US012559564B2

(12) United States Patent
Robson et al.

(10) Patent No.: US 12,559,564 B2
(45) Date of Patent: Feb. 24, 2026

(54) COMPOSITIONS AND METHODS FOR PREVENTING OR REVERSING T-CELL EXHAUSTION THROUGH ECTONUCLEOTIDASE INHIBITION AND ANTIBODY-MEDIATED TARGET CYTOSIS

(71) Applicants: Beth Israel Deaconess Medical Center, Inc., Boston, MA (US); Antagen Institute for Biomedical Research, Boston, MA (US)

(72) Inventors: Simon C. Robson, Weston, MA (US); Yan Wu Shang, North Reading, MA (US); Wenda Gao, Sharon, MA (US); Haohai Zhang, Brighton, MA (US); Paola De Andrade Mello, Cambridge, MA (US)

(73) Assignees: Beth Israel Deaconess Medical Center, Inc., Boston, MA (US); Antagen Institute for Biomedical Research, Boston, MA (US)

( * ) Notice: Subject to any disclaimer, the term of this patent is extended or adjusted under 35 U.S.C. 154(b) by 675 days.

(21) Appl. No.: 17/251,507

(22) PCT Filed: Jun. 14, 2019

(86) PCT No.: PCT/US2019/037312

§ 371 (c)(1),
(2) Date: Dec. 11, 2020

(87) PCT Pub. No.: WO2019/241707

PCT Pub. Date: Dec. 19, 2019

(65) Prior Publication Data

US 2021/0253731 A1 Aug. 19, 2021

Related U.S. Application Data

(60) Provisional application No. 62/685,176, filed on Jun. 14, 2018.

(51) Int. Cl.
*C07K 16/28* (2006.01)
*A61K 39/00* (2006.01)
*A61K 45/06* (2006.01)

(52) U.S. Cl.
CPC .......... *C07K 16/2896* (2013.01); *A61K 45/06* (2013.01); *A61K 2039/505* (2013.01);
(Continued)

(58) Field of Classification Search
CPC ............ C07K 16/2896; C07K 2317/24; C07K 2317/31; C07K 2317/41; C07K 2317/565;
(Continued)

(56) References Cited

U.S. PATENT DOCUMENTS

2010/0303828 A1 12/2010 Levy et al.
2013/0273062 A1 10/2013 Bensussan et al.
(Continued)

FOREIGN PATENT DOCUMENTS

WO WO-2008068048 A2 * 6/2008 .............. A61P 31/10
WO WO-2017089334 A1 * 6/2017 .............. A61P 35/00
(Continued)

OTHER PUBLICATIONS

Wang et al., Tailoring Biomaterials for Cancer Immunotherapy: Emerging Trends and Future Outlook, May 26, 2017, Advanced Materials, vol. 29, Issue 29, pp. 1-24. (Year: 2017).*
(Continued)

*Primary Examiner* — Aurora M Fontainhas
*Assistant Examiner* — Selam Berhane
(74) *Attorney, Agent, or Firm* — Clark & Elbing LLP

(57) ABSTRACT

In combination with conventional therapies (e.g., targeted therapy, chemotherapy, and angiogenesis inhibitors etc.), immunotherapies targeting checkpoint molecules have shown promise in the treatment of solid or liquid tumors. However, apoptotic regulatory T cells (Treg) induced by
(Continued)

such therapies often become more suppressive in the tumor microenvironment (TME), through increased generation of adenosine tightly controlled by ectonucleotidases, viz. CD39 and CD73. CD39/ENTPD1, a novel checkpoint molecule, is highly expressed and activated on the tumor vasculature and infiltrating immune cells, promoting tumor growth. Deletion or blockade of CD39 enhances anti-tumor activity by augmenting anti-tumor immune responses and inhibiting tumor angiogenesis. The present invention is based at least in part on the development of anti-CD39 antibodies which mediate CD39 downregulation on immune cells, such as T-cells with markers of T-cell exhaustion, and the demonstrated utility of these antibodies in blocking tumor growth with minimal side effects in pre-clinical models.

6 Claims, 59 Drawing Sheets

Specification includes a Sequence Listing.

(52) U.S. Cl.
CPC ...... *C07K 2317/24* (2013.01); *C07K 2317/31* (2013.01); *C07K 2317/41* (2013.01); *C07K 2317/565* (2013.01); *C07K 2317/732* (2013.01)

(58) Field of Classification Search
CPC .............. C07K 2317/732; A61K 45/06; A61K 2039/505
See application file for complete search history.

(56) References Cited

U.S. PATENT DOCUMENTS

| | | | |
|---|---|---|---|
| 2016/0137747 A1 | 5/2016 | Levy et al. | |
| 2017/0355756 A1* | 12/2017 | Julien | A61P 25/00 |
| 2017/0362321 A1 | 12/2017 | Campbell et al. | |
| 2018/0086846 A1 | 3/2018 | Wiltzius et al. | |

FOREIGN PATENT DOCUMENTS

| | | |
|---|---|---|
| WO | WO-2017/157948 A1 | 9/2017 |
| WO | WO-2017/220988 A1 | 12/2017 |

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Kussie, Paul H., "A Single Engineered Amino Acid Substitution Changes Antibody Fine Specificity", 1994, Journal of Immunology 152(1): pp. 146-152. (Year: 1994).*

Extended European Search Report for European Patent Application No. 19819158.7 dated Apr. 7, 2022 (12 pages).

Shields et al., "Lack of Fucose on Human IgG1 N-Linked Oligosaccharide Improves Binding to Human FcgammaRIII and Antibody-dependent Cellular Toxicity," J Biol Chem. 277(30):26733-26740 (2002).

Bastid et al., "Inhibition of CD39 Enzymatic Function at the Surface of Tumor Cells Alleviates Their Immunosuppressive Activity," Cancer Immunol Res. 3(3)254-265 (2015).

"Purified anti-mouse CD39 Antibody," BioLegend, <https://www.biolegend.com/en-us/products/purified-anti-mouse-cd39-antibody-6236>, retrieved on Mar. 23, 2022 (2 pages).

Canale et al., "CD39 Expression Defines Cell Exhaustion in Tumor-Infiltrating CD8+ T Cells," Cancer Res. 78(1):115-28 (2018).

International Search Report and Written Opinion for International Application No. PCT/US2019/037312, mailed Oct. 2, 2019 (18 pages).

Kashyap et al., "Antisense oligonucleotide targeting CD39 improves anti-tumor T cell immunity," J Immunother Cancer. 7(1):67 (2019) (12 pages).

Sela-Culang et al., "The structural basis of antibody-antigen recognition," Front Immunol. 4:302 (Oct. 2013) (13 pages).

Caldas et al., "Humanization of the anti-CD18 antibody 6.7: An unexpected effect of a framework residue in binding to antigen," Mol Immunol. 39(15):941-52 (May 2003).

Communication pursuant to Article 94(3) EPC for European Patent Application No. 19819159.7 dated Jul. 10, 2025 (10 Pages).

* cited by examiner

Fig. 28

| Sample name | BUN (18-29mg/dl) | ALT (28-132mg/dl) | AST (59-247mg/dl) |
|---|---|---|---|
| CTX1 | 20 | 33 | 29 |
| CTX2 | 18 | 0 | 27 |
| CTX3 | 16 | 42 | 29 |
| CTX4 | 34 | 17 | 31 |
| CTX5 | 13 | 27 | 27 |
| CTX6 | 12 | 26 | 25 |
| CTX7 | 16 | 23 | 21 |
| CTX8 | 14 | 15 | 27 |
| CTX9 | 15 | 13 | 14 |
| CTX10 | 11 | 24 | 17 |

*$P < 0.05$
**$P < 0.01$
***$P < 0.001$

*P < 0.05
**P < 0.01
***P < 0.001

*P < 0.05
**P < 0.01
***P < 0.001

*P < 0.05
**P < 0.01
***P < 0.001

*P < 0.05
**P < 0.01
***P < 0.001

*$P$ < 0.05
**$P$ < 0.01
***$P$ < 0.001

*P < 0.05
**P < 0.01
***P < 0.001

*P < 0.05
**P < 0.01
***P < 0.001

*P < 0.05
**P < 0.01
***P < 0.001

*P < 0.05
**P < 0.01
***P < 0.001

Within coculture: Chimeric mAb/hIgG1

Coculture/B cells alone

Within coculture: Chimeric mAb/hIgG1

Coculture/B cells alone

Within coculture: Chimeric mAb/hIgG1

Coculture/B cells alone

Within coculture: Chimeric mAb/hIgG1

Coculture/B cells alone

COMPOSITIONS AND METHODS FOR PREVENTING OR REVERSING T-CELL EXHAUSTION THROUGH ECTONUCLEOTIDASE INHIBITION AND ANTIBODY-MEDIATED TARGET CYTOSIS

STATEMENT REGARDING FEDERALLY SPONSORED RESEARCH

This invention was made with government support under Grant Nos. CA221702, CA164970, HL094400, and HL063972 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 13, 2019 is named "01948-260WO2_Sequence_Listing_06.13.19_ST25" and is 69,641 bytes in size.

BACKGROUND OF THE INVENTION

The discovery of tumor-associated antigens and tumor-reactive immune cells led to a promise of a new cancer therapy based on tumor antigen-specific immune responses. Despite the success of immunotherapies in advanced cancers based on inhibitory antibodies to programmed cell death protein 1 (PD1), PD1 ligand 1 (PD11) and cytotoxic T lymphocyte antigen 4 (CTLA4) therapies in advanced cancer, a considerable proportion of patients remain unresponsive to these treatments (known as innate resistance). In addition, one-third of patients relapse after initial response (known as adaptive resistance). Preventing successful immunotherapy of cancer is the occurrence of multiple non-redundant immunosuppressive mechanisms coexisting within the tumour microenvironment.

Extracellular adenosine has been known as an inhibitor of immune functions. While intracellular adenosine is involved in energy metabolism, nucleic acid metabolism, and the methionine cycle, extracellular adenosine plays an important role in intercellular signaling. Its signal is transmitted by G protein-coupled adenosine receptors on the cell surface, and it affects diverse physiological functions including neurological, cardiovascular, and immunological systems. Extracellular concentration of adenosine can increase in response to metabolic change. When cells are deprived of nutrients or oxygen, insufficient ATP biosynthesis tends to lower the ATP/adenosine ratio. To reduce ATP expenditure, cells may suspend energy-consuming activities such as cell proliferation, which requires biosynthesis of a large amount of cellular components.

Immunosuppressive adenosine 3'5'-monophosphate (cAMP)-mediated pathway signaling through adenosine A2A receptor (A2AR), can inhibit T lymphocytes and natural killer (NK) cells in hypoxic, inflamed, and cancerous microenvironment. In addition, blocking the adenosine-generating pathway CD39/CD73 also induces regression of breast cancer, colorectal cancer and melanoma animal models. However, because of the potential for deleterious effects, such as inflammation and exacerbation of inflammatory/autoimmune diseases, the use of A2AR inhibitors can have unwanted systemic effects that cause adverse event conditions requiring dosing limitation/de-escalation or even discontinuation of drug to cancer patients. In the case of anti-CD39 and anti-CD73 antibody therapies, which focus predominantly on the inhibition of ATP catabolism to adenosine through binding to these cell surface adenosine generating enzymes ("ectonucleotidases"), not only is the risk of systemic side-effects present, but the antibodies do not address the full range of activities these cell surface proteins may have. This is especially evident when upregulated in the generation of exhausted T-cells in the tumor infiltrated lymphocyte (TILs) that can contribute to resistance to immuno-oncology therapies (such as anti-PD-1) in significant percentages of patients. Accordingly, new methods of treatment are needed.

SUMMARY OF THE INVENTION

The present invention is based on the discovery that certain antibodies to an ectonucleoside triphosphate diphosphohydrolase, such as CD39, are capable of preventing or reversing T-cell exhaustion and enhancing immune responses through a process of antibody-mediated target cytosis (removal) of CD39 on CD45+ immune cells.

One aspect of the present invention provides methods and therapeutic agents for decreasing T-cell exhaustion in a subject in need thereof, comprising administering to a subject an effective amount of a pharmaceutical composition of an anti-CD39 agent comprising an antigen binding domain that binds ectonucleoside triphosphate diphosphohydrolase-1 ("CD39") and an FcγRIIIa binding moiety that binds FcγRIIIa, administration of which antibody results in a reduction of detectable CD39 levels on CD45+ immune cells.

In certain embodiments, the FcγRIIIa binding moiety is selected from an Fc domain, an antibody or fragment thereof that binds to FcγRIIIa, and an FcγRIIIa binding peptide.

In certain embodiments, the antigen binding domain is an Fab, Fab', $F(ab')_2$, Fv or single chain Fv (scFv).

In certain embodiments, the anti-CD39 agent causes antibody-mediated target cytosis of CD39 on CD45+ immune cells. In certain embodiments, the anti-CD39 agent reduces percentage of exhausted T-cells (e.g., T-cells phenotypic for T-cell exhaustion) in the tumor.

In certain embodiments, the anti-CD39 agent causes antibody-mediated target cytosis of CD39 from tumor vascular endothelium. In certain embodiments, the anti-CD39 agent is antiangiogenic or otherwise disrupts or collapses the vasculature network in the tumor.

In certain embodiments, the anti-CD39 agent is an antibody or antigen-binding fragment thereof comprising a heavy chain variable region that at least 60% (e.g., 70%, 80%, 90%, 95%, 97%, 99%, or 100%) identical to the variable region of SEQ ID NO: 3, 5, 7, 9 or 11, and a light chain variable region that is at least 60% (e.g., 70%, 80%, 90%, 95%, 97%, 99%, or 100%) identical to the variable region SEQ ID NO: 4, 6, 8, 10 or 12, which antibody is able to specifically bind human CD39.

In certain embodiments, the anti-CD39 agent is an antibody or antigen-binding fragment thereof comprising a heavy chain having CDRs at least 60% (e.g., 70%, 80%, 90%, 95%, 97%, 99%, or 100%) identical to the CDRs of SEQ ID NO: 3, 5, 7, 9 or 11, and a light chain having CDRs at least 60% (e.g., 70%, 80%, 90%, 95%, 97%, 99%, or 100%) identical to the CDRs of SEQ ID NO: 4, 6, 8, 10 or 12, which antibody is able to specifically bind human CD39.

In certain embodiments, the anti-CD39 agent is an antibody or antigen-binding fragment thereof comprising a heavy chain having the CDRs of SEQ ID NO: 3 and a light chain having the CDRs of SEQ ID NO: 4, and human framework sequences to form humanized heavy and light chains with an antigen binding site able to specifically bind human CD39.

In certain embodiments, the anti-CD39 agent is an antibody or antigen-binding fragment thereof comprising a heavy chain having the CDRs of SEQ ID NO: 5 and a light chain having the CDRs of SEQ ID NO: 6, and human framework sequences to form humanized heavy and light chains with an antigen binding site able to specifically bind human CD39.

In certain embodiments, the anti-CD39 agent is an antibody comprising a heavy chain having the CDRs of SEQ ID NO: 7 and a light chain having the CDRs of SEQ ID NO: 8, and human framework sequences to form humanized heavy and light chains with an antigen binding site able to specifically bind human CD39.

In certain embodiments, the anti-CD39 agent is an antibody comprising a heavy chain having the CDRs of SEQ ID NO: 9 and a light chain having the CDRs of SEQ ID NO: 10, and human framework sequences to form humanized heavy and light chains with an antigen binding site able to specifically bind human CD39.

In certain embodiments, the anti-CD39 agent is an antibody comprising a heavy chain having the CDRs of SEQ ID NO: 11 and a light chain having the CDRs of SEQ ID NO: 12, and human framework sequences to form humanized heavy and light chains with an antigen binding site able to specifically bind human CD39.

In certain embodiments, the anti-CD39 agent is administered as part of an antitumor therapy.

In certain embodiments, the anti-CD39 agent is administered as part of an anti-infective therapy, such as antiviral therapy (including treatment of HIV and HBV infection), treatment for *Mycobacterium tuberculosis*, and visceral leishmaniasis.

Another aspect of the present invention provides methods and therapeutic agents for promoting an anti-tumor immune response comprising administering to a human patient having a tumor an anti-CD39 antibody that binds ectonucleoside triphosphate diphosphohydrolase-1 ("CD39"), and which antibody binds FcγRIIa, retains antibody-dependent cellular cytotoxicity (ADCC), and administration of the antibody to the human patient results in a reduction of CD39 expression on immune cells in the tumor.

In certain embodiments, the anti-CD39 antibody causes antibody-mediated target cytosis of CD39 on CD45+ immune cells. In certain embodiments, the anti-CD39 agent reduces percentage (e.g., by 10%, 20%, 30%, 40%, 50%, 60%, 70%, 80%, 90%, 95%, or 100%) of exhausted T-cells (e.g., T-cells phenotypic for T-cell exhaustion) in the tumor.

In certain embodiments, the anti-CD39 agent causes antibody-mediated target cytosis of CD39 from tumor vascular endothelium. In certain embodiments, the anti-CD39 agent is antiangiogenic or otherwise disrupts or collapses the vasculature network in the tumor.

In certain embodiments, the anti-CD39 antibody is an IgG1 or IgG3 isotype.

In certain embodiments, the anti-CD39 antibody is hypofucosylated or afucosylated.

In certain embodiments, the anti-CD39 antibody is a human antibody or humanized antibody.

In certain embodiments, anti-CD39 antibody (or more generally, the anti-CD39 agent) is a multispecific (e.g., bispecific) antibody (or multispecific anti-CD39 agent) including at least one additional antigen binding site for a tumor antigen, immune checkpoint or costimulatory receptor, wherein if the additional antigen binding site is for an immune checkpoint it functions as a checkpoint inhibitor and wherein if the additional antigen binding site is for a costimulatory receptor it functions as a costimulatory agonist. For instance, the additional antigen binding site can be one which binds to a checkpoint protein, such as selected from the group consisting of PD-1, PD-L1, CTLA-4/B7-1/B7-2, PD-L2, NKG2A, KIR, LAG-3, TIM-3, CD96, VISTA and TIGIT, wherein the additional antigen binding site is a checkpoint inhibitor. In certain preferred embodiments, the additional antigen binding site binds a checkpoint protein upregulated on T-cells and associated with T-cell exhaustion. The additional antigen binding site can also be one which binds to an immune costimulatory receptor, such as selected from the group consisting of MHCI molecules, BTLA receptor, OX40, CD27, CD28, CDS, ICAM-1, LFA-1 (CD11a/CD18), ICOS (CD278) and 4-1 BB (CD137), wherein the additional antigen binding site is a costimulatory agonist.

In certain embodiments, the anti-CD39 antibody (or more generally, the anti-CD39 agent) is administered as part of an antitumor therapy for treating a solid or liquid tumor. Exemplary solid tumors that can be treated by the subject method include is pancreatic cancer, liver cancer, lung cancer, stomach cancer, esophageal cancer, head and neck squamous cell carcinoma, prostate cancer, colon cancer, breast cancer, lymphoma, gallbladder cancer, renal cancer, multiple myeloma, ovarian cancer, cervical cancer or glioma. Exemplary liquid tumors that can be treated by the subject method include leukemias such as myelogenous or granulocytic leukemia, lymphatic, lymphocytic, or lymphoblastic leukemia, and polycythemia vera or erythremia.

The anti-CD39 agent, such as the anti-CD39 antibody, can be administered as part of a therapy involving one or more chemotherapeutic agents, anti-angiogenetic agents, immuno-oncology agents and/or radiation. Exemplary inhibitors (e.g., antagonists) of checkpoint molecules include PD-1 antagonists, PD-L1 antagonists, CTLA-4 antagonists, LAG-3 antagonists, TIM-3 antagonists and TIGIT antagonists. Exemplary activators (e.g., agonists) of costimulatory molecules include GITR agonists, CD27 agonists, 4-1 BB agonists, OX40 agonists, CD137 agonists, ICOS agonists and CD28 agonists. Examples of other therapeutic agents that can be administered as part of the therapy with an anti-CD39 agent include VEGF/VEGFR antagonists (such as an anti-VEGF-2 antibodies like Cyramza), an EGF/EGFR antagonist (such as an anti-EGFR antibody like Necitumumab), an IDO inhibitor (such as NLG919) or an IDO1 inhibitor (such as Epacadostat), an HDAC inhibitor (such as entiostat), a PI3K delta inhibitor (such as TGR-1202), an IL-15 agonist (such as IL15Ra-Fc fusion protein ALT-803), a CXCR4 antagonist (such as Ulocuplumab, Plerixafor and BL-8040), a CXCL12 antagonist (such as the Spiegelmer NOX-A12), a DNMT inhibitor (such as azacitidine), interleukin-21, an anti-KIR antibody (such as Lirilumab), an anti-CSF-1R antibody (such as FPA008 or RO5509554), an anti-CCR4 antibody (such as Mogamulizumab), GMCSF (such as sargamostim), an anti-PS antibody (such as Bavituximab), an anti-CD30 antibody-aurstatin E conjugate (such as Adcetris), an anti-CD19 antibody (such as MEDI-551), an anti-CEA IL-2 antibody (such as RG7813), an anti-NY-ESO-1 antibody (such as CDX-1401), an anti-NKG2A antibody (such as IPH2201), a STING agonist (such as ADU-S100, MK-1454 or SB 11285), a TRL7/8 agonist (such as MEDI9197), a RIG-1 agonist (such as RGT100), or an anti-CD73 antibody (such as MEDI9447).

The subject methods of the present invention can also be used as part of therapies including tumor vaccines, adoptive cell therapy (including CAR-T and ACTR therapies), anti-tumor gene therapies, inhibitory nucleic acid therapies (such as siRNA, shRNA, antisense, CRISPR and TALEN therapies) or oncolytic viral therapies.

Yet another aspect of the invention provides a method for preventing or reversing T-cell exhaustion and enhancing an immune response against a tumor, comprising (i) identifying a cancer patient having a degree of tumor infiltrated lymphocytes expressing one or more markers of T-cell exhaustion above a predetermined threshold; and (ii) administering to the patient an anti-CD39 antibody that binds ectonucleoside triphosphate diphosphohydrolase-1 ("CD39") and FcγRIIIa, reduces detectable CD39 levels on the tumor infiltrated lymphocytes and thereby reverses T-cell exhaustion.

In certain embodiments, the anti-CD39 antibody causes antibody-mediated target cytosis of CD39 on CD45+ immune cells. In certain embodiments, the anti-CD39 agent reduces percentage of exhausted T-cells (e.g., T-cells phenotypic for T-cell exhaustion) in the tumor.

In certain embodiments, the anti-CD39 agent causes antibody-mediated target cytosis of CD39 from tumor vascular endothelium. In certain embodiments, the anti-CD39 agent is antiangiogenic or otherwise disrupts or collapses the vasculature network in the tumor.

In certain embodiments, the anti-CD39 antibody is an IgG1 or IgG3 isotype.

In certain embodiments, the anti-CD39 antibody is hypofucosylated or afucosylated.

In certain embodiments, the anti-CD39 antibody is a human antibody or humanized antibody.

In certain embodiments, the anti-CD39 antibody is a multispecific (e.g., bispecific) antibody including at least one additional antigen binding site for a tumor antigen, immune checkpoint or costimulatory receptor, wherein if the additional antigen binding site is for an immune checkpoint it functions as a checkpoint inhibitor and wherein if the additional antigen binding site is for a costimulatory receptor it functions as a costimulatory agonist. For instance, the additional antigen binding site can be one which binds to a checkpoint protein, such as selected from the group consisting of PD-1, PD-L1, CTLA-4/B7-1/B7-2, PD-L2, NKG2A, KIR, LAG-3, TIM-3, CD96, VISTA and TIGIT, wherein the additional antigen binding site is a checkpoint inhibitor. In certain preferred embodiments, the additional antigen binding site binds a checkpoint protein upregulated on T-cells and associated with T-cell exhaustion. The additional antigen binding site can also be one which binds to an immune costimulatory receptor, such as selected from the group consisting of MHCI molecules, BTLA receptor, OX40, CD27, CD28, CDS, ICAM-1, LFA-1 (CD11a/CD18), ICOS (CD278) and 4-1BB (CD137), wherein the additional antigen binding site is a costimulatory agonist.

In certain embodiments, the anti-CD39 antibody is administered as part of an antitumor therapy for treating a tumor, e.g., a solid or liquid tumor. Exemplary solid tumors that can be treated by the subject method include sarcomas, carcinomas, and lymphomas, such as pancreatic cancer, liver cancer, lung cancer, stomach cancer, esophageal cancer, head and neck squamous cell carcinoma, prostate cancer, colon cancer, breast cancer, lymphoma, gallbladder cancer, renal cancer, multiple myeloma, ovarian cancer, cervical cancer and gliomas, as well as lymphomas (both Hodgkin lymphoma and Non-Hodgkin lymphoma). Exemplary liquid tumors that can be treated by the subject method include leukemias such as myelogenous or granulocytic leukemia, lymphatic, lymphocytic, or lymphoblastic leukemia, and plycythemia vera or erythremia.

The anti-CD39 antibody can be administered as part of a therapy involving one or more chemotherapeutic agents, anti-angiogenetic agents, immuno-oncology agents and/or radiation.

Exemplary inhibitors (antagonists) of checkpoint molecules include PD-1 antagonists, PD-L1 antagonists, CTLA-4 antagonists, LAG-3 antagonists, TIM-3 antagonists and TIGIT antagonists. Exemplary activators (agonists) of costimulatory molecules include GITR agonists, CD27 agonists, 4-1 BB agonists, OX40 agonists, CD137 agonists, ICOS agonists and CD28 agonists. Examples of other therapeutic agents that can be administered as part of the therapy with an anti-CD39 agent include VEGFR/VEGF antagonists, EGFR/EGF antagonists, IDO inhibitors (including IDO1 and IDO2 inhibitors), HDAC inhibitors, PI3K delta inhibitors, IL-15 agonists, CXCR4 antagonists, CXCL12 antagonists, DNMT inhibitors, interleukin-21, anti-KIR antibodies, anti-CSF-1R antibodies, anti-CCR4 antibodies, GMCSF, anti-PS antibodies, anti-CD30 antibody-drug (e.g., aurstatin E) conjugate, anti-CD19 antibodies, anti-CEA IL-2 antibodies, anti-NY-ESO-1 antibodies, anti-NKG2A antibodies, STING agonists, TRL7/8 agonists, RIG-1 agonists, anti-CD73 antibodies, P2X7 antagonists and Adenosine A2a receptor antagonists.

The subject methods of the present invention can also be used as part of therapies including tumor vaccines, adoptive cell therapy (including CAR-T and ACTR therapies), anti-tumor gene therapies, inhibitory nucleic acid therapies (such as siRNA, shRNA, antisense, CRISPR and TALEN therapies) or oncolytic viral therapies.

In certain embodiments, step (i) further includes detecting the number or percentage of cells or intensity of antibody staining indicating the degree of upregulation of one or more of CD39, PD-1, CTLA-4, TIM-3, LAG-3, CD160, BTLA, or 2B4 on tumor infiltrating lymphocytes. In those embodiments, the status of other upregulated markers of T-cell exhaustion can be used to determine eligibility of patients for receiving administration of an anti-CD39 antibody, e.g., the antibody is administered to patients having a degree of tumor infiltrated lymphocytes expressing one or more markers of T-cell exhaustion above the predetermined threshold. Such T-cell exhausted markers can be prevalent in patients suffering from, e.g., non-Small Cell Lung Carcinoma (NSCLC), Colorectal Cancer, Advanced Melanoma, Renal Cell Carcinoma (RCC), Breast Cancer (including Triple Negative Breast Cancer, Gastric Cancer, Esophageal Cancer, Urothelial Carcinoma (UC), or Hepatocellular Carcinoma (HCC).

Still another aspect of the invention provides a pharmaceutical preparation for decreasing T-cell exhaustion in a subject in need thereof, comprising a therapeutically effective amount of an antibody that binds ectonucleoside triphosphate diphosphohydrolase-1 ("CD39") and binds FcγRIIIa, which when administrators results in a reduction of detectable CD39 levels on CD45+ immune cells and is effective to restore T-cell function in T-cells exhibiting T-cell exhaustion or T-cell anergy.

In certain embodiments, the anti-CD39 antibody causes antibody-mediated target cytosis of CD39 on CD45+ immune cells. In certain embodiments, the anti-CD39 agent reduces percentage of exhausted T-cells (e.g., T-cells phenotypic for T-cell exhaustion) in the tumor.

In certain embodiments, the anti-CD39 agent causes antibody-mediated target cytosis of CD39 from tumor vascular endothelium. In certain embodiments, the anti-CD39 agent is antiangiogenic or otherwise disrupts or collapses the vasculature network in the tumor.

In certain embodiments, the anti-CD39 antibody is an IgG1 or IgG3 isotype.

In certain embodiments, the anti-CD39 antibody is hypofucosylated or afucosylated.

In certain embodiments, the anti-CD39 antibody is a human antibody or humanized antibody.

In certain embodiments, the anti-CD39 antibody is a multispecific (e.g., bispecific) antibody including at least one additional antigen binding site for a tumor antigen, immune checkpoint or costimulatory receptor, wherein if the additional antigen binding site is for an immune checkpoint it functions as a checkpoint inhibitor and wherein if the additional antigen binding site is for a costimulatory receptor it functions as a costimulatory agonist. For instance, the additional antigen binding site can be one which binds to a checkpoint protein, such as selected from the group consisting of PD-1, PD-L1, CTLA-4/B7-1/B7-2, PD-L2, NKG2A, KIR, LAG-3, TIM-3, CD96, VISTA and TIGIT, wherein the additional antigen binding site is a checkpoint inhibitor. In certain preferred embodiments, the additional antigen binding site binds a checkpoint protein upregulated on T-cells and associated with T-cell exhaustion. The additional antigen binding site can also be one which binds to an immune costimulatory receptor, such as selected from the group consisting of MHCI molecules, BTLA receptor, OX40, CD27, CD28, CDS, ICAM-1, LFA-1 (CD11a/CD18), ICOS (CD278) and 4-1BB (CD137), wherein the additional antigen binding site is a costimulatory agonist.

In certain embodiments, the anti-CD39 antibody is formulated for administration to a human patient as part of an antitumor therapy for treating a solid or liquid tumor. Exemplary solid or liquid tumors that can be treated by the subject method include is pancreatic cancer, liver cancer, lung cancer, stomach cancer, esophageal cancer, head and neck squamous cell carcinoma, prostate cancer, colon cancer, breast cancer, gallbladder cancer, renal cancer, multiple myeloma, ovarian cancer, cervical cancer and gliomas, as well as lymphomas (both Hodgkin lymphoma and Non-Hodgkin lymphoma). Exemplary liquid tumors that can be treated by the subject method include leukemias such as myelogenous or granulocytic leukemia, lymphatic, lymphocytic, or lymphoblastic leukemia, and plycythemia vera or erythremia.

In certain embodiments, the anti-CD39 antibody can be formulated with or present in a kit for co-administration with one or more chemotherapeutic agents, anti-angiogenetic agents, immuno-oncology agents and/or radiation. Exemplary inhibitors (antagonists) of checkpoint molecules include PD-1 antagonists, PD-L1 antagonists, CTLA-4 antagonists, LAG-3 antagonists, TIM-3 antagonists and TIGIT antagonists. Exemplary activators (agonists) of costimulatory molecules include GITR agonists, CD27 agonists, 4-1BB agonists, OX40 agonists, CD137 agonists, ICOS agonists and CD28 agonists. Examples of other therapeutic agents that can be administered as part of the therapy with an anti-CD39 agent include VEGFR/VEGF antagonists, EGFR/EGF antagonists, IDO inhibitors (including IDO1 and IDO2 inhibitors), HDAC inhibitors, PI3K delta inhibitors, IL-15 agonists, CXCR4 antagonists, CXCL12 antagonists, DNMT inhibitors, interleukin-21, anti-KIR antibodies, anti-CSF-1R antibodies, anti-CCR4 antibodies, GMCSF, anti-PS antibodies, anti-CD30 antibody-drug (e.g., aurstatin E) conjugate, anti-CD19 antibodies, anti-CEA IL-2 antibodies, anti-NY-ESO-1 antibodies, anti-NKG2A antibodies, STING agonists, TRL7/8 agonists, RIG-1 agonists, anti-CD73 antibodies, P2X7 antagonists and Adenosine A2a receptor antagonists.

The subject methods of the present invention can also be used as part of therapies including tumor vaccines, adoptive cell therapy (including CAR-T and ACTR therapies), antitumor gene therapies, inhibitory nucleic acid therapies (such as siRNA, shRNA, antisense, CRISPR and TALEN therapies) or oncolytic viral therapies.

In certain embodiments, step (i) further includes detecting the number or percentage of cells or intensity of antibody staining indicating the degree of upregulation of one or more of CD39, PD-1, CTLA-4, TIM-3, LAG-3, CD160, BTLA, or 2B4 on tumor infiltrating lymphocytes. In those embodiments, the status of other upregulated markers of T-cell exhaustion can be used to determine eligibility of patients for receiving administration of an anti-CD39 antibody, e.g., the antibody is administered to patients having a degree of tumor infiltrated lymphocytes expressing one or more markers of T-cell exhaustion above the predetermined threshold. Such T-cell exhausted markers can be prevalent in patients suffering from, to illustrate, non-Small Cell Lung Carcinoma (NSCLC), Colorectal Cancer, Advanced Melanoma, Renal Cell Carcinoma (RCC), Breast Cancer (including Triple Negative Breast Cancer, Gastric Cancer, Esophageal Cancer, Urothelial Carcinoma (UC), or Hepatocellular Carcinoma (HCC).

Another aspect of the invention provides a pharmaceutical preparation for decreasing T-cell exhaustion in a subject in need thereof, including a therapeutically effective amount of an antibody that binds ectonucleoside triphosphate diphosphohydrolase-1 ("CD39") and binds FcγRIIIa, which when administrators results in a reduction of detectable CD39 levels on CD45+ immune cells and is effective to restore T-cell function in T-cells exhibiting T-cell exhaustion or T-cell anergy. The antibody may include:

a) a heavy chain having the CDRs of SEQ ID NO: 3 and a light chain having the CDRs of SEQ ID NO: 4,
b) a heavy chain having the CDRs of SEQ ID NO: 5 and a light chain having the CDRs of SEQ ID NO: 6,
c) a heavy chain having the CDRs of SEQ ID NO: 7 and a light chain having the CDRs of SEQ ID NO: 8,
d) a heavy chain having the CDRs of SEQ ID NO: 9 and a light chain having the CDRs of SEQ ID NO: 10, or
e) a heavy chain having the CDRs of SEQ ID NO: 11 and a light chain having the CDRs of SEQ ID NO: 12.

The heavy and light chains may further include human framework sequences to form humanized heavy and light chains with an antigen binding site able to specifically bind human CD39.

Another aspect of the invention provides a bispecific antibody comprising a first binding part specifically binding to human CD39 and a second binding part specifically binding to a tumor antigen, immune checkpoint or costimulatory receptor, wherein if the additional antigen binding site is for an immune checkpoint it functions as a checkpoint inhibitor and wherein if the additional antigen binding site is for a costimulatory receptor it functions as a costimulatory agonist, wherein the bispecific antibody causes antibody-mediated target cytosis of CD39 on CD45+ immune cells.

BRIEF DESCRIPTION OF THE DRAWINGS

FIG. 2A shows a control with saline, FIG. 2B shows tumor growth when treated with 5F2-mIgG2c, and FIG. 2C shows tumor growth treated with Afuc 5F2-mIgG2c.

FIG. 4A shows a control with saline, and FIG. 4B shows tumor growth when treated with WT 5F2-mIgG1.

FIG. 6A shows tumor growth when treated with WT 5F2-mIgG1, FIG. 6B shows tumor growth when treated with Afuc 5F2-mIgG1, FIG. 6C shows tumor growth when treated with 5F2-mIgG2c, and FIG. 6D shows tumor growth when treated with Afuc 5F2-mIgG2c.

FIG. 28 is a table showing that no significant cytotoxicity is noted as evaluated for liver (ALT and AST) and renal (BUN) functions in tumor-free mice treated with 1000 μg afuc 5F2 IgG2c three times (CTX8-10). Liver and renal functions were evaluated, and no significant toxicity was found.

FIG. 37A shows control mice treated with saline, FIG. 37B shows tumor growth in mice treated with WT 5F2-mIgG1, FIG. 37C shows tumor growth in mice treated with Afuc 5F2-mIgG1, FIG. 37D shows tumor growth in mice treated with 5F2-mIgG2c, and FIG. 37E shows tumor growth in mice treated with Afuc 5F2-mIgG2c.

FIG. 49A shows PB1, FIG. 49B shows PB3, FIG. 49C shows PB4, and FIG. 49D shows PB5.

DETAILED DESCRIPTION OF THE INVENTION

I. Overview

Figure 1A:
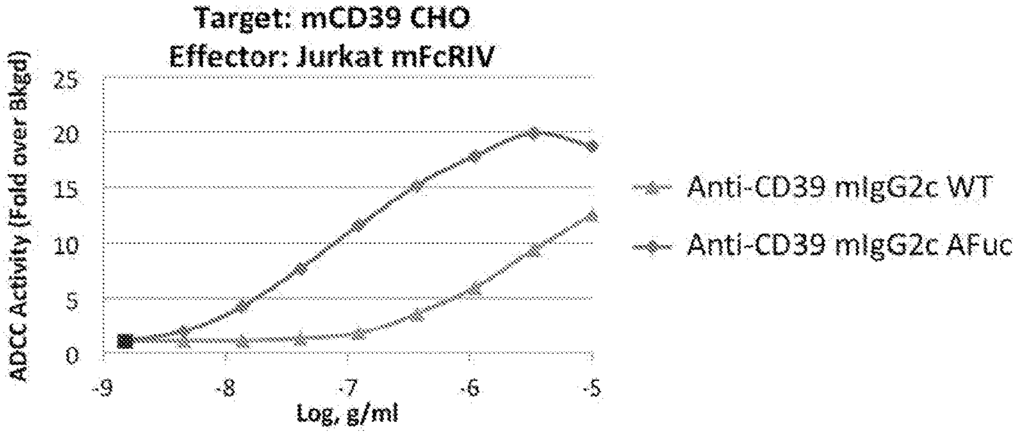
FIGS. 1A-1B are graphs showing that anti-CD39 5F2 antibody demonstrates ADCC activities against mouse and human CD39 positive cells. CHO cells expressing mCD39 (FIG. 1A) or Raji cells expressing hCD39 (FIG. 1B) were used as target cells, respectively. Jurkat cells transfected with a plasmid encoding luciferase were purchased from Promega, and further infected with pLentiTdT-mFcγRIV. TdTomato positive Jurkat cells were FACS-sorted and used as effector cells. Wildtype (WT) or afucosylated (Afuc) 5F2-mIgG2c was added at serially diluted concentrations. ADCC in fold increase of luciferase activity over background was measured after 6 hours of incubation of antibodies with target and effector cells.

To inactivate the adenosine-dependent immunosuppression, it would be beneficial to think about the metabolism of extracellular adenosine. The source of extracellular adenosine is believed to be ATP in the extracellular compartment. There are nucleotidases on the cell surface called CD39 and CD73. CD39 catalyzes hydrolysis of ATP/ADP to AMP, and CD73 converts AMP to adenosine. Tissue hypoxia can induce accumulation of extracellular adenosine by increasing adenosine production and by decreasing adenosine removal. Hypoxia induces the mRNA levels and enzymatic activities of CD39 and CD73 leading to an increase in adenosine production. The rate of adenosine removal can be reduced by hypoxia-dependent inhibition of adenosine kinase, resulting in further accumulation of adenosine.

The ability of CD8+ T lymphocytes to eliminate tumors is limited by their countervailing ability to create an immunosuppressive microenvironment. Evidence has emerged recently that a subset of tumor-infiltrating CD8+ T cells are marked by high expression levels of CD39. The frequency of $CD39^{high}$CD8+ T cells increased with tumor growth but was absent in lymphoid organs. Tumor-infiltrating CD8+ T cells with high CD39 expression exhibited features of exhaustion, such as reduced production of TNF and IL2 and expression of coinhibitory receptors. Exhausted CD39+ CD8+ T cells from mice hydrolyzed extracellular ATP, confirming that CD39 is enzymatically active. Furthermore, exhausted CD39+CD8+ T cells inhibited IFNγ production by responder CD8+ T cells. In specimens from breast cancer and melanoma patients, CD39+CD8+ T cells were present within tumors and invaded or metastatic lymph nodes, but were barely detectable within noninvaded lymph nodes and absent in peripheral blood. These cells exhibited an exhausted phenotype with impaired production of IFNγ, TNF, IL2, and high expression of coinhibitory receptors. Although T-cell receptor engagement was sufficient to induce CD39 on human CD8+ T cells, exposure to IL6 and IL27 promoted CD39 expression on stimulated CD8+ T cells from human or murine sources. These observations indicate how the tumor microenvironment drives the acquisition of CD39 as an immune regulatory molecule on CD8+ T cells, with implications for defining a biomarker of T-cell dysfunction and a target for immunotherapeutic intervention. Exhausted T cells express multiple co-inhibitory molecules that impair their function and limit immunity to chronic viral infection. CD39 is a marker of exhausted CD8+ T cells in connection with chronic viral infections and in microbial and parasitic pathogen infections. CD39 expressed by CD8+ T cells in chronic infection is enzymatically active, co-expressed with PD-1, marks cells with a transcriptional signature of T cell exhaustion and correlates with viral load in HIV and HCV. In the mouse model of chronic Lymphocytic Choriomeningitis Virus infection, virus-specific CD8+ T cells contain a population of $CD39^{high}$ CD8+ T cells that is absent in functional memory cells elicited by acute infection. This $CD39^{high}$ CD8+ T cell population is enriched for cells with the phenotypic and functional profile of terminal exhaustion. This implicates the purinergic pathway in the regulation of T cell exhaustion connected to chronic infections The present invention is based at least in part on the discovery that certain antibodies to ectonucleoside triphosphate diphosphohydrolase, such as CD39, are capable of preventing or reversing T-cell exhaustion and enhancing immune responses through a process of trogocytosis—oncologic trogocytosis in the case of cancer.

In certain embodiments, the present invention provides pharmaceutical compositions comprising an antibody that binds to an ectonucleoside triphosphate diphosphohydrolase-1 ("CD39"), and also binds to FcγRIII (such as FcγRIIIa and/or FcγRIIIc) and, when administered to a patient having a $CD39^{high}$CD45+ immunes cells (such as $CD39^{high}$ CD8+ T cells), results in a reduction of $CD39^{high}$ CD45+ immunes cells, preferably without a substantial decrease in the number of CD45+ immune cells. While not wishing to be bound by any particular theory, the reduction of $CD39^{high}$ CD45+ immunes cells, such as $CD39^{high}$ CD8+ T cells, is apparently the consequence of the FcγRIII binding-dependent removal (a process referred to CD39 trogocytosis, as defined below) of CD39 from immune cells, e.g., without depleting the immune cell population by way of cell killing. The result is preservation of the immune cell numbers but with reversion from the exhausted phenotype to an immune competent state.

In certain embodiments, the anti-CD39 agent causes antibody-mediated target cytosis of CD39 from tumor vascular endothelium. In certain embodiments, the anti-CD39 agent is antiangiogenic or otherwise disrupts or collapses the vasculature network in the tumor.

II. Definitions

To facilitate an understanding of the present invention, a number of terms and phrases are defined below.

"CD39", also referred to as "Cluster of Differentiation 39", "ectonucleoside triphosphate diphosphohydrolase-1" or (gene) "ENTPD1" and (protein) "NTPDase1" is a cell surface-located ectonucleotidase with an extracellularly facing catalytic site that catalyse the hydrolysis of γ- and β-phosphate residues of triphospho- and diphosphonucleosides to the monophosphonucleoside derivative (ENZYME entry: EC 3.6.1.5), such as to hydrolyzes P2 receptor ligands such as ATP, ADP, UTP and UDP. A representative human NTPDase1 protein sequence is provided in the UniProtKB entry "P49961 (ENTP1_HUMAN)", and a representative human coding sequence for the enzyme is provided in GenBank Accession S73813.

A "CD39 antibody" (alternatively an "anti-CD39 antibody") refers to an antibody that selectively binds to one or more epitopes of the NTPDase1 protein, and includes monoparatopic antibodies, as well as biparatopic and other multiparatopic format antibodies.

"Antibody-mediated Target Cytosis" or "AMTC" in the context of the present invention refers to antibody-mediated depletion of CD39 from the surface of CD45+ immune cells without a substantial decrease in the number of CD45+ immune cells, e.g., through a process other than induction of CD45+ cell death. As described herein, the preferred CD39 Antibody binds to an extracellular epitope of NTPDase1 and also binds FcγRIII (e.g., through an Fc domain of the antibody or other FcγRIII binding moiety), and even more preferably is able to mediate FcγRIII binding-dependent Antibody-mediated Target Cytosis of CD39 from CD45+ immune cells.

a. Antibodies and Other Polypeptides

The term "antibody" as used herein refers to an immunoglobulin molecule that recognizes and specifically binds a target, such as a protein, polypeptide, peptide, carbohydrate, polynucleotide, lipid, or a combination of any of the foregoing, through at least one antigen-binding site wherein the antigen-binding site is usually within the variable region of the immunoglobulin molecule. As used herein, the term encompasses intact polyclonal antibodies, intact monoclonal antibodies, antigen-binding fragments (such as Fab, Fab', F(ab')2, and Fv fragments), single chain Fv (scFv) antibodies provided those fragments have been formatted to include an Fc or other FcγRIII binding domain, multispecific antibodies, bispecific antibodies, monospecific antibodies, monovalent antibodies, chimeric antibodies, humanized antibodies, human antibodies, fusion proteins comprising an antigen-binding site of an antibody (formatted to include an Fc or other FcγRIII binding domain), and any other modified immunoglobulin molecule comprising an antigen-binding site as long as the antibodies exhibit the desired biological activity.

The term "antigen-binding portion" of an antibody, as used herein, refers to one or more fragments of an antibody that retain the ability to specifically bind to an antigen (e.g., human CD39). It has been shown that the antigen-binding function of an antibody can be performed by fragments of a full-length antibody. Examples of binding fragments encompassed within the term "antigen-binding portion" of an antibody, e.g., an anti-CD39 antibody described herein, include (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Such single chain antibodies are also intended to be encompassed within the term "antigen-binding portion" of an antibody. These and other potential constructs are described at Chan & Carter (2010) Nat. Rev. Immunol. 10:301. These antigen-binding fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "variable region" of an antibody refers to the variable region of an antibody light chain, or the variable region of an antibody heavy chain, either alone or in combination. Generally, the variable region of heavy and light chains each consist of four framework regions (FR) and three complementarity determining regions (CDRs), also known as "hypervariable regions". The CDRs in each chain are held together in close proximity by the framework regions and, with the CDRs from the other chain, contribute to the formation of the antigen-binding sites of the antibody. There are at least two techniques for determining CDRs: (1) an approach based on cross-species sequence variability (e.g., Kabat et al., 1991, Sequences of Proteins of Immunological Interest, 5th Edition, National Institutes of Health, Bethesda Md.), and (2) an approach based on crystallographic studies of antigen-antibody complexes (Al Lazikani et al., 1997, J. Mol. Biol., 273:927-948). In addition, combinations of these two approaches are sometimes used in the art to determine CDRs.

While the antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively, the preferred CD39 antibody is an IgG1 and IgG3 isotype in order to engage FcγRIII most effectively (e.g., with a Kd of $10^{-7}$ or smaller).

In certain embodiments, the antibody is "hypofucosylated" and may even be "afucosylated". A "hypofucosylated" antibody preparation refers to an antibody preparation in which less than 50% of the oligosaccharide chains contain α-1,6-fucose. Typically, less than about 40%, less than about 30%, less than about 20%, less than about 10%, or less than 5% or less than 1% of the oligosaccharide chains contain α-1,6-fucose in a "hypofucosylated" antibody preparation. An "afucosylated" antibody lacks α-1,6-fucose in the carbohydrate attached to the CH2 domain of the IgG heavy chain.

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animal (e.g., a transgenic mouse having a genome comprising a human heavy chain transgene and a light chain transgene), to an immortalized cell.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability. In some instances, the Fv framework region residues of a human immunoglobulin are replaced with the corresponding residues in an antibody from a non-human species. The humanized antibody can be further modified by the substitution of additional residues either in the Fv framework region and/or within the replaced non-human residues to refine and optimize antibody specificity, affinity, and/or binding capability. The humanized antibody may comprise variable domains containing all or substantially all of the CDRs that correspond to the non-human immunoglobulin whereas all or substantially all of the framework regions are those of a human immunoglobulin sequence. In some embodiments, the variable domains comprise the framework regions of a human immunoglobulin sequence. In some embodiments, the variable domains comprise the framework regions of a human immunoglobulin consensus sequence. The humanized antibody can also comprise at least a portion of an immunoglobulin constant region or domain (Fc), typically that of a human immunoglobulin. A humanized antibody is usually considered distinct from a chimeric antibody.

The term "human antibody" as used herein refers to an antibody produced by a human or an antibody having an amino acid sequence corresponding to an antibody produced by a human made using any of the techniques known in the art.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions are homologous to the sequences in antibodies derived from another species (usually human) to avoid eliciting an immune response in that species.

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (Fc□RIIB) receptor.

An "FcγRIII binding moiety" is a peptide, protein, nucleic acid or other moiety which, when associated with an antigen binding site of an anti-CD39 antibody, is able to bind to FcγRIII (CD16) and mediate Antibody-mediated Target Cytosis.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 1 (e.g., 2, 3, 4, 5, 6, 7, 8, 9, 10, or more) amino acids in a unique spatial conformation.

As used herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of less than or equal to 1 μM, 100 nM, 10 nM, 1 nM, or even 0.1 nM. In certain embodiments, an antibody specifically binds to an epitope on a protein that is conserved among the protein from different species. In another embodiment, specific binding can include, but does not require exclusive binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies or other members of the immunoglobulin superfamily, in certain embodiments, the polypeptides can occur as single chains or as associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

A "conservative amino acid substitution" is one in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble proteins, and/or antibodies of the invention do not abrogate the binding of the polypeptide, soluble protein, or antibody containing the amino acid sequence, to the target binding site. Methods of identifying amino acid conservative substitutions which do not eliminate binding are well-known in the art.

A polypeptide, soluble protein, antibody, polynucleotide, vector, cell, or composition which is "isolated" is a polypeptide, soluble protein, antibody, polynucleotide, vector, cell, or composition which is in a form not found in nature. Isolated polypeptides, soluble proteins, antibodies, polynucleotides, vectors, cells, or compositions include those which have been purified to a degree that they are no longer in a form in which they are found in nature. In some embodiments, a polypeptide, soluble protein, antibody, polynucleotide, vector, cell, or composition which is isolated is substantially pure.

The term "substantially pure" as used herein refers to material which is at least 50% pure (e.g., free from contaminants), at least 90% pure, at least 95% pure, at least 98% pure, or at least 99% pure.

The term "fusion protein" or "fusion polypeptide" as used herein refers to a hybrid protein expressed by a nucleic acid molecule comprising nucleotide sequences of at least two genes.

The term "linker" or "linker region" as used herein refers to a linker inserted between a first polypeptide (e.g., an anti-CD39 antibody) and a second polypeptide (e.g., an Fc or other FcγRIII binding moiety; an scFV, Vhh domain or the like the binds a different protein to create a bispecific antibody format maintaining the bivalency for CD39). In some embodiments, the linker is a peptide linker. Linkers should not adversely affect the expression, secretion, or bioactivity of the polypeptides. Preferably, linkers are not antigenic and do not elicit an immune response.

b. Nucleic Acids

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

As used herein, the term "nucleic acid molecule encoding", "DNA sequence encoding," and "DNA encoding" refer to the order or sequence of nucleotides along a strand of deoxyribonucleic acid deoxyribonucleotides. The order of these deoxyribonucleotides determines the order of amino acids along the polypeptide (protein) chain. Thus, a nucleic acid sequence encoding the amino acid sequence.

When used in reference to nucleotide sequences, "sequence" as used herein, the term grammatical and other forms may comprise DNA or RNA, and may be single or double stranded. Nucleic acid sequences may be mutated. Nucleic acid sequence may have any length, for example 2 to 000,000 or more nucleotides (or any integral value above or between) a nucleic acid, for example a length of from about 100 to about 10,000, or from about 200 nucleotides to about 500 nucleotides.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

As used herein, the term "transfection" refers to an exogenous nucleic acid into a eukaryotic cell. Transfection can be achieved by various means known in the art, including calcium phosphate -DNA co-precipitation, DEAE-dextran-mediated transfection, polybrene-mediated transfection, electroporation, microinjection, liposome fusion, lipofection, protoplast fusion, retroviral infection, and biolistics technology (biolistics).

The term "carrier" as used herein is an isolated nucleic acid comprising the isolated nucleic acid can be used to deliver a composition to the interior of the cell. It is known in the art a number of carriers including, but not limited to the linear polynucleotides, polynucleotides associated with ionic or amphiphilic compounds, plasmids, and viruses. Thus, the term "vector" includes an autonomously replicating plasmid or virus. The term should also be construed to include facilitate transfer of nucleic acid into cells of the non-plasmid and non-viral compounds, for example, polylysine compounds, liposomes, and the like. Examples of viral vectors include, but are not limited to adenoviral vectors, adeno-associated virus vectors, retroviral vectors and the like.

As used herein, the term "expression vector" refers to a vector comprising a recombinant polynucleotide comprising expression control sequence and a nucleotide sequence to be expressed operably linked. The expression vector comprises sufficient cis-acting elements (cis-acting elements) used for expression; other elements for expression can be supplied by the host cell or in vitro expression system. Expression vectors include all those known in the art, such as cosmids, plasmids (e.g., naked or contained in liposomes) and viruses (e.g., lentivirus, retroviruses, adenoviruses and adeno-associated viruses).

As used herein, the term "operably linked" refers to functional linkage between the regulatory sequence and a heterologous nucleic acid sequence is connected to a connection results in the expression of the latter. For example, when the first nucleic acid sequence and a second nucleic acid sequence is a functional relationship between the first nucleic acid sequence and the second nucleic acid sequence is operably linked. For example, if the promoter affects the transcription or expression of the coding sequence, the promoter is operably linked to a coding sequence. Typically, DNA sequencing operably linked are contiguous, and to join two protein coding regions in the same reading frame as necessary.

As used herein, the term "promoter" is defined as a promoter DNA sequence recognized by the synthetic machinery required for the synthesis machinery of the cell specific transcription of a polynucleotide sequence or introduced.

The term "constitutive expression" as used herein refers to all expressed under physiological conditions.

The term "inducible expression" as used herein refers to expression under certain conditions, the conditions such as occurs when a T cell antigen binding. How those skilled in the routine "induce expression."

The term "electroporation" refers to the use of a transmembrane electric field pulse to induce microscopic pathways (pores) in a bio-membrane; their presence allows biomolecules such as plasmids or other oligonucleotide to pass from one side of the cellular membrane to the other.

c. Checkpoint Inhibitors, Co-Stimulatory Agonists and Chemotherapeutics

A "checkpoint molecule" refers to proteins that are expressed by tissues and/or immune cells and reduce the efficacy of an immune response in a manner dependent on the level of expression of the checkpoint molecule. When these proteins are blocked, the "brakes" on the immune system are released and, for example, T cells are able to kill cancer cells more effectively. Examples of checkpoint proteins found on T cells or cancer cells include PD-1/PD-L1 and CTLA-4/B7-1/B7-2, PD-L2, NKG2A, KIR, LAG-3, TIM-3, CD96, VISTA and TIGIT.

A "checkpoint inhibitor" refers to a drug entity that reverses the immunosuppressive signaling from a checkpoint molecule.

A "costimulatory molecule" refers to an immune cell such as a T cell cognate binding partner which specifically binds to costimulatory ligands thereby mediating co-stimulation, such as, but not limited to proliferation. Costimulatory molecules are cell surface molecules other than the antigen receptor or ligand which facilitate an effective immune response. Co-stimulatory molecules include, but are not limited to MHCI molecules, BTLA receptor and Toll ligands, and OX40, CD27, CD28, CDS, ICAM-1, LFA-1 (CD11a/CD18), ICOS (CD278) and 4-1 BB (CD137). Examples of costimulatory molecules include but are not limited to: CDS, ICAM-1, GITR, BAFFR, HVEM (LIGHTR), SLAMF7, NKp80 (KLRF1), NKp44, NKp30, NKp46, CD160, CD19, CD4, CD8a, CD83, IL2Rp3, IL2Ry, IL7Ra, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244,2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and CD83 ligand.

A "costimulatory agonists" refers to a drug entity that activates (agonizes) the costimulatory molecule, such as costimulatory ligand would do, and produces an immunostimulatory signal or otherwise increases the potency or efficacy of an immune response.

A "chemotherapeutic agent" is a chemical compound useful in the treatment of cancer. Examples of chemotherapeutic agents include alkylating agents such as thiotepa and cyclophosphamide (CYTOXAN); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL); beta-lapachone; lapachol; colchicines; betulinic acid; a camptothecin (including the synthetic analogue topotecan (HYCAMTIN), CPT-11 (irinotecan, CAMPTOSAR), acetylcamptothecin, scopolectin, and 9-aminocamptothecin)); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammalI and calicheamicin omegaI1 (see, e.g., Nicolaou et al., Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN, morpholino-doxorubicin, cyanomorpholino-doxorubicin, 2-pyrrolino-doxorubicin, doxorubicin HCl liposome injection (DOXIL) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR), tegafur (UFTORAL), capecitabine (XELODA), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE, FILDESIN); dacarbazine; mannomustine; mitobronitol; mitolactol; pipobroman; gacytosine; arabinoside ("Ara-C"); thiotepa; taxoids, e.g., paclitaxel (TAXOL), albumin-engineered nanoparticle formulation of paclitaxel (ABRAXANE), and doxetaxel (TAXOTERE); chloranbucil; 6-thioguanine; mercaptopurine; methotrexate; platinum analogs such as cisplatin and carboplatin; vinblastine (VELBAN); platinum; etoposide (VP-16); ifosfamide; mitoxantrone; vincristine (ONCOVIN); oxaliplatin; leucovovin; vinorelbine (NAVELBINE); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX tamoxifen), raloxifene (EVISTA), droloxifene, 4-hydroxytamoxifen, trioxifene, keoxifene, LY117018, onapristone, and toremifene (FARESTON); anti-progesterones; estrogen receptor down-regulators (ERDs); estrogen receptor antagonists such as fulvestrant (FASLODEX); agents that function to suppress or shut down the ovaries, for example, leutinizing hormone-releasing hormone (LHRH) agonists such as leuprolide acetate (LUPRON and ELIGARD), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE), exemestane (AROMASIN), formestanie, fadrozole, vorozole (RIVISOR), letrozole (FEMARA), and anastrozole (ARIMIDEX). In addition, such definition of chemotherapeutic agents includes bisphosphonates such as clodronate (for example, BONEFOS or OSTAC), etidronate (DIDROCAL), NE-58095, zoledronic acid/zoledronate (ZOMETA), alendronate (FOSAMAX), pamidronate (AREDIA), tiludronate (SKELID), or risedronate (ACTONEL); as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE vaccine and gene therapy vaccines, for example, ALLOVECTIN vaccine, LEUVECTIN vaccine, and VAXID vaccine; topoisomerase 1 inhibitor (e.g., LURTOTECAN); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1α, IL-2, IL-3, IL-4, IL-5, IL-6, IL-7, IL-8, IL-9, IL10, IL-11, IL-12, IL-13, IL-15, IL-17A-F, IL-18 to IL-29 (such as IL-23), IL-31, including PROLEUKIN rIL-2; a tumor-necrosis factor such as TNF-α or TNF-β, TGF-β1-3; and other polypeptide factors including leukemia inhibitory factor ("LIF"), ciliary neurotrophic factor ("CNTF"), CNTF-like cytokine ("CLC"), cardiotrophin ("CT"), and kit ligand ("KL").

As used herein, the term "chemokine" refers to soluble factors (e.g., cytokines) that have the ability to selectively induce chemotaxis and activation of leukocytes. They also trigger processes of angiogenesis, inflammation, wound healing, and tumorigenesis. Example chemokines include IL-8, a human homolog of murine keratinocyte chemoattractant (KC).

d. Treatments

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g., increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors.

"Enhancing T-cell function" means to induce, cause or stimulate a T-cell to have a sustained or amplified biological function, or renew or reactivate exhausted or inactive T-cells. Examples of enhancing T-cell function include: increased secretion of y-interferon from CD8+ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, or 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased levels of CD39. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (noncancerous) or malignant (cancerous) including pre-cancerous lesions. Tumor growth is generally uncontrolled and progressive, does not induce or inhibit the proliferation of normal cells. Tumor can affect a variety of cells, tissues or organs, including but not limited to selected from bladder, bone, brain, breast, cartilage, glial cells, esophagus, fallopian tube, gall bladder, heart, intestine, kidney, liver, lung, lymph node, neural tissue, ovary, pancreas, prostate, skeletal muscle, skin, spinal cord, spleen, stomach, testis, thymus, thyroid, trachea, urethra, ureter, urethra, uterus, vagina organ or tissue or the corresponding cells. Tumors include cancers, such as sarcoma, carcinoma, plasmacytoma or (malignant plasma cells). Tumors of the present invention, may include, but are not limited to leukemias (e.g., acute leukemia, acute lymphoblastic leukemia, acute myeloid leukemia, acute myeloid leukemia, acute promyelocytic leukemia, acute myeloid-monocytic leukemia, acute monocytic leukemia, acute leukemia, chronic leukemia, chronic myeloid leukemia, chronic lymphocytic leukemia, polycythemia vera), lymphomas (Hodgkin's disease, non-Hodgkin's disease), primary macroglobulinemia disease, heavy chain disease, and solid tumors such as sarcomas cancer (e.g., fibrosarcoma, myxosarcoma, liposarcoma, chondrosarcoma, osteosarcoma, chordoma, endothelium sarcoma, lymphangiosarcoma, angiosarcoma, lymphangioendothelio sarcoma, synovioma vioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, carcinoma, bronchogenic carcinoma, medullary carcinoma, renal cell carcinoma, hepatoma, Nile duct carcinoma, choriocarcinoma, spermatogonia Tumor, embryonal carcinoma, Wilms' tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, retinoblastoma), esophageal cancer, gallbladder, kidney cancer, multiple myeloma. Preferably, a "tumor" includes, but is not limited to: pancreatic cancer, liver cancer, lung cancer, stomach cancer, esophageal cancer, head and neck squamous cell carcinoma, prostate cancer, colon cancer, breast cancer, lymphoma, gallbladder cancer, renal cancer, leukemia, multiple myeloma, ovarian cancer, cervical cancer and glioma.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "effective amount" as used herein refers to an amount to provide therapeutic or prophylactic benefit.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

The term "treatment" as used herein refers to the individual trying to change the process or treatment of a clinical disease caused by intervention of a cell, may be either preventive intervention course of clinical pathology. Including but not limited to treatment to prevent the occurrence or recurrence of disease, alleviation of symptoms, reducing the direct or indirect pathological consequences of any disease, preventing metastasis, slow the rate of disease progression, amelioration or remission of disease remission or improved prognosis.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The terms "agonist" and "agonistic" as used herein refer to or describe an anti-CD39 antibody that is capable of, directly or indirectly, substantially inducing, activating, promoting, increasing, or enhancing the biological activity of a target and/or a pathway. The term "agonist" is used herein to include any agent that partially or fully induces, activates, promotes, increases, or enhances the activity of a protein or other target of interest.

The terms "antagonist" and "antagonistic" as used herein refer to or describe an anti-CD39 antibody that is capable of, directly or indirectly, partially or fully blocking, inhibiting, reducing, or neutralizing a biological activity of a target and/or pathway. The term "antagonist" is used herein to include any agent that partially or fully blocks, inhibits, reduces, or neutralizes the activity of a protein or other target of interest.

The terms "modulation" and "modulate" as used herein refer to a change or an alteration in a biological activity.

Modulation includes, but is not limited to, stimulating an activity or inhibiting an activity. Modulation may be an increase in activity or a decrease in activity, a change in binding characteristics, or any other change in the biological, functional, or immunological properties associated with the activity of a protein, a pathway, a system, or other biological targets of interest.

The term "immune response" as used herein includes responses from both the innate immune system and the adaptive immune system. It includes both cell-mediated and/or humoral immune responses. It includes both T-cell and B-cell responses, as well as responses from other cells of the immune system such as natural killer (NK) cells, monocytes, macrophages, etc.

The term "pharmaceutically acceptable" refers to a substance approved or approvable by a regulatory agency of the Federal government or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one agent of the present disclosure, and which does not destroy the pharmacological activity thereof and is nontoxic when administered in doses sufficient to deliver a therapeutic effect. In general, those of skill in the art and the U.S. FDA consider a pharmaceutically acceptable excipient, carrier, or adjuvant to be an inactive ingredient of any formulation.

The terms "effective amount" or "therapeutically effective amount" or "therapeutic effect" refer to an amount of an anti-CD39 antibody described herein (e.g., a fusion protein, a soluble receptor, an antibody, a polypeptide, a polynucleotide, a small organic molecule, or other drug) effective to "treat" a disease or disorder in a subject such as, a mammal. In the case of cancer or a tumor, the therapeutically effective amount of an anti-CD39 antibody (e.g., polypeptide, soluble protein, or antibody) has a therapeutic effect and as such can boost the immune response, boost the anti-tumor response, increase cytolytic activity of immune cells, increase killing of tumor cells by immune cells, reduce the number of tumor cells; decrease tumorigenicity, tumorigenic frequency or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects.

The terms "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented. In the case of cancer or a tumor, a subject is successfully "treated" according to the methods of the present invention if the patient shows one or more of the following: an increased immune response, an increased anti-tumor response, increased cytolytic activity of immune cells, increased killing of tumor cells by immune cells, a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

e. Miscellaneous

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

As used herein, reference to "about" or "approximately" a value or parameter includes (and describes) embodiments that are directed to that value or parameter. For example, description referring to "about X" includes description of "X".

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

III. Anti-CD39 Antibodies a. Monoclonal Antibodies

The anti-CD39 antibodies may be a monoclonal antibody. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the CD39 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

b. Human and Humanized Antibodies

The anti-CD39 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-329 (1988); and Presta, Curr. Op. Struct. Biol., 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

The antibodies may also be affinity matured using known selection and/or mutagenesis methods as described above.

Preferred affinity matured antibodies have an affinity which is five times, more preferably 10 times, even more preferably 20 or 30 times greater than the starting antibody (generally murine, humanized or human) from which the matured antibody is prepared.

c. Bispecific Antibodies

Anti-CD39 antibodies described herein include bispecific molecules. An anti-CD39 antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody described herein may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antigen-binding fragment, peptide or binding mimetic, such that a bispecific molecule results.

Accordingly, provided herein are bispecific molecules comprising at least one first binding specificity for CD39 and a second binding specificity for a second target epitope. In an embodiment described herein in which the bispecific molecule is multi-specific, the molecule can further include a third binding specificity.

In certain embodiments, the subject bispecific (or multi-specific as the case may be) includes one or more binding domains for immune checkpoints, e.g., which are checkpoint inhibitors, such as PD-1, PD-L1, CTLA-4/B7-1/B7-2, PD-L2, NKG2A, KIR, LAG-3, TIM-3, CD96, VISTA and/or TIGIT. In certain embodiments, the multi-specific includes binding domains that bind checkpoint proteins on T-cells, especially checkpoints associated with T-cell exhaustion such as LAG-3, TIM-3 or TIGIT. In certain embodiments, the multi-specific binds to CD39 and one or more other T-cell associated checkpoints and leads to antibody-mediated target cytosis of both CD39 and the other checkpoint proteins to which it binds.

In certain embodiments, the subject bispecific (or multi-specific as the case may be) includes one or more binding domains for immune costimulatory receptors, e.g., which are costimulatory agonists (activators), such as agonists of MHCI molecules, BTLA receptor and Toll ligands, and OX40, CD27, CD28, CDS, ICAM-1, LFA-1 (CD11a/CD18), ICOS (CD278) and 4-1 BB (CD137). Examples of costimulatory molecules that can be included in the multi-specific include but are not limited to: CDS, ICAM-1, GITR, BAFFR, HVEM (LIGHTR), SLAMF7, NKp80 (KLRF1), NKp44, NKp30, NKp46, CD160, CD19, CD4, CD8a, CD83, IL2Rp3, IL2Ry, IL7Ra, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244,2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and CD83 ligand.

In one embodiment, the bispecific molecules described herein comprise as a binding specificity at least one antibody, or an antigen-binding fragment thereof, including, e.g., an Fab, Fab', $F(ab')_2$, Fv, or a single chain Fv. The antibody may also be a light chain or heavy chain dimer, or any minimal fragment thereof such as a Fv or a single chain (scFv) construct.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan).

Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies can be prepared as full length antibodies or antigen-binding fragments (e.g., $F(ab')_2$ bispecific antibodies). Techniques for generating bispecific antibodies from antigen-binding fragments have been described in the literature. For example, bispecific antibodies can be prepared can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., J. Exp. Med. 175:217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antigen-binding fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antigen-binding fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antigen-binding fragments by the use of single-chain Fv (sFv) dimers has also been reported. See, Gruber et al., J. Immunol. 152:5368 (1994).

Antibodies with more than two valencies are contemplated. As one nonlimiting example, trispecific antibodies can be prepared. See, e.g., Tutt et al., J. Immunol. 147:60 (1991).

d. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

e. Effector Function Engineering

It may be desirable to modify the antibody of the invention with respect to effector function, so as to enhance, e.g., the effectiveness of the anti-CD39 antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med., 176: 1191-1195 (1992) and Shopes, J. Immunol., 148: 2918-2922 (1992). In certain preferred embodiments, the effector function being engineered is the ability of the anti-CD39 antibody to induce FcγRIII binding-dependent removal (such as by anti-CD39 antibody mediated target cytosis) of CD39 from immune cells, e.g., without depleting the immune cell population by way of cell killing.

Homodimeric antibodies with enhanced anti-tumor activity may also be prepared using heterobifunctional cross-linkers as described in Wolff et al. Cancer Research, 53: 2560-2565 (1993). Alternatively, an antibody can be engineered that has dual Fc regions and may thereby have enhanced CD39 trogocytosis capabilities. See Stevenson et al., Anti-Cancer Drug Design, 3: 219-230 (1989).

In some embodiment, anti-CD39 antibodies were generated which were mouse antibodies. For instance, the murine monoclonal 5F2 specifically binds to mouse CD39 with cross-reactivity to human CD39. The amino acid sequences of the light and heavy chains of the 5F2 antibody were determined using standard techniques. The light chain variable region sequence of this antibody is:

DIQLTQSPASLSVATGEKVTIRCIT-STDVDDDMNWFQQKPGEPPNL-LISEGDTLRPGVPSRFSSS GYGTDFVF-TIENTLSEDVADYYCLQSDNMPLTFGGGTKLEIK (SEQ ID NO:1)

and the heavy chain variable regions sequence of this antibody is:

EVQLEESGPGLVQPSQRLSITCTISGFSLTSY-GIHWVRQSPGKGLEWLGVIWSGGNTDYNAAFIS RLSISKDNSKSQVFFKMNSLQVGDTATYYCAR-NGHGSNIPWFVYWGQGTLVTVST (SEQ ID NO:2).

In some embodiments, the anti-CD39 antibody or antigen-binding fragment thereof, is a humanized version of the murine 5F2 antibody.

In some embodiments, the anti-CD39 antibody or antigen-binding fragment thereof comprises at least one light chain variable is at least 60% identical to SEQ ID NO: 1, and even more preferably at least 65%, 70%, 75%, 80%, 85%, 90%, 95%, 97%, 99%, or 100% identical to SEQ ID NO: 1, and able to specifically bind human CD39.

In some embodiments, the anti-CD39 antibody or antigen-binding fragment thereof comprises at least one heavy chain variable is at least 60% identical to SEQ ID NO: 2, and even more preferably at least 65%, 70%, 75%, 80%, 85%, 90%, 95%, 97%, 99%, or 100% identical to SEQ ID NO: 2, and able to specifically bind human CD39.

In certain embodiments, the anti-CD39 antibody is a humanized antibody comprising the CDRs of SEQ ID NO: 1 and/or 2, or CDRs at least 65%, 70%, 75%, 80%, 85%, 90%, 95%, 97%, 99%, or 100% identical to SEQ ID NO: 1 or 2, and human framework sequences to form humanized heavy and light chains with an antigen binding site able to specifically bind human CD39.

In certain embodiments, an antibody provided herein is a chimeric antibody. In one example, a chimeric antibody comprises a non-human variable region (e.g., a variable region derived from a mouse, rat, hamster, rabbit, or non-human primate, such as a monkey), such as one or both variable regions from SEQ ID NO: 1 or 2, and a human constant region. Chimeric antibodies of interest herein include "primatized" antibodies comprising variable domain antigen-binding sequences derived from a non-human primate (e.g., Old World Monkey, such as baboon, rhesus or cynomolgus monkey) and human constant region sequences. In a further example, a chimeric antibody is a "class switched" antibody in which the class or subclass has been changed from that of the parent antibody. Chimeric antibodies include antigen-binding fragments thereof.

In other embodiments, anti-CD39 antibodies which were generated were rabbit monoclonal antibodies. For instance, the monoclonal antibodies designated herein as PB1, PB2, PB3, PB4 and PB5, are monoclonal antibodies that specifically binds to human CD39. The amino acid sequences of the light and heavy chains of the PB1-PB5 antibodies were determined using standard techniques, and the heavy and light chain sequences are as follows:

PB1
Heavy chain:

(SEQ ID NO: 3)

METGLRWLLLVAVLKGVQCQEQLVESGGDLVQPGASLTLTCTTSGFSFSSNYWICWVRQAPGKGLEWI

GCIYTGSDTTYYASWAKGRFTISKTSSTTVTLQMTSLTAADTATYSCARGGAVYAAYAGVFFGLWGPGSL

VTVSSGQPKAPSVFPLAPCCGDTPSSTVTLGCLVKGYLPEPVTVTWNSGTLTNGVRTFPSVRQSSGLYS

LSSVVSVTSSSQPVTCNVAHPATNTKVDKTVAPSTCSKPMCPPPELPGGPSVFIFPPKPKDTLMISRTPE

VTCVVVDVSQDDPEVQFTWYINNEQVRTARPPLREQQFNSTIRVVSTLPIAHQDWLRGKEFKCKVHNKA

LPAPIEKTISKARGQPLEPKVYTMGPPREELSSRSVSLTCMINGFYPSDISVEWEKNGKAEDNYKTTPTVL

DSDGSYFLYSKLSVPTSEWQRGDVFTCSVMHEALHNHYTQKSISRSPGK

Light chain:

(SEQ ID NO: 4)

MDTRAPTQLLGLLLLWLPGARCADVVMTQTPASVSEPVGGTVTIKCQASESIYSGLAWYQQKPGQPPKL

LIYGASTLASGVPSRFKGSGSGTEFTLTISDLECADAATYYCQSYFGIGGYGLAFGGGTEVVVLGDPVAPT

VLIFPPAADQVATGTVTIVCVANKYFPDVTVTWEVDGTTQTTGIENSKTPQNSADCTYNLSSTLTLTSTQY

NSHKEYTCKVTQGTTSVVQSFNRGDC

PB2
Heavy chain:

(SEQ ID NO: 5)

METGLRWLLLVAVLKGVQCQSLEESGGDLVKPGASLTLTCTASGIDFSDYGYMCWVRQAPGKGLEWIG

CIYVGSSGSTYYATWAKGRFTVSRPSSTTVTLQMTSLTAADTATYFCVRRVNGYGLWGPGTLVTVSSGQ

PKAPSVFPLAPCCGDTPSSTVTLGCLVKGYLPEPVTVTWNSGTLTNGVRTFPSVRQSSGLYSLSSVVSVT

SSSQPVTCNVAHPATNTKVDKTVAPSTCSKPMCPPPELPGGPSVFIFPPKPKDTLMISRTPEVTCVVVDV

SQDDPEVQFTWYINNEQVRTARPPLREQQFNSTIRVVSTLPIAHQDWLRGKEFKCKVHNKALPAPIEKTIS

KARGQPLEPKVYTMGPPREELSSRSVSLTCMINGFYPSDISVEWEKNGKAEDNYKTTPTVLDSDGSYFL

YSKLSVPTSEWQRGDVFTCSVMHEALHNHYTQKSISRSPGK

Light chain:

(SEQ ID NO: 6)

MDTRVPTQLLGLLLLWLPGARCADVVMTQTPASVSEPVGGTVTIKCQASENIYTGLAWYQQRPGQPPKL

LIYAASTLASGVSSRFKGSRSGTEYTLTISDLECADAATYYCQGCYGISSYGDSFGGGTEVVVRGDPVAP

TVLIFPPAADQVATGTVTIVCVANKYFPDVTVTWEVDGTTQTTGIENSKTPQNSADCTYNLSSTLTLTSTQ

YNSHKEYTCKVTQGTTSVVQSFNRGDC

PB3
Heavy chain:

(SEQ ID NO: 7)

METGLRWLLLVAVLKGVQCQSLEESGGDLVKPGASLTLTCTASGFSFSKNYWMCWVRQAPGKGLEWIG

CIYTGSDSRYYASWVNGRFSISKSSSTTVTLQMTSLTAADTATYFCASDSGAPGSSDSTLWGPGTLVTVS

SGQPKAPSVFPLAPCCGDTPSSTVTLGCLVKGYLPEPVTVTWNSGTLTNGVRTFPSVRQSSGLYSLSSV

VSVTSSSQPVTCNVAHPATNTKVDKTVAPSTCSKPMCPPPELPGGPSVFIFPPKPKDTLMISRTPEVTCV

VVDVSQDDPEVQFTWYINNEQVRTARPPLREQQFNSTIRVVSTLPIAHQDWLRGKEFKCKVHNKALPAPI

-continued

EKTISKARGQPLEPKVYTMGPPREELSSRSVSLTCMINGFYPSDISVEWEKNGKAEDNYKTTPTVLDSDG

SYFLYSKLSVPTSEWQRGDVFTCSVMHEALHNHYTQKSISRSPGK

Light chain:

(SEQ ID NO: 8)

MDTRVPTQLLGLLLLWLPGARCADVVMTQTPASVEAAVGGTVTIKCQASENIYSGLAWYQQKPGQPPKL

LIYLASTLASGVSSRFKGSRSGTEYTLTISDLECADAATYYCQSYYALSTYGTAFGGGTEVVVKGDPVAPT

VLIFPPAADQVATGTVTIVCVANKYFPDVTVTWEVDGTTQTTGIENSKTPQNSADCTYNLSSTLTLTSTQY

NSHKEYTCKVTQGTTSVVQSFNRGDC

PB4

Heavy chain:

(SEQ ID NO: 9)

METGLRWLLLVAVLKGVQCQEQLVESGGGLVQPEGSLTLTCTASGFSFSSSYYMCWVRQAPGKGLEWI

GCIYIGSSTTYYATWAKGRFTISKTSSTAVTLQMTGLTAADTATYFCARDQYDDSGNLWGPGTLVTVSSG

QPKAPSVFPLAPCCGDTPSSTVTLGCLVKGYLPEPVTVTWNSGTLTNGVRTFPSVRQSSGLYSLSSVVS

VTSSSQPVTCNVAHPATNTKVDKTVAPSTCSKPMCPPPELPGGPSVFIFPPKPKDTLMISRTPEVTCVVV

DVSQDDPEVQFTWYINNEQVRTARPPLREQQFNSTIRVVSTLPIAHQDWLRGKEFKCKVHNKALPAPIEK

TISKARGQPLEPKVYTMGPPREELSSRSVSLTCMINGFYPSDISVEWEKNGKAEDNYKTTPTVLDSDGSY

FLYSKLSVPTSEWQRGDVFTCSVMHEALHNHYTQKSISRSPGK

Light chain:

(SEQ ID NO: 10)

MDTRAPTQLLGLLLLWLPGARCADVVMTQTPASVSEPVGGTVTIKCQASQSIYSGLAWYQQKPGQPPNL

LIYKASNLASGVSSRFKGSRSGTEYTLTISDLECADAATYYCQNWYGISSYGRAFGGGTEVVVKGDPVAP

TVLIFPPAADQVATGTVTIVCVANKYFPDVTVTWEVDGTTQTTGIENSKTPQNSADCTYNLSSTLTLTSTQ

YNSHKEYTCKVTQGTTSVVQSFNRGDC

PB5

Heavy chain:

(SEQ ID NO: 11)

METGLRWLLLVAVLKGVQCQEQLEESGGGLVQPEGSLTLTCKASGFALSSSYYMCWVRQAPGKGLEWI

GCIYIGSGTTYYASWAKGRFTISKTSSTAVTLQMTGLTAADTATYFCARDQYDDSGNLWGPGTLVTVSSG

QPKAPSVFPLAPCCGDTPSSTVTLGCLVKGYLPEPVTVTWNSGTLTNGVRTFPSVRQSSGLYSLSSVVS

VTSSSQPVTCNVAHPATNTKVDKTVAPSTCSKPMCPPPELPGGPSVFIFPPKPKDTLMISRTPEVTCVVV

DVSQDDPEVQFTWYINNEQVRTARPPLREQQFNSTIRVVSTLPIAHQDWLRGKEFKCKVHNKALPAPIEK

TISKARGQPLEPKVYTMGPPREELSSRSVSLTCMINGFYPSDISVEWEKNGKAEDNYKTTPTVLDSDGSY

FLYSKLSVPTSEWQRGDVFTCSVMHEALHNHYTQKSISRSPGK

Light chain:

(SEQ ID NO: 12)

MDTRVPTQLLGLLLLWLPGARCADIVMTQTPASVSEPVGGTVTIKCQASQNIYSGLAWYQQKPGQPPKLL

IYKASNLASGVSSRFKGSRSGTEYTLTISDLECADAATYYCQNWYGISTYGRAFGGGTEVVVKGDPVAPT

VLIFPPAADQVATGTVTIVCVANKYFPDVTVTWEVDGTTQTTGIENSKTPQNSADCTYNLSSTLTLTSTQY

NSHKEYTCKVTQGTTSVVQSFNRGDC

In some embodiments, the anti-CD39 antibody or antigen-binding fragment thereof, is a humanized version of the PB1, PB2, PB3, PB4 or PB5 antibodies.

In some embodiments, the anti-CD39 antibody or antigen-binding fragment thereof comprises at least one heavy chain variable is at least 60% identical to the variable region of SEQ ID NO: 3, and even more preferably at least 65%, 70%, 75%, 80%, 85%, 90%, 95%, 97%, 99%, or 100% identical to the variable region of SEQ ID NO: 3, and able to specifically bind human CD39.

In some embodiments, the anti-CD39 antibody or antigen-binding fragment thereof comprises at least one heavy chain variable is at least 60% identical to the variable region of SEQ ID NO: 5, and even more preferably at least 65%, 70%, 75%, 80%, 85%, 90%, 95%, 97%, 99%, or 100% identical to the variable region of SEQ ID NO: 5, and able to specifically bind human CD39.

In some embodiments, the anti-CD39 antibody or antigen-binding fragment thereof comprises at least one heavy chain variable is at least 60% identical to the variable region of SEQ ID NO: 7, and even more preferably at least 65%, 70%, 75%, 80%, 85%, 90%, 95%, 97%, 99%, or 100% identical to the variable region of SEQ ID NO: 7, and able to specifically bind human CD39.

In some embodiments, the anti-CD39 antibody or antigen-binding fragment thereof comprises at least one heavy chain variable is at least 60% identical to the variable region of SEQ ID NO: 9, and even more preferably at least 65%, 70%, 75%, 80%, 85%, 90%, 95%, 97%, 99%, or 100% identical to the variable region of SEQ ID NO: 9, and able to specifically bind human CD39.

In some embodiments, the anti-CD39 antibody or antigen-binding fragment thereof comprises at least one heavy chain variable is at least 60% identical to the variable region of SEQ ID NO: 11, and even more preferably at least 65%, 70%, 75%, 80%, 85%, 90%, 95%, 97%, 99%, or 100% identical to the variable region of SEQ ID NO: 11, and able to specifically bind human CD39.

In some embodiments, the anti-CD39 antibody or antigen-binding fragment thereof comprises at least one light chain variable region which is at least 60% identical to the variable region of SEQ ID NO: 4, and even more preferably at least 65%, 70%, 75%, 80%, 85%, 90%, 95%, 97%, 99%, or 100% identical to the variable region of SEQ ID NO: 4, and able to specifically bind human CD39.

In some embodiments, the anti-CD39 antibody or antigen-binding fragment thereof comprises at least one light chain variable region which is at least 60% identical to the variable region of SEQ ID NO: 6, and even more preferably at least 65%, 70%, 75%, 80%, 85%, 90%, 95%, 97%, 99%, or 100% identical to the variable region of SEQ ID NO: 6, and able to specifically bind human CD39.

In some embodiments, the anti-CD39 antibody or antigen-binding fragment thereof comprises at least one light chain variable region which is at least 60% identical to the variable region of SEQ ID NO: 48 and even more preferably at least 65%, 70%, 75%, 80%, 85%, 90%, 95%, 97%, 99%, or 100% identical to the variable region of SEQ ID NO: 8, and able to specifically bind human CD39.

In some embodiments, the anti-CD39 antibody or antigen-binding fragment thereof comprises at least one light chain variable region which is at least 60% identical to the variable region of SEQ ID NO: 10, and even more preferably at least 65%, 70%, 75%, 80%, 85%, 90%, 95%, 97%, 99%, or 100% identical to the variable region of SEQ ID NO: 10, and able to specifically bind human CD39.

In some embodiments, the anti-CD39 antibody or antigen-binding fragment thereof comprises at least one light chain variable region which is at least 60% identical to the variable region of SEQ ID NO: 12, and even more preferably at least 65%, 70%, 75%, 80%, 85%, 90%, 95%, 97%, 99%, or 100% identical to the variable region of SEQ ID NO: 12, and able to specifically bind human CD39.

In certain embodiments, the Fc domain of the heavy chain is a human IgG1 or IgG3 Fc isotype. Exemplary sequences for PB1-PB5 chimeras including a human IgG1 Fc are as follows:

```
PB1
                                                          (SEQ ID NO: 13)
METGLRWLLLVAVLKGVQCQEQLVESGGDLVQPGASLTLTCTTSGFSFSSNYWICWVRQAPGKGLEWI

GCIYTGSDTTYYASWAKGRFTISKTSSTTVTLQMTSLTAADTATYSCARGGAVYAAYAGVFFGLWGPGSL

VTVSSGQPKAPSVFPLAPCCGDTPSSTVTLGCLVKGYLPEPVTVTWNSGTLTNGVRTFPSVRQSSGLYS

LSSVVSVTSSSQPVTCNVAHPATNTKVDKTVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGKGSGLNDIFEAQKIE

WHE

PB2
                                                          (SEQ ID NO: 14)
METGLRWLLLVAVLKGVQCQSLEESGGDLVKPGASLTLTCTASGIDFSDYGYMCWVRQAPGKGLEWIG

CIYVGSSGSTYYATWAKGRFTVSRPSSTTVTLQMTSLTAADTATYFCVRRVNGYGLWGPGTLVTVSSGQ

PKAPSVFPLAPCCGDTPSSTVTLGCLVKGYLPEPVTVTWNSGTLTNGVRTFPSVRQSSGLYSLSSVVSVT

SSSQPVTCNVAHPATNTKVDKTVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGKGSGLNDIFEAQKIEWHE

PB3
                                                          (SEQ ID NO: 15)
METGLRWLLLVAVLKGVQCQSLEESGGDLVKPGASLTLTCTASGFSFSKNYWMCWVRQAPGKGLEWIG

CIYTGSDSRYYASWVNGRFSISKSSSTTVTLQMTSLTAADTATYFCASDSGAPGSSDSTLWGPGTLVTVS

SGQPKAPSVFPLAPCCGDTPSSTVTLGCLVKGYLPEPVTVTWNSGTLTNGVRTFPSVRQSSGLYSLSSV

VSVTSSSQPVTCNVAHPATNTKVDKTVEPKSCDKTHTCPPCPAPELLGGPSVFLFPPKPKDTLMISRTPE
```

-continued

VTCVVVDVSHEDPEVKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGKGSGLNDIFEAQKIEWHE

PB4

(SEQ ID NO: 16)

METGLRWLLLVAVLKGVQCQEQLVESGGGLVQPEGSLTLTCTASGFSFSSSYYMCWVRQAPGKGLEWI

GCIYIGSSTTYYATWAKGRFTISKTSSTAVTLQMTGLTAADTATYFCARDQYDDSGNLWGPGTLVTVSSG

QPKAPSVFPLAPCCGDTPSSTVTLGCLVKGYLPEPVTVTWNSGTLTNGVRTFPSVRQSSGLYSLSSVVS

VTSSSQPVTCNVAHPATNTKVDKTVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGKGSGLNDIFEAQKIEWHE

PB5

(SEQ ID NO: 17)

METGLRWLLLVAVLKGVQCQEQLEESGGGLVQPEGSLTLTCKASGFALSSSYYMCWVRQAPGKGLEWI

GCIYIGSGTTYYASWAKGRFTISKTSSTAVTLQMTGLTAADTATYFCARDQYDDSGNLWGPGTLVTVSSG

QPKAPSVFPLAPCCGDTPSSTVTLGCLVKGYLPEPVTVTWNSGTLTNGVRTFPSVRQSSGLYSLSSVVS

VTSSSQPVTCNVAHPATNTKVDKTVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGKGSGLNDIFEAQKIEWHE

In certain embodiments, the anti-CD39 antibody is a further humanized antibody comprising a heavy chain having the CDRs of SEQ ID NO: 3 and/or a light chain having the CDRs of SEQ ID NO: 4, or CDRs which are at least 65%, 70%, 75%, 80%, 85%, 90%, 95%, 97%, 99%, or 100% identical to those of SEQ ID NO: 3 and/or 4, and human framework sequences to form humanized heavy and light chains with an antigen binding site able to specifically bind human CD39.

In certain embodiments, the anti-CD39 antibody is a further humanized antibody comprising a heavy chain having the CDRs of SEQ ID NO: 35 and/or a light chain having the CDRs of SEQ ID NO: 6, or CDRs which are at least 65%, 70%, 75%, 80%, 85%, 90%, 95%, 97%, 99%, or 100% identical to those of SEQ ID NO: 5 and/or 6, and human framework sequences to form humanized heavy and light chains with an antigen binding site able to specifically bind human CD39.

In certain embodiments, the anti-CD39 antibody is a further humanized antibody comprising a heavy chain having the CDRs of SEQ ID NO: 7 and/or a light chain having the CDRs of SEQ ID NO: 8, or CDRs which are at least 65%, 70%, 75%, 80%, 85%, 90%, 95%, 97%, 99%, or 100% identical to those of SEQ ID NO: 7 and/or 8, and human framework sequences to form humanized heavy and light chains with an antigen binding site able to specifically bind human CD39.

In certain embodiments, the anti-CD39 antibody is a further humanized antibody comprising a heavy chain having the CDRs of SEQ ID NO: 9 and/or a light chain having the CDRs of SEQ ID NO: 10, or CDRs which are at least 65%, 70%, 75%, 80%, 85%, 90%, 95%, 97%, 99%, or 100% identical to those of SEQ ID NO: 9 and/or 10, and human framework sequences to form humanized heavy and light chains with an antigen binding site able to specifically bind human CD39.

In certain embodiments, the anti-CD39 antibody is a further humanized antibody comprising a heavy chain having the CDRs of SEQ ID NO: 11 and/or a light chain having the CDRs of SEQ ID NO: 12, or CDRs which are at least 65%, 70%, 75%, 80%, 85%, 90%, 95%, 97%, 99%, or 100% identical to those of SEQ ID NO: 11 and/or 12, and human framework sequences to form humanized heavy and light chains with an antigen binding site able to specifically bind human CD39.

In certain embodiments, the anti-CD39 antibody is a humanized antibody comprising a heavy chain having a CDR3 sequence selected from the group consisting of CARGGAVYAAYAGVFFGLW, CVRRVNGYGLW, CASDSGAPGSSDSTLW, CARDQYDDSGNLW and CARDQYDDSGNLW, and a light chain having a CDR3 sequence selected from the group consisting of CQSYFGIGGYGLAF, CQGCYGISSYGDSF, CQSYYALSTYGTAF, CQNWYGISSYGRAF and CQNWYGISTYGRAF.

In other embodiments, the heavy and light chains of the anti-CD39 antibody can be encoded by a nucleic acid which is identical to, or hybridizes under stringent conditions (such as the 6× sodium chloride/sodium citrate (SSC) at 45° C., and washing in 0.2×SSC/0.1% SDS at 50-65° C.) to the heavy and light chain (correspondingly) coding sequences for PB1, PB2, PB3, PB4 or PB5 monoclonals:

PB1
Heavy Chain:

(SEQ ID NO: 18)

5'ATGGAGACTGGGCTGCGCTGGCTTCTCCTGGTCGCTGTGCTCAAAGGTGTCCAGTGTCAGGAGCA

GCTGGTGGAGTCCGGGGGAGACCTGGTCCAGCCTGGGGCATCCCTGACACTCACCTGCACAACTT

CTGGATTCTCCTTCAGTAGCAATTACTGGATATGCTGGGTCCGCCAGGCTCCAGGGAAGGGGCTGG

AGTGGATCGGATGCATTTATACTGGTAGTGATACCACTTACTACGCGAGCTGGGCGAAAGGCCGATT

CACCATCTCCAAAACCTCGTCGACCACGGTGACTCTGCAGATGACCAGTCTGACAGCCGCGGACAC

GGCCACCTATTCCTGTGCGAGAGGGGGGGCTGTTTATGCTGCTTATGCTGGTGTCTTCTTTGGCTTG

TGGGGCCCAGGCTCCCTGGTCACCGTCTCCTCAGGGCAACCTAAGGCTCCATCAGTCTTCCCACTG

GCCCCCTGCTGCGGGGACACACCCAGCTCCACGGTGACCCTGGGCTGCCTGGTCAAAGGCTACCT

CCCGGAGCCAGTGACCGTGACCTGGAACTCGGGCACCCTCACCAATGGGGTACGCACCTTCCCGT

CCGTCCGGCAGTCCTCAGGCCTCTACTCGCTGAGCAGCGTGGTGAGCGTGACCTCAAGCAGCCAG

CCCGTCACCTGCAACGTGGCCCACCCAGCCACCAACACCAAAGTGGACAAGACCGTTGCGCCCTCG

ACATGCAGCAAGCCCATGTGCCCACCCCCTGAACTCCCGGGGGGACCGTCTGTCTTCATCTTCCCC

CCAAAACCCAAGGACACCCTCATGATCTCACGCACCCCCGAGGTCACATGCGTGGTGGTGGACGTG

AGCCAGGATGACCCCGAGGTGCAGTTCACATGGTACATAAACAACGAGCAGGTGCGCACCGCCCG

GCCGCCGCTACGGGAGCAGCAGTTCAACAGCACGATCCGCGTGGTCAGCACCCTCCCCATCGCGC

ACCAGGACTGGCTGAGGGGCAAGGAGTTCAAGTGCAAAGTCCACAACAAGGCACTCCCGGCCCCC

ATCGAGAAAACCATCTCCAAAGCCAGAGGGCAGCCCCTGGAGCCGAAGGTCTACACCATGGGCCCT

CCCCGGGAGGAGCTGAGCAGCAGGTCGGTCAGCCTGACCTGCATGATCAACGGCTTCTACCCTTCC

GACATCTCGGTGGAGTGGGAGAAGAACGGGAAGGCAGAGGACAACTACAAGACCACGCCGACCGT

GCTGGACAGCGACGGCTCCTACTTCCTCTACAGCAAGCTCTCAGTGCCCACGAGTGAGTGGCAGCG

GGGCGACGTCTTCACCTGCTCCGTGATGCACGAGGCCTTGCACAACCACTACACGCAGAAGTCCAT

CTCCCGCTCTCCGGGTAAATAG-3'

Light Chain:

(SEQ ID NO: 19)

5'ATGGACACGAGGGCCCCCACTCAGCTGCTGGGGCTCCTGCTGCTCTGGCTCCCAGGTGCCAGAT

GTGCCGATGTTGTGATGACCCAGACTCCAGCCTCCGTGTCTGAACCTGTGGGAGGCACAGTCACCA

TCAAGTGCCAGGCCAGTGAGAGCATTTATAGTGGTTTGGCCTGGTATCAGCAGAAACCAGGGCAGC

CTCCCAAGCTCCTGATCTATGGTGCATCCACTCTGGCATCTGGGGTCCCGTCGCGGTTCAAAGGCA

GTGGATCTGGGACAGAGTTCACTCTCACCATCAGCGACCTGGAGTGTGCCGATGCTGCCACTTACT

ACTGTCAAAGCTATTTTGGTATTGGTGGTTATGGTCTTGCTTTCGGCGGAGGGACCGAGGTGGTGGT

CTTGGGTGATCCAGTTGCACCTACTGTCCTCATCTTCCCACCAGCTGCTGATCAGGTGGCAACTGGA

ACAGTCACCATCGTGTGTGTGGCGAATAAATACTTTCCCGATGTCACCGTCACCTGGGAGGTGGATG

GCACCACCCAAACAACTGGCATCGAGAACAGTAAAACACCGCAGAATTCTGCAGATTGTACCTACAA

CCTCAGCAGCACTCTGACACTGACCAGCACACAGTACAACAGCCACAAAGAGTACACCTGCAAGGT

GACCCAGGGCACGACCTCAGTCGTCCAGAGCTTCAATAGGGGTGACTGTTAG-3'

PB2
Heavy Chain:

(SEQ ID NO: 20)

5'ATGGAGACTGGGCTGCGCTGGCTTCTCCTGGTCGCTGTGCTCAAAGGTGTCCAGTGTCAGTCGTT

GGAGGAGTCCGGGGGAGACCTGGTCAAGCCTGGGGCATCCCTGACACTCACCTGTACAGCCTCTG

GAATCGACTTCAGTGACTATGGCTACATGTGCTGGGTCCGCCAGGCTCCAGGGAAGGGGCTGGAGT

GGATCGGATGTATTTATGTTGGTAGTAGTGGTAGCACTTATTATGCGACCTGGGCGAAAGGCCGATT

-continued

CACCGTCTCCAGGCCCTCGTCGACCACGGTGACTCTGCAAATGACCAGTCTGACAGCCGCGGACAC

GGCCACTTATTTCTGTGTGAGAAGGGTTAATGGTTATGGGTTGTGGGGCCCAGGCACCCTGGTCAC

CGTCTCCTCAGGGCAACCTAAGGCTCCATCAGTCTTCCCACTGGCCCCCTGCTGCGGGGACACACC

CAGCTCCACGGTGACCCTGGGCTGCCTGGTCAAAGGCTACCTCCCGGAGCCAGTGACCGTGACCT

GGAACTCGGGCACCCTCACCAATGGGGTACGCACCTTCCCGTCCGTCCGGCAGTCCTCAGGCCTCT

ACTCGCTGAGCAGCGTGGTGAGCGTGACCTCAAGCAGCCAGCCCGTCACCTGCAACGTGGCCCAC

CCAGCCACCAACACCAAAGTGGACAAGACCGTTGCGCCCTCGACATGCAGCAAGCCCATGTGCCCA

CCCCCTGAACTCCCGGGGGGACCGTCTGTCTTCATCTTCCCCCCAAAACCCAAGGACACCCTCATG

ATCTCACGCACCCCCGAGGTCACATGCGTGGTGGTGGACGTGAGCCAGGATGACCCCGAGGTGCA

GTTCACATGGTACATAAACAACGAGCAGGTGCGCACCGCCCGGCCGCCGCTACGGGAGCAGCAGT

TCAACAGCACGATCCGCGTGGTCAGCACCCTCCCCATCGCGCACCAGGACTGGCTGAGGGGCAAG

GAGTTCAAGTGCAAAGTCCACAACAAGGCACTCCCGGCCCCCATCGAGAAAACCATCTCCAAAGCC

AGAGGGCAGCCCCTGGAGCCGAAGGTCTACACCATGGGCCCTCCCCGGGAGGAGCTGAGCAGCA

GGTCGGTCAGCCTGACCTGCATGATCAACGGCTTCTACCCTTCCGACATCTCGGTGGAGTGGGAGA

AGAACGGGAAGGCAGAGGACAACTACAAGACCACGCCGACCGTGCTGGACAGCGACGGCTCCTAC

TTCCTCTACAGCAAGCTCTCAGTGCCCACGAGTGAGTGGCAGCGGGGCGACGTCTTCACCTGCTCC

GTGATGCACGAGGCCTTGCACAACCACTACACGCAGAAGTCCATCTCCCGCTCTCCGGGTAAATAG-

3'

Light Chain:

(SEQ ID NO: 21)

5'ATGGACACGAGGGTCCCCACTCAGCTGCTGGGGCTCCTGCTGCTCTGGCTCCCAGGTGCCAGAT

GTGCCGATGTTGTGATGACCCAGACTCCAGCCTCCGTGTCTGAACCTGTGGGAGGCACAGTCACCA

TCAAGTGCCAGGCCAGTGAGAACATTTATACTGGTTTGGCCTGGTATCAGCAGAGACCAGGGCAGC

CTCCCAAACTCCTGATCTATGCTGCATCCACTCTGGCATCTGGGGTCTCATCGCGGTTCAAAGGCAG

TAGATCTGGGACAGAGTACACTCTCACCATCAGCGACCTGGAGTGTGCCGATGCTGCCACTTACTAC

TGTCAGGGCTGCTATGGTATTAGTAGTTATGGTGATTCTTTCGGCGGAGGGACCGAGGTGGTGGTC

AGAGGTGATCCAGTTGCACCTACTGTCCTCATCTTCCCACCAGCTGCTGATCAGGTGGCAACTGGAA

CAGTCACCATCGTGTGTGTGGCGAATAAATACTTTCCCGATGTCACCGTCACCTGGGAGGTGGATG

GCACCACCCAAACAACTGGCATCGAGAACAGTAAAACACCGCAGAATTCTGCAGATTGTACCTACAA

CCTCAGCAGCACTCTGACACTGACCAGCACACAGTACAACAGCCACAAAGAGTACACCTGCAAGGT

GACCCAGGGCACGACCTCAGTCGTCCAGAGCTTCAATAGGGGTGACTGTTAG-3'

PB3

Heavy Chain:

(SEQ ID NO: 22)

5'ATGGAGACTGGGCTGCGCTGGCTTCTCCTGGTCGCTGTGCTCAAAGGTGTCCAGTGTCAGTCGTT

GGAGGAGTCCGGGGGAGACCTGGTCAAGCCGGGGGCATCCCTGACACTCACCTGCACAGCCTCTG

GATTCTCCTTCAGTAAGAACTACTGGATGTGCTGGGTCCGCCAGGCTCCAGGGAAGGGTCTGGAGT

GGATCGGATGCATTTATACTGGTAGTGATAGTAGATACTACGCGAGCTGGGTGAATGGCCGATTCTC

CATCTCCAAATCCTCGTCGACCACGGTGACTCTGCAAATGACCAGTCTGACAGCCGCGGACACGGC

CACTTATTTCTGTGCGAGCGATAGTGGTGCTCCTGGTAGTAGTGATTCAACTTTGTGGGGCCCAGGC

ACCCTGGTCACCGTCTCCTCAGGGCAACCTAAGGCTCCATCAGTCTTCCCACTGGCCCCCTGCTGC

GGGGACACACCCAGCTCCACGGTGACCCTGGGCTGCCTGGTCAAAGGCTACCTCCCGGAGCCAGT

GACCGTGACCTGGAACTCGGGCACCCTCACCAATGGGGTACGCACCTTCCCGTCCGTCCGGCAGT

-continued

CCTCAGGCCTCTACTCGCTGAGCAGCGTGGTGAGCGTGACCTCAAGCAGCCAGCCCGTCACCTGCA

ACGTGGCCCACCCAGCCACCAACACCAAAGTGGACAAGACCGTTGCGCCCTCGACATGCAGCAAGC

CCATGTGCCCACCCCCTGAACTCCCGGGGGGACCGTCTGTCTTCATCTTCCCCCCAAAACCCAAGG

ACACCCTCATGATCTCACGCACCCCCGAGGTCACATGCGTGGTGGTGGACGTGAGCCAGGATGACC

CCGAGGTGCAGTTCACATGGTACATAAACAACGAGCAGGTGCGCACCGCCCGGCCGCCGCTACGG

GAGCAGCAGTTCAACAGCACGATCCGCGTGGTCAGCACCCTCCCCATCGCGCACCAGGACTGGCT

GAGGGGCAAGGAGTTCAAGTGCAAAGTCCACAACAAGGCACTCCCGGCCCCCATCGAGAAAACCAT

CTCCAAAGCCAGAGGGCAGCCCCTGGAGCCGAAGGTCTACACCATGGGCCCTCCCCGGGAGGAGC

TGAGCAGCAGGTCGGTCAGCCTGACCTGCATGATCAACGGCTTCTACCCTTCCGACATCTCGGTGG

AGTGGGAGAAGAACGGGAAGGCAGAGGACAACTACAAGACCACGCCGACCGTGCTGGACAGCGAC

GGCTCCTACTTCCTCTACAGCAAGCTCTCAGTGCCCACGAGTGAGTGGCAGCGGGGCGACGTCTTC

ACCTGCTCCGTGATGCACGAGGCCTTGCACAACCACTACACGCAGAAGTCCATCTCCCGCTCTCCG

GGTAAATAG-3'

Light Chain:

(SEQ ID NO: 23)

5'ATGGACACGAGGGTCCCCACTCAGCTGCTGGGGCTCCTGCTGCTCTGGCTCCCAGGTGCCAGAT

GTGCCGATGTTGTGATGACCCAGACTCCAGCCTCCGTGGAGGCAGCTGTGGGAGGCACAGTCACC

ATCAAGTGCCAGGCCAGTGAGAACATTTATAGTGGTTTGGCCTGGTATCAGCAGAAACCAGGGCAG

CCTCCCAAACTCCTGATCTATCTGGCATCCACTCTGGCATCTGGGGTCTCATCGCGGTTCAAAGGCA

GTAGATCTGGGACAGAGTACACTCTCACCATCAGCGACCTGGAGTGTGCCGATGCTGCCACTTACTA

CTGTCAAAGCTATTATGCGCTTAGTACTTATGGTACTGCTTTCGGCGGAGGGACCGAGGTGGTGGTC

AAAGGTGATCCAGTTGCACCTACTGTCCTCATCTTCCCACCAGCTGCTGATCAGGTGGCAACTGGAA

CAGTCACCATCGTGTGTGTGGCGAATAAATACTTTCCCGATGTCACCGTCACCTGGGAGGTGGATG

GCACCACCCAAACAACTGGCATCGAGAACAGTAAAACACCGCAGAATTCTGCAGATTGTACCTACAA

CCTCAGCAGCACTCTGACACTGACCAGCACACAGTACAACAGCCACAAAGAGTACACCTGCAAGGT

GACCCAGGGCACGACCTCAGTCGTCCAGAGCTTCAATAGGGGTGACTGTTAG-3'

PB4

Heavy Chain:

(SEQ ID NO: 24)

5'ATGGAGACTGGGCTGCGCTGGCTTCTCCTGGTCGCTGTGCTCAAAGGTGTCCAGTGTCAGGAGCA

GCTGGTGGAGTCCGGGGGAGGCCTGGTCCAGCCTGAGGGATCCCTGACACTCACCTGCACAGCTT

CTGGATTCTCCTTCAGTAGCAGCTACTACATGTGCTGGGTCCGCCAGGCTCCAGGGAAGGGGCTGG

AGTGGATCGGATGCATTTATATTGGTAGTTCTACCACTTACTACGCGACCTGGGCGAAAGGCCGATT

CACCATCTCCAAAACCTCGTCGACCGCGGTGACTCTGCAAATGACCGGTCTGACAGCCGCGGACAC

GGCCACCTATTTCTGTGCGAGAGATCAATATGATGATAGTGGTAATTTGTGGGGCCCAGGCACCCTG

GTCACCGTCTCCTCAGGGCAACCTAAGGCTCCATCAGTCTTCCCACTGGCCCCCTGCTGCGGGGAC

ACACCCAGCTCCACGGTGACCCTGGGCTGCCTGGTCAAAGGCTACCTCCCGGAGCCAGTGACCGT

GACCTGGAACTCGGGCACCCTCACCAATGGGGTACGCACCTTCCCGTCCGTCCGGCAGTCCTCAG

GCCTCTACTCGCTGAGCAGCGTGGTGAGCGTGACCTCAAGCAGCCAGCCCGTCACCTGCAACGTG

GCCCACCCAGCCACCAACACCAAAGTGGACAAGACCGTTGCGCCCTCGACATGCAGCAAGCCCATG

TGCCCACCCCCTGAACTCCCGGGGGGACCGTCTGTCTTCATCTTCCCCCCAAAACCCAAGGACACC

CTCATGATCTCACGCACCCCCGAGGTCACATGCGTGGTGGTGGACGTGAGCCAGGATGACCCCGA

GGTGCAGTTCACATGGTACATAAACAACGAGCAGGTGCGCACCGCCCGGCCGCCGCTACGGGAGC

-continued

AGCAGTTCAACAGCACGATCCGCGTGGTCAGCACCCTCCCCATCGCGCACCAGGACTGGCTGAGG

GGCAAGGAGTTCAAGTGCAAAGTCCACAACAAGGCACTCCCGGCCCCCATCGAGAAAACCATCTCC

AAAGCCAGAGGGCAGCCCCTGGAGCCGAAGGTCTACACCATGGGCCCTCCCCGGGAGGAGCTGAG

CAGCAGGTCGGTCAGCCTGACCTGCATGATCAACGGCTTCTACCCTTCCGACATCTCGGTGGAGTG

GGAGAAGAACGGGAAGGCAGAGGACAACTACAAGACCACGCCGACCGTGCTGGACAGCGACGGCT

CCTACTTCCTCTACAGCAAGCTCTCAGTGCCCACGAGTGAGTGGCAGCGGGGCGACGTCTTCACCT

GCTCCGTGATGCACGAGGCCTTGCACAACCACTACACGCAGAAGTCCATCTCCCGCTCTCCGGGTA

AATAG-3'

Light Chain:

(SEQ ID NO: 25)

5'ATGGACACGAGGGCCCCCACTCAGCTGCTGGGGCTCCTGCTGCTCTGGCTCCCAGGTGCCAGAT

GTGCCGATGTTGTGATGACCCAGACTCCAGCCTCCGTGTCTGAACCTGTGGGAGGCACAGTCACCA

TCAAGTGCCAGGCCAGTCAGAGCATTTACAGTGGTTTGGCCTGGTATCAGCAGAAACCAGGGCAGC

CTCCCAACCTCCTGATCTACAAGGCATCCAATCTGGCATCTGGGGTCTCATCGCGGTTCAAAGGCAG

TAGATCTGGGACAGAGTACACTCTCACCATCAGCGACCTGGAGTGTGCCGATGCTGCCACTTACTAC

TGTCAAAACTGGTATGGTATTAGTAGTTATGGTCGGGCTTTCGGCGGAGGGACCGAGGTGGTGGTC

AAAGGTGATCCAGTTGCACCTACTGTCCTCATCTTCCCACCAGCTGCTGATCAGGTGGCAACTGGAA

CAGTCACCATCGTGTGTGTGGCGAATAAATACTTTCCCGATGTCACCGTCACCTGGGAGGTGGATG

GCACCACCCAAACAACTGGCATCGAGAACAGTAAAACACCGCAGAATTCTGCAGATTGTACCTACAA

CCTCAGCAGCACTCTGACACTGACCAGCACACAGTACAACAGCCACAAAGAGTACACCTGCAAGGT

GACCCAGGGCACGACCTCAGTCGTCCAGAGCTTCAATAGGGGTGACTGTTAG-3'

PB5

Heavy Chain:

(SEQ ID NO: 26)

5'ATGGAGACTGGGCTGCGCTGGCTTCTCCTGGTCGCTGTGCTCAAAGGTGTCCAGTGTCAGGAGCA

GCTGGAGGAGTCCGGGGGAGGCCTGGTCCAGCCTGAGGGATCCCTGACACTCACCTGCAAAGCCT

CTGGATTCGCCCTCAGTAGCAGCTACTACATGTGCTGGGTCCGCCAGGCTCCAGGGAAGGGGCTG

GAGTGGATCGGATGCATTTATATTGGTAGTGGTACCACTTACTACGCGAGCTGGGCGAAAGGCCGA

TTCACCATCTCCAAAACCTCGTCGACCGCGGTGACTCTGCAAATGACCGGTCTGACAGCCGCGGAC

ACGGCCACCTATTTCTGTGCGAGAGATCAATATGATGATAGTGGTAATTTGTGGGGCCCAGGCACCC

TGGTCACCGTCTCCTCAGGGCAACCTAAGGCTCCATCAGTCTTCCCACTGGCCCCCTGCTGCGGGG

ACACACCCAGCTCCACGGTGACCCTGGGCTGCCTGGTCAAAGGCTACCTCCCGGAGCCAGTGACC

GTGACCTGGAACTCGGGCACCCTCACCAATGGGGTACGCACCTTCCCGTCCGTCCGGCAGTCCTCA

GGCCTCTACTCGCTGAGCAGCGTGGTGAGCGTGACCTCAAGCAGCCAGCCCGTCACCTGCAACGT

GGCCCACCCAGCCACCAACACCAAAGTGGACAAGACCGTTGCGCCCTCGACATGCAGCAAGCCCAT

GTGCCCACCCCCTGAACTCCCGGGGGGACCGTCTGTCTTCATCTTCCCCCCAAAACCCAAGGACAC

CCTCATGATCTCACGCACCCCCGAGGTCACATGCGTGGTGGTGGACGTGAGCCAGGATGACCCCG

AGGTGCAGTTCACATGGTACATAAACAACGAGCAGGTGCGCACCGCCCGGCCGCCGCTACGGGAG

CAGCAGTTCAACAGCACGATCCGCGTGGTCAGCACCCTCCCCATCGCGCACCAGGACTGGCTGAG

GGGCAAGGAGTTCAAGTGCAAAGTCCACAACAAGGCACTCCCGGCCCCCATCGAGAAAACCATCTC

CAAAGCCAGAGGGCAGCCCCTGGAGCCGAAGGTCTACACCATGGGCCCTCCCCGGGAGGAGCTGA

GCAGCAGGTCGGTCAGCCTGACCTGCATGATCAACGGCTTCTACCCTTCCGACATCTCGGTGGAGT

GGGAGAAGAACGGGAAGGCAGAGGACAACTACAAGACCACGCCGACCGTGCTGGACAGCGACGGC

-continued

```
TCCTACTTCCTCTACAGCAAGCTCTCAGTGCCCACGAGTGAGTGGCAGCGGGGCGACGTCTTCACC

TGCTCCGTGATGCACGAGGCCTTGCACAACCACTACACGCAGAAGTCCATCTCCCGCTCTCCGGGT

AAATAG-3'

Light Chain:
                                                                  (SEQ ID NO: 27)
5'ATGGACACGAGGGTCCCCACTCAGCTGCTGGGGCTCCTGCTGCTCTGGCTCCCAGGTGCCAGAT

GTGCCGATATTGTGATGACCCAGACTCCAGCCTCCGTGTCTGAACCTGTGGGAGGCACAGTCACCA

TCAAGTGCCAGGCCAGTCAGAACATTTACAGTGGTTTGGCCTGGTATCAGCAGAAACCAGGGCAGC

CTCCCAAGCTCCTAATCTACAAGGCATCCAATCTGGCATCTGGGGTCTCATCGCGGTTCAAAGGCAG

TAGATCTGGGACAGAGTACACTCTCACCATCAGCGACCTGGAGTGTGCCGATGCTGCCACTTACTAC

TGTCAAAACTGGTATGGTATTAGTACTTATGGTCGGGCTTTCGGCGGAGGGACCGAGGTGGTGGTC

AAAGGTGATCCAGTTGCACCTACTGTCCTCATCTTCCCACCAGCTGCTGATCAGGTGGCAACTGGAA

CAGTCACCATCGTGTGTGTGGCGAATAAATACTTTCCCGATGTCACCGTCACCTGGGAGGTGGATG

GCACCACCCAAACAACTGGCATCGAGAACAGTAAAACACCGCAGAATTCTGCAGATTGTACCTACAA

CCTCAGCAGCACTCTGACACTGACCAGCACACAGTACAACAGCCACAAAGAGTACACCTGCAAGGT

GACCCAGGGCACGACCTCAGTCGTCCAGAGCTTCAATAGGGGTGACTGTTAG-3'
```

In other embodiments, the variable regions of the heavy and light chains of the anti-CD39 antibody can be encoded by a nucleic acid which is identical to, or hybridizes under stringent conditions (such as the 6× sodium chloride/sodium citrate (SSC) at 45° C., and washing in 0.2×SSC/0.1% SDS at 50-65° C.) to the variable regions of the heavy and light chain (correspondingly) coding sequences for PB1, PB2, PB3, PB4 or PB5 monoclonals (above).

In other embodiments, the CDRs of the heavy and light chains of the anti-CD39 antibody can be encoded by a nucleic acid which is identical to, or hybridizes under stringent conditions (such as the 6× sodium chloride/sodium citrate (SSC) at 45° C., and washing in 0.2×SSC/0.1% SDS at 50-65° C.) to the CDRs of the heavy and light chain (correspondingly) coding sequences for PB1, PB2, PB3, PB4 or PB5 monoclonals (above).

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J Biol. Chem. 271:22611-22618 (1996)).

In certain embodiments, an anti-CD39 antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

For instance, human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE technology; U.S. Pat. No. 5,770,429 describing HuMAB technology; U.S. Pat. No. 7,041,870 describing K-M MOUSE technology, and U.S. Patent Application Publication No. US 2007/0061900, describing VELOCIMOUSE technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage, yeast or bacterial display libraries. Such variable domain sequences may then be combined with a desired human constant domain. Techniques for selecting human antibodies from antibody libraries are described below.

To illustrate, anti-CD39 antibodies of the invention may be isolated by screening combinatorial libraries for antibodies with the desired activity or activities. For example, a variety of methods are known in the art for generating phage or yeast display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

As an example of phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antigen-binding fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antigen-binding fragments isolated from human antibody libraries are considered human antibodies or human antigen-binding fragments herein.

FcγRIII binding can also be increased by methods according to the state of the art, e.g., by modifying the amino acid sequence of the Fc part or the glycosylation of the Fc part of the antibody (see e.g., EP2235061). In certain embodiments, the subject antibodies are produced by cells in which, when glycosylated, less than 50% of the oligosaccharide chains on the antibody contain α-1,6-fucose. Typically, less than about 40%, less than about 30%, less than about 20%, less than about 10%, or less than 5% or less than 1% of the oligosaccharide chains contain α-1,6-fucose in a "hypofucosylated" antibody preparation. An "afucosylated" antibody lacks α-1,6-fucose in the carbohydrate attached to the CH2 domain of the IgG heavy chain. Mori, K et al., Cytotechnology 55 (2007)109 and Satoh M, et al., Expert Opin Biol Ther. 6 (2006) 1161-1173 relate to a FUT8 (α-1,6-fucosyltransferase) gene knockout CHO line for the generation of afucosylated antibodies.

IV. Expression Vectors

In certain embodiments, a recombinant expression vector is used to amplify and express DNA encoding the anti-CD39 antibody described herein. For example, a recombinant expression vector can be a replicable DNA construct which has synthetic or cDNA-derived DNA fragments encoding the polypeptide chains of the anti-CD39 antibody operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host cell. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Suitable host cells for expression of the polypeptide chains of the anti-CD39 antibody (or a protein to use as a target) include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described below. Cell-free translation systems may also be employed. Appropriate cloning and expression vectors for use with bacterial, fungal, yeast, and mammalian cellular hosts are well known by those skilled in the art.

Various mammalian cell culture systems are used to express recombinant polypeptides. Expression of recombinant proteins in mammalian cells can be preferred because such proteins are generally correctly folded, appropriately modified, and biologically functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), and HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

In certain embodiments, the polynucleotide comprises a polynucleotide encoding an antibody light chain comprising a variable region at least 60% identical to SEQ ID NO: 1, and even more preferably at least 65%, 70%, 75%, 80%, 85%, 90%, 95%, 97%, 99%, or 100% identical to SEQ ID NO: 1, and able to specifically bind human CD39.

In certain embodiments, the polynucleotide comprises a polynucleotide encoding an antibody heavy chain comprising a variable region at least 60% identical to SEQ ID NO: 2, and even more preferably at least 65%, 70%, 75%, 80%, 85%, 90%, 95%, 97%, 99%, or 100% identical to SEQ ID NO: 2, and able to specifically bind human CD39.

V. Encoded Anti-CD39 Antibodies for In Vivo Delivery

Therapeutic vectors for delivering the coding sequence for an anti-CD39 antibody to be expressed in the patient can be viral, non-viral, or physical. See, for example, Rosenberg et al., Science, 242:1575-1578, 1988, and Wolff et al., Proc. Natl. Acad. Sci. USA 86:9011-9014 (1989). Discussion of methods and compositions for use in gene therapy include Eck et al., in Goodman & Gilman's The Pharmacological Basis of Therapeutics, Ninth Edition, Hardman et al., eds., McGraw-Hill, New York, (1996), Chapter 5, pp. 77-101; Wilson, Clin. Exp. Immunol. 107 (Suppl. 1):31-32, 1997; Wivel et al., Hematology/Oncology Clinics of North America, Gene Therapy, S. L. Eck, ed., 12(3):483-501, 1998; Romano et al., Stem Cells, 18:19-39, 2000, and the references cited therein. U.S. Pat. No. 6,080,728 also provides a discussion of a wide variety of gene delivery methods and compositions. The routes of delivery include, for example, systemic administration and administration in situ. Well-known viral delivery techniques include the use of adenovirus, retrovirus, lentivirus, foamy virus, herpes simplex virus, vaccinia virus and adeno-associated virus vectors.

a. Viral Vectors

Preferred viral vectors are based on non-cytopathic eukaryotic viruses in which non-essential genes have been replaced with the nucleic acid construct carrying the nucleic acid sequences encoding the epitopes and targeting sequences of interest. Preferred viruses for certain embodiments of the invention are the adenoviruses and adeno-associated (AAV) viruses, which are double-stranded DNA viruses that have already been approved for human use in gene therapy. In addition, preferred vectors for tolerizing do not include immune-stimulating sequences.

Adenovirus Vectors

One illustrative method for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized. In a specific embodiment, the delivery vector pertains to commercially available ORF of cytochrome b5 reductase 3 (CYB5R3), transcript variant 1 in adenoviral vector pAd, with C terminal Flag and His tag, (Vigene Biosciences Product code AH889428). PCT Publication No. WO/2015/050364 also teaches vectors with expression constructs including a Cyb5r3 gene.

Adenoviral vectors are highly immunogenic and therefore are less preferred for administration to induce tolerance by presenting antigens, or in the case of autoimmune diseases. These vectors can be used, however to induce immunity, for example in treatment of infectious diseases and the like, include, for example, influenza, HBV, HCV and HIV.

Adeno-Associated Virus Vectors (AAV)

AAV is a good choice of delivery vehicles due to its safety, e.g., genetically engineered (recombinant) does not integrate into the host genome. Likewise, AAV is not pathogenic and not associated with any disease. The removal of viral coding sequences minimizes immune reactions to viral gene expression, and therefore, rAAV does not evoke an inflammatory response. According to a specific embodiment, an AAV vector containing an epitope sequence containing nucleic acid construct described herein is useful for transducing APCs.

Typically, viral vectors containing an epitope containing nucleic acid construct are assembled from polynucleotides encoding the desired epitopes, suitable regulatory elements and elements necessary for epitope expression which mediate cell transduction. In one embodiment, adeno-associated viral (AAV) vectors are employed. In a more specific embodiment, the AAV vector is an AAV1, AAV6, or AAV8.

The AAV expression vector which harbors the DNA molecule of interest bounded by AAV ITRs, can be constructed by directly inserting the selected sequence(s) into an AAV genome which has had the major AAV open reading frames ("ORFs") excised therefrom. Examples of constitutive promoters which may be included in the AAV of this invention include, without limitation, the exemplified CMV immediate early enhancer/chicken β-actin (CBA) promoter.

For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' ITR sequence. In one embodiment, the bovine growth hormone polyA may be used.

Selection of these and other common vector and regulatory elements are conventional, and many such sequences are available. See, e.g., Sambrook et al., and references cited therein at, for example, pages 3.18-3.26 and 16.17-16.27 and Ausubel et al., Current Protocols in Molecular Biology, John Wiley & Sons, New York, 1989). Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct.

Retrovirus Vectors

In a certain embodiments, the viral vector may be a retroviral vector. "Retroviruses" are viruses having an RNA genome. In particular embodiments, a retroviral vector contains all of the cis-acting sequences necessary for the packaging and integration of the viral genome, e.g., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail regarding retroviral vectors can be found in Boesen, et al., 1994, Biotherapy 6:291-302; Clowes, et ai, 1994, J. Clin. Invest. 93:644-651; Kiem, et al., 1994, Blood 83: 1467-1473; Salmons and Gunzberg, 1993, Human Gene Therapy 4: 129-141; Miller, et al., 1993, Meth. Enzymol. 217:581-599; and Grossman and Wilson, 1993, Curr. Opin. in Genetics and Devel. 3: 110-1 14.

"Gammaretroviruses" refers to a genus of the retroviridae family. Exemplary gammaretroviruses include mouse stem cell virus, murine leukemia virus, feline leukemia virus, feline sarcoma virus, and avian reticuloendotheliosis viruses.

Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., J. Virol. 66:2731-2739, 1992; Johann et al., J. Virol. 66: 1635-1640, 1992; Sommerfelt et al., Virol. 176:58-59, 1990; Wilson et al., J. Virol. 63:2374-2378, 1989; Miller et al., J. Virol. 65:2220-2224, 1991; and PCT/US94/05700).

Lentiviral vectors refer to a genus of retroviruses that are capable of infecting dividing and non-dividing cells and typically produce high viral titers. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

In particular embodiments, other retroviral vectors can be used. These include, e.g., vectors based on human foamy virus (HFV) or other viruses in the Spumavirus genera. Foamy viruses (FVes) are the largest retroviruses known today and are widespread among different mammals, including all non-human primate species, however are absent in humans. This complete apathogenicity qualifies FV vectors as ideal gene transfer vehicles for genetic therapies in humans and clearly distinguishes FV vectors as gene delivery system from HIV-derived and also gammaretrovirus-derived vectors.

Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (e.g., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are known to those of skill in the art.

The retroviral genome contains three genes, gag, pol, and env that code for capsid proteins, polymerase enzyme, and envelope components, respectively. A sequence found upstream from the gag gene contains a signal for packaging of the genome into virions. Retroviral vectors are gene transfer plasmids wherein the heterologous nucleic acid resides between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764). These two long terminal repeat (LTR) sequences are present at the 5' and 3' ends of the viral genome. These contain strong promoter and enhancer sequences and are also required for integration in the host cell genome (Coffin, 1990). In order to construct a retroviral vector, a nucleic acid encoding one or more oligonucleotide or polynucleotide sequences of interest is inserted into the viral genome in the place of certain viral sequences to produce a virus that is replication-defective. Also included are episomal or non-integrating forms of retroviral vectors based on lentiviruses (e.g., a type of retrovirus).

Lentiviral vectors are useful when stable expression is needed, but lentiviral vectors can be immunogenic, and possibly have other undesirable effects. Therefore, although lentiviral vectors are convenient for research, care should be taken when using them for human administration, particularly where it is desired to induce tolerance rather than immunity. Lentiviruses are suitable for engineering T cells or dendritic cells or other antigen presenting cells ex vivo for cancer therapy, although mRNA electroporation is more safe. However, two recent advances have made the use of lentiviruses safer and more clinically translatable. First, the coexpression of a suicide gene along with the antigens whose products become functional when a drug is administered. A typical example is Herpes simplex virus thymidine kinase (HSV-Tk). Cells that express these genes can metabolize the drug ganciclovir into a cytotoxic product that induces cell death. Thus, in case some transduced cells become malignant, they can be eradicated. About a dozen such systems exist (Duarte et al., Cancer Letters, 324:160-170, 2012). Second, there are now non-integrating lentiviral vectors being developed that are therefore non-oncogenic (Nightingale et al., 2006, Mol. Ther., 13:1121-1132). These methods can be used with the invention according to the judgement of the person of skill in the art.

Suitable retroviral vectors for use herein are described, for example, in U.S. Pat. Nos. 5,399,346 and 5,252,479; and in PCT Publication Nos. WO 92/07573, WO 90/06997, WO 89/05345, WO 92/05266 and WO 92/14829, which provide a description of methods for efficiently introducing nucleic acids into human cells using such retroviral vectors. Other retroviral vectors include, for example, mouse mammary tumor virus vectors (e.g., Shackleford et al., Proc. Natl. Acad. Sci. U.S.A. 85:9655-9659, 1998), lentiviruses, and the like. An exemplary viral vector is plentilox-IRES-GFP.

Additional retroviral viral delivery systems that can be readily adapted for delivery of a transgene encoding a Anti-CD39 antibody Agent include, merely to illustrate Published PCT Applications WO/2010/045002, WO/2010/148203, WO/2011/126864, WO/2012/058673, WO/2014/066700, WO/2015/021077, WO/2015/148683, and WO/2017/040815, the disclosures of each of which are incorporated by reference herein.

In certain embodiments, the retrovirus is a recombinant replication competent retrovirus comprising: a nucleic acid sequence encoding a retroviral GAG protein; a nucleic acid sequence encoding a retroviral POL protein; a nucleic acid sequence encoding a retroviral envelope; an oncoretroviral polynucleotide sequence comprising Long-Terminal Repeat (LTR) sequences at the 5' and 3' end of the oncoretroviral polynucleotide sequence; a cassette comprising an internal ribosome entry site (IRES) operably linked to a coding sequence for a Anti-CD39 antibody Agent, wherein the cassette is positioned 5' to the U3 region of the 3' LTR and 3' to the sequence encoding the retroviral envelope; and cis-acting sequences for reverse transcription, packaging and integration in a target cell.

In certain embodiments, the retrovirus is a recombinant replication competent retrovirus comprising: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, the promoter being suitable for expression in a mammalian cell, a gag nucleic acid domain, a pol nucleic acid domain and an env nucleic acid domain; a cassette comprising a Anti-CD39 antibody Agent coding sequence operably linked to a heterologous polynucleotide, wherein the cassette is positioned 5' to the 3' LTR and is operably linked and 3' to the env nucleic acid domain encoding the retroviral envelope; and cis-acting sequences necessary for reverse transcription, packaging and integration in a target cell.

In certain preferred embodiments of the recombinant replication competent retrovirus, the envelope is chosen from one of amphotropic, polytropic, xenotropic, 10A1, GALV, Baboon endogenous virus, RD114, rhabdovirus, alphavirus, measles or influenza virus envelopes. In certain preferred embodiments of the recombinant replication competent retrovirus, the retroviral polynucleotide sequence is engineered from a virus selected from the group consisting of murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV).

In certain preferred embodiments of the recombinant replication competent retrovirus, retrovirus is a gammaretrovirus.

In certain preferred embodiments of the recombinant replication competent retrovirus, there is a second cassette comprising a coding sequence for a second therapeutic protein, such as another checkpoint inhibitor polypeptide, a co-stimulatory polypeptide and/or a immunostimulatory cytokine (merely as examples), e.g., downstream of the cassette. In certain instances, the second cassette can include an internal ribosome entry site (IRES) or a minipromoter or a polIII promoter operably linked to the coding sequence for the second therapeutic protein.

In certain preferred embodiments of the recombinant replication competent retrovirus, it is a nonlytic, amphotropic retroviral replicating vector which, preferably, selectively infects and replicates in the cells of the tumor microenvironment.

Other Viral Vectors as Expression Constructs

Other viral vectors may be employed as expression constructs in the present invention for the delivery of oligonucleotide or polynucleotide sequences to a host cell. Vectors derived from viruses such as vaccinia virus, polioviruses and herpes viruses may be employed. They offer several attractive features for various mammalian cells. Also included are hepatitis B viruses.

b. Non-Viral Vectors

Plasmid Vectors

Other vectors include plasmid vectors. Plasmid vectors have been extensively described in the art and are well known to those of skill in the art. See e.g., Sambrook et al., 1989, cited above. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide epitope encoded by nucleic acid within the plasmid. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Thus, in one aspect, a plasmid is provided for expression of the epitope containing nucleic acid construct which includes an expression cassette; also referred to as a transcription unit. When a plasmid is placed in an environment suitable for epitope expression, the transcriptional unit will express the polynucleotide including a sequence encoding the epitopes, ETS and MHCII activator sequence, or sequence encoding the epitopes and secretion signal sequence, and anything else encoded in the construct. The transcription unit includes a transcriptional control sequence, which is transcriptionally linked with a cellular immune response element coding sequence. Transcriptional control sequence may include promoter/enhancer sequences such as cytomegalovirus (CMV) promoter/enhancer sequences. However, those skilled in the art will recognize that a variety of other promoter sequences suitable for expression in eukaryotic cells are known and can similarly be used in the constructs disclosed herein. The level of expression of the nucleic acid product will depend on the associated promoter and the presence and activation of an associated enhancer element.

In certain embodiments, a sequence encoding the desired epitopes and targeting sequence can be cloned into an expression plasmid which contains the regulatory elements for transcription, translation, RNA stability and replication (e.g., including a transcriptional control sequence). Such expression plasmids are well known in the art and one of ordinary skill would be capable of designing an appropriate expression construct with a polynucleotide including a sequence encoding a cellular immune response element or fragment thereof in such a manner that the cellular immune response element is expressible. There are numerous examples of suitable expression plasmids into which a polynucleotide including a sequence could be cloned such as pCI-neo, pUMVC or pcDNA3.

Large quantities of a bacterial host harboring a plasmid for expression of cellular immune response element or fragment thereof may be fermented and the plasmid can be purified for subsequent use. Current human clinical trials using plasmids utilize this approach. Recombinant DNA Advisory Committee Data Management Report, Human Gene Therapy 6: 535-548, 1994. Current DNA isolation methods known in the art include removal of lipopolysaccharides (endotoxins) that are contaminants from the bacteria used to propagate the plasmids. This step is most preferably taken for use of tolerogenic DNA vaccines as endotoxins act as strong adjuvants and can produce undesired immune stimulation.

The purpose of the plasmid is the efficient delivery of nucleic acid sequences to and expression of therapeutic epitopes in a cell or tissue. In particular, the purpose of the plasmid may be to achieve high copy number, avoid potential causes of plasmid instability and provide a means for plasmid selection. As for expression, the nucleic acid cassette contains the necessary elements for expression of the nucleic acid within the cassette. Expression includes the efficient transcription of an inserted gene, nucleic acid sequence, or nucleic acid cassette with the plasmid. Expression products may be proteins, polypeptides or RNA. The nucleic acid sequence can be contained in a nucleic acid cassette. Expression of the nucleic acid can be continuous or regulated.

Minicircle

Embodiments of nucleic acid constructs described herein may be processed in the form of minicircle DNA. Minicircle DNA pertains to small (2-4 kb) circular plasmid derivatives that have been freed from all prokaryotic vector parts. Since minicircle DNA vectors contain no bacterial DNA sequences, they are less likely to be perceived as foreign and destroyed. (Typical transgene delivery methods involve plasmids, which contain foreign DNA.) As a result, these vectors can be expressed for longer periods of time (in order of weeks or months) compared to conventional plasmids (days to weeks). The smaller size of minicircles also extends their cloning capacity and facilitates their delivery into cells. Kits for producing minicircle DNA are known in the art and are commercially available (System Biosciences, Inc., Palo Alto, Calif.). Information on minicircle DNA is provided in Dietz et al., Vector Engineering and Delivery Molecular Therapy (2013); 21 8, 1526-1535 and Hou et al., Molecular Therapy—Methods & Clinical Development, Article number: 14062 (2015) doi:10.1038/mtm.2014.62. More information on Minicircles is provided in Chen Z Y, He C Y, Ehrhardt A, Kay M A. Mol Ther. 2003 September; 8(3): 495-500 and Minicircle DNA vectors achieve sustained expression reflected by active chromatin and transcriptional level. Gracey Maniar L E, Maniar J M, Chen Z Y, Lu J, Fire A Z, Kay M A. Mol Ther. 2013 January; 21(1):131-8

As an initial step in the process of ultimately obtaining expression of a product encoded by a nucleic acid, is to effect the uptake of the nucleic acid by cells. Uptake of nucleic acid by cells is dependent on a number of factors, one of which is the length of time during which a nucleic acid is in proximity to a cellular surface. For instance, after intramuscular (i.m.) administration of plasmid DNA in buffer, a marked reduction in gene expression was observed if the muscle is massaged, presumably due to DNA leakage out of the muscle either directly or via lymphatic vessels (Human Gene Therapy 4:151-159; 1993). Accordingly, it may be desirable to formulate nucleic acids with compounds which would retard the rate at which nucleic acids diffuse or are carried away from a site at which cellular uptake of the nucleic acid is desired. Further, these compounds could be suitable for administration to an organism by means such as injection while maintaining or regaining the physical characteristics necessary to increase cellular uptake of nucleic acids.

In order to effect expression of oligonucleotide or polynucleotide sequences, the expression construct must be delivered into a cell. In certain embodiments of the invention, an expression construct comprising one or more oligonucleotide or polynucleotide sequences may simply consist of naked recombinant DNA or plasmids.

To prime immunity, DNA vaccine vectors of any type preferably are engineered to be CpG-rich (to stimulate TLR9 on immune cells) or conversely are engineered to remove CpG, and when possible, replace CpG motifs with GpG motifs (Ho et al., J. Immunol. 71(9):4920-6, 2003; Ho et al., J. Immunol. 175(9):6226-34, 2005). DNA vaccines can be engineered to contain the antigen(s)/epitope(s), and also can contain additional genes for co-expression with the antigens to act as adjuvants or immunomodulators (multiple promoter vectors. These DNA vaccines have been found to be safe clinically, for example in T1 D patients (Roep et al., Sci. Transl. Med. 5(191):191 ra82, 2013).

Mechanical Delivery Systems

Additional non-viral delivery methods include but are not limited to mechanical delivery systems that can be used in vitro such as the approach described in Woffendin et al., Proc. Natl. Acad. Sci. USA 91(24):11581, 1994; deposition of photopolymerized hydrogel materials or use of ionizing radiation (see, e.g., U.S. Pat. No. 5,206,152 and WO 92/11033); the use of a hand-held gene transfer particle gun (see, e.g., U.S. Pat. No. 5,149,655); and the use of ionizing radiation for activating transferred gene (see, e.g., U.S. Pat. No. 5,206,152 and WO 92/11033). Delivery devices can also be biocompatible, and may also be biodegradable. The formulation preferably provides a relatively constant level of active component release. On the other hand, a more rapid rate of release immediately upon administration may be desired. The formulation of such compositions is well within the level of ordinary skill in the art using known techniques.

Physical methods to enhance delivery include electroporation (where short pulses of high voltage carries the nucleic acid across the membrane), a gene gun (where DNA is loaded onto gold particles and forced to achieve penetration of the DNA into the cells), sonoporation, magnetofection, hydrodynamic delivery and the like, all of which are known to those of skill in the art. DNA also can be encapsulated in liposomes, preferably cationic liposomes, or polymersomes (synthetic liposomes) which can interact with the cell membrane and fuse or undergo endocytosis to effect DNA transfer into the cell. The DNA also can be formed into complexes with polymers (polyplexes) or with dendrimers which can directly release there load into the cytoplasm of a cell.

Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active agent contained within a sustained release formulation depends upon the site of implantation, the rate and expected duration of release and the nature of the condition to be treated or prevented.

Biodegradable microspheres (e.g., polylactate polyglycolate) may be employed as carriers for compositions. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which can have the added benefit when used intratumorally to deliver the coding sequence for a Anti-CD39 antibody Agent of being capable of inducing an MHC I-restricted cytotoxic T lymphocyte responses targeted tumor tissues of the patient.

Biodegradable polymeric nanoparticles facilitate nonviral nucleic acid transfer to cells. Small (approximately 200 nm), positively charged (approximately 10 mV) particles are formed by the self-assembly of cationic, hydrolytically degradable poly(beta-amino esters) and plasmid DNA.

Polynucleotides may also be administered to cells by direct microinjection, temporary cell permeabilizations (e.g., co-administration of repressor and/or activator with a cell permeabilizing agent), fusion to membrane translocating peptides, and the like.

In certain particular embodiments of the present disclosure, the gene construct is introduced into target cells via electroporation. Electroporation involves the exposure of cells (or tissues) and DNA (or a DNA complex) to a high-voltage electric discharge. In vivo electroporation is a gene delivery technique that has been used successfully for efficient delivery of plasmid DNA to many different tissues. Studies have reported the administration of in vivo electroporation for delivery of plasmid DNA to B16 melanomas and other tumor tissues. Systemic and local expression of a gene or cDNA encoded by a plasmid can be obtained with administration of in vivo electroporation. Use of in vivo electroporation enhances plasmid DNA uptake in tumor tissue, resulting in expression within the tumor, and delivers plasmids to muscle tissue, resulting in systemic expression of secreted proteins, such as cytokines (see, e.g., U.S. Pat. No. 8,026,223). Exemplary techniques, vectors and devices for electroporating Anti-CD39 antibody Agent transgenes into cells in vivo include PCT Publications WO/2017/106795, WO/2016/161201, WO/2016/154473, WO/2016/112359 and WO/2014/066655.

U.S. Pat. No. 7,245,963 describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the ceil between the plurality of electrodes. The entire content of U.S. Pat. No. 7,245,963 is hereby incorporated by reference.

U.S. Patent Pub. 2005/0052630 describes an electroporation device which may be used to effectively facilitate the introduction of a biomolecule into ceils of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk (see, e.g., U.S. Patent Pub. 2005/0052630) is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes.

Typically, the electric fields needed for in vivo cell electroporation are generally similar in magnitude to the fields required for cells in vitro. In one embodiment, the magnitude of the electric field range from approximately, 10 V/cm to about 1500 V/cm, preferably from about 300 V/cm to 1500 V/cm and preferably from about 1000 V/cm to 1500 V/cm. Alternatively, lower field strengths (from about 10 V/cm to 100 V/cm, and more preferably from about 25 V/cm to 75 V/cm) the pulse length is long. For example, when the nominal electric field is about 25-75 V/cm, if is preferred that the pulse length is about 10 msec.

The pulse length can be about 10 s to about 100 ms. There can be any desired number of pulses, typically one to 100 pulses per second. The delay between pulses sets can be any desired time, such as one second. The waveform, electric field strength and pulse duration may also depend upon the type of cells and the type of molecules that are to enter the cells via electroporation.

Also encompassed are electroporation devices incorporating electrochemical impedance spectroscopy ("EIS"). Such devices provide real-time information on in vivo, in particular, intratumoral electroporation efficiency, allowing for the the optimization of conditions. Examples of electroporation devices incorporating EIS can be found, e.g., in WO2016/161201, which is hereby incorporated by reference.

Uptake of the non-viral delivery vectors of the present invention may also be enhanced by plasma electroporation also termed avalanche transfection. Briefly, microsecond discharges create cavitation microbubbles at electrode surface. The mechanical force created by the collapsing microbubbles combined with the magnetic field serve to increase transport efficiency across the cell membrane as compared with the diffusion mediated transport associated with conventional electroporation. The technique of plasma electroporation is described in U.S. Pat. Nos. 7,923,251 and 8,283,171. This technique may also be employed in vivo for the transformation of cells. Chaiberg, et al (2006) Investigative Ophthalmology & Visual Science 47:4083-4090; Chaiberg, et al United States Patent No 8, 101 169 Issued Jan. 24, 2012.

Other alternative electroporation technologies are also contemplated. In vivo plasmid delivery can also be performed using cold plasma. Plasma is one of the four fundamental states of matter, the others being solid, liquid, and gas. Plasma is an electrically neutral medium of unbound positive and negative particles (e.g., the overall charge of a plasma is roughly zero). A plasma can be created by heating a gas or subjecting it to a strong electromagnetic field, applied with a laser or microwave generator. This decreases or increases the number of electrons, creating positive or negative charged particles called ions (Luo, et al. (1998) Phys. Plasma 5:2868-2870) and is accompanied by the dissociation of molecular bonds, if present.

Cold plasmas (e.g., non-thermal plasmas) are produced by the delivery of pulsed high voltage signals to a suitable electrode. Cold plasma devices may take the form of a gas jet device or a dielectric barrier discharge (DBD) device. Cold temperature plasmas have attracted a great deal of enthusiasm and interest by virtue of their provision of plasmas at relatively low gas temperatures. The provision of plasmas at such a temperature is of interest to a variety of applications, including wound healing, anti-bacterial processes, various other medical therapies and sterilization. As noted earlier, cold plasmas (e.g., non-thermal plasmas) are produced by the delivery of pulsed high voltage signals to a suitable electrode. Cold plasma devices may take the form of a gas jet device, a dielectric barrier discharge (DBD) device or multi-frequency harmonic-rich power supply.

Dielectric barrier discharge device, relies on a different process to generate the cold plasma. A dielectric barrier discharge (DBD) device contains at least one conductive electrode covered by a dielectric layer. The electrical return path is formed by the ground that can be provided by the target substrate undergoing the cold plasma treatment or by providing an in-built ground for the electrode. Energy for the dielectric barrier discharge device can be provided by a high voltage power supply, such as that mentioned above. More generally, energy is input to the dielectric barrier discharge device in the form of pulsed DC electrical voltage to form the plasma discharge. By virtue of the dielectric layer, the discharge is separated from the conductive electrode and electrode etching and gas heating is reduced. The pulsed DC electrical voltage can be varied in amplitude and frequency to achieve varying regimes of operation. Any device incorporating such a principle of cold plasma generation (e.g., a DBD electrode device) falls within the scope of various embodiments of the present invention.

Cold plasma has been employed to transfect cells with foreign nucleic acids. In particular, transfection of tumor cells (see, e.g., Connolly, et al. (2012) Human Vaccines & Immune-therapeutics 8: 1729-1733; and Connolly et al (2015) Bioelectrochemistry 103: 15-21).

In certain illustrative embodiments, the transgene construct encoding the Anti-CD39 antibody Agent of the present invention is delivered using an electroporation device comprising: an applicator; a plurality of electrodes extending from the applicator, the electrodes being associated with a cover area; a power supply in electrical communication with the electrodes, the power supply configured to generate one or more electroporating signals to cells within the cover area; and a guide member coupled to the electrodes, wherein the guide member is configured to adjust the cover area of the electrodes. At least a portion of the electrodes can be positioned within the applicator in a conical arrangement. The one or more electroporating signals may be each associated with an electric field. The device may further comprise a potentiometer coupled to the power supply and electrodes. The potentiometer may be configured to maintain the electric field substantially within a predetermined range.

The one or more electroporating signals may be each associated with an electric field. The device may further comprise a potentiometer coupled to the power supply and the electrodes. The potentiometer may be configured to maintain the electric field within a predetermined range so as to substantially prevent permanent damage in the cells within the cover area and/or substantially minimize pain. For instance, potentiometer may be configured to maintain the electric field to about 1300 V/cm.

The power supply may provide a first electrical signal to a first electrode and a second electrical signal to a second electrode. The first and second electrical signals may combine to produce a wave having a beat frequency. The first and second electrical signals may each have at least one of a unipolar waveform and a bipolar waveform. The first electrical signal may have a first frequency and a first amplitude. The second electrical signal may have a second frequency and a second amplitude. The first frequency may be different from or the same as the second frequency. The first amplitude may be different from or the same as the second amplitude.

In certain embodiments, the present invention provides a method for treating a subject having a tumor, the method comprising: injecting the tumor with an effective dose of plasmid coding for an anti-CD39 antibody agent; and administering electroporation therapy to the tumor. In certain embodiments, the electroporation therapy further comprises the administration of at least one voltage pulse of about 200 V/cm to about 1500 V/cm over a pulse width of about 100 microseconds to about 20 milliseconds.

In certain embodiments, the plasmid (or a second electroporated plasmid) further encodes at least one immunostimulatory cytokine, such as selected from the group encoding IL-12, IL-15, and a combination of IL-12 and IL-15.

Lipids and Polycationic Molecules for Delivering Anti-CD39 Antibody Encoding Nucleic Constructs Lipid-mediated nucleic acid delivery and expression of foreign nucleic acids, including mRNA, in vitro and in vivo has been very successful. Lipid based non-viral formulations provide an alternative to adenoviral gene therapies. Current in vivo lipid delivery methods use subcutaneous, intradermal, intratumoral, or intracranial injection. Advances in lipid formulations have improved the efficiency of gene transfer in vivo (see PCT Publication WO 98/07408). For instance, a lipid formulation composed of an equimolar ratio of 1,2-bis(oleoyloxy)-3-(trimethyl ammonio)propane (DOTAP) and cholesterol can significantly enhances systemic in vivo gene transfer. The DOTAP:cholesterol lipid formulation forms unique structure termed a “sandwich liposome”. This formulation is reported to “sandwich” DNA between an invaginated bi-layer or ‘vase’ structure. Beneficial characteristics of these lipid structures include a positive p, colloidal stabilization by cholesterol, two dimensional nucleic acid packing and increased serum stability.

Cationic liposome technology is based on the ability of amphipathic lipids, possessing a positively charged head group and a hydrophobic lipid tail, to bind to negatively charged DNA or RNA and form particles that generally enter cells by endocytosis. Some cationic liposomes also contain a neutral co-lipid, thought to enhance liposome uptake by mammalian cells. Similarly, other polycations, such as polylysine and polyethylene-imine, complex with nucleic acids via charge interaction and aid in the condensation of DNA or RNA into nanoparticles, which are then substrates for endosome-mediated uptake. Several of these cationic-nucleic acid complex technologies have been developed as potential clinical products, including complexes with plasmid DNA (pDNA), oligodeoxynucleotides, and various forms of synthetic RNA.

The nucleic acid constructs disclosed herein may be associated with polycationic molecules that serve to enhance uptake into cells. Complexing the nucleic acid construct with polycationic molecules also helps in packaging the construct such their size is reduced, which is believed to assist with cellular uptake. Once in the endosome, the complex dissociates due to the lower pH, and the polycationic molecules can disrupt the endosome’s membrane to facilitate DNA escape into the cytoplasm before it can be degraded. Preliminary data shows that the nucleic acid construct embodiments had enhanced uptake into SCs over DCs when complexed with the polycationic molecules polylysine or polyethyleneimine.

One example of polycationic molecules useful for complexing with nucleic acid constructs includes cell penetrating peptides (CPP), examples include polylysine (described above), polyarginine and Tat peptides. Cell penetrating peptides (CPP) are small peptides which can bind to DNA and, once released, penetrate cell membranes to facilitate escape of the DNA from the endosome to the cytoplasm. Another example of a CPP pertains to a 27 residue chimeric peptide, termed MPG, was shown some time ago to bind ss- and ds-oligonucleotides in a stable manner, resulting in a non-covalent complex that protected the nucleic acids from degradation by DNase and effectively delivered oligonucleotides to cells in vitro (Mahapatro A, et al., J Nanobiotechnol, 2011, 9:55). The complex formed small particles of approximately 150 nm to 1 um when different peptide:DNA ratios were examined, and the 10:1 and 5:1 ratios (150 nm and 1 um respectively). Another CPP pertains to a modified tetrapeptide (tetralysine containing guanidinocarbonylpyrrole (GCP) groups (TL-GCP)), which was reported to bind with high affinity to a 6.2 kb plasmid DNA resulting in a positive charged aggregate of 700-900 nm Li et al., Agnew Chem Int Ed Enl 2015; 54(10):2941-4). RNA can also be complexed by such polycationic molecules for in vivo delivery.

Other examples of polycationic molecules that may be complexed with the nucleic acid constructs described herein include polycationic polymers commercially available as JETPRIME® and in vivo JET (Polypus-transfection, S.A., Illkirch, France).

VI. Methods of Use and Pharmaceutical Compositions

The anti-CD39 antibodies of the invention are useful in a variety of applications including, but not limited to, therapeutic treatment methods, such as immunotherapy for cancer. In certain embodiments, an anti-CD39 antibody described herein is useful for activating, promoting, increasing, and/or enhancing an immune response, inhibiting tumor growth, reducing tumor volume, inducing tumor regression, increasing tumor cell apoptosis, and/or reducing the tumorigenicity of a tumor. In certain embodiments, the anti-CD39 antibody of the invention are also useful for immunotherapy against pathogens, such as viruses. In certain embodiments, an anti-CD39 antibody described herein is useful for inhibiting viral infection, reducing viral infection, increasing virally-infected cell apoptosis, and/or increasing killing of virus-infected cells. The methods of use may be in vitro, ex vivo, or in vivo methods.

The present invention provides methods for activating an immune response in a subject using an anti-CD39 antibody described herein. In some embodiments, the invention provides methods for promoting an immune response in a subject using an anti-CD39 antibody described herein. In some embodiments, the invention provides methods for increasing an immune response in a subject using an anti-CD39 antibody described herein. In some embodiments, the invention provides methods for enhancing an immune response in a subject using an anti-CD39 antibody described herein. In some embodiments, the activating, promoting, increasing, and/or enhancing of an immune response comprises increasing cell-mediated immunity. In some embodiments, the activating, promoting, increasing, and/or enhancing of an immune response comprises increasing Th1-type responses. In some embodiments, the activating, promoting, increasing, and/or enhancing of an immune response comprises increasing T-cell activity. In some embodiments, the activating, promoting, increasing, and/or enhancing of an immune response comprises increasing CD4+ T-cell activity. In some embodiments, the activating, promoting, increasing, and/or enhancing of an immune response comprises increasing CD8+ T-cell activity. In some embodiments, the activating, promoting, increasing, and/or enhancing of an immune response comprises increasing CTL activity. In some embodiments, the activating, promoting, increasing, and/or enhancing of an immune response comprises increasing NK cell activity. In some embodiments, the activating, promoting, increasing, and/or enhancing of an immune response comprises increasing T-cell activity and increasing NK cell activity. In some embodiments, the activating, promoting, increasing, and/or enhancing of an immune response comprises increasing CU activity and increasing NK cell activity. In some embodiments, the activating, promoting, increasing, and/or enhancing of an immune response comprises inhibiting or decreasing the suppressive activity of Treg cells. In some embodiments, the activating, promoting, increasing, and/or enhancing of an immune response comprises inhibiting or decreasing the suppressive activity of MDSCs. In some embodiments, the activating, promoting, increasing, and/or enhancing of an immune response comprises increasing the number of the percentage of memory T-cells. In some embodiments, the activating, promoting, increasing, and/or enhancing of an immune response comprises increasing long-term immune memory function. In some embodiments, the activating, promoting, increasing, and/or enhancing of an immune response comprises increasing long-term memory. In some embodiments, the activating, promoting, increasing, and/or enhancing of an immune response comprises no evidence of substantial side effects and/or immune-based toxicities. In some embodiments, the activating, promoting, increasing, and/or enhancing of an immune response comprises no evidence of cytokine release syndrome (CRS) or a cytokine storm. In some embodiments, the immune response is a result of antigenic stimulation. In some embodiments, the antigenic stimulation is a tumor cell. In some embodiments, the antigenic stimulation is cancer. In some embodiments, the antigenic stimulation is a pathogen. In some embodiments, the antigenic stimulation is a virally-infected cell.

In vivo and in vitro assays for determining whether an anti-CD39 antibody modulates, activates, or inhibits an immune response are known in the art or are being developed.

In certain embodiments of the methods described herein, a method of inducing a persistent or long-term immunity which inhibits tumor relapse or tumor regrowth comprises administering to a subject a therapeutically effective amount of an anti-CD39 antibody.

In some embodiments, the tumor is a solid tumor. In certain embodiments, the tumor is a tumor selected from the group consisting of: colorectal tumor, pancreatic tumor, lung tumor, ovarian tumor, liver tumor, breast tumor, kidney tumor, prostate tumor, neuroendocrine tumor, gastrointestinal tumor, melanoma, cervical tumor, bladder tumor, glioblastoma, lymphoma and head and neck tumor. In certain embodiments, the tumor is a colorectal tumor. In certain embodiments, the tumor is an ovarian tumor. In some embodiments, the tumor is a lung tumor. In certain embodiments, the tumor is a pancreatic tumor. In certain embodiments, the tumor is a melanoma tumor. In some embodiments, the tumor is a bladder tumor.

In some embodiments, the tumor is a liquid tumor. In certain embodiments, the tumor is a leukemia, such as myelogenous or granulocytic leukemia, lymphatic, lymphocytic, or lymphoblastic leukemia, and plycythemia vera or erythremia.

In some embodiments, the tumor expresses or overexpresses a tumor antigen targeted by the anti-CD39 antibody, such as a bispecific agent which comprises an antigen-binding site that specifically binds the tumor antigen.

The present invention further provides methods for treating cancer in a subject comprising administering to the subject a therapeutically effective amount of an anti-CD39 antibody described herein. In some embodiments, the anti-CD39 antibody and inhibits or reduces growth of the cancer.

The present invention provides for methods of treating cancer comprising administering to a subject (e.g., a subject in need of treatment) a therapeutically effective amount of an anti-CD39 antibody described herein. In certain embodiments, the subject is a human. In certain embodiments, the subject has a cancerous tumor. In certain embodiments, the subject has had a tumor removed.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, neuroendocrine cancer, bladder cancer, brain cancer, glioblastoma, and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer. In certain embodiments, the cancer is prostate cancer. In certain embodiments, the cancer is lung cancer. In certain embodiments, the cancer is melanoma. In some embodiments, the cancer is bladder cancer.

The present invention provides compositions comprising an anti-CD39 antibody described herein. The present invention also provides pharmaceutical compositions comprising an anti-CD39 antibody described herein and a pharmaceutically acceptable vehicle. In some embodiments, the pharmaceutical compositions find use in immunotherapy. In some embodiments, the pharmaceutical compositions find use in immuno-oncology. In some embodiments, the compositions find use in inhibiting tumor growth. In some embodiments, the pharmaceutical compositions find use in inhibiting tumor growth in a subject (e.g., a human patient). In some embodiments, the compositions find use in treating cancer. In some embodiments, the pharmaceutical compositions find use in treating cancer in a subject (e.g., a human patient).

Formulations are prepared for storage and use by combining a purified agent of the present invention with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

In some embodiments, the anti-CD39 antibody is lyophilized and/or stored in a lyophilized form. In some embodiments, a formulation comprising an anti-CD39 antibody described herein is lyophilized.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (Remington: The Science and Practice of Pharmacy, 22.sup.nd Edition, 2012, Pharmaceutical Press, London).

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The anti-CD39 antibody can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington: The Science and Practice of Pharmacy, 22.sup.nd Edition, 2012, Pharmaceutical Press, London.

In certain embodiments, pharmaceutical formulations include an anti-CD39 antibody complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations comprising the anti-CD39 antibody can be produced. Suitable examples of sustained-release preparations include semi-permeable matrices of solid hydrophobic polymers containing an anti-CD39 antibody, where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), sucrose acetate isobutyrate, and poly-D-(−)-3-hydroxybutyric acid.

In certain embodiments, in addition to administering an anti-CD39 antibody, the method or treatment further comprises administering at least one additional immune response stimulating agent. In some embodiments, the additional immune response stimulating agent includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), a checkpoint inhibitor, an antibody that blocks immunosuppressive functions (e.g., an anti-CTLA-4 antibody, anti-CD28 antibody, anti-CD3 antibody), a toll-like receptor (e.g., TLR4, TLR7, TLR9), or a member of the B7 family (e.g., CD80, CD86). An additional immune response stimulating agent can be administered prior to, concurrently with, and/or subsequently to, administration of the anti-CD39 antibody. Pharmaceutical compositions comprising an anti-CD39 antibody and the immune response stimulating agent(s) are also provided. In some embodiments, the immune response stimulating agent comprises 1, 2, 3, or more immune response stimulating agents.

In certain embodiments, in addition to administering an anti-CD39 antibody, the method or treatment further comprises administering at least one additional therapeutic agent. An additional therapeutic agent can be administered prior to, concurrently with, and/or subsequently to, administration of the anti-CD39 antibody. Pharmaceutical compositions comprising an anti-CD39 antibody and the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the anti-CD39 antibody. Combination therapy may decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, the combination of an anti-CD39 antibody and at least one additional therapeutic agent results in additive or synergistic results. In some embodiments, the combination therapy results in an increase in the therapeutic index of the anti-CD39 antibody. In some embodiments, the combination therapy results in an increase in the therapeutic index of the additional therapeutic agent(s). In some embodiments, the combination therapy results in a decrease in the toxicity and/or side effects of the anti-CD39 antibody. In some embodiments, the combination therapy results in a decrease in the toxicity and/or side effects of the additional therapeutic agent(s).

Useful classes of therapeutic agents include, for example, anti-tubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, anti-folates, anti-metabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, *vinca* alkaloids, or the like. In certain embodiments, the second therapeutic agent is an alkylating agent, an antimetabolite, an antimitotic, a topoisomerase inhibitor, or an angiogenesis inhibitor.

Therapeutic agents that may be administered in combination with the anti-CD39 antibody described herein include chemotherapeutic agents. Thus, in some embodiments, the method or treatment involves the administration of an anti-CD39 antibody in combination with a chemotherapeutic agent or in combination with a cocktail of chemotherapeutic agents. Treatment with an anti-CD39 antibody can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in The Chemotherapy Source Book, 4.sup.th Edition, 2008, M. C. Perry, Editor, Lippincott, Williams & Wilkins, Philadelphia, Pa.

Chemotherapeutic agents useful in the present invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g., paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin.

In certain embodiments of the methods described herein, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments of the methods described herein, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1.

In certain embodiments of the methods described herein, it is anticipated that the subject anti-CD39 agent will have a greater combinatorial effect (perhaps even synergy) with those chemotherapeutic agents that induce the release of ATP in the tumor and/or cause upregulation of CD39 or CD73 intratumorally. There are a wide range of chemotherapeutic agents that cause the release of ATP into the extracellular space as they induce tumor cell death, such as (but not limited to) anthracyclines (such as doxorubicin, daunorubicin, epirubicin and idarubicin), platinum-based drugs (such as cisplatin, carboplatin, and oxaliplatin), and proteasome inhibitors (such as bortezomib). Radiotherapy and photodynamic therapy (PDT) may also result in ATP release and/or upregulation of intratumoral levels of CD39 and/or CD73.

In some embodiments of the methods described herein, an additional therapeutic agent comprises an agent such as a small molecule. For example, treatment can involve the combined administration of an anti-CD39 antibody with a small molecule that acts as an inhibitor against tumor-associated antigens including, but not limited to, EGFR, HER2 (ErbB2), and/or VEGF. In some embodiments, an anti-CD39 antibody is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor.

In certain embodiments of the methods described herein, the additional therapeutic agent is a small molecule that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an inhibitor of the Hippo pathway. In some embodiments, the additional therapeutic agent is an inhibitor of the mTOR/AKR pathway. In some embodiments, the additional therapeutic agent is an inhibitor of the RSPO/LGR pathway.

In some embodiments of the methods described herein, an additional therapeutic agent comprises a biological molecule, such as an antibody. For example, treatment can involve the combined administration of an anti-CD39 antibody with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an antibody that inhibits β-catenin signaling. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

I/O Combinations—Representative Checkpoint Inhibitors and Co-Stimulatory Agonists In some embodiments of the methods described herein, the additional therapeutic agent is an antibody that modulates the immune response. In some embodiments, the additional therapeutic agent is an anti-PD-1 antibody, an anti-PD-L1 antibody, an anti-CTLA-4 antibody, an anti-LAG-3 antibody, and anti-TIM-3 antibody or an anti-TIGIT antibody.

For instance, the therapy can further include administering an inhibitor of immune checkpoint molecule or an activator of a costimulatory molecule, or a combination thereof. Exemplary inhibitors of immune checkpoints include inhibitors of one or more of PD-1, CTLA-4, TIM-3, LAG-3, CEACAM, VISTA, BTLA, TIGIT, LAIR1, CD160, 2B4, NLRP1, NRLP3, STING or TGFR beta. Exemplary activators of costimulatory molecules include agonists of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand. Exemplary inhibitor of immune checkpoints and exemplary activators of costimulatory molecules can be found in PCT Publication WO 2016/054555, which is incorporated by reference herein.

PD-1 Antagonists

The PD-1 gene is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Daeron, M (1997) Immunol Today 18:286-91). Two ligands for PD-1 have been identified, PD-L1 and PD-L2, that have been shown to downregulate T cell activation upon binding to PD-1 (Freeman et al. (2000) J Exp Med 192: 1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members. PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170: 1257-66)

As used herein, the terms "Programmed Death 1," "Programmed Cell Death 1," "Protein PD-1," "PD-1," PD1," "PDCD1," "hPD-1" and "hPD-I" are used interchangeably, and include variants, isoforms, species homologs of human PD-1, and analogs having at least one common epitope with human PD-1. The complete human PD-1 sequence can be found under GenBank Accession No. U64863.

As used herein, the terms "Programmed Cell Death 1 Ligand 1", "PD-L1", "PD11", "PDCD1 L1 "PDCD1LG1", "CD274", "B7 homolog 1", "B7-H1", "B7-H", and "B7H1" are used interchangeably, and include variants, isoforms, species homologs of human PD1-1, and analogs having at least one common epitope with human PD1-1. The complete human PD-L1 amino acid sequence—isoform a precursor—can be found under GenBank Accession No. NP_054862.1. The complete human PD-L1 amino acid sequence—isoform b precursor—can be found under GenBank Accession No. NP_001254635.1.

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 described herein. In another specific aspect, a PD-1 binding antagonist is Merck 3745 described herein. In another specific aspect, a PD-1 binding antagonist is CT-011 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPD13280A described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

PD-1 pathway: Members of the PD-1 pathway are all proteins which are associated with PD-1 signaling. On the one hand these might be proteins which induce PD-1 signaling upstream of PD-1 as e.g., the ligands of PD-1 PD-L1 and PD-L2 and the signal transduction receptor PD-1. On the other hand, these might be signal transduction proteins downstream of PD-1 receptor. Particularly preferred as members of the PD-1 pathway in the context of the present invention are PD-1, PD-L1 and PD-L2.

PD-1 pathway inhibitor: In the context of the present invention, a PD-1 pathway inhibitor is preferably defined herein as a compound capable to impair the PD-1 pathway signaling, preferably signaling mediated by the PD-1 receptor. Therefore, the PD-1 pathway inhibitor may be any inhibitor directed against any member of the PD-1 pathway capable of antagonizing PD-1 pathway signaling. In this context, the inhibitor may be an antagonistic antibody as defined herein, targeting any member of the PD-1 pathway, preferably directed against PD-1 receptor, PD-L1 or PD-L2. This antagonistic antibody may also be encoded by a nucleic acid. Such encoded antibodies are also called "intrabodies" as defined herein. Also, the PD-1 pathway inhibitor may be a fragment of the PD-1 receptor or the PD1—receptor blocking the activity of PD1 ligands. B7-1 or fragments thereof may act as PD1—inhibiting ligands as well. Furthermore, the PD-1 pathway inhibitor may be si NA (small interfering RNA) or antisense RNA directed against a member of the PD-1 pathway, preferably PD-1, PD-L1 or PD-L2. Additionally, a PD-1 pathway inhibitor may be a protein comprising (or a nucleic acid coding for) an amino acid sequence capable of binding to PD-1 but preventing PD-1 signaling, e.g., by inhibiting PD-1 and B7-H1 or B7-DL interaction. Additionally, a PD-1 pathway inhibitor may be a small molecule inhibitor capable of inhibiting PD-1 pathway signaling, e.g., a PD-1 binding peptide or a small organic molecule.

In certain embodiments, PD-1 antagonists of the invention include agents that bind to ligands of PD-1 and interfere with, reduce, or inhibit the binding of one or more ligands to the PD-1 receptor, or bind directly to the PD-1 receptor, without engaging in signal transduction through the PD-1 receptor. In one embodiment, the PD-1 antagonist binds directly to PD-1 and blocks PD-1 inhibitory signal transduction. In another embodiment, the PD-1 antagonist binds to one or more ligands of PD-1 (e.g., PD-L1 and PD-L2) and reduces or inhibits the ligand(s) from triggering inhibitory signal transduction through the PD-1. In one embodiment, the PD-1 antagonist binds directly to PD-L1, inhibiting or preventing PD-L1 from binding to PD-1, thereby blocking PD-1 inhibitory signal transduction.

PD-1 antagonists used in the methods and compositions of the present invention include PD-1 binding scaffold proteins and include, but are not limited to, PD-ligands, antibodies and multivalent agents. In a particular embodiment, the antagonist is a fusion protein, such as AMP-224.

In another embodiment, the antagonist is an anti-PD-1 antibody ("PD-1 antibody"). Anti-human-PD-1 antibodies (or VH and/or VL domains derived therefrom) suitable for use in the invention can be generated using methods well known in the art. Alternatively, art recognized anti-PD-1 antibodies can be used. For example, antibodies MK-3475 or CT-011 can be used. Additionally, monoclonal antibodies 5C4, 17D8, 2D3, 4H1, 4A11, 7D3, and 5F4, described in WO 2006/121168, the teachings of which are hereby incorporated by reference, can be used. Antibodies that compete with any of these art-recognized antibodies for binding to PD-1 also can be used.

In another embodiment, the PD-1 antagonist is an anti-PD-L1 antibody. Anti-human-PD-L1 antibodies (or VH and/or VL domains derived therefrom) suitable for use in the invention can be generated using methods well known in the art. Alternatively, art recognized anti-PD-L1 antibodies can be used. For example, MEDI4736 (also known as Anti-B7-HI) or MPD13280A (also known as RG7446) can be used. Additionally, monoclonal antibodies 12A4, 3G10, 10A5, 5F8, 10H10, 1B12, 7H1, 11E6, 12B7, and 13G4 described in WO 2007/005874 and U.S. Pat. No. 7,943,743, the teachings of which are hereby incorporated by reference, can be used. Antibodies that compete with any of these art-recognized antibodies for binding to PD-L1 also can be used.

An exemplary anti-PD-L1 antibody is 12A4 (WO 2007/005874 and U.S. Pat. No. 7,943,743). In one embodiment, the antibody comprises the heavy and light chain CDRs or VRs of 12A4. Accordingly, in one embodiment, the antibody comprises the CDR1, CDR2, and CDR3 domains of the VH region of 12A4 having the sequence shown in SEQ ID NO: 1 and the CDR1, CDR2 and CDR3 domains of the VL region of 12A4 having the sequence shown in SEQ ID NO: 3. In another embodiment, the antibody comprises the heavy chain CDR1, CDR2 and CDR3 domains having the sequences set forth in SEQ ID NOs: 5, 6, and 7, respectively, and the light chain CDR1, CDR2 and CDR3 domains having the sequences set forth in SEQ ID NOs: 8, 9, and 10, respectively. In another embodiment, the antibody comprises VH and/or VL regions of 12A4 having the amino acid sequences set forth in SEQ ID NO: 1 and/or SEQ ID NO: 3, respectively. In another embodiment, the antibody comprises the heavy chain variable (VH) and/or light chain variable (VL) regions encoded by the nucleic acid sequences set forth in SEQ ID NO: 2 and/or SEQ ID NO: 4, respectively. In another embodiment, the antibody competes for binding with, and/or binds to the same epitope on PD-L1 as, the above-mentioned antibodies. In another embodiment, the antibody has at least about 90% variable region amino acid sequence identity with the above-mentioned antibodies (e.g., at least about 90%, 95% or 99% variable region identity 12A4 with SEQ ID NO: 1 or SEQ ID NO: 3).

Anti-PD-1 or anti-PD-L1 antibodies may bind to PD-1 or PD-L1, respectively, with a KD of $10^{-7}$ M, $5\times10^{-8}$ M, $10^{-8}$ M, $5\times10^{-9}$ M, $10^{-9}$ M, $5\times10^{-10}$ M, $10^{-10}$ M or less.

In one embodiment, the PD-1 inhibitor is an anti-PD-1 antibody chosen from Nivolumab, Pembrolizumab or Pidilizumab. A preferred PD-1 inhibitor is Nivolumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 (incorporated by reference) and WO 2006/121168 (incorporated by reference). In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) New England Journal of Medicine 369 (2): 134-44, WO 2009/114335 (incorporated by reference), and U.S. Pat. No. 8,354,509 (incorporated by reference).

In some embodiments, the anti-PD-1 antibody is Pidilizumab. Pidilizumab (CT-011; Cure Tech) is a humanized IgGlk monoclonal antibody that binds to PD1. Pidilizumab and other humanized anti-PD-1 monoclonal antibodies are disclosed in WO2009/101611. Other anti-PD1 antibodies are disclosed in U.S. Pat. No. 8,609,089, US 2010028330, and/or US 20120114649. Other anti-PD1 antibodies include AMP 514 (Amplimmune).

In some embodiments, the PD-1 inhibitor is an immunoadhesin {e.g., an immunoadhesin comprising an extracellular or PD-1 binding portion of PD-L1 or PD-L2 fused to a constant region {e.g., an Fc region of an immunoglobulin sequence). In some embodiments, the PD-1 inhibitor is AMP-224. In some embodiments, the PD-L1 inhibitor is anti-PD-L1 antibody. In some embodiments, the anti-PD-L1 inhibitor is YW243.55.S70, MPD13280A, MEDI-4736, MSB-0010718C, or MDX-1105.

In one embodiment, the PD-L1 inhibitor is MDX-1105. MDX-1105, also known as BMS-936559, is an anti-PD-L1 antibody described in WO 2007/005874. In one embodiment, the PD-L1 inhibitor is YW243.55.S70. The YW243.55.S70 antibody is an anti-PD-L1 described in WO 2010/077634 (incorporated by reference) (heavy and light chain variable region sequences shown in SEQ ID Nos. 20 and 21, respectively).

In one embodiment, the PD-L1 inhibitor is MDPL3280A (Genentech/Roche). MDPL3280A is a human Fc optimized IgGI monoclonal antibody that binds to PD-L1. MDPL3280A and other human monoclonal antibodies to PD-L1 are disclosed in U.S. Pat. No. 7,943,743 (incorporated by reference) and U.S. Publication No.: 2012/0039906 (incorporated by reference). In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO 2010/027827 (incorporated by reference) and WO 2011/066342 (incorporated by reference)).

In certain embodiments, the PD-1 pathway inhibitor is a small molecule antagonist of PD-1 pathway signaling. Such small molecule antagonists include those agents that bind to one or more of PD-1, PD-1L and/or PD-1 L2 and inhibits the interaction of PD-1 with PD-1 L1 and/or PD-1 L2.

Exemplary small molecule antagonist of PD-1 pathway signaling can be found in, inter alia, published US applications 2014/0294898 and 2014/0199334, and published PCT Applications WO 2013/132317 and WO 2012/168944, each of which is incorporated by reference herein.

Merely to illustrate, the subject combination therapy can be practiced with small molecule antagonist selected from the group consisting of 2a

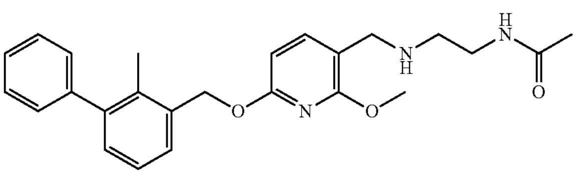

(BMS-202)

2b

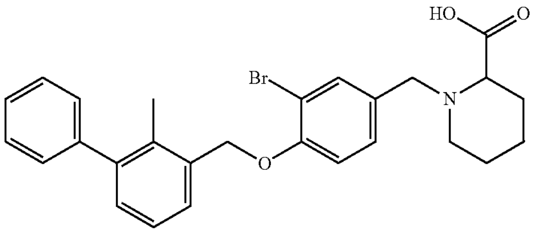

(BMS-8)

2c

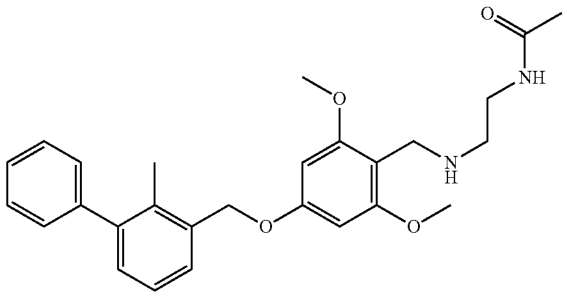

(BMS-37)

2c1

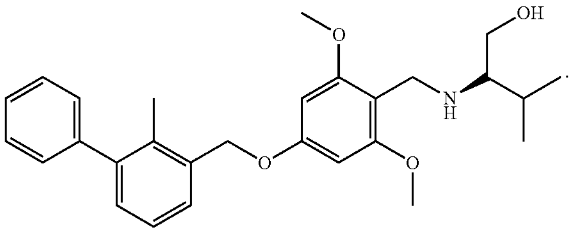

(BMS-242)

In other embodiments, the small molecule antagonist is represented in the general formula

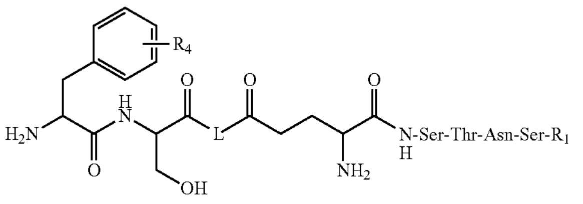

wherein, $R_1$ is free C-terminal or amidated C-terminal of Ser;

L is a linker selected from —$NH(CH_2)_nNH$—or —$NH(CH_2CH_2O)_nNH$—;

$R_4$ is selected from hydrogen, amino($C_1$-$C_{20}$)alkyl, —$NHCOCH_3$ or —$NHCONH_2$;

or retro analogue or a pharmaceutically acceptable stereoisomer or a pharmaceutically acceptable salt thereof.

In still other embodiments, the small molecule antagonist is represented in the general formula

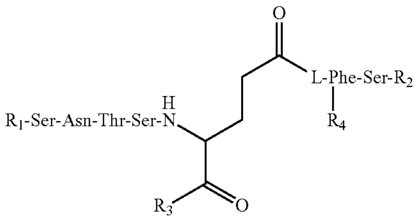

wherein, $R_1$ is N-terminal of Ser; or ($C_1$-$C_{20}$)acyl substituted with either hydroxyl group or amino group of Ser;

L is a linker selected from —$NH(CH_2)_nNH$—, —$NH(CH_2)_nCH(NH_2)CO$—, —$OOC(CH_2)_mCOO$—, —$NH(CH_2)_nCO$—, —$NH(CH_2CH_2O)_nNH$—, —$NH(CH_2CH_2O)_nCO$— or —$CO(CH_2CH_2O)_nCO$—;

$R_2$ is free C-terminal, amidated C-terminal or N-terminal of $Am_2$; or Y—$R_5$;

Y is an optional linker selected from —$OOC(CH_2)_mCOO$—, —$CO(CH_2)_nNH$—, —$CO(CH_2CH_2O)_nNH$— or —$COCH_2(OCH_2CH_2)_nNH$—;

$R_5$ is an albumin binding moiety such as maleimido propionic acid;

$R_3$ is OH or $NH_2$;

$R_4$ is a substituent on phenyl group of Phe and is selected from hydrogen, amino($C_1$-$C_{20}$)alkyl, —$NHCOCH_3$ or —$NHCONH_2$;

n is an integer having values selected from 2 to 10, both inclusive;

m is an integer having values selected from 0 to 8, both inclusive; and one of the peptide bond (—CONH—) of Ser-Asn, Asn-Thr or Thr-Ser may be replaced with a modified peptide bond of

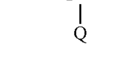

wherein Q is hydrogen, —CO($C_1$-$C_{20}$)alkyl or —COO($C_1$-$C_{20}$)alkyl group; wherein one or more or all amino acids may be in the D-configuration;

or retro analogue or a pharmaceutically acceptable stereoisomer or a pharmaceutically acceptable salt thereof.

For instance, the small molecule antagonist can be selected from the group consisting of

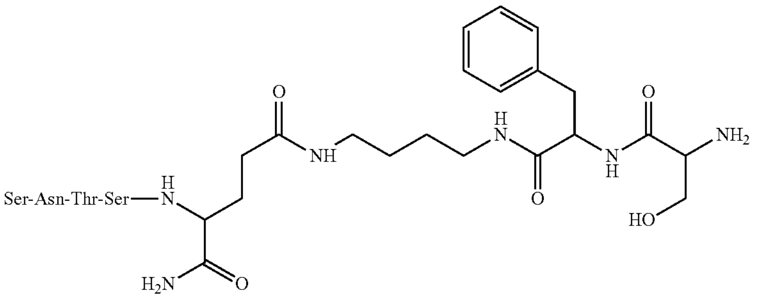
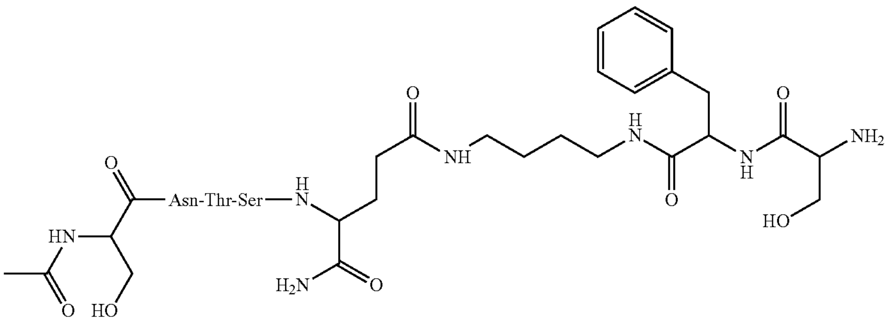
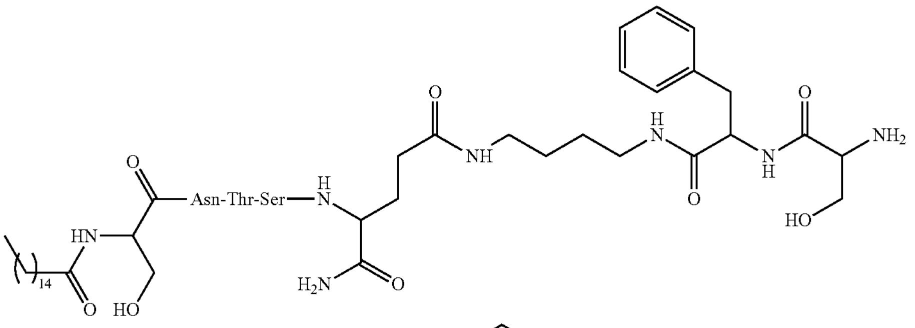
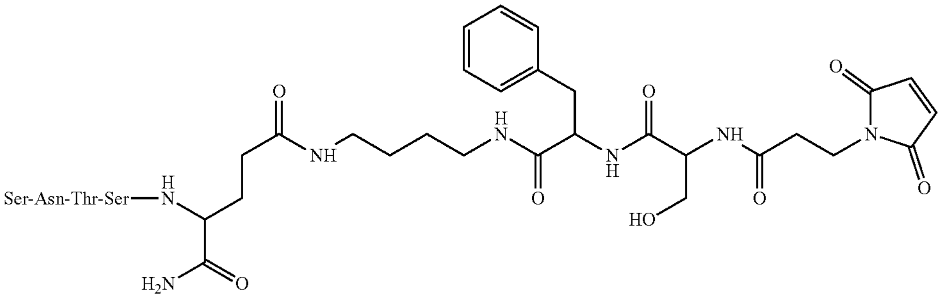
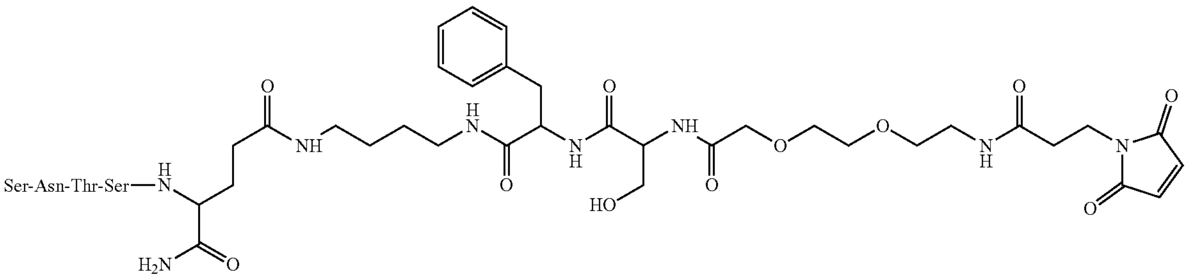
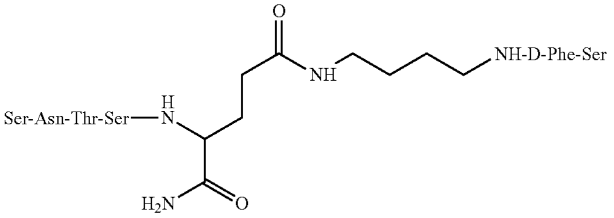

-continued
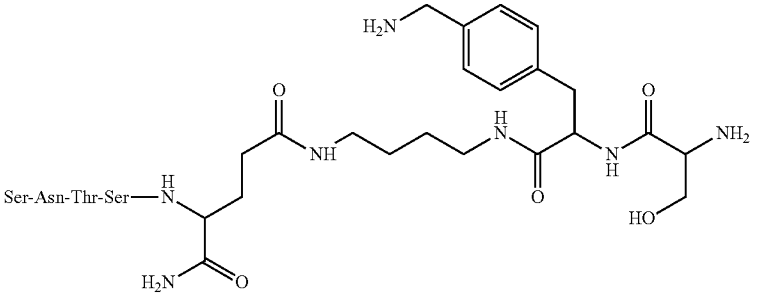
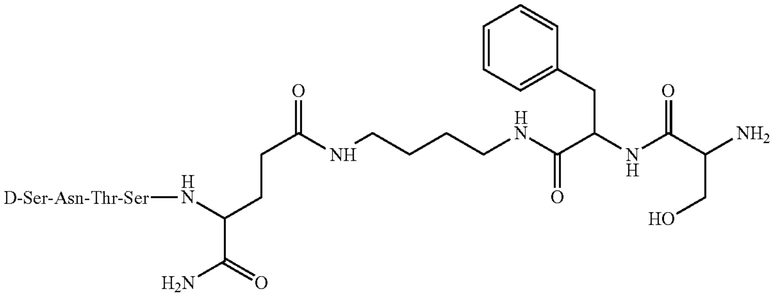
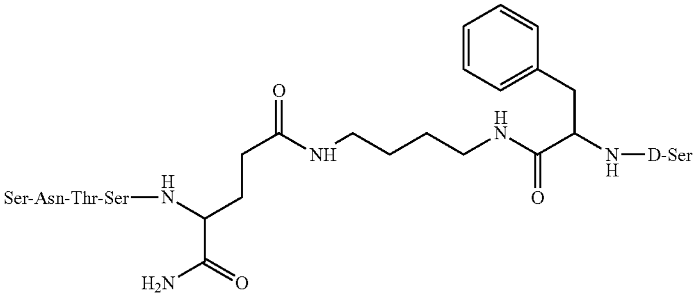
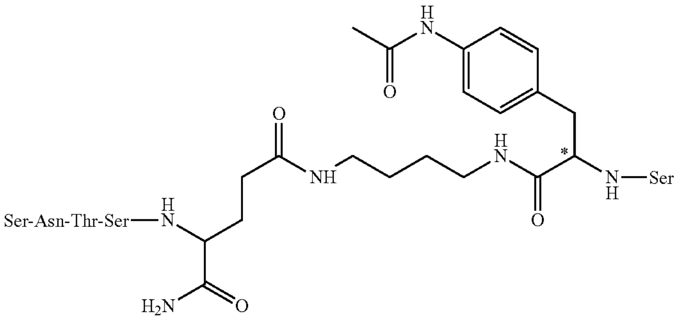
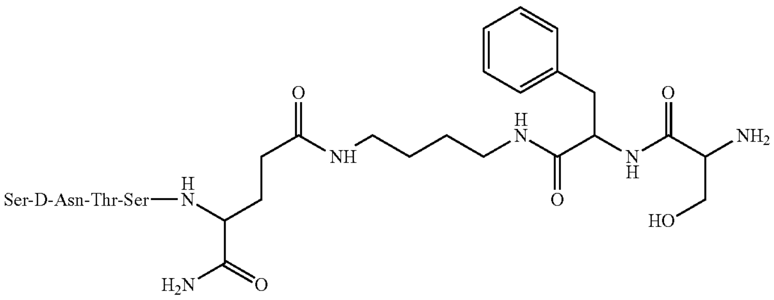

-continued
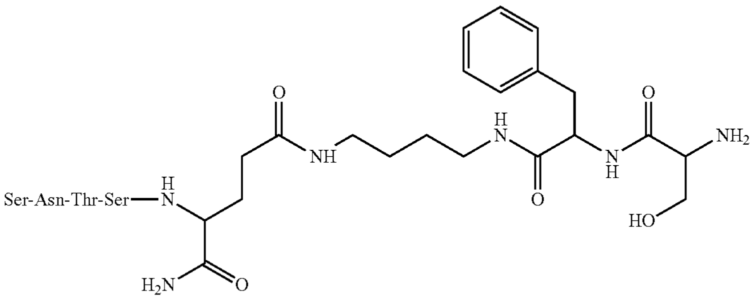
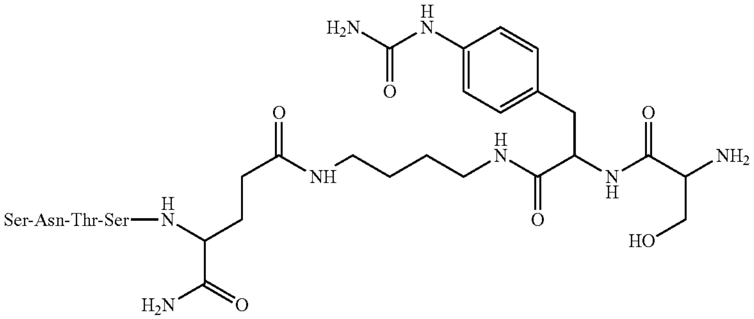
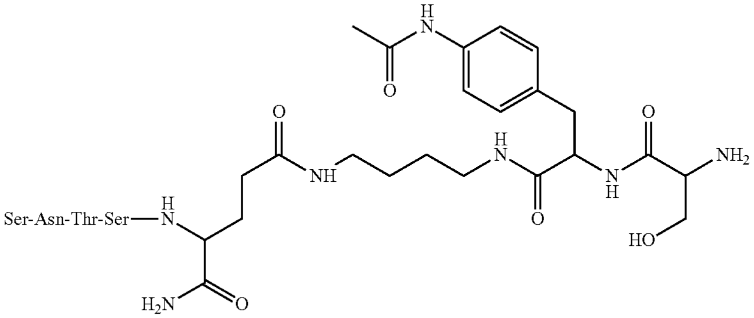
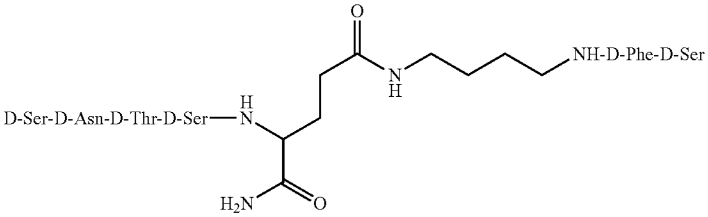
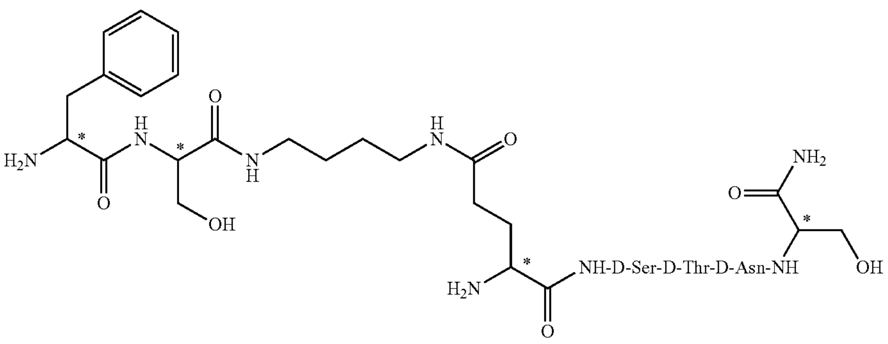

-continued
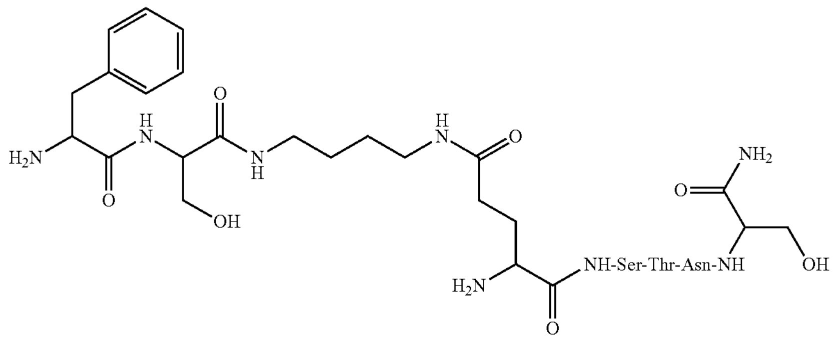
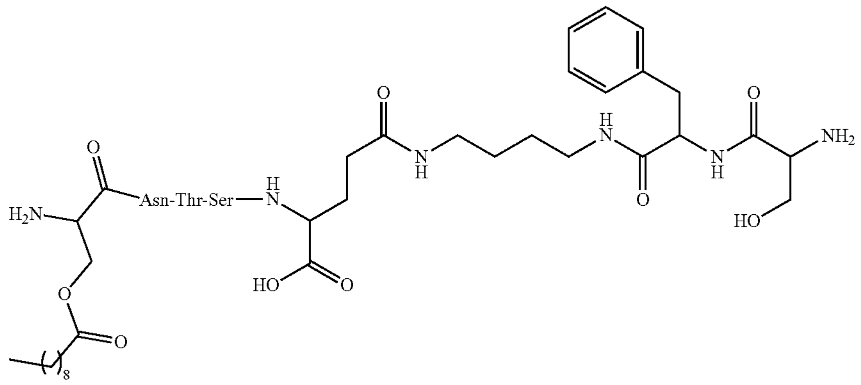
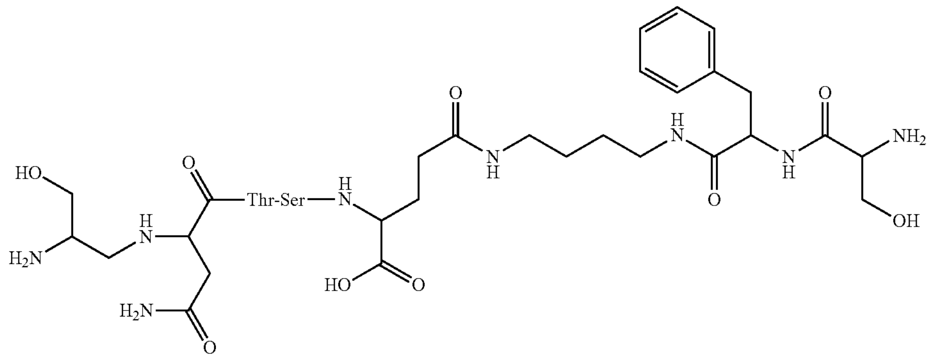
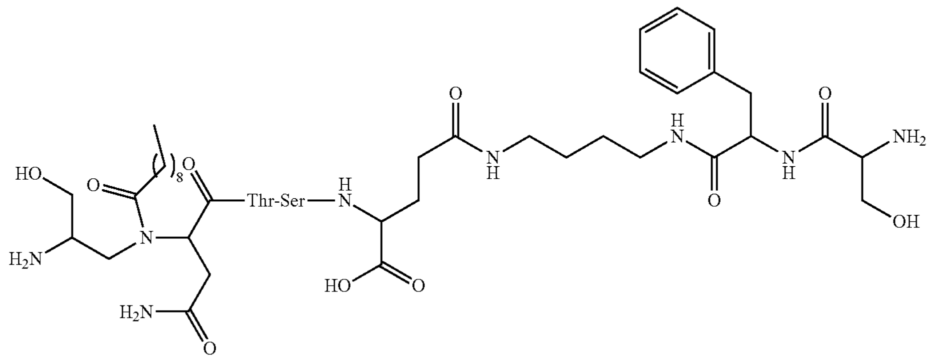

-continued
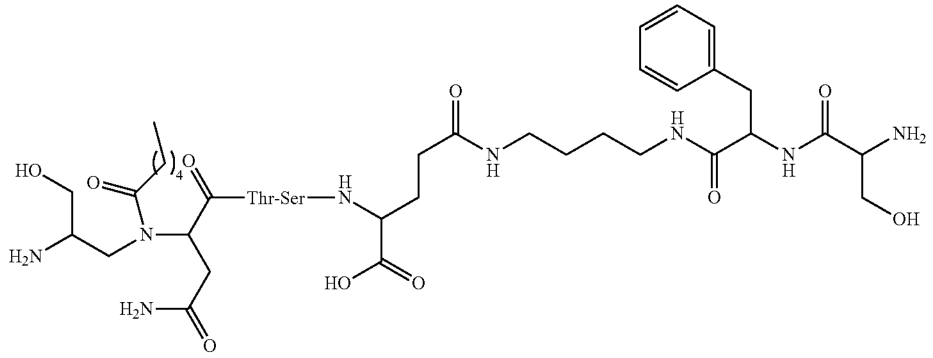
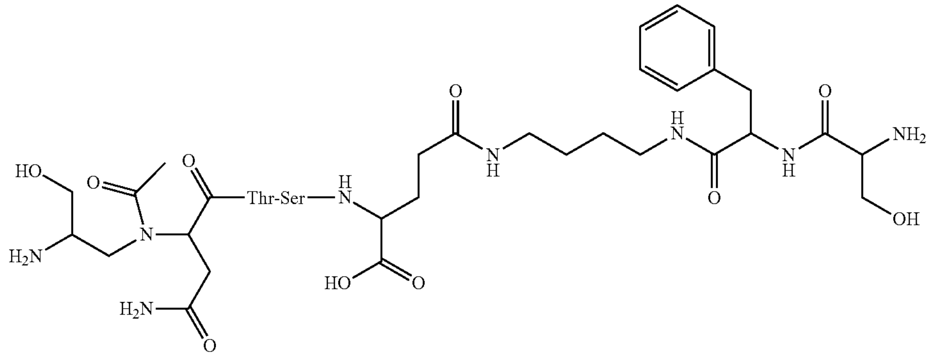
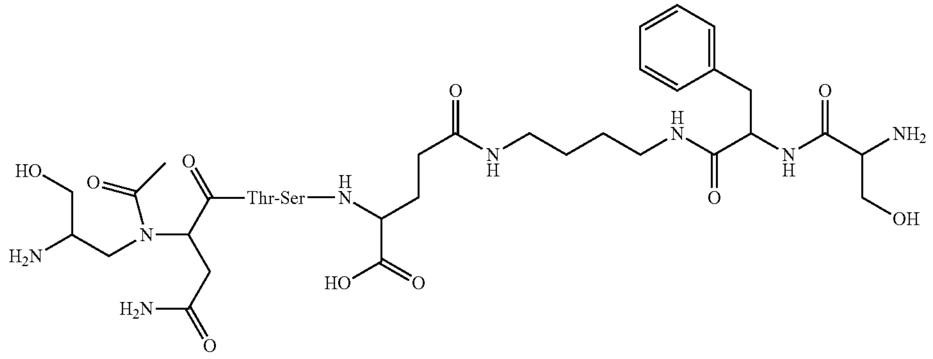
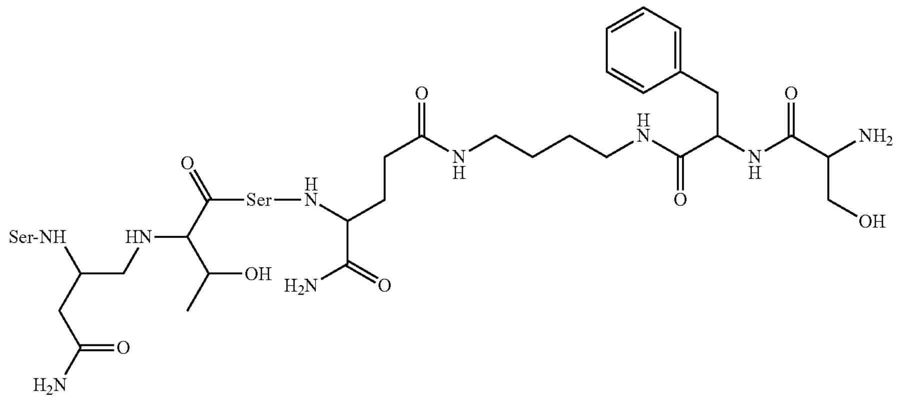

-continued
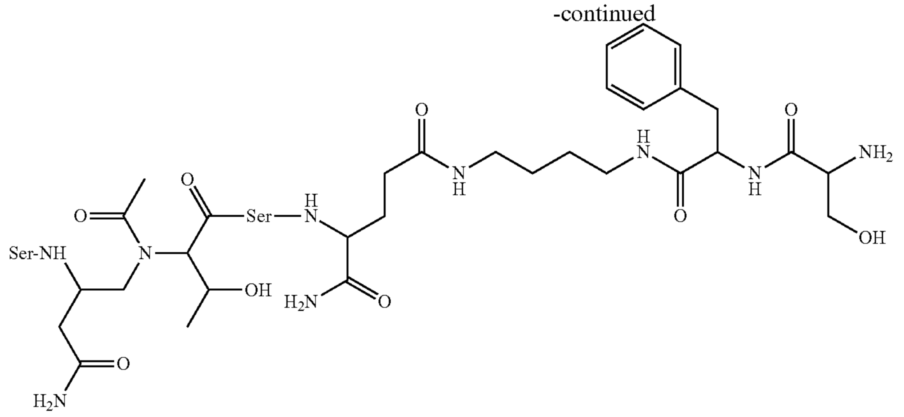
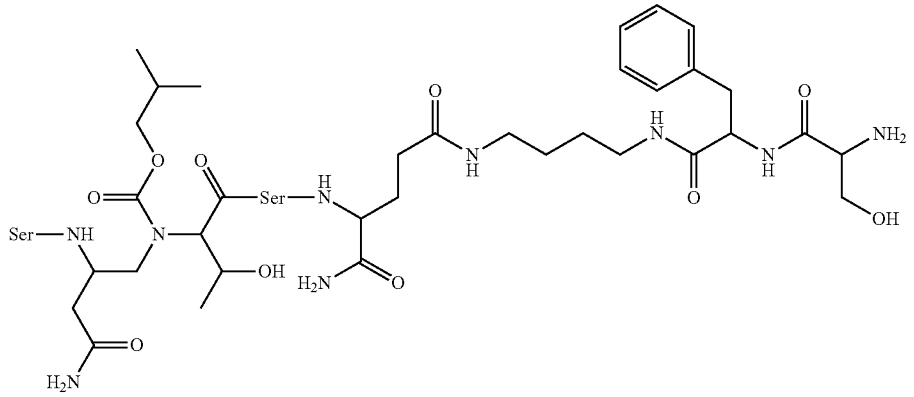
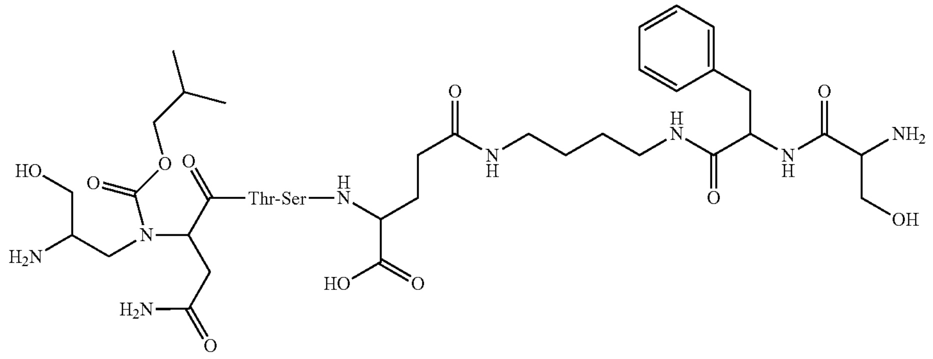
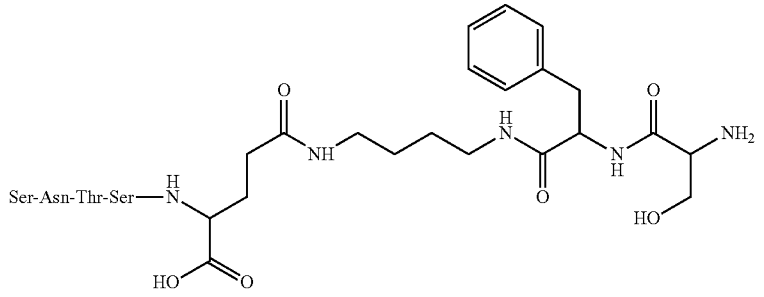

-continued

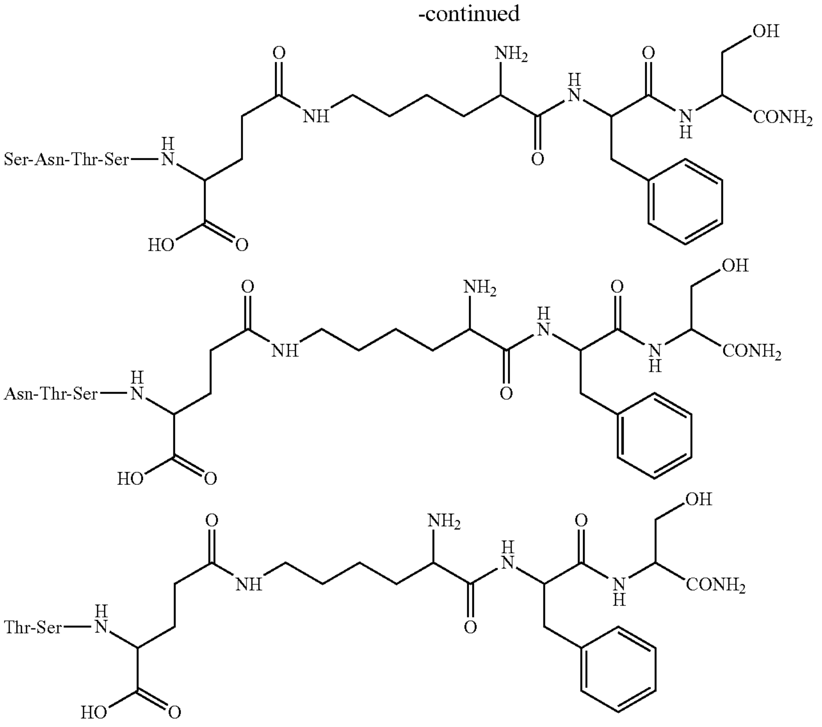

CTLA-4 Antagonists

In certain embodiments, a combination described herein also includes a CTLA-4 inhibitor. Exemplary anti-CTLA-4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

Information regarding tremelimumab (or antigen-binding fragments thereof) for use in the methods provided herein can be found in U.S. Pat. No. 6,682,736 (incorporated by reference) (where it is referred to as 11.2.1), the disclosure of which is incorporated herein by reference in its entirety. Tremelimumab (also known as CP-675,206, CP-675, CP-675206, and ticilimumab) is a human IgG2 monoclonal antibody that is highly selective for CTLA-4 and blocks binding of CTLA-4 to CD80 (B7.1) and CD86 (B7.2). It has been shown to result in immune activation in vitro and some patients treated with tremelimumab have shown tumor regression.

Tremelimumab for use in the methods provided herein comprises a heavy chain and a light chain or a heavy chain variable region and a light chain variable region. In a specific aspect, tremelimumab or an antigen-binding fragment thereof for use in the methods provided herein comprises a light chain variable region comprising the amino acid sequences shown herein above and a heavy chain variable region comprising the amino acid sequence shown herein above. In a specific aspect, tremelimumab or an antigen-binding fragment thereof for use in the methods provided herein comprises a heavy chain variable region and a light chain variable region, wherein the heavy chain variable region comprises the Kabat-defined CDR1, CDR2, and CDR3 sequences shown herein above, and wherein the light chain variable region comprises the Kabat-defined CDR1, CDR2, and CDR3 sequences shown herein above. Those of ordinary skill in the art would easily be able to identify Chothia-defined, Abm-defined or other CDR definitions known to those of ordinary skill in the art. In a specific aspect, tremelimumab or an antigen-binding fragment thereof for use in the methods provided herein comprises the variable heavy chain and variable light chain CDR sequences of the antibody as disclosed in U.S. Pat. No. 6,682,736, which is herein incorporated by reference in its entirety.

The present invention also contemplates utilizing small molecule inhibitors of CTLA-4, such as described by Huxley et al. 2004 Cell Chemical Biology 11:1651-1658, which includes compounds of the formula:

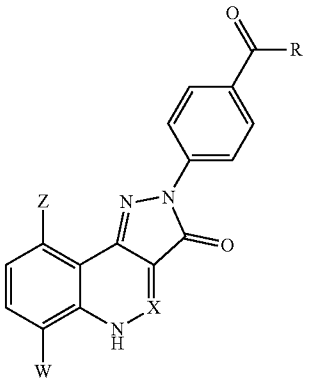

| Compound | W | Z | X | R |
|---|---|---|---|---|
| 1 | F | H | CH | OH |
| 2 | F | H | CH | $NHCH_2CH_2CH_2NMe_2$ |

-continued

| Compound | W | Z | X | R |
|---|---|---|---|---|
| 3 | H | H | N | 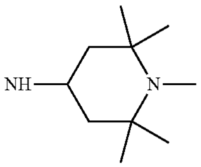 |
| 4 | F | H | N | 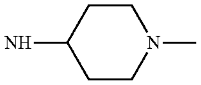 |
| 5 | F | H | N | 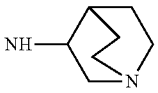 |
| 6 | F | F | N | 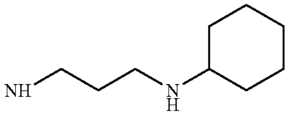 |

Other small molecule CTLA-4 antagonists include

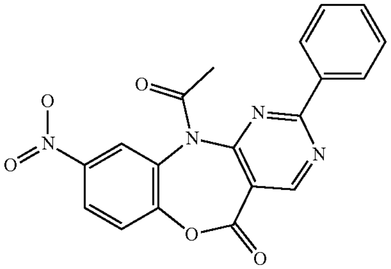

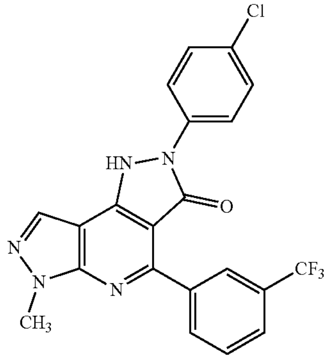

In one embodiment, the combination includes an immuno-DASH inhibitor, an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Other exemplary anti-CTLA-4 antibodies are disclosed, e.g., in U.S. Pat. No. 5,811,097.

In some embodiments of the methods described herein, the additional therapeutic agent is an antibody that modulates the immune response. In some embodiments, the additional therapeutic agent is an anti-PD-1 antibody, an anti-LAG-3 antibody, an anti-CTLA-4 antibody, an anti-TIM-3 antibody, or an anti-TIGIT antibody.

In some embodiments, the LAG3 antibody is IMP701, IMP731, BMS-986016, LAG525, and GSK2831781. In some embodiments, the LAG3 antagonist includes a soluble LAG3 receptor, for example, IMP321.

In some embodiments, an immune response stimulating agent is selected from the group consisting of: a CD28 agonist, a 4-1 BB agonist, an OX40 agonist, a CD27 agonist, a CD80 agonist, a CD86 agonist, a CD40 agonist, and a GITR agonist. In some embodiments, the OX40 agonist includes OX40 ligand, or an OX40-binding portion thereof. For example, the OX40 agonist may be MEDI6383. In some embodiments, the OX40 agonist is an antibody that specifically binds OX40. In some embodiments, the antibody that binds OX40 is MEDI6469, MED10562, or MOXR0916 (RG7888). In some embodiments, the OX40 agonist is a vector (e.g., an expression vector or virus, such as an adenovirus) capable of expressing OX40 ligand. In some embodiments the OX40-expressing vector is Delta-24-RG-DOX or DNX2401.

In some embodiments, the 4-11BB (CD137) agonist is a binding molecule, such as an anticalin. In some embodiments, the anticalin is PRS-343. In some embodiments, the 4-1 BB agonist is an antibody that specifically binds 4-1 BB. In some embodiments, antibody that binds 4-1 BB is PF-2566 (PF-05082566) or urelumab (BMS-663513).

In some embodiments, the CD27 agonist is an antibody that specifically binds CD27. In some embodiments, the antibody that binds CD27 is varlilumab (CDX-1127).

In some embodiments, the GITR agonist comprises GITR ligand or a GITR-binding portion thereof. In some embodiments, the GITR agonist is an antibody that specifically binds GITR. In some embodiments, the antibody that binds GITR is TRX518, MK-4166, or INBRX-110.

In certain embodiments, an anti-CD39 antibody is combined with STING agonist, preferably as part of a pharmaceutical composition. The cyclic-di-nucleotides (CDNs) cyclic-di-AMP (produced by *Listeria monocytogenes* and other bacteria) and its analogs cyclic-di-GMP and cyclic-GMP-AMP are recognized by the host cell as a pathogen associated molecular pattern (PAMP), which bind to the pathogen recognition receptor (PRR) known as Stimulator of INterferon Genes (STING). STING is an adaptor protein in the cytoplasm of host mammalian cells which activates the TANK binding kinase (TBK1)-IRF3 and the NF-κB signaling axis, resulting in the induction of IFN-γ and other gene products that strongly activate innate immunity. It is now recognized that STING is a component of the host cytosolic surveillance pathway (Vance et al., 2009), that senses infection with intracellular pathogens and in response induces the production of IFN-γ, leading to the development of an adaptive protective pathogen-specific immune response consisting of both antigen-specific CD4+ and CD8+ T cells as well as pathogen-specific antibodies. U.S. Pat. Nos. 7,709,458 and 7,592,326; PCT Publication Nos. WO2007/054279, WO2014/093936, WO2014/179335, WO2014/189805, WO2015/185565, WO2016/096174, WO2016/145102, WO2017/027645, WO2017/027646, and WO2017/075477; and Yan et al., Bioorg. Med. Chem Lett. 18:5631-4, 2008.

Exemplary Combinations

In a preferred embodiment, the invention is directed to the combination of an anti-CD39 antibody with an antitumor platinum coordination complex in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer, brain cancer and lymphoma. This chemotherapeutic group includes, but is not limited to cisplatin, oxaliplatin, carboplatin, triplatin tetranitrate (BBR3464), satraplatin, tetraplatin, ormiplatin, iproplatin, nedaplatin and lobaplatin. Particularly preferred is the combination of an anti-CD39 antibody with cisplatin, oxaliplatin, carboplatin, triplatin tetranitrate, satraplatin, tetraplatin, ormiplatin, iproplatin, nedaplatin and lobaplatin, and even more preferred is the combination with cisplatin and oxaliplatin in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer and brain cancer. In another preferred embodiment, the invention is directed to the combination of an anti-CD39 antibody with an antimetabolite in the treatment of cancer, and more particularly in the treatment of a cancer selected from lung cancer, sarcoma, malignant melanoma, bladder carcinoma, prostate cancer, pancreas carcinoma, gastric carcinoma, ovarian cancer, hepatoma, breast cancer, colorectal cancer, kidney cancer, esophageal cancer, brain cancer, anal cancer, leukaemia and lymphoma. This chemotherapeutic group includes, but is not limited to 5-fluorouracil, gemcitabine, cytarabine, capecitabine, decitabine, floxuridine, fludarabine, aminopterin, methotrexate, pemetrexed, raltitrexed, cladribine, clofarabine, mercaptopurine, pentostatin, and thioguanine. Particularly preferred is the combination of an anti-CD39 antibody with 5-fluorouracil, gemcitabine, cytarabine, capecitabine, decitabine, floxuridine, fludarabine, aminopterin, methotrexate, pemetrexed, raltitrexed, cladribine, clofarabine, mercaptopurine, pentostatin, and thioguanine, and even more preferred is the combination with 5-fluorouracil, gemcitabine, cytarabine and methotrexate in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer, brain cancer, leukemia and lymphoma.

In another preferred embodiment, the invention is directed to the combination of an anti-CD39 antibody with a mitotic inhibitor in the treatment of cancer, and more particularly in the treatment of a cancer selected from lung cancer, sarcoma, prostate cancer, gastric carcinoma, ovarian cancer, hepatoma, breast cancer, colorectal cancer, kidney cancer, brain cancer, leukemia, and lymphoma. This chemotherapeutic group includes, but is not limited to paclitaxel, docetaxel, vinblastine, vincristine, vindesine, and vinorelbine. Particularly preferred is the combination of an anti-CD39 antibody with paclitaxel, docetaxel, vinblastine, vincristine, vindesine, and vinorelbine, and even more preferred is the combination with paclitaxel, docetaxel, vincristine and vinorelbine in the treatment of cancer, and more particularly in the treatment of a cancer selected from lung cancer, sarcoma, prostate cancer, gastric carcinoma, ovarian cancer, hepatoma, breast cancer, colorectal cancer, kidney cancer and brain cancer.

In another preferred embodiment, the invention is directed to the combination of anti-CD39 antibody with an anticancer antibiotic in the treatment of cancer, and more particularly in the treatment of lung cancer, sarcoma, malignant melanoma, bladder carcinoma, prostate cancer, pancreas carcinoma, thyroid cancer, gastric carcinoma, ovarian cancer, hepatoma, breast cancer, colorectal cancer, kidney cancer, neuroblastoma, brain cancer, anal cancer, testicular cancer, leukemia, multiple myeloma and lymphoma. This chemotherapeutic group includes, but is not limited to daunorubicin, doxorubicin, epirubicin, idarubicin, mitoxantrone, pixantrone, valrubicin, mitomycin C, bleomycin, actinomycin A and mithramycin. Particularly preferred is the combination of an anti-CD39 antibody with daunorubicin, doxorubicin, epirubicin, idarubicin, mitoxantrone, pixantrone, valrubicin, mitomycin C, bleomycin, actinomycin D and mithramycin, and even more preferred is the combination with daunorubicin, doxorubicin, mitomycin C and actinomycin D in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, brain cancer, leukemia and lymphoma.

In another preferred embodiment, the invention is directed to the combination of anti-CD39 antibody with a topoisomerase I and/or II inhibitor in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, neuroblastoma, brain cancer, cervical cancer, testicular cancer, leukemia and lymphoma. This chemotherapeutic group includes, but is not limited to topotecan, SN-38, irinotecan, camptothecin, rubitecan, etoposide, amsacrine and teniposide. Particularly preferred is the combination of PM00104, or a pharmaceutically acceptable salt thereof, with topotecan, SN-38, irinotecan, camptothecin, rubitecan, etoposide, amsacrine and teniposide, and even more preferred is the combination with topotecan, irinotecan and etoposide in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, and brain cancer.

In another preferred embodiment, the invention is directed to the combination of an anti-CD39 antibody with a proteosome inhibitor in the treatment of cancer, and more particularly in the treatment of lung cancer, prostate cancer, pancreas carcinoma, gastric carcinoma, hepatoma, colorectal cancer, brain cancer, multiple myeloma and lymphoma. This chemotherapeutic group includes, but is not limited to bortezomib, disulfiram, epigallocatechin gallate, and salinosporamide A. Particularly preferred is the combination of an anti-CD39 antibody with bortezomib, disulfiram, epigallocatechin gallate, and salinosporamide A, and even more preferred is the combination with bortezomib in the treatment of cancer, and more particularly in the treatment of lung cancer, prostate cancer, pancreas carcinoma, gastric carcinoma, hepatoma, colorectal cancer and brain cancer.

In another preferred embodiment, the invention is directed to the combination of an anti-CD39 antibody with a histone deacetylase inhibitor in the treatment of cancer, and more particularly in the treatment of lung cancer, sarcoma, prostate cancer, pancreas carcinoma, gastric carcinoma, ovarian cancer, breast cancer, colorectal cancer, kidney cancer, brain cancer and lymphoma. This chemotherapeutic group includes, but is not limited to romidepsin, panobinostat, vorinostat, mocetinostat, belinostat, entinostat, resminostat, PCI-24781, AR-42, CUDC-101, and valproic acid. Particularly preferred is the combination of an anti-CD39 antibody with romidepsin, panobinostat, vorinostat, mocetinostat, belinostat, entinostat, resminostat, PCI-24781, AR-42, CUDC-101, and valproic acid, and even more preferred is the combination with vorinostat in the treatment of cancer, and more particularly in the treatment of lung cancer, sarcoma, prostate cancer, pancreas carcinoma, gastric carcinoma, ovarian cancer, breast cancer, colorectal cancer, kidney cancer and brain cancer.

In another preferred embodiment, the invention is directed to the combination of an anti-CD39 antibody with a nitrogen mustard alkylating agent in the treatment of cancer, and more particularly in the treatment of lung cancer, sarcoma, bladder carcinoma, gastric carcinoma, ovarian cancer, hepatoma, breast cancer, colorectal cancer, kidney cancer, leukemia, multiple myeloma and lymphoma. This chemotherapeutic group includes, but is not limited to melphalan, ifosfamide, chlorambucil, cyclophosphamide, mechlorethamine, uramustine, estramustine and bendamustine. Particularly preferred is the combination of an anti-CD39 antibody with melphalan, ifosfamide, chlorambucil, cyclophosphamide, mechlorethamine, uramustine, estramustine and bendamustine, and even more preferred is the combination with cyclophosphamide in the treatment of cancer, and more particularly in the treatment of lung cancer, sarcoma, gastric carcinoma, ovarian cancer, hepatoma, breast cancer, colorectal cancer and kidney cancer. In another preferred embodiment, the invention is directed to the combination of an anti-CD39 antibody with a nitrosourea alkylating agent in the treatment of cancer, and more particularly in the treatment of lung cancer, ovarian cancer, breast cancer, brain cancer, multiple myeloma and lymphoma. This chemotherapeutic group includes, but is not limited to lomustine, semustine, carmustine, fotemustine and streptozotocin. Particularly preferred is the combination of an anti-CD39 antibody with lomustine, semustine, carmustine, fotemustine and streptozotocin, and even more preferred is the combination with carmustine in the treatment of cancer, and more particularly in the treatment of lung cancer, ovarian cancer and breast cancer.

In another preferred embodiment, the invention is directed to the combination of an anti-CD39 antibody with a nonclassical alkylating agent in the treatment of cancer, and more particularly in the treatment of lung cancer, sarcoma, malignant melanoma, pancreas carcinoma, gastric carcinoma, ovarian cancer, breast cancer, colorectal cancer, kidney cancer, brain cancer, leukemia and lymphoma. This chemotherapeutic group includes, but is not limited to procarbazine, dacarbazine, temozolomide and altretamine. Particularly preferred is the combination of an anti-CD39 antibody with procarbazine, dacarbazine, temozolomide and altretamine, and even more preferred is the combination with dacarbazine and tezolomide in the treatment of lung cancer, sarcoma, malignant melanoma, gastric carcinoma, ovarian cancer, breast cancer, colorectal cancer, kidney cancer and brain cancer. In another preferred embodiment, the invention is directed to the combination of an anti-CD39 antibody with an estrogen antagonist in the treatment of cancer, and more particularly in the treatment of breast cancer. This chemotherapeutic group includes, but is not limited to toremifene, fulvestrant, tamoxifen and nafoxidine. Particularly preferred is the combination of an anti-CD39 antibody with toremifene, fulvestrant, tamoxifen and nafoxidine, and even more preferred is the combination with tamoxifen in the treatment of breast cancer.

In another preferred embodiment, the invention is directed to the combination of an anti-CD39 antibody with an androgen antagonist in the treatment of cancer, and more particularly in the treatment of prostate cancer. This chemotherapeutic group includes, but is not limited to bicalutamide, flutamide, MDV3100 and nilutamide. Particularly preferred is the combination of an anti-CD39 antibody with bicalutamide, flutamide, MDV3100 and nilutamide, and even more preferred is the combination with flutamide in the treatment of prostate cancer.

In another preferred embodiment, the invention is directed to the combination of an anti-CD39 antibody with a mTOR inhibitor in the treatment of cancer, and more particularly in the treatment of lung cancer, sarcoma, malignant melanoma, prostate cancer, pancreas carcinoma, gastric carcinoma, ovarian cancer, breast cancer, colorectal cancer, kidney cancer and brain cancer. This chemotherapeutic group includes, but is not limited to sirolimus, temsirolimus, everolimus, ridaforolimus, KU-0063794 and WYE-354. Particularly preferred is the combination of an anti-CD39 antibody with sirolimus, temsirolimus, everolimus, ridaforolimus, KU-0063794 and WYE-354, and even more preferred is the combination with temsirolimus in the treatment of lung cancer, sarcoma, malignant melanoma, prostate cancer, pancreas carcinoma, gastric carcinoma, ovarian cancer, breast cancer, colorectal cancer and brain cancer.

In another preferred embodiment, the invention is directed to the combination of an anti-CD39 antibody with a tyrosine kinase inhibitor in the treatment of cancer, and more particularly in the treatment of a cancer selected from lung cancer, sarcoma, prostate cancer, pancreas carcinoma, gastric carcinoma, ovarian cancer, hepatoma, breast cancer, colorectal cancer, kidney cancer and brain cancer. This chemotherapeutic group includes, but is not limited to erlotinib, sorafenib, axitinib, bosutinib, cediranib, crizotinib, dasatinib, gefitinib, imatinib, canertinib, lapatinib, lestaurtinib, neratinib, nilotinib, semaxanib, sunitinib, vatalanib and vandetanib. Particularly preferred is the combination of an anti-CD39 antibody with erlotinib, sorafenib, axitinib, bosutinib, cediranib, crizotinib, dasatinib, gefitinib, imatinib, canertinib, lapatinib, lestaurtinib, neratinib, nilotinib, semaxanib, sunitinib, vatalanib and vandetanib, and even more preferred is the combination with erlotinib in the treatment of cancer, and more particularly in the treatment of a cancer selected from lung cancer, sarcoma, prostate cancer, pancreas carcinoma, gastric carcinoma, ovarian cancer, hepatoma, breast cancer, colorectal cancer, kidney cancer and brain cancer.

Another aspect of the present invention relates to any one of the foregoing methods, further comprising administering to the patient a MAP kinase pathway inhibitor or a WNT pathway inhibitor.

In some embodiments, the MAP kinase pathway inhibitor is selected from the group consisting of a BRAF inhibitor, a MEK inhibitor, a PI3K inhibitor and a c-KIT inhibitor.

In some embodiments, the BRAF inhibitor is selected from the group consisting of GDC-0879, PLX-4720, sorafenib tosylate, dabrafenib and LGX818.

In some embodiments, the MEK inhibitor is selected from the group consisting of GSK1120212, selumetinib and MEK162.

In some embodiments, the WNT pathway inhibitor is a β-catenin inhibitor or a frizzled inhibitor.

In some embodiments, the β-catenin inhibitor is selected from the group consisting of niclosamide, XAV-939, FH 535 and ICG 001.

Another aspect of the present invention relates to any one of the foregoing methods, further comprising administering to the patient a cancer vaccine. In some embodiments, the cancer vaccine is a dendritic cell vaccine.

Another aspect of the present invention relates to any one of the foregoing methods, further comprising administering to the patient an adoptive cell transfer.

In some embodiments, the adoptive cell transfer is a CAR-T cell therapy.

Another aspect of the present invention relates to any one of the foregoing methods, further comprising administering to the patient an antibody therapy.

Another aspect of the present invention relates to any one of the foregoing methods, wherein administration of the anti-CD39 antibody enhances antibody-dependent cell-mediated cytotoxicity of the antibody therapy.

In some embodiment, the antibody therapy is selected from the group consisting of trastuzamab, cetuximab, bevacizumab, and rituximab.

Furthermore, treatment with anti-CD39 antibody can include combination treatment with other biologic molecules, such as one or more cytokines (e.g., lymphokines, interleukins, tumor necrosis factors, and/or growth factors) or can be accompanied by surgical removal of tumors, removal of cancer cells, or any other therapy deemed necessary by a treating physician. In some embodiments, the additional therapeutic agent is an immune response stimulating agent.

In some embodiments of the methods described herein, the anti-CD39 antibody can be combined with a growth factor selected from the group consisting of: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-α, TGF-β, TNF-α, VEGF, P1GF, IL-1, IL-2, IL-3, IL-4, IL-5, IL-6, IL-7, IL-12, IL-15, and IL-18.

In some embodiments of the methods described herein, the additional therapeutic agent is an immune response stimulating agent. In some embodiments, the immune response stimulating agent is selected from the group consisting of granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1) or interleukin 2 (IL-2).

Administration Scheduling

In certain embodiments of the methods described herein, the treatment involves the administration of an anti-CD39 antibody in combination with radiation therapy. Treatment with an anti-CD39 antibody can occur prior to, concurrently with, or subsequent to administration of radiation therapy. Dosing schedules for such radiation therapy can be determined by the skilled medical practitioner.

In certain embodiments of the methods described herein, the treatment involves the administration of an anti-CD39 antibody in combination with anti-viral therapy. Treatment with an anti-CD39 antibody can occur prior to, concurrently with, or subsequent to administration of antiviral therapy. The anti-viral drug used in combination therapy will depend upon the virus the subject is infected with.

Combined administration can include co-administration, either in a single pharmaceutical formulation or using separate formulations, or consecutive administration in either order but generally within a time period such that all active agents can exert their biological activities simultaneously.

It will be appreciated that the combination of an anti-CD39 antibody and at least one additional therapeutic agent may be administered in any order or concurrently. In some embodiments, the anti-CD39 antibody will be administered to patients that have previously undergone treatment with a second therapeutic agent. In certain other embodiments, the anti-CD39 antibody and a second therapeutic agent will be administered substantially simultaneously or concurrently. For example, a subject may be given an anti-CD39 antibody while undergoing a course of treatment with a second therapeutic agent (e.g., chemotherapy). In certain embodiments, an anti-CD39 antibody will be administered within 1 year of the treatment with a second therapeutic agent. In certain alternative embodiments, an anti-CD39 antibody will be administered within 10, 8, 6, 4, or 2 months of any treatment with a second therapeutic agent. In certain other embodiments, an anti-CD39 antibody will be administered within 4, 3, 2, or 1 weeks of any treatment with a second therapeutic agent. In some embodiments, an anti-CD39 antibody will be administered within 5, 4, 3, 2, or 1 days of any treatment with a second therapeutic agent. It will further be appreciated that the two (or more) agents or treatments may be administered to the subject within a matter of hours or minutes (e.g., substantially simultaneously).

For the treatment of a disease, the appropriate dosage of an anti-CD39 antibody depends on the type of disease to be treated, the severity and course of the disease, the responsiveness of the disease, whether the anti-CD39 antibody is administered for therapeutic or preventative purposes, previous therapy, the patient's clinical history, and so on, all at the discretion of the treating physician. The anti-CD39 antibody can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual agent. The administering physician can determine optimum dosages, dosing methodologies, and repetition rates. In certain embodiments, dosage is from 0.01 μg to 100 mg/kg of body weight, from 0.1 μg to 100 mg/kg of body weight, from 1 μg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, the dosage of the anti-CD39 antibody is from about 0.1 mg to about 20 mg/kg of body weight. In some embodiments, the dosage of the anti-CD39 antibody is about 0.1 mg/kg of body weight. In some embodiments, the dosage of the anti-CD39 antibody is about 0.25 mg/kg of body weight. In some embodiments, the dosage of the anti-CD39 antibody is about 0.5 mg/kg of body weight. In some embodiments, the dosage of the anti-CD39 antibody is about 1 mg/kg of body weight. In some embodiments, the dosage of the anti-CD39 antibody is about 1.5 mg/kg of body weight. In some embodiments, the dosage of the anti-CD39 antibody is about 2 mg/kg of body weight. In some embodiments, the dosage of the anti-CD39 antibody is about 2.5 mg/kg of body weight. In some embodiments, the dosage of the anti-CD39 antibody is about 5 mg/kg of body weight. In some embodiments, the dosage of the anti-CD39 antibody is about 7.5 mg/kg of body weight. In some embodiments, the dosage of the anti-CD39 antibody is about 10 mg/kg of body weight. In some embodiments, the dosage of the anti-CD39 antibody is about 12.5 mg/kg of body weight. In some embodiments, the dosage of the anti-CD39 antibody is about 15 mg/kg of body weight. In certain embodiments, the dosage can be given once or more daily, weekly, monthly, or yearly. In certain embodiments, the anti-CD39 antibody is given once every week, once every two weeks, once every three weeks, or once every four weeks.

In some embodiments, an anti-CD39 antibody may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

In some embodiments, the dosing schedule may be limited to a specific number of 35 administrations or "cycles". In some embodiments, the anti-CD39 antibody is administered for 3, 4, 5, 6, 7, 8, or more cycles. For example, the anti-CD39 antibody is administered every 2 weeks for 6 cycles, the anti-CD39 antibody is administered every 3 weeks for 6 cycles, the anti-CD39 antibody is administered every 2 weeks for 4 cycles, the anti-CD39 antibody is administered every 3 weeks for 4 cycles, etc. Dosing schedules can be decided upon and subsequently modified by those skilled in the art.

Thus, the present invention provides methods of administering to a subject the anti-CD39 antibody described herein comprising using an intermittent dosing strategy for administering one or more agents, which may reduce side effects and/or toxicities associated with administration of an anti-CD39 antibody, chemotherapeutic agent, etc. In some embodiments, a method for treating cancer in a human subject comprises administering to the subject a therapeutically effective dose of an anti-CD39 antibody in combination with a therapeutically effective dose of a chemotherapeutic agent, wherein one or both of the agents are administered according to an intermittent dosing strategy. In some embodiments, the intermittent dosing strategy comprises administering an initial dose of an anti-CD39 antibody to the subject, and administering subsequent doses of the anti-CD39 antibody about once every 2 weeks. In some embodiments, the intermittent dosing strategy comprises administering an initial dose of an anti-CD39 antibody to the subject, and administering subsequent doses of the anti-CD39 antibody about once every 3 weeks. In some embodiments, the intermittent dosing strategy comprises administering an initial dose of an anti-CD39 antibody to the subject, and administering subsequent doses of the anti-CD39 antibody about once every 4 weeks. In some embodiments, the anti-CD39 antibody is administered using an intermittent dosing strategy and the chemotherapeutic agent is administered weekly.

Anti-Infective Therapeutic Combinations

In an embodiment, the invention provides methods for treating subjects using an an anti-CD39 antibody, wherein the subject suffers from a viral infection. In one embodiment, the viral infection is infection with a virus selected from the group consisting of human immunodeficiency virus (HIV), hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment, the invention provides methods for treating subjects using an an anti-CD39 antibody, wherein the subject suffers from a bacterial infection. In one embodiment, the bacterial infection is infection with a bacterium selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium diphtheriae, Salmonella*, bacilli, *Vibrio cholerae, Clostridium tetan, Clostridium botulinum, Bacillus anthricis, Yersinia pestis, Mycobacterium leprae, Mycobacterium* lepromatosis, and Borriella.

In an embodiment, the invention provides methods for treating subjects using an an anti-CD39 antibody, wherein the subject suffers from a fungal infection. In one embodiment, the fungal infection is infection with a fungus selected from the group consisting of *Candida* (*albicans, krusei, glabrata, tropicalis*, etc.), *Cryptococcus neoformans, Aspergillus* (*fumigatus, niger*, etc.), Genus Mucorales (*mucor, absidia, rhizopus*), *Sporothrix schenkii, Blastomyces dermatitidis, Paracoccidioides brasiliensis, Coccidioides immitis* and *Histoplasma capsulatum.*

In an embodiment, the invention provides methods for treating subjects using an an anti-CD39 antibody, wherein the subject suffers from a parasitic infection. In one embodiment, the parasitic infection is infection with a parasite selected from the group consisting of *Entamoeba histolytica, Balantidium coli, Naegleria fowleri, Acanthamoeba, Giardia lambia, Cryptosporidium, Pneumocystis carinii, Plasmodium vivax, Babesia microti, Trypanosoma brucei, Trypanosoma cruzi, Leishmania donovani, Toxoplasma gondii* and Nippostrongylus *brasiliensis.*

VII. Anti-CD39 Antibody Conjugates

The anti-CD39 antibodies disclosed herein may also be conjugated to a chemical moiety. The chemical moiety may be, inter alia, a polymer, a radionuclide or a cytotoxic factor.

For instance, featured is an anti-CD39 antibody conjugated to a therapeutic moiety, e.g., a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs". Accordingly, in one aspect, the anti-CD39 antibody according to any above-described aspect or embodiment is conjugated to a therapeutic moiety. Exemplary therapeutic moieties include a cytotoxic moiety, a radioisotope, a cytokine, and a lytic peptide.

In certain embodiments, the anti-CD39 antibody is capable of inducing cytotoxicity in a CD39-expressing cells by internalization of the antibody conjugated to or associated with a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine;

colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin.

In one embodiment, the anti-CD39 antibody is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and anti-fungal activity (Pettit et al., (1998) Antimicrob. Agents and Chemother. 42:2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In another embodiment, the anti-CD39 antibody is conjugated to pyrrolo[2,1-c][1,4]-benzodiazepine (PDB) or an analog, derivative or prodrug thereof. Suitable PDBs and PDB derivatives, and related technologies are described in, e.g., Hartley J. A. et al., Cancer Res 2010; 70(17): 6849-6858; Antonow D. et al., Cancer J 2008; 14(3):154-169; Howard P. W. et al., Bioorg Med Chem Lett 2009; 19: 6463-6466 and Sagnou et al., Bioorg Med Chem Lett 2000; 10(18): 2083-2086.

In another embodiment, the anti-CD39 antibody is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof.

In a particular embodiment, the anti-CD39 antibody is conjugated to an anthracycline or an analog, derivative or prodrug thereof. In another particular embodiment, the antibody is conjugated to maytansine or an analog, derivative or prodrug thereof. In another particular embodiment, the antibody is conjugated to calicheamicin or an analog, derivative or prodrug thereof. In another particular embodiment, the antibody is conjugated to duocarmycin or an analog, derivative or prodrug thereof. In another particular embodiment, the antibody is conjugated to rachelmycin (CC-1065) or an analog, derivative or prodrug thereof. In another particular embodiment, the antibody is conjugated to dolastatin 10 or an analog, derivative or prodrug thereof. In another particular embodiment, the antibody is conjugated to dolastatin 15 or an analog, derivative or prodrug thereof. In another particular embodiment, the antibody is conjugated to monomethyl auristatin E or an analog, derivative or prodrug thereof. In another particular embodiment, the antibody is conjugated to monomethyl auristatin F or an analog, derivative or prodrug thereof. In another particular embodiment, the antibody is conjugated to pyrrolo[2,1-c][1,4]-benzodiazepine or an analog, derivative or prodrug thereof. In another particular embodiment, the antibody is conjugated to irinotecan or an analog, derivative or prodrug thereof.

In one embodiment, an anti-CD39 antibody of the invention is conjugated to a nucleic acid or nucleic acid-associated molecule. In one such embodiment, the conjugated nucleic acid is a cytotoxic ribonuclease (RNase) or deoxyribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In another embodiment, a CD39-specific antibody of the invention is conjugated to an aptamer or a ribozyme.

In one embodiment, an anti-CD39 antibody of the invention is conjugated, e.g., as a fusion protein, to a lytic peptide such as CLIP, Magainin 2, mellitin, Cecropin and P18.

In one embodiment, the anti-CD39 antibody is conjugated to a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFNα, IFNβ, IFNγ, GM-CSF, CD40L, Flt3 ligand, stem cell factor, ancestim, and TNFα.

In certain embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)).

The anti-CD39 antibodies may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th $^{40}$K, $^{157}$Gd, $^{55}$Mn, $^{52}$Tr, and $^{56}$Fe.

The anti-CD39 antibodies may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibodies and antigen-binding fragments thereof of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies and fragments are conventional and very well known in the art.

VIII. Pharmaceutical Compositions

Anti-CD39 antibodies, antigen-binding fragments, nucleic acids, or vectors of the invention can be formulated in compositions, especially pharmaceutical compositions. Such compositions comprise a therapeutically or prophylactically effective amount of an anti-CD39 antibody, antigen-binding fragment, nucleic acid, or vector of the invention in admixture with a suitable carrier, e.g., a pharmaceutically acceptable agent. Typically, anti-CD39 antibodies, antigen-binding fragments, nucleic acids, or vectors of the invention are sufficiently purified for administration to an animal before formulation in a pharmaceutical composition.

Pharmaceutically acceptable agents for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions can include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also can be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition can be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly (ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, Hnoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, NJ.), polyethyl glycol, polypropyl glycol, and copolymers of ethylene and propylene glycol (e.g., Pluronics, PF68 etc.). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replem'shers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) and/or increased stability or half-life in a particular local environment. The compositions can include the formulation of anti-CD39 antibodies, antigen-binding fragments, nucleic acids, or vectors of the invention with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies). See, for example, the description of controlled release porous polymeric microparticles for the delivery of pharmaceutical compositions in PCT Application Publication WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly (2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(~)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al, Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals. Microencapsulation of recombinant proteins for sustained release has been performed successfully with human growth hormone (rhGH), interferon- (rhIFNγ), interleukin-2, and MNrgpl20. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,48 IA, U.S. Pat. No. 3,887,699, EP 158,277A, Canadian Patent No. 1176565, U. Sidman et al., Biopolymers 22, 547 (1983), R. Langer et al., Chem. Tech. 12, 98 (1982), Sinha et al., J. Control. Release 90, 261 (2003), Zhu et al., Nat. Biotechnol. 18, 24 (2000), and Dai et al., Colloids Surf B Biointerfaces 41, 117 (2005).

Bioadhesive polymers are also contemplated for use in or with compositions of the present invention. Bioadhesives are synthetic and naturally occurring materials able to adhere to biological substrates for extended time periods. For example, Carbopol and polycarbophil are both synthetic cross-linked derivatives of poly (acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humour of the eye. Esterified derivatives of hyaluronic acid have been used to produce microspheres for use in delivery that are biocompatible and biodegradable (see for example, Cortivo et al., Biomaterials (1991) 12:727-730; European Publication No. 517,565; International Publication No. WO 96/29998; Ilium et al., J. Controlled Rel. (1994) 29:133-141). Exemplary hyaluronic acid containing compositions of the present invention comprise a hyaluronic acid ester polymer in an amount of approximately 0.1% to about 40% (w/w) of an IL-1/3 binding antibody or fragment to hyaluronic acid polymer. Both biodegradable and non-biodegradable polymeric matrices can be used to deliver compositions of the present invention, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which can be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), polyethylene oxide), polyethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see for example International Publication Nos. WO 04/009664, WO 05/087201, and Sawhney, et al., Macromolecules, 1993, 26, 581-587,) that can absorb up to about 90% of its weight in water and further, optionally is cross-linked with multivalent ions or other polymers.

Delivery systems also include non-polymer systems that are lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324).

Alternatively or additionally, the compositions can be administered locally via implantation into the affected area of a membrane, sponge, or other appropriate material on to which an anti-CD39 antibody, antigen-binding fragment, nucleic acid, or vector of the invention has been absorbed or encapsulated. Where an implantation device is used, the device can be implanted into any suitable tissue or organ, and delivery of an anti-CD39 antibody, antigen-binding fragment, nucleic acid, or vector of the invention can be directly through the device via bolus, or via continuous administration, or via catheter using continuous infusion.

A pharmaceutical composition comprising an anti-CD39 antibody, antigen-binding fragment, nucleic acid, or vector of the invention can be formulated for inhalation, such as for example, as a dry powder. Inhalation solutions also can be formulated in a liquefied propellant for aerosol delivery. In yet another formulation, solutions may be nebulized. Additional pharmaceutical composition for pulmonary administration include, those described, for example, in PCT Application Publication WO 94/20069, which discloses pulmonary delivery of chemically modified proteins. For pulmonary delivery, the particle size should be suitable for delivery to the distal lung. For example, the particle size can be from 1 μm to 5 μm; however, larger particles may be used, for example, if each particle is fairly porous.

Certain formulations containing anti-CD39 antibody, antigen-binding fragments, nucleic acids, or vectors of the invention can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

Another preparation can involve an effective quantity of an anti-CD39 antibody, antigen-binding fragment, nucleic acid, or vector of the invention in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

IX. Exemplary Methods

Figure 1B:
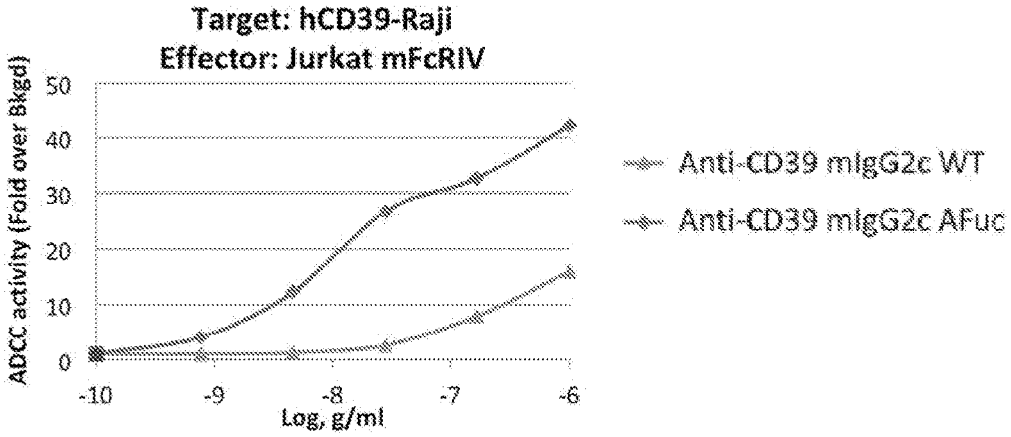
Figure 2A:
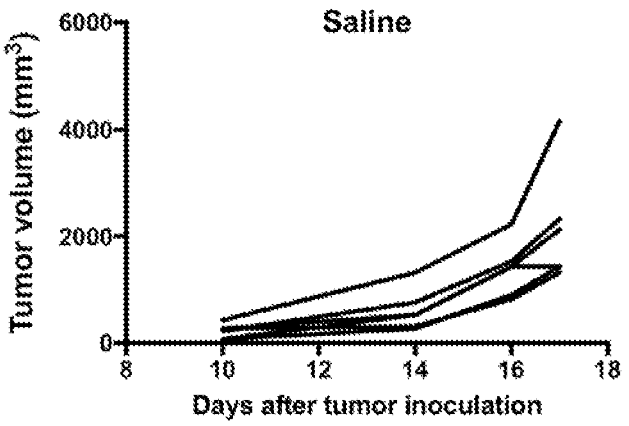
FIGS. 2A-2C are a set of graphs showing kinetics of B16/F10 tumor growth in each individual mouse post 5F2-mIgG2c mAb treatment.
Figure 2B:
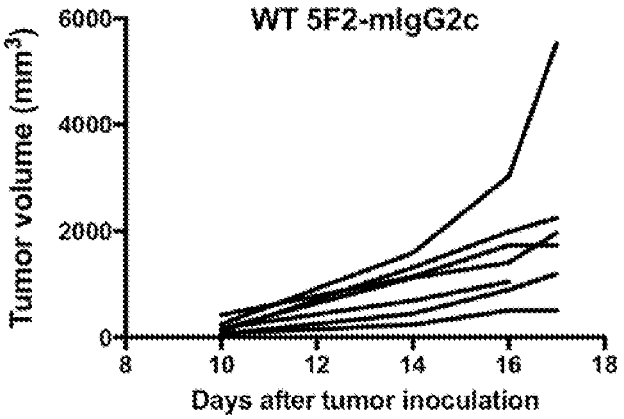
Figure 2C:
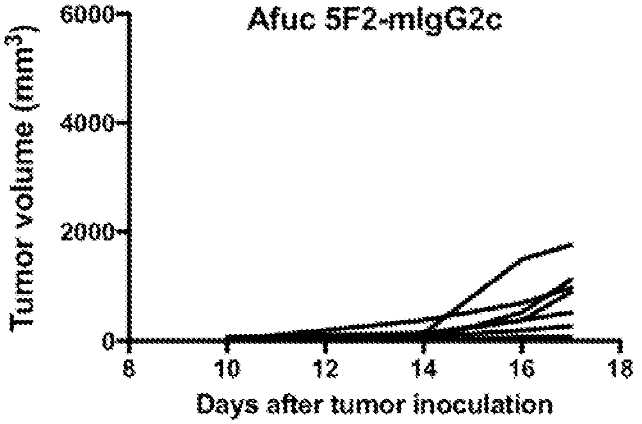
Figure 3A:
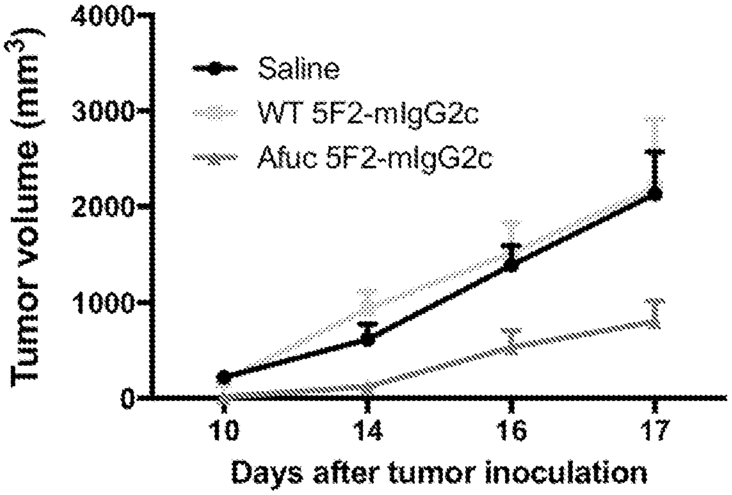
FIGS. 3A-3B are a set of graphs showing average tumor volume (FIG. 3A) and tumor weight (FIG. 3B) of B16/F10-bearing mice post 5F2-mIgG2c mAb treatment.
Figure 3B:
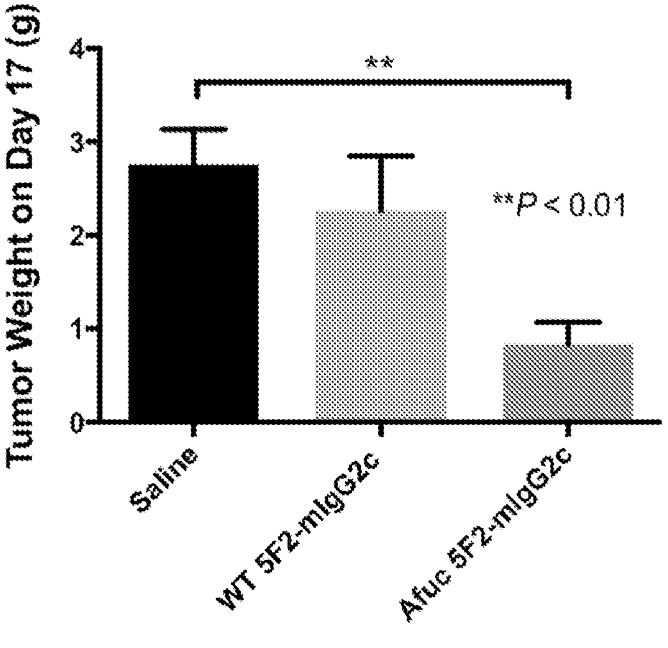
Figure 4A:
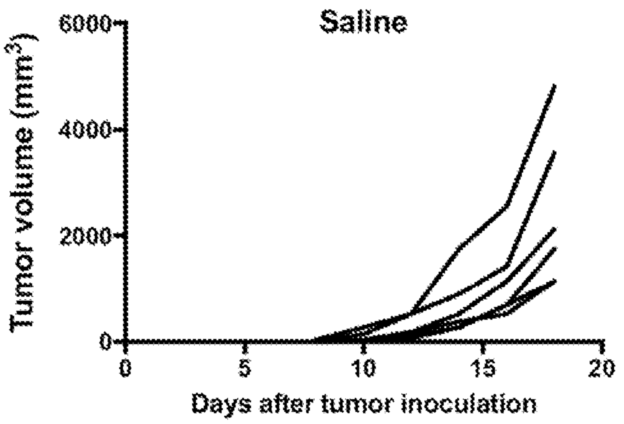
FIGS. 4A and 4B are a set of graphs showing kinetics of B16/F10 tumor growth in each individual mouse post WT 5F2-mIgG1 mAb treatment.
Figure 4B:
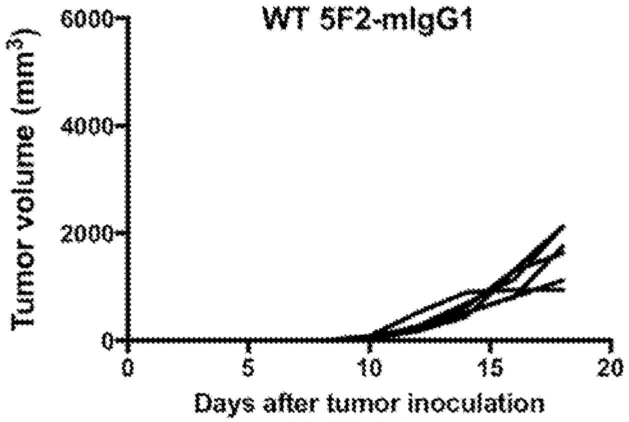
Figure 5A:
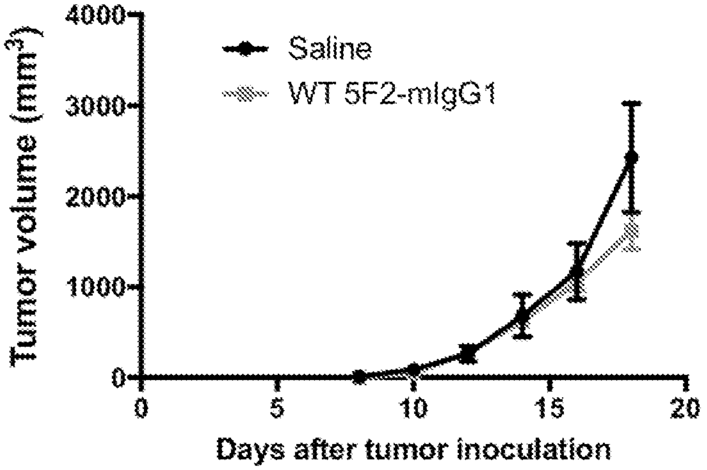
FIGS. 5A-5B are a set of graphs showing average tumor volume (FIG. 5A) and tumor weight (FIG. 5B) of B16/F10-bearing mice post WT 5F2-mIgG1 mAb treatment.
Figure 5B:
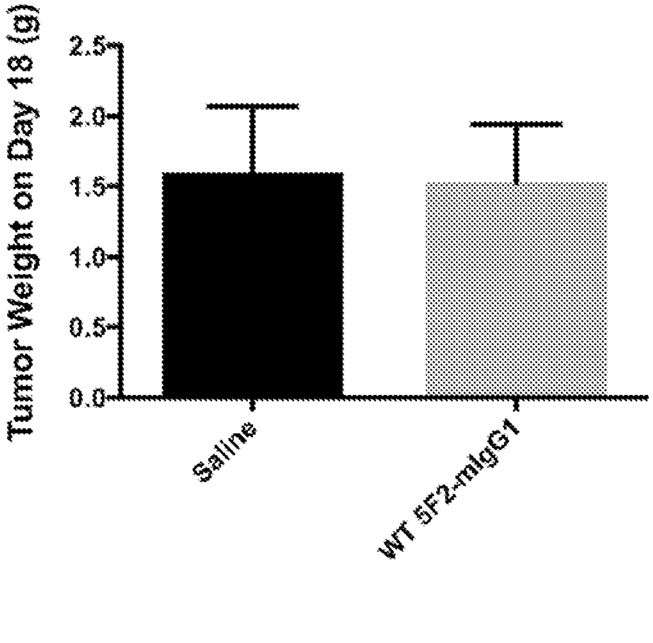
Figure 6A:
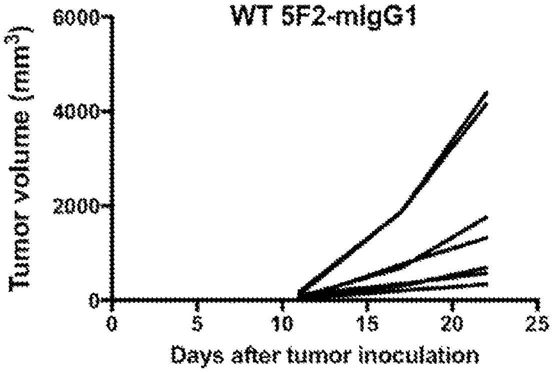
FIGS. 6A-6D are a set of graphs showing kinetics of B16/F10 tumor growth in each individual mouse post various types of 5F2 mAb treatment.
Figure 6B:
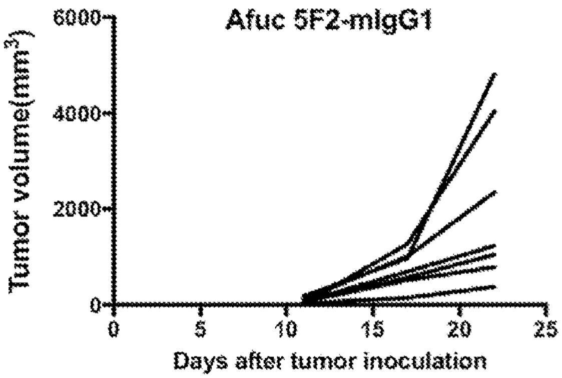
Figure 6C:
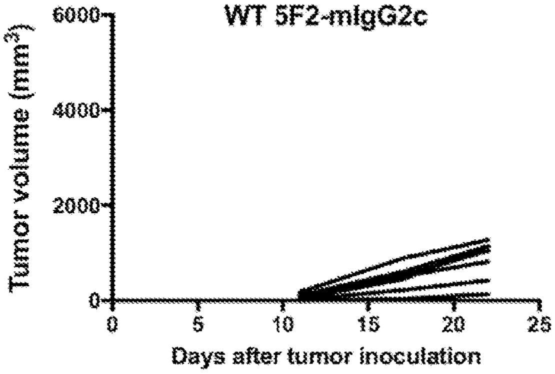
Figure 6D:
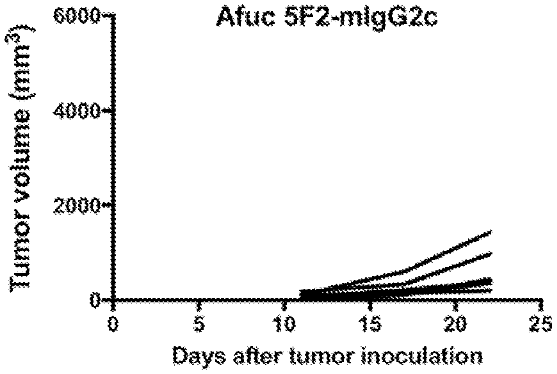
Figure 7:
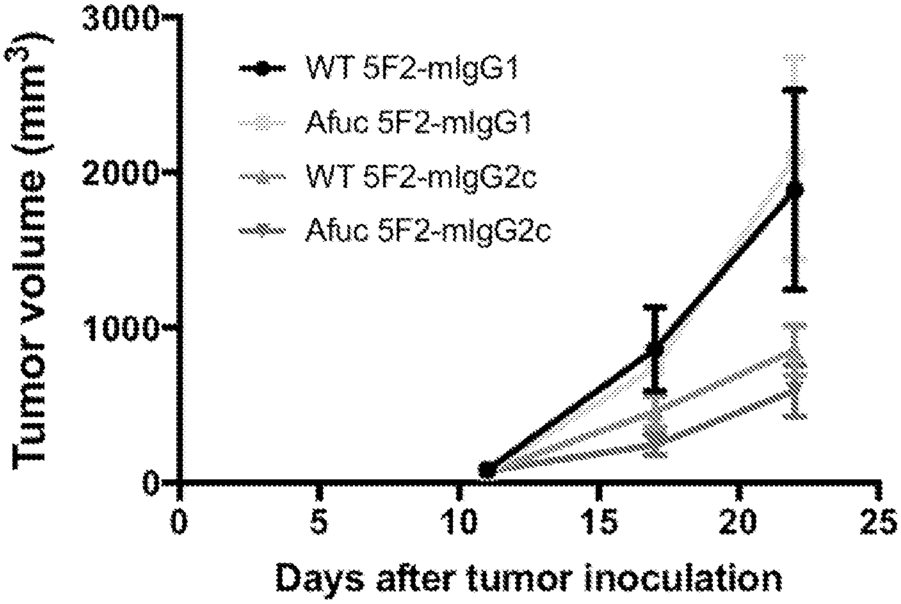
FIG. 7 is a a graph showing average tumor volume of B16/F10-bearing mice post 5F2 mAb treatment.
Figure 8:
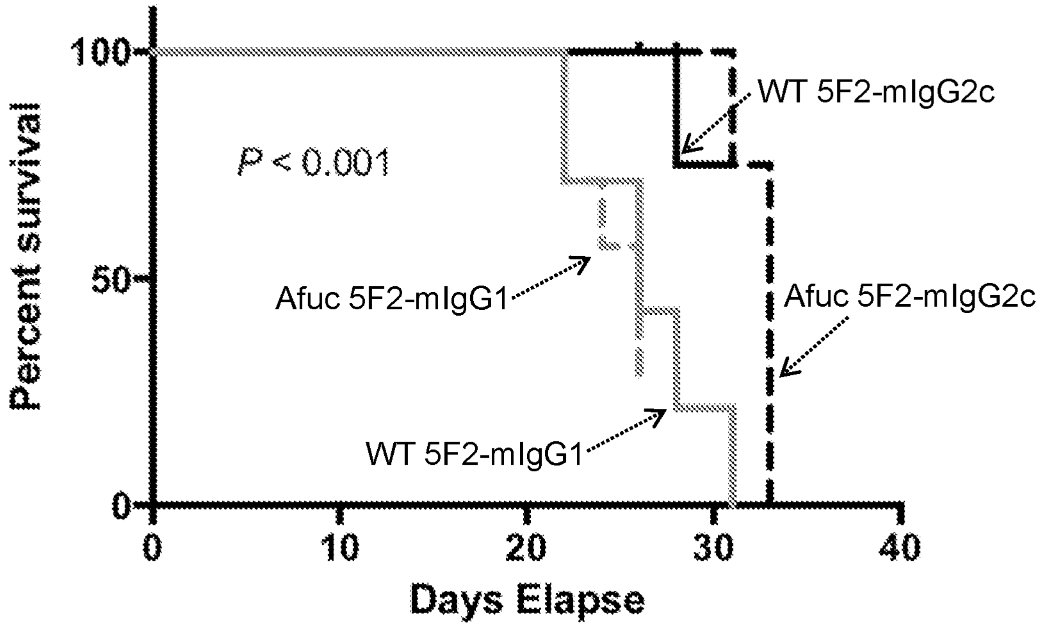
FIG. 8 is a graph showing percentage of survival (time-to-euthanasia) of B16/F10-bearing mice post 5F2 mAb treatment.
Figure 9A:
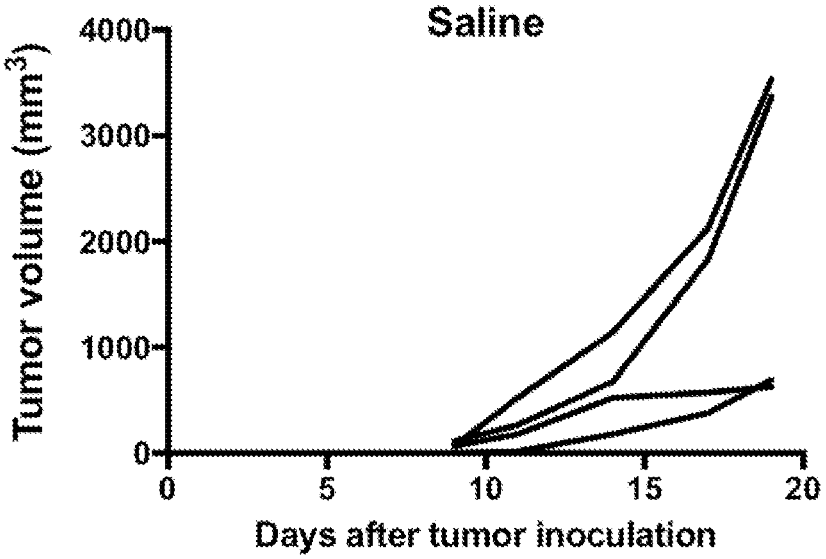
FIGS. 9A and 9B are a set of graphs showing kinetics of B16/F10 tumor growth in each individual mouse post Afuc 5F2-mIgG2c mAb treatment (FIG. 9B) or treated with saline (FIG. 9A).
Figure 9B:
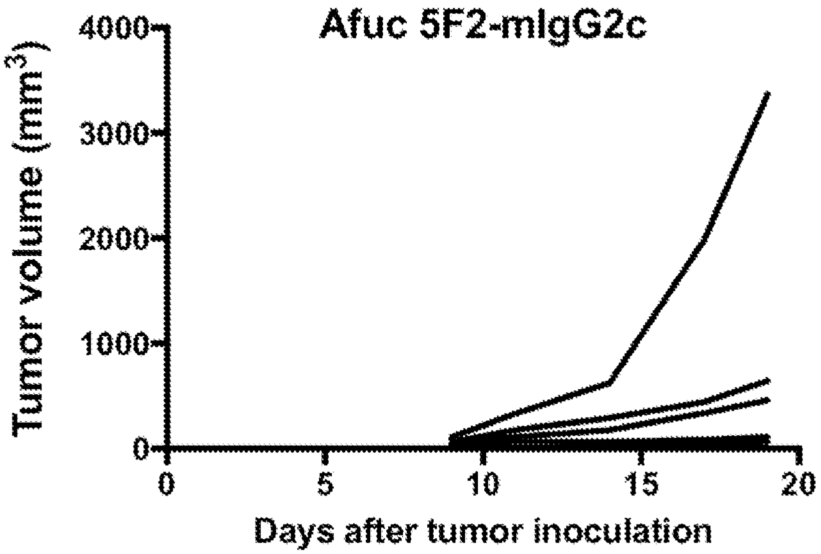
Figure 10:
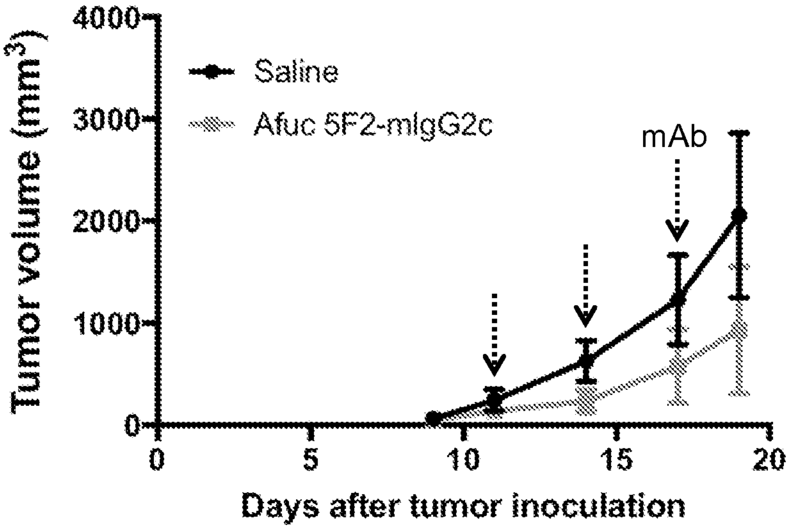
FIG. 10 is a graph showing average tumor volume of B16/F10-bearing mice post Afuc 5F2-mIgG2c mAb treatment.
Figure 11:
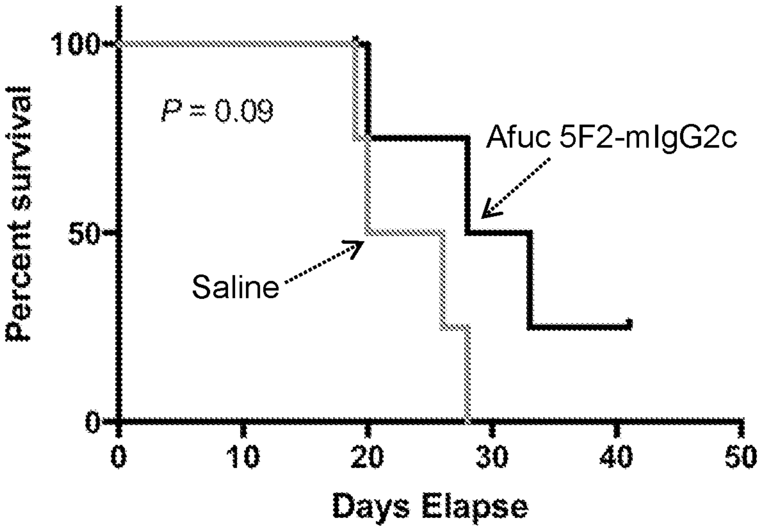
FIG. 11 is a graph showing percentage of survival (time-to-euthanasia) of B16/F10-bearing mice post Afuc 5F2-mIgG2c mAb treatment.

FIGS. 1A and 1B

Anti-CD39 5F2 antibody demonstrates ADCC activities against mouse and human CD39 positive cells. CHO cells expressing mCD39 (FIG. 1A) or Raji cells expressing hCD39 (FIG. 1B) were used as target cells, respectively. Jurkat cells transfected with a plasmid encoding luciferase were purchased from Promega, and further infected with pLentiTdT-mFcγRIV. TdTomato positive Jurkat cells were FACS-sorted and used as effector cells. Wildtype (WT) or afucosylated (Afuc) 5F2-mIgG2c was added at serially diluted concentrations. ADCC in fold increase of luciferase activity over background was measured after 6 hours of incubation of antibodies with target and effector cells.

FIGS. 2A-12B are B16/F10 data.

Afucosylated anti-CD39 monoclonal antibody (mAb) 5F2-mIgG2c demonstrates anti-tumor activity toward B16/F10 melanoma in vivo. $1.6\times10^5$ luc-B16/F10 cells (B16/F10 endogenously overexpressing luciferase) were injected subcutaneously (s.c.) into the right lower flank of C57BL/6 mice (males at ages of 8 weeks; obtained from Taconic) on day 0, followed by treatment with 200 μg of Wildtype (WT) or afucosylated (Afuc) 5F2-mIgG2c in 200 μl of saline via i.p. on days 1, 4 and 7. Mice received 200 μl of saline served as controls. Perpendicular tumor diameters were directly measured when tumor became palpable and 2-3 times per week thereafter using a digital caliper. Tumor volume was determined by integration: $\Sigma t_1+t_2+\ldots t_n$ ($t=t=a^2\times b\times0.52$; a=the smaller tumor diameter, b=the larger tumor diameter). Studies were terminated when any tumor volume reaches around 4000 $mm^3$. n=5-7 per group.

Wildtype (WT) 5F2-mIgG1 fails to block B16/F10 tumor growth in vivo. $1.8\times10^5$ luc-B16/F10 cells were s.c. implanted into the right lower flank of C57BL/6 mice (males at ages of 8 weeks; obtained from Taconic) on day 0, followed by treatment with Wildtype (WT) 5F2-mIgG1 (200 μg in 200 μl of saline via i.p.) on days 1, 4 and 7. Saline treated mice were considered as the control group. Tumor volume was determined as above. Studies were terminated on day 18. n=6 per group.

Afucosylated 5F2-mIgG2c shows superior in-vivo tumor-inhibitory activity against established B16/F10 melanoma to any other types of 5F2 mAbs. $1.0\times10^5$ luc-B16/F10 cells were injected (s.c.) into the right lower flank of C57BL/6 mice (males at ages of 10 weeks; obtained from The Jackson Laboratory) on day 0. Antibody treatment (200 μg of each mAb in 200 μl of saline via i.p.) started when the tumors have reached an average volume of 50-100 $mm^3$. Mice were randomized to four groups based on tumor volume. Specifically, three doses were given on days 11, 14 and 17. Tumor volume was measured as described above. Animals were euthanized when the tumor volume reaches around 3500-4000 $mm^3$. Earlier euthanasia was performed when tumor ulceration occurred. n=7 per group.

Treatment with afucosylated 5F2-mIgG2c leads to tumor regression and prolonged survival in B16/F10-bearing wild-type FoxP3-GFP knock-in mice. $1.0\times10^5$ luc-B16/F10 cells were injected (s.c.) into the right lower flank of wildtype FoxP3-GFP knock-in mice of the C57BL/6 strain (a reporter mouse strain expresses Green Fluorescent Protein (GFP) in $FoxP3^+$ Treg cells); males at ages of 12-16 weeks; in house) on day 0. Afuc 5F2-mIgG2c mAb (200 μg in 200 μl of saline via i.p.) were given to tumor-bearing mice on days 11, 14 and 17 (mice were randomized to two groups based on tumor volume). Mice received 200 μl of saline were used as controls. Tumor volume was measured as described above. Animals were euthanized when the tumor volume reaches around 3500-4000 $mm^3$. n=4-5 per group.

Optimization of Afucosylated 5F2-mIgG2c mAb Treatment Strategy. Two Doses of Afuc 5F2-mIgG2c is Able to Induce B16/F10 Tumor Regression in Wildtype FoxP3-GFP Knock-In Mice.

Figure 12A:
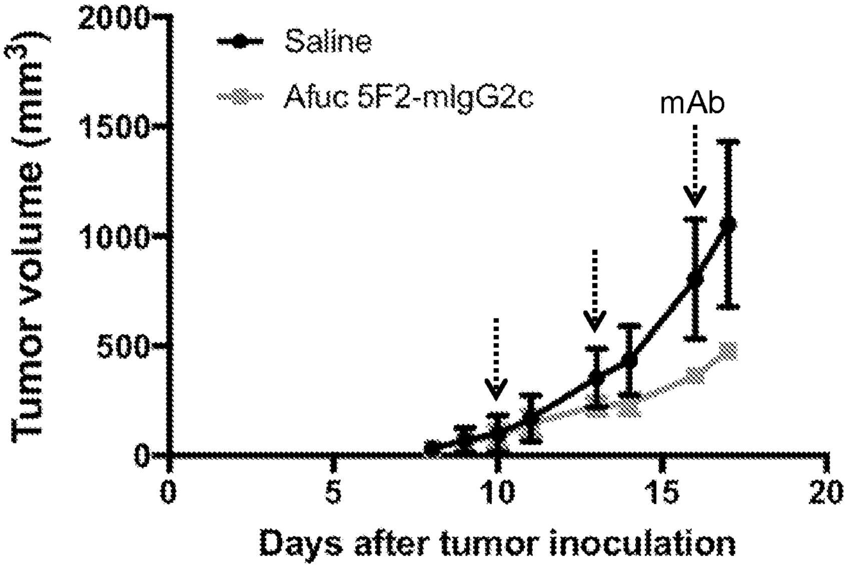
FIG. 12A is a graph showing average tumor volume of B16/F10-bearing mice received three Afuc 5F2-mIgG2c mAb treatments. $1.6\times10^5$ luc-B16/F10 cells were injected (s.c.) into the right lower flank of wildtype FoxP3-GFP knock-in reporter mice (females at ages of 16-18 weeks; in house) on day 0. Afuc 5F2-mIgG2c mAb (200 μg in 200 μl of saline via i.p.) were given to tumor-bearing mice on days 9, 13 and 16 (mice were randomized to two groups based on tumor volume). Mice received 200 μl of saline served as controls. Tumor volume was measured as described above and studies were terminated on day 17. n=3 per group.

FIG. 12A. Average tumor volume of B16/F10-bearing mice received three Afuc 5F2-mIgG2c mAb treatments. $1.6\times10^5$ luc-B16/F10 cells were injected (s.c.) into the right lower flank of wildtype FoxP3-GFP knock-in reporter mice (females at ages of 16-18 weeks; in house) on day 0. Afuc 5F2-mIgG2c mAb (200 μg in 200 μl of saline via i.p.) were given to tumor-bearing mice on days 9, 13 and 16 (mice were randomized to two groups based on tumor volume). Mice received 200 μl of saline served as controls. Tumor volume was measured as described above and studies were terminated on day 17. n=3 per group.

Figure 12B:
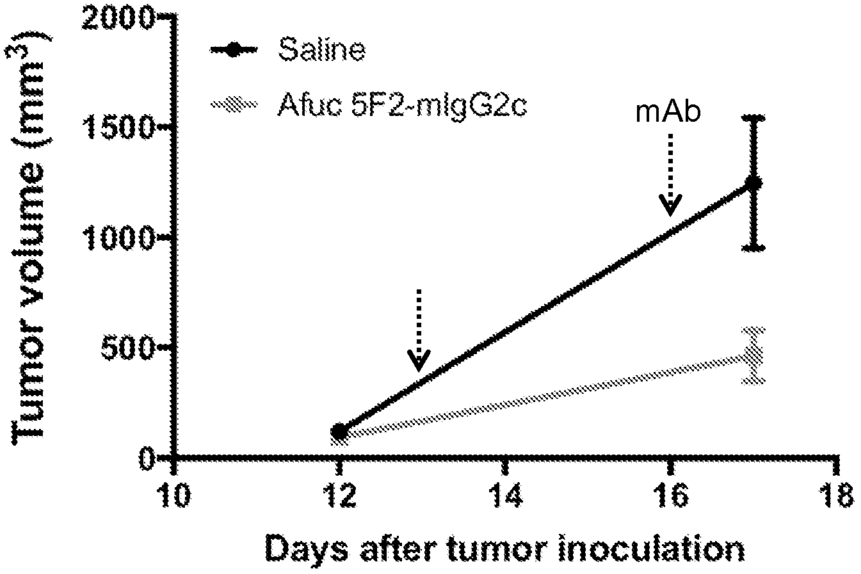
FIG. 12B is a graph showing average tumor volume of B16/F10-bearing mice received two Afuc 5F2-mIgG2c mAb treatments. $1.0\times10^5$ luc-B16/F10 cells were injected (s.c.) into the right lower flank of wildtype FoxP3-GFP knock-in reporter mice (females at ages of 8 weeks; in house) on day 0. Afuc 5F2-mIgG2c mAb (200 μg in 200 μl of saline via i.p.) were given to tumor-bearing mice on days 13 and 16 (mice were randomized to two groups based on tumor volume). Mice received 200 μl of saline were used as controls. Tumor volume was measured as described above and studies were terminated on day 17. n=4-5 per group.
Figure 13A:
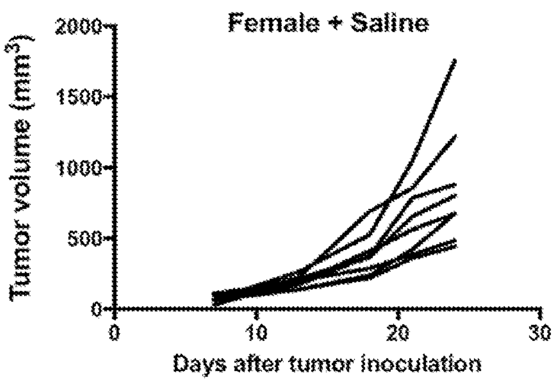
FIGS. 13A-13D are a set of graphs showing kinetics of MC38 tumor growth in each individual mouse post Afuc 5F2-mIgG2c mAb treatment. Mice were either male or female (FIGS. 13B and 13D). Controls were treated with saline (FIGS. 13A and 13C).
Figure 13B:
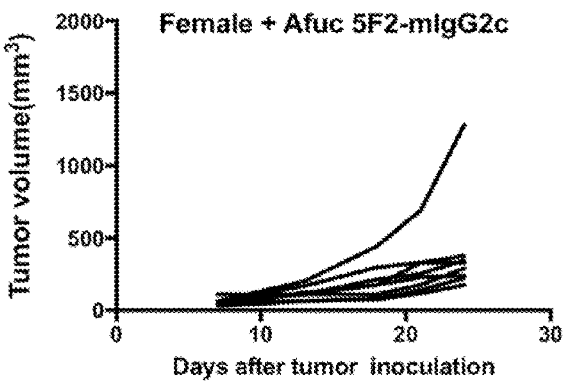
Figure 13C:
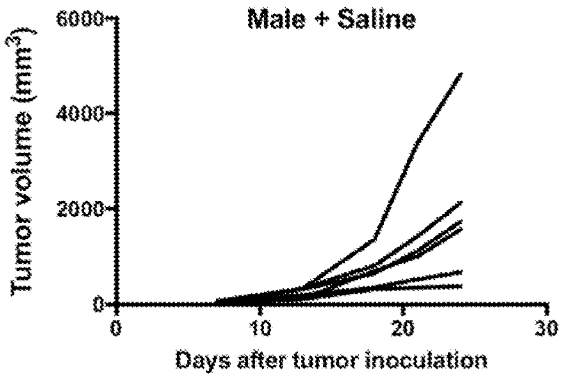
Figure 13D:
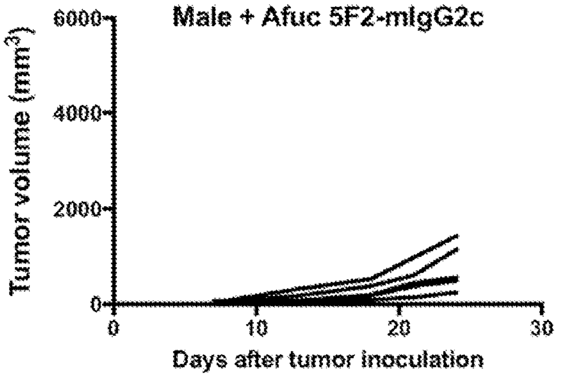
Figure 14A:
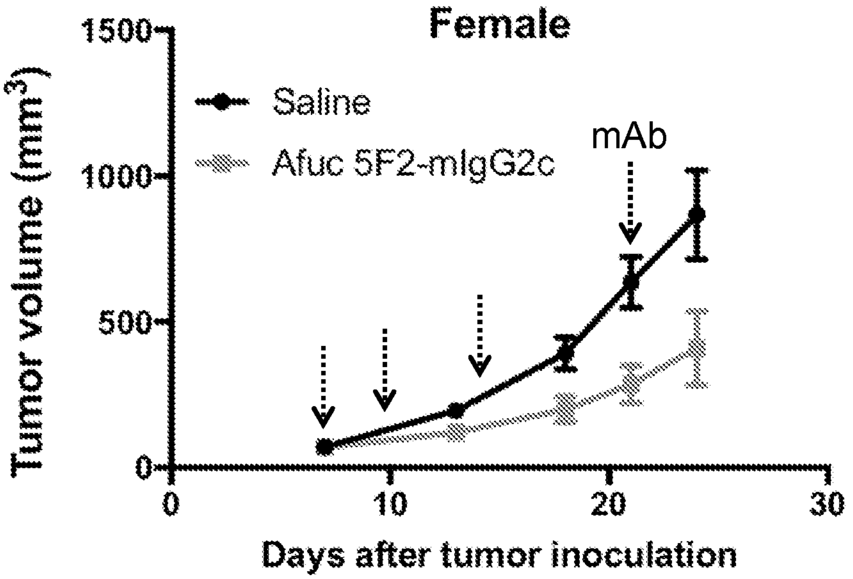
FIGS. 14A and 14B are a set of graphs showing average tumor volume of MC38-bearing male (FIG. 14B) or female (FIG. 14A) mice post Afuc 5F2-mIgG2c mAb treatment.
Figure 14B:
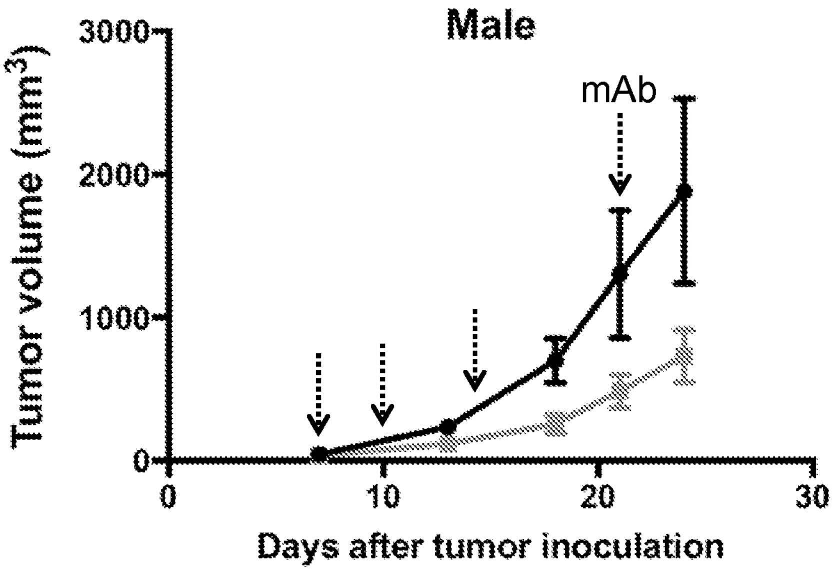
Figure 15:
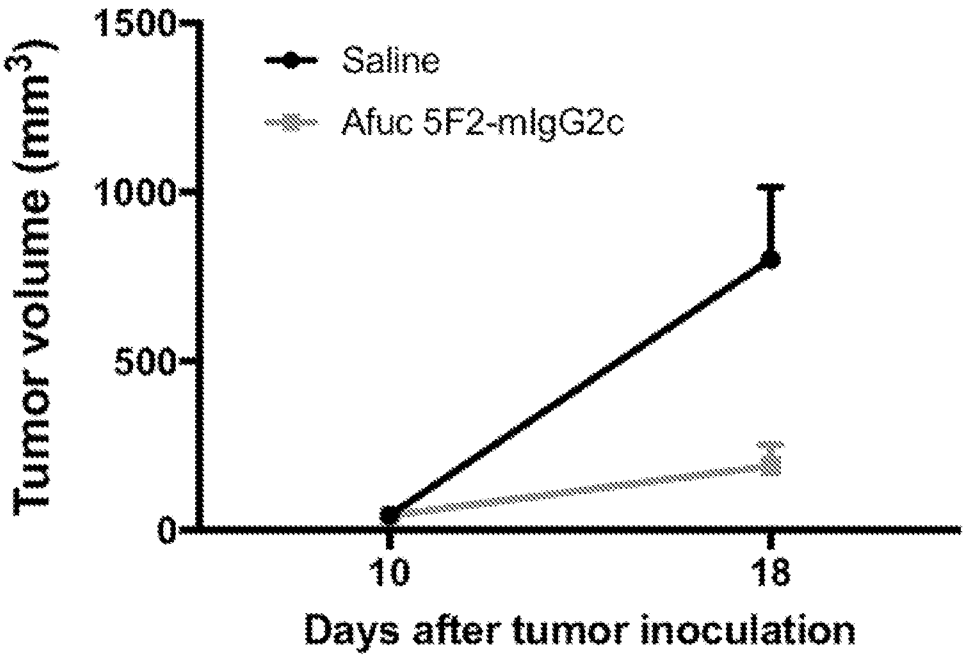
FIG. 15 is a graph showing average tumor volume of MC38-bearing mice post Afuc 5F2-mIgG2c mAb treatment.
Figure 16:
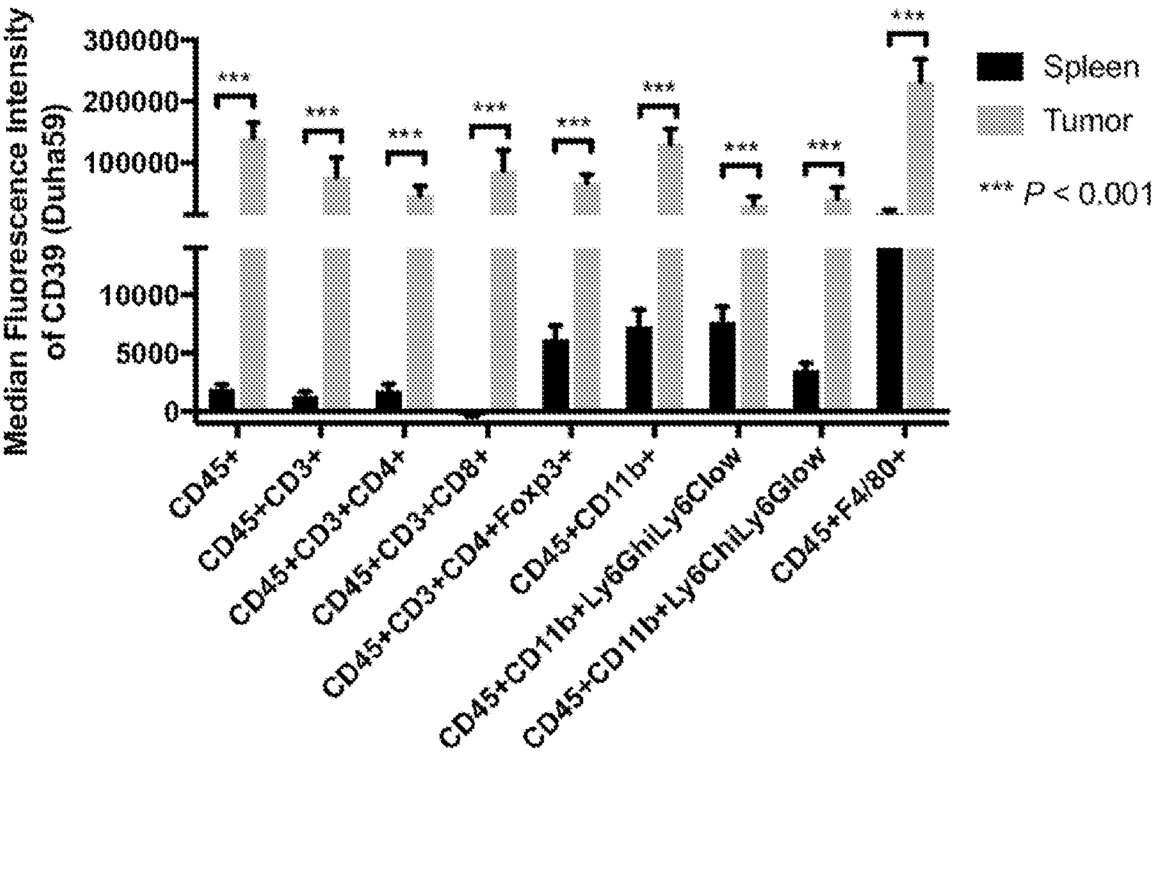
FIG. 16 is a graph showing that CD39 expression is dramatically elevated inside the tumor after Afuc 5F2-mIgG2c mAb treatment, in contrast to spleen.
Figure 17A:
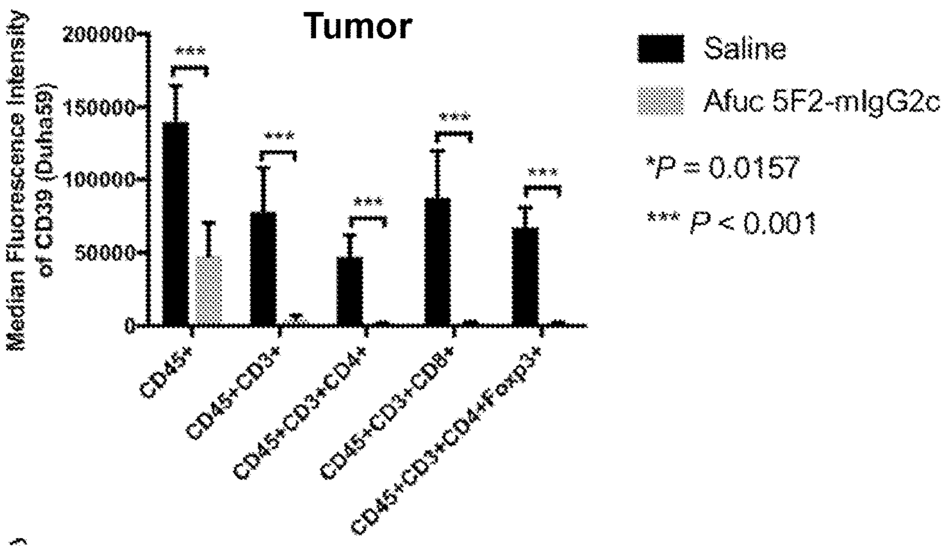
FIGS. 17A-17C are a set of graphs showing that in the tumor, Afuc 5F2-mIgG2c mAb treatment leads to marked decreases of CD39 expression in T cell subtypes ($CD45^+$ $CD3^+$), myeloid derived cells ($CD45^+CD11$ $b^+$/or $F4/80^+$) (FIGS. 17A and 17B) as well as non-lymphocytes (CD45−) (FIG. 17C), in comparison with saline treated mice.
Figure 17B:
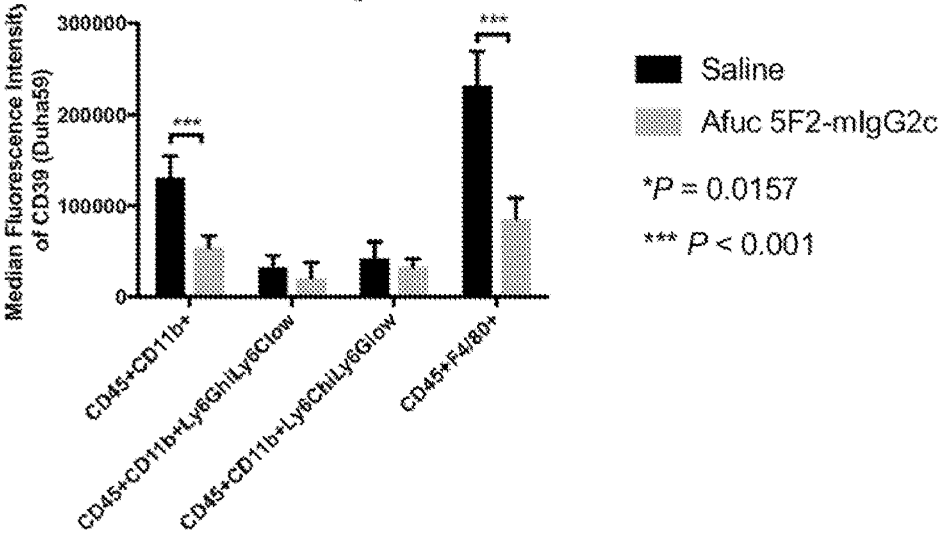
Figure 17C:
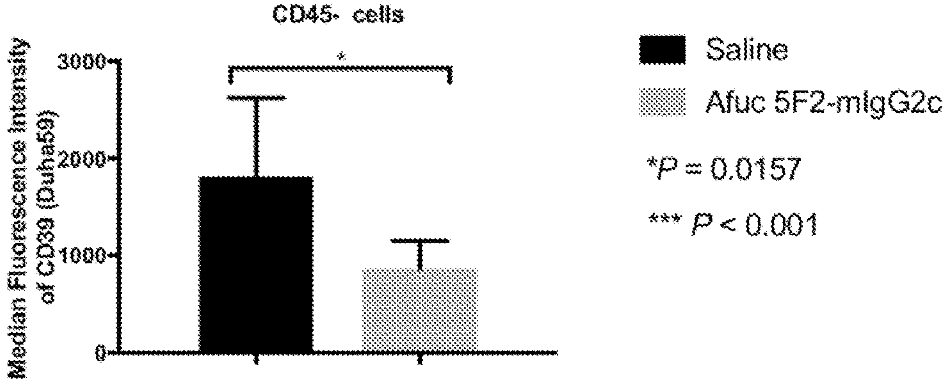
Figure 18A:
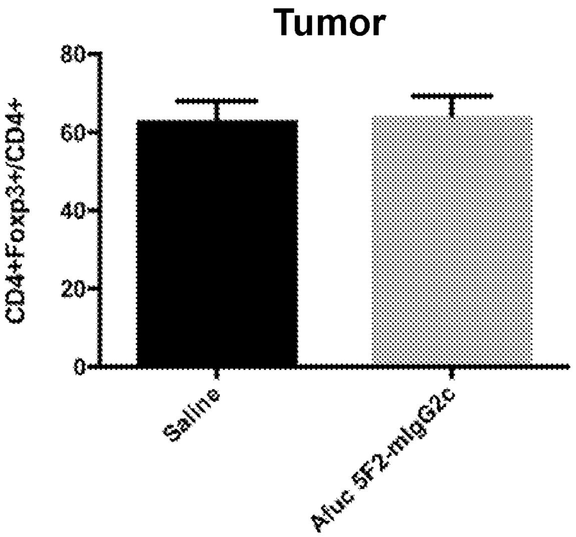
FIGS. 18A and 18B are a set of graphs showing that no depletion of Treg cells ($CD4^+FoxP3^+/CD4^+$) (FIG. 18A) and increased levels of F4/80 macrophages ($CD11$ $b^+F4/80^+$/ $CD11$ $b^+$) (FIG. 18B) were noted within the tumor post Afuc 5F2-mIgG2c mAb treatment.
Figure 18B:
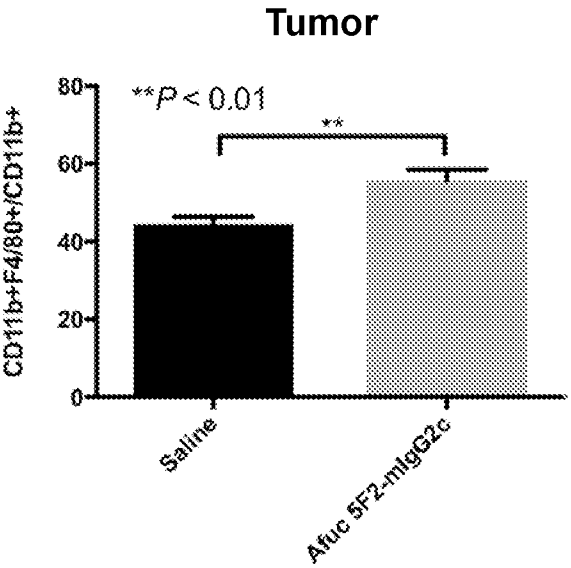
Figure 19A:
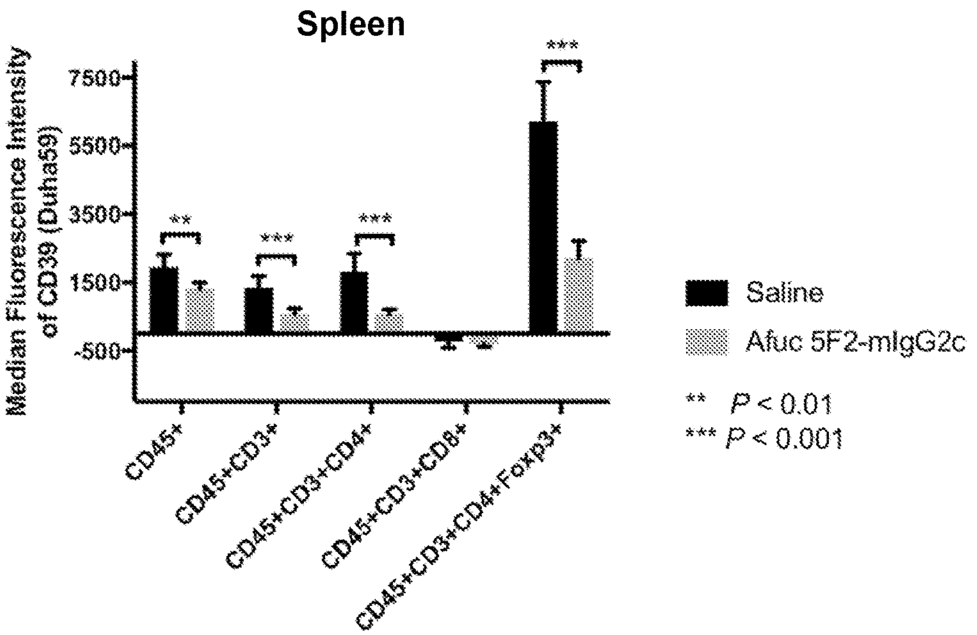
FIGS. 19A and 19B are a set of graphs showing that in the spleen, decreases of CD39 expression were noted on T cell subtypes ($CD45^+CD3^+$) (FIG. 19A) and myeloid derived cells ($CD45^+CD11$ $b^+$/or $F4/80^+$) (FIG. 19B) post Afuc 5F2-mIgG2c mAb treatment, as compared to saline treated mice.
Figure 19B:
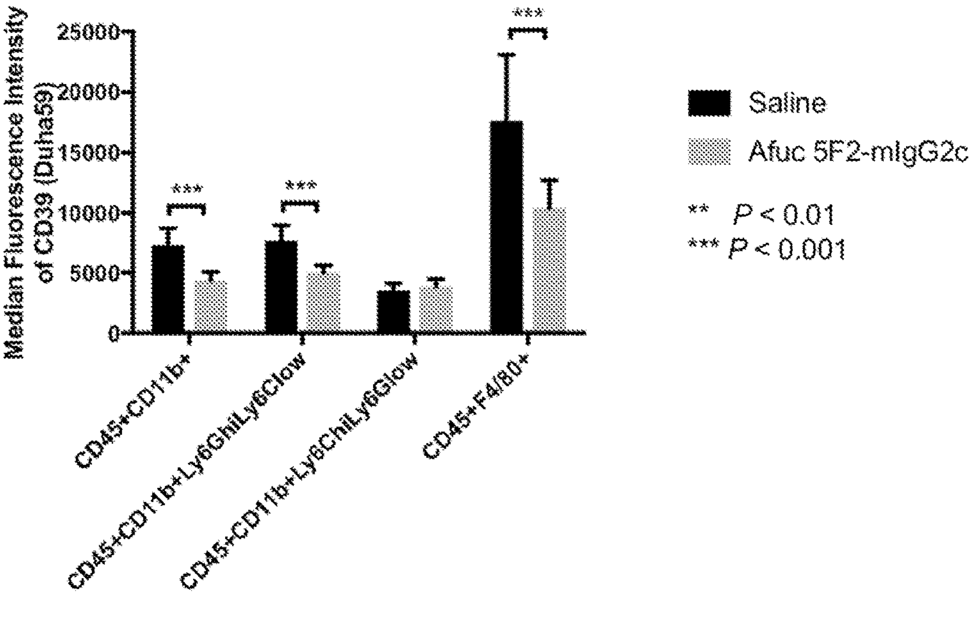
Figure 20A:
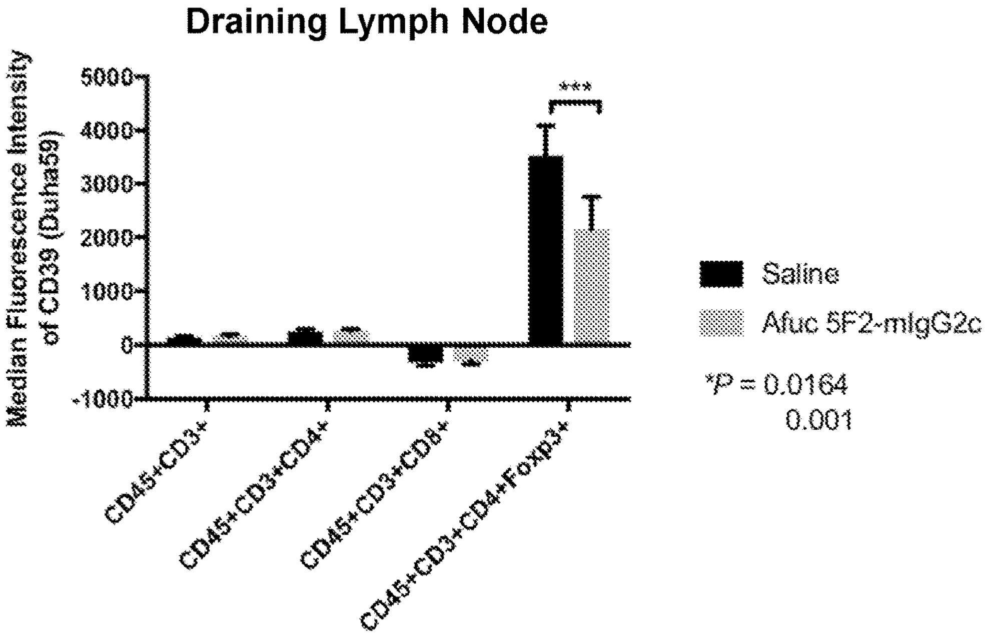
FIGS. 20A and 20B are a set of graphs showing that in the draining lymph node, decreases of CD39 expression were observed on Treg ($CD45^+CD3^+CD4^+FoxP3^+$) (FIG. 20A) and $CD45^+CD11$ $b^+$ (FIG. 20B) cells post Afuc 5F2-mIgG2c mAb treatment, when compared with saline treated controls.
Figure 20B:
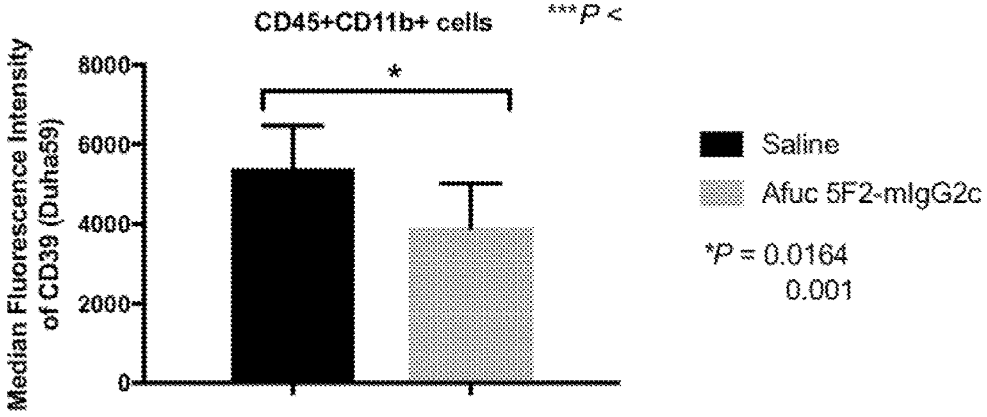
Figure 21A:
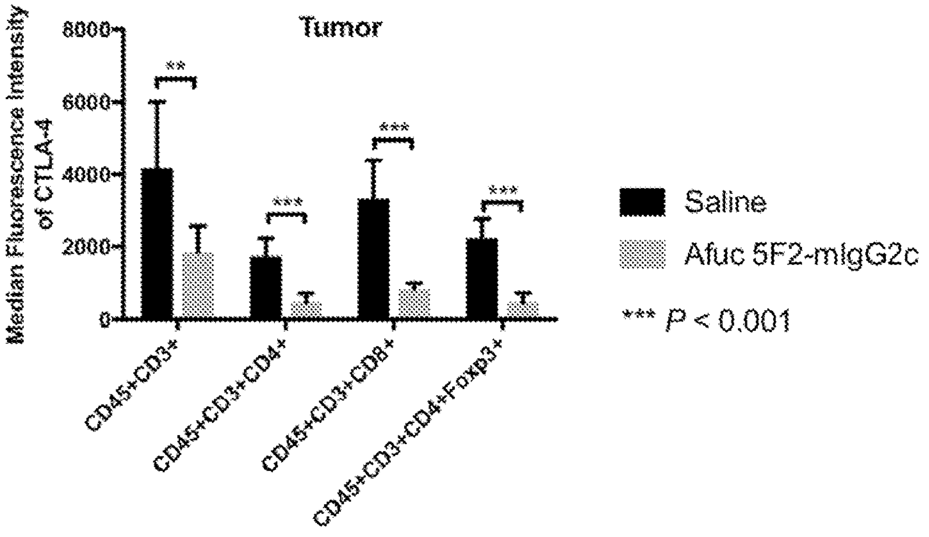
FIGS. 21A-21C are a set of graphs showing that Afuc 5F2-mIgG2c mAb treatment results in significant reductions of CTLA4 expression on T cell subtypes ($CD45^+CD3^+$) in the tumor (FIG. 21A) and spleen (FIG. 21B), but not draining lymph node (FIG. 21C), as compared to saline treated mice.
Figure 21B:
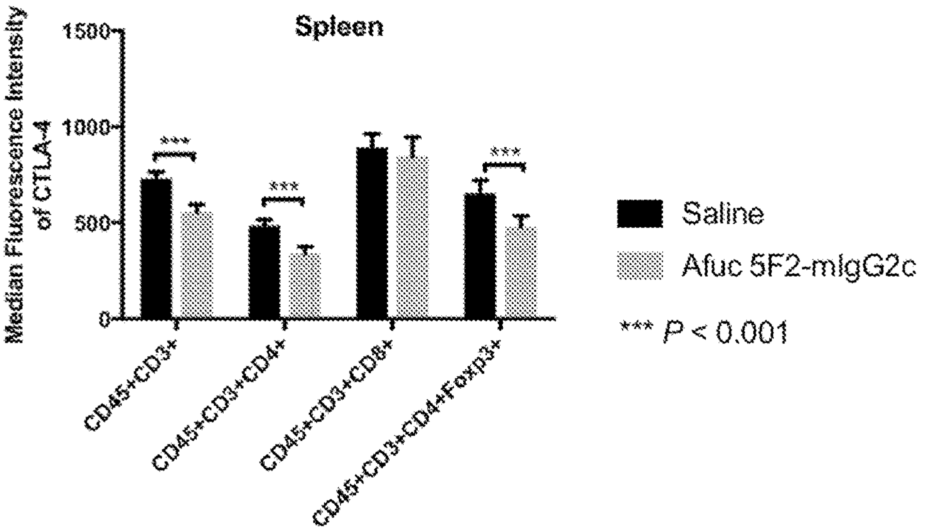
Figure 21C:
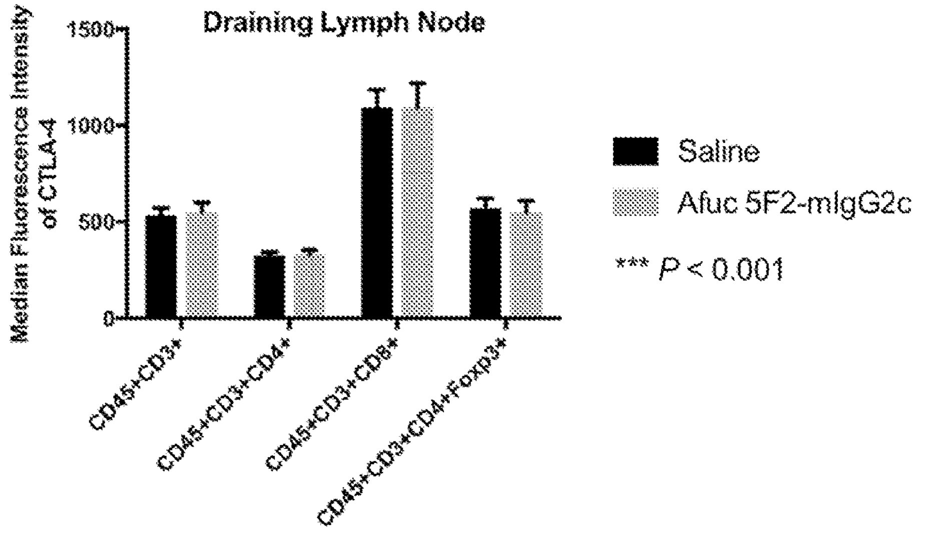
Figure 22A:
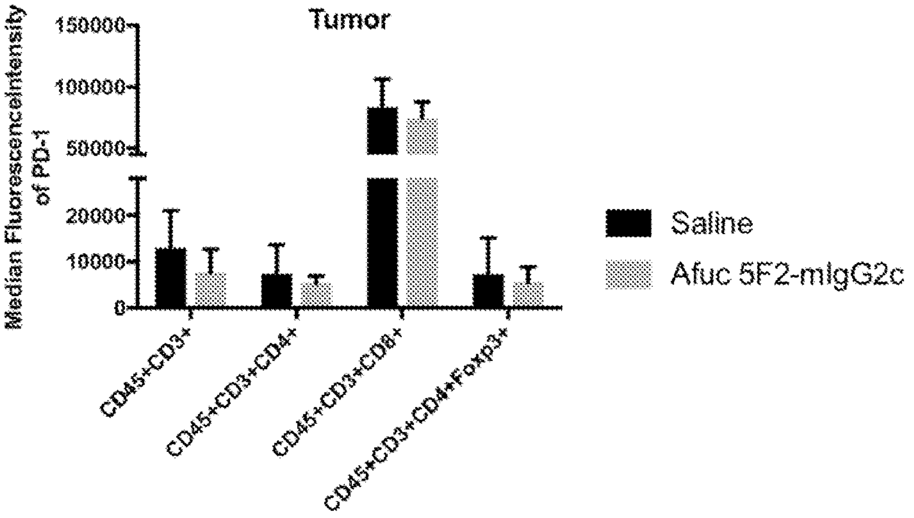
FIGS. 22A-22C are a set of graphs showing that PD-1 expression on T cell subtypes ($CD45^+CD3^+$) in tumor (FIG. 22A), spleen (FIG. 22B) or draining lymph node (FIG. 22C) is not altered by Afuc 5F2-mIgG2c mAb treatment, as compared to saline treated mice.
Figure 22B:
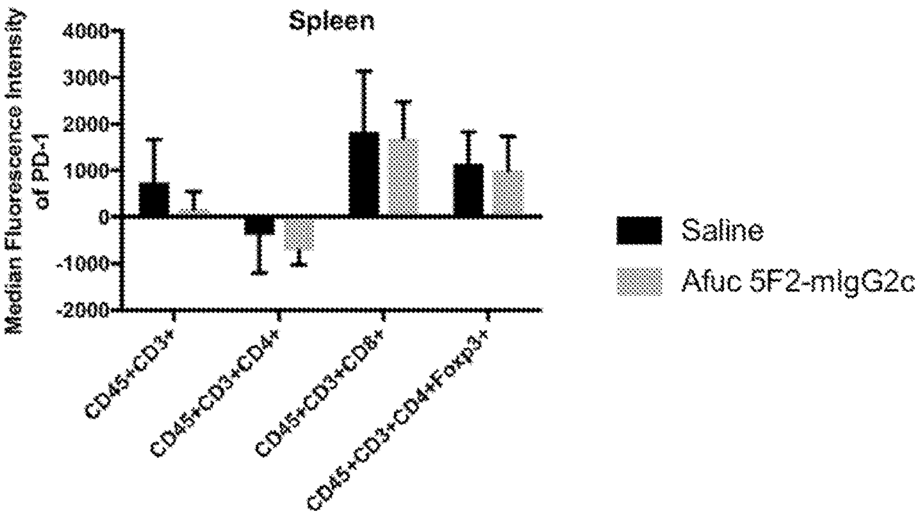
Figure 22C:
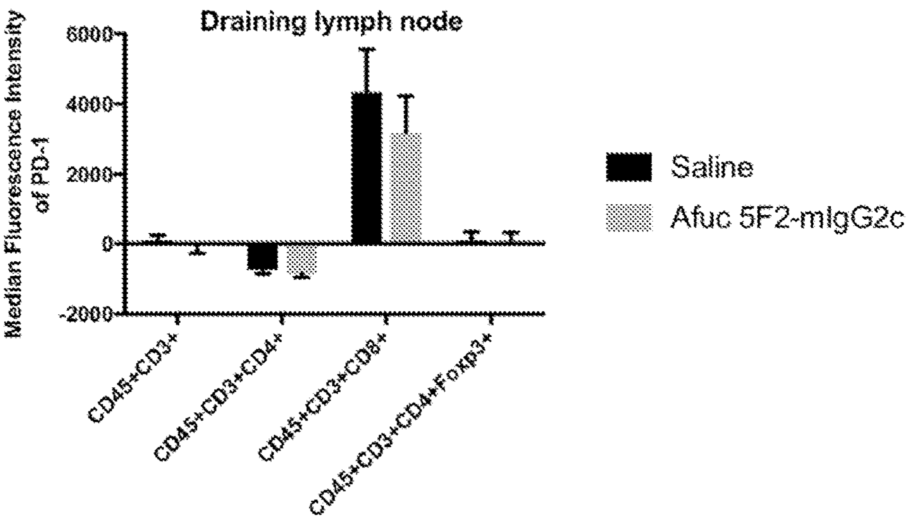
Figure 23A:
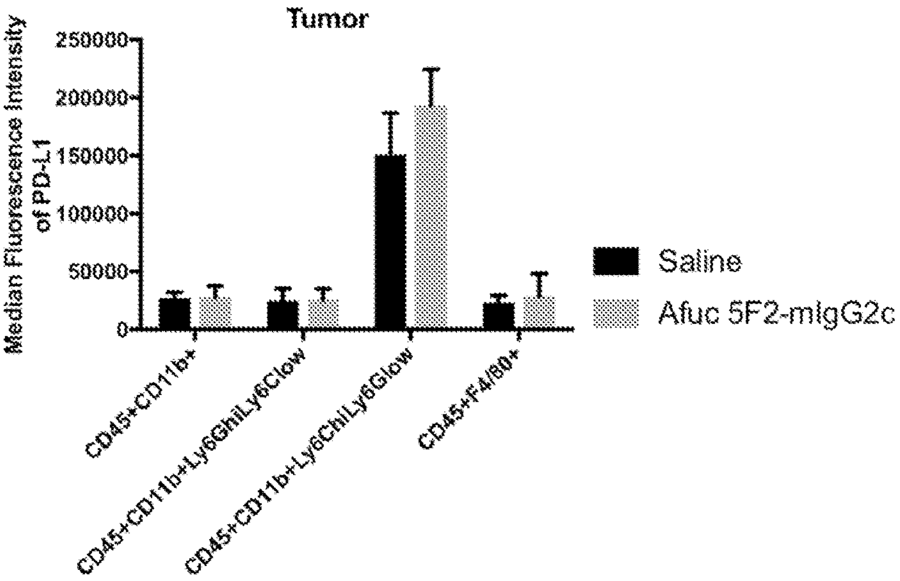
FIGS. 23A-23C are a set of graphs showing that PD-L1 expression on myeloid derived cells ($CD45^+CD11$ $b^+$) in tumor (FIG. 23A), spleen (FIG. 23B) or draining lymph node (FIG. 23C) is not altered by Afuc 5F2-mIgG2c mAb treatment, as compared to saline treated mice.
Figure 23B:
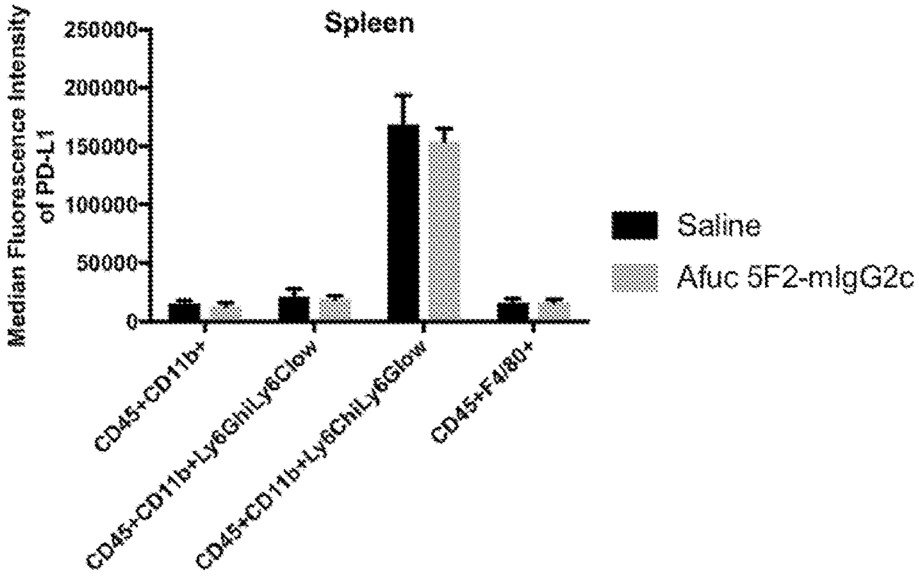
Figure 23C:
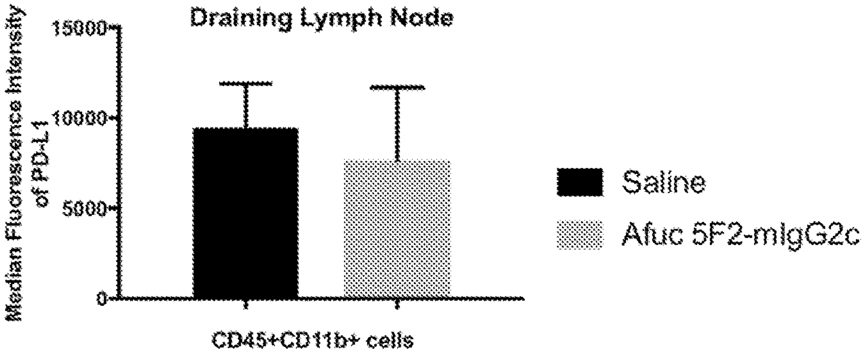
Figure 24A:
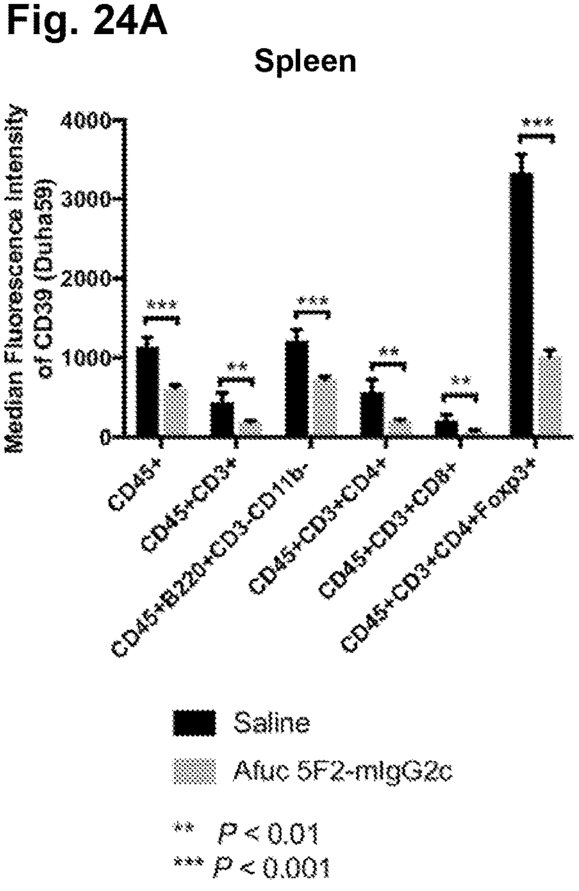
FIGS. 24A and 24B are a set of graphs showing that in the spleen, decreases of CD39 expression are noted in all major lymphocytes ($CD45^+$) post Afuc 5F2-mIgG2c mAb treatment, in contrast with saline treated mice.
Figure 24B:
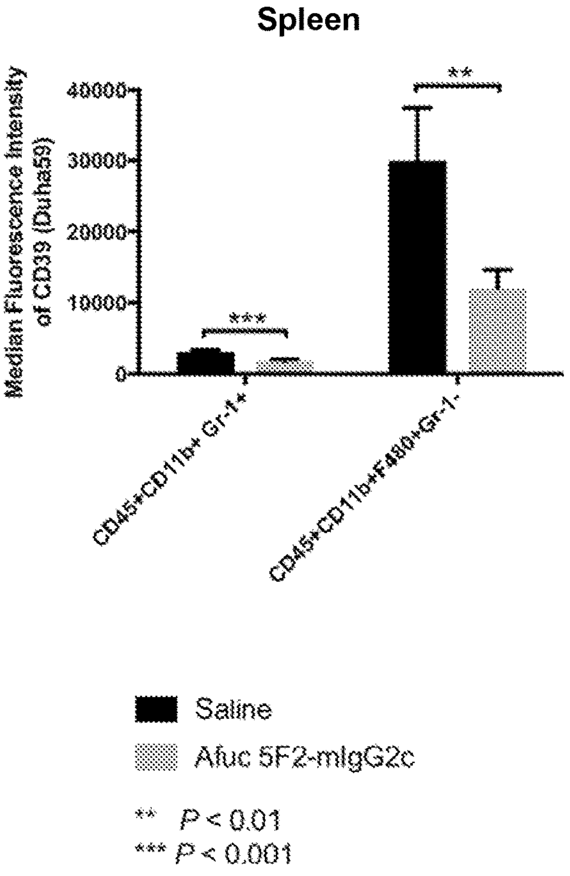
Figure 25A:
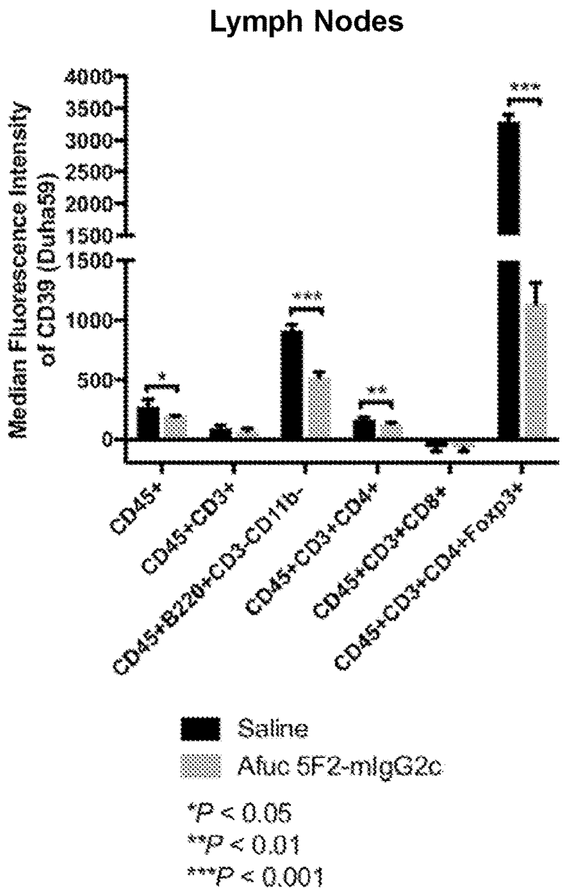
FIGS. 25A and 25B are a set of graphs showing that in lymph nodes, decreases of CD39 expression are noted in select lymphocyte populations ($CD45^+$) post Afuc 5F2-mIgG2c mAb treatment, as compared to saline treated mice.
Figure 25B:
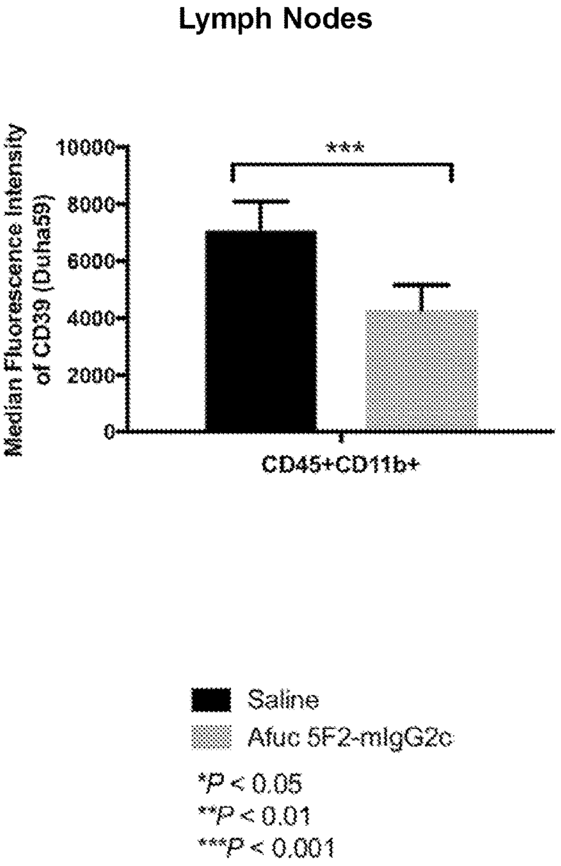
Figure 26:
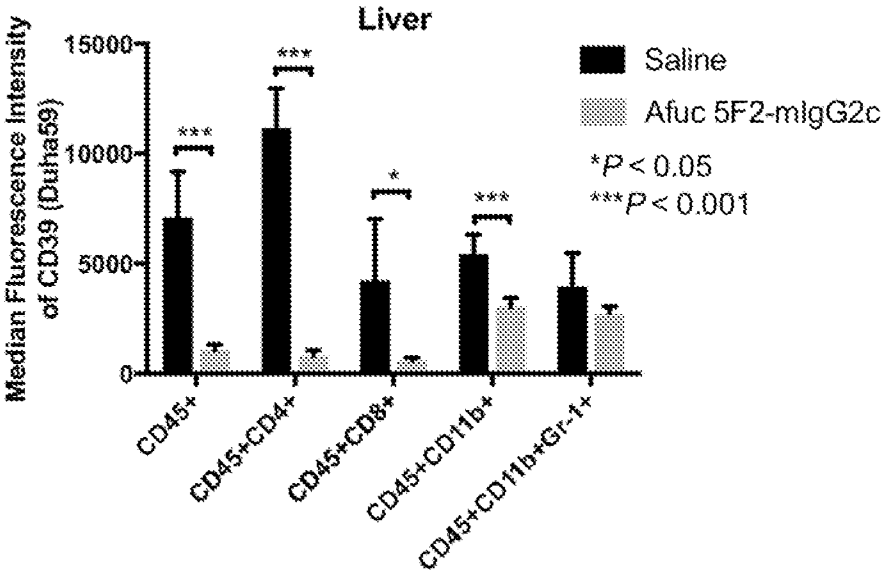
FIG. 26 is a graph showing that in the liver, decreases of CD39 expression are noted in most lymphocyte populations (CD45$^+$) post Afuc 5F2-mIgG2c mAb treatment, when compared to saline treated mice.
Figure 27:
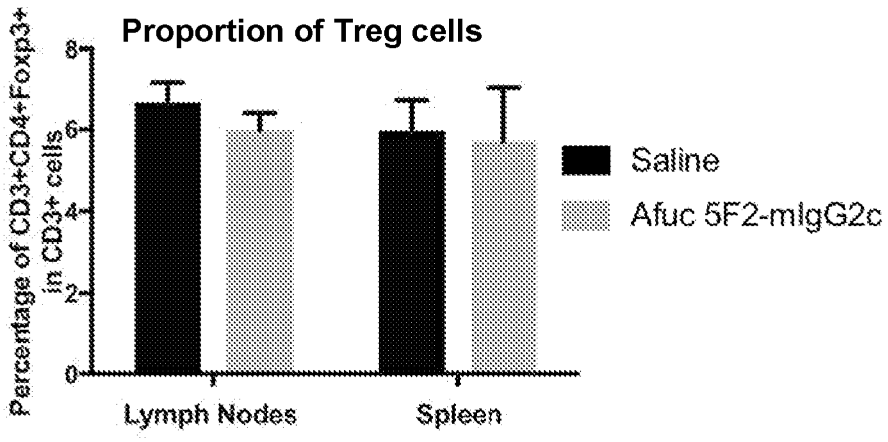
FIG. 27 is a graph showing that no depletion of Treg cells (CD3$^+$CD4$^+$FoxP3$^+$/CD3$^+$) is noted in the lymph nodes or spleen post Afuc 5F2-mIgG2c mAb treatment, when compared to control mice.
Figure 29A:
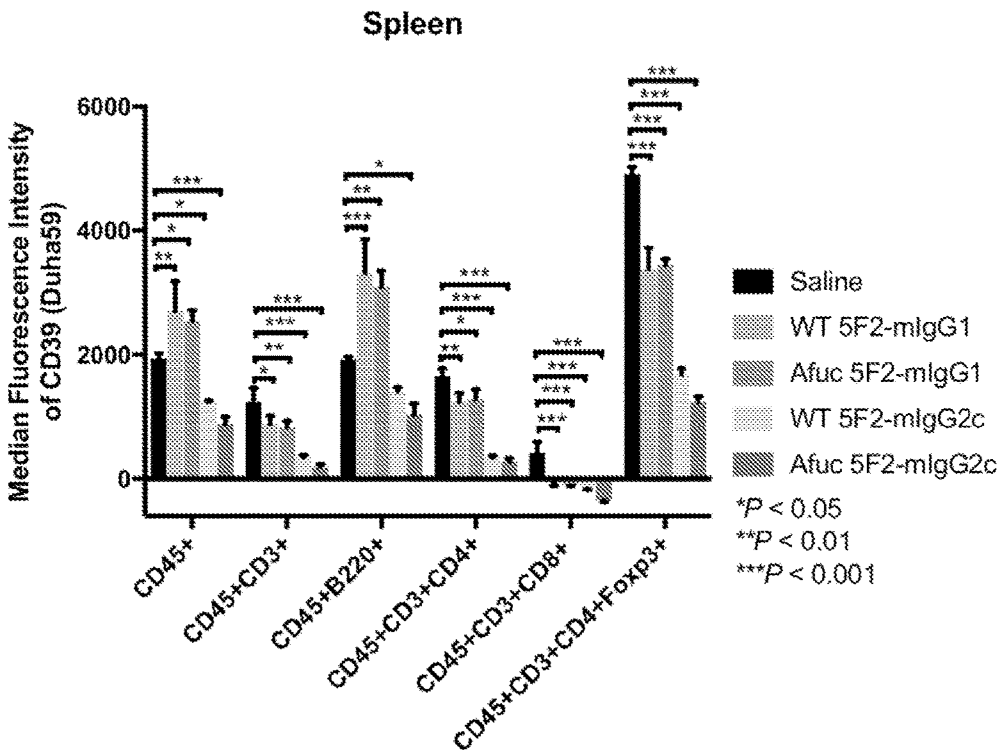
FIGS. 29A and 29B are a set of graphs showing that in the spleen, Afuc 5F2-mIgG2c mAb treatment leads to the largest decreases of CD39 expression in all major lymphocytes (CD45$^+$), when compared to saline- or any other types of 5F2 mAb-treated mice.
Figure 29B:
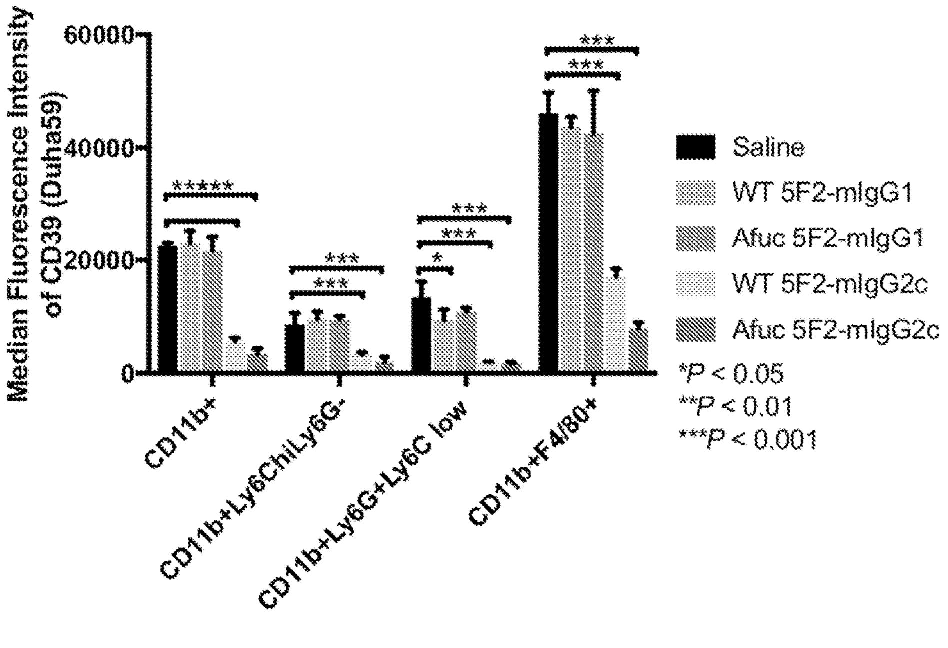
Figure 30A:
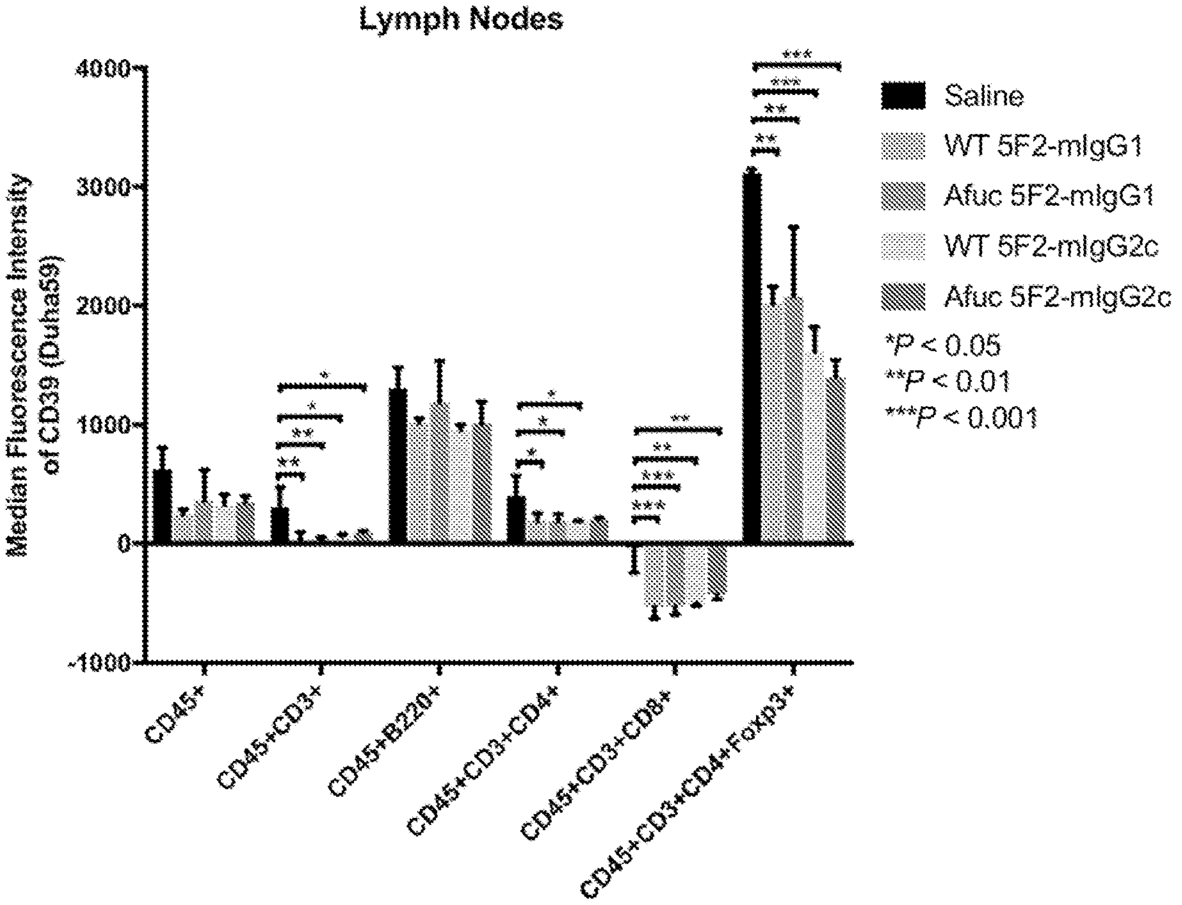
FIGS. 30A and 30B are a set of graphs showing that in the lymph nodes, 5F2 mAbs lead to decreases of CD39 expression in T cell subtypes (CD45$^+$CD3$^+$) when compared to saline treated mice.
Figure 30B:
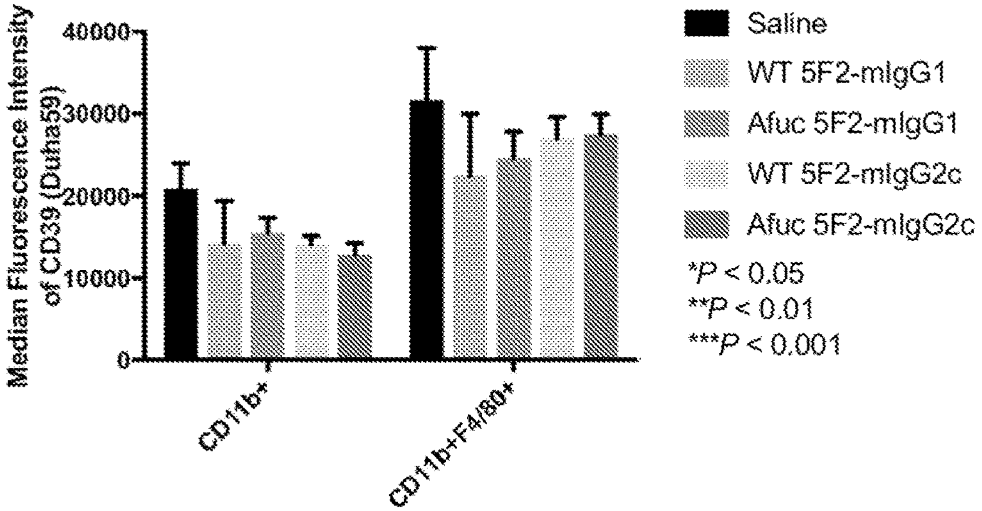
Figure 31A:
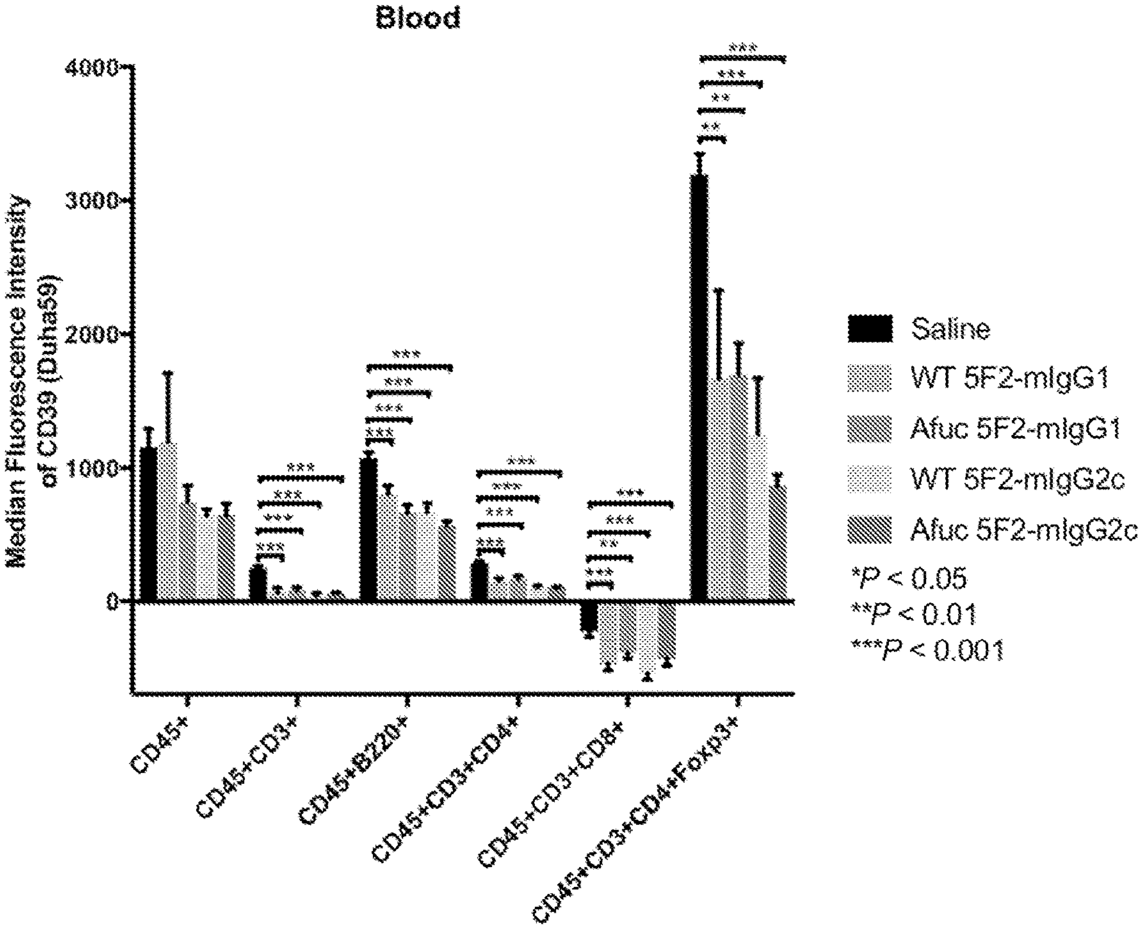
FIGS. 31A and 31B are a set of graphs showing that in the blood, 5F2 mAbs lead to decreases of CD39 expression in select lymphocyte populations (CD45$^+$), as compared with saline treated mice.
Figure 31B:
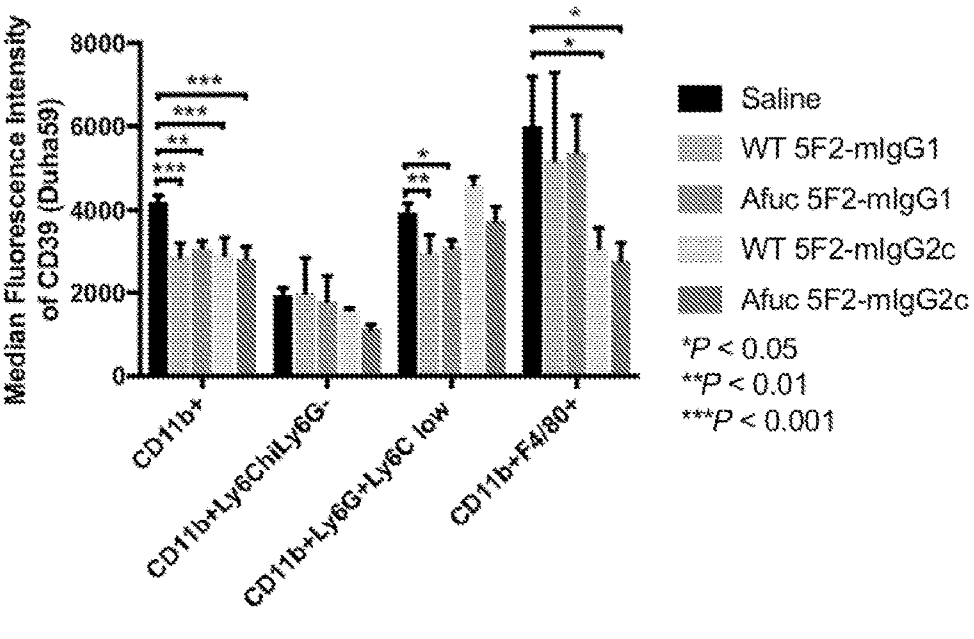
Figure 32:
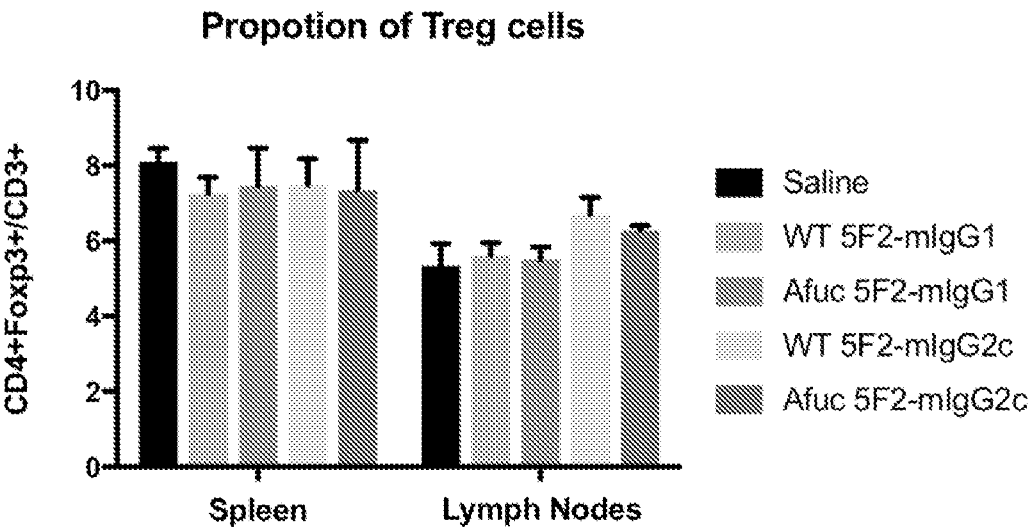
FIG. 32 is a graph showing that no depletion of Treg cells (CD4$^+$FoxP3$^+$/CD3$^+$) is noted in the spleen nor lymph nodes post various 5F2 mAb treatments, when compared to the control mice.
Figure 33A:
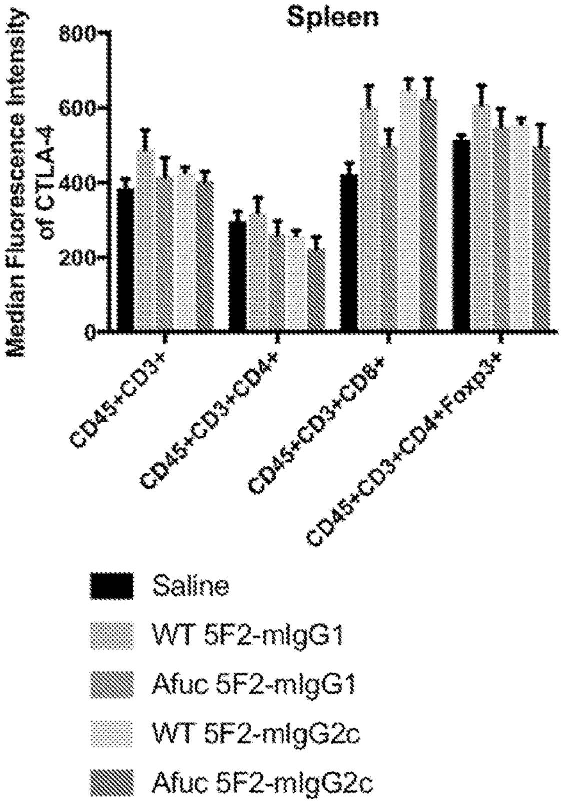
FIGS. 33A-33C are a set of graphs showing that CTLA4 expression on T cell subtypes (CD45$^+$CD3$^+$) in the spleen (FIG. 33A), lymph nodes (FIG. 33B), or blood (FIG. 33C) is not altered by 5F2 mAb treatment, in contrast with saline treated mice.
Figure 33B:
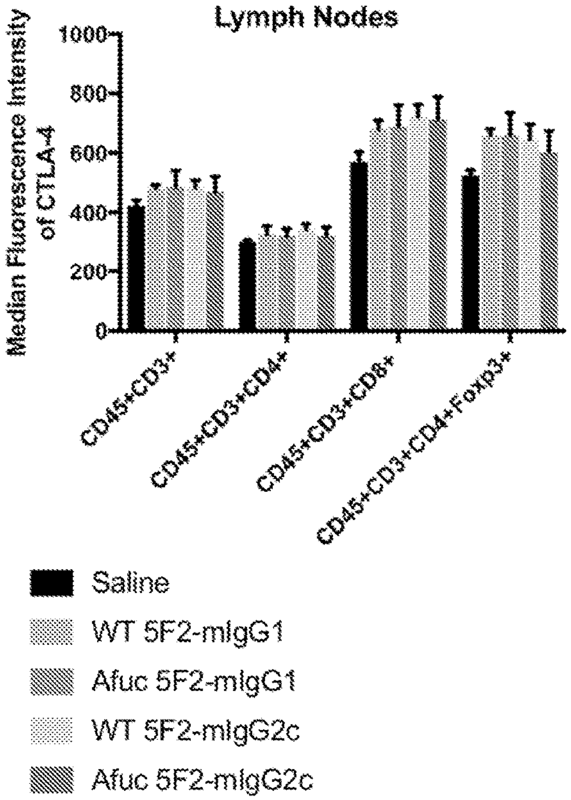
Figure 33C:
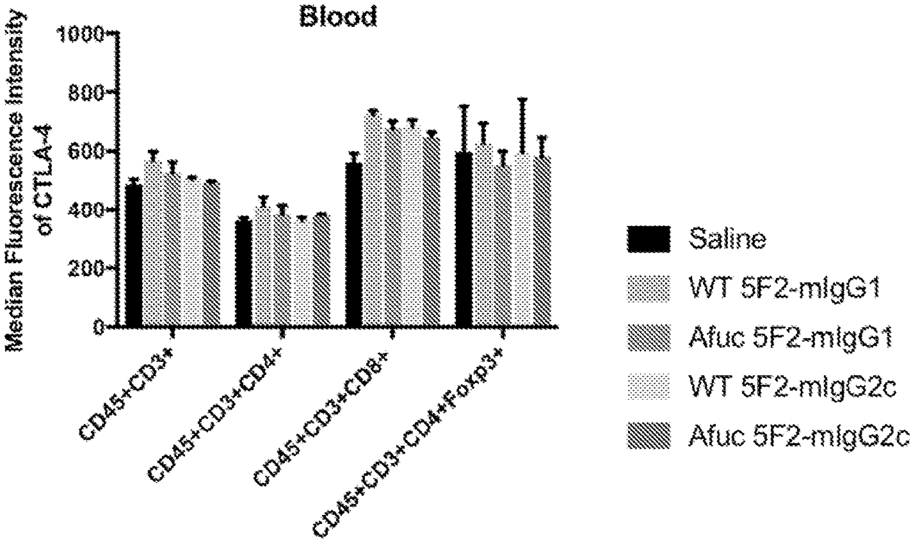
Figure 34A:
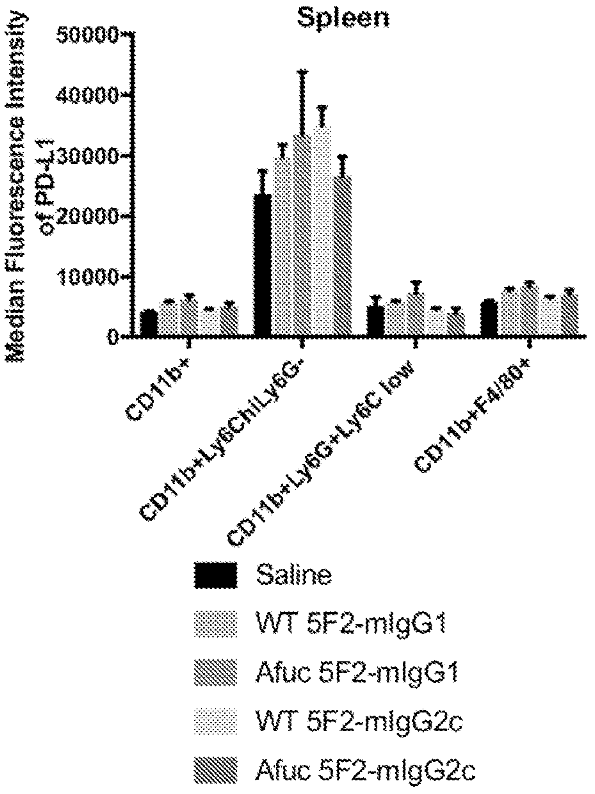
FIG. 34A-34C are a set of graphs showing that PD-L1 expression on myeloid derived cell populations (CD11 b$^+$) in the spleen (FIG. 34A), lymph nodes (FIG. 34B), or blood (FIG. 34C) is not altered by 5F2 mAb treatment, as compared with saline treated mice.
Figure 34B:
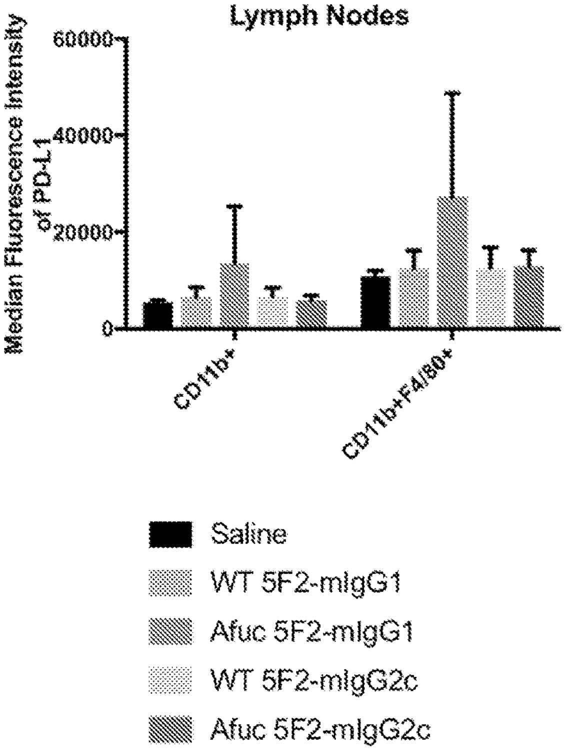
Figure 34C:
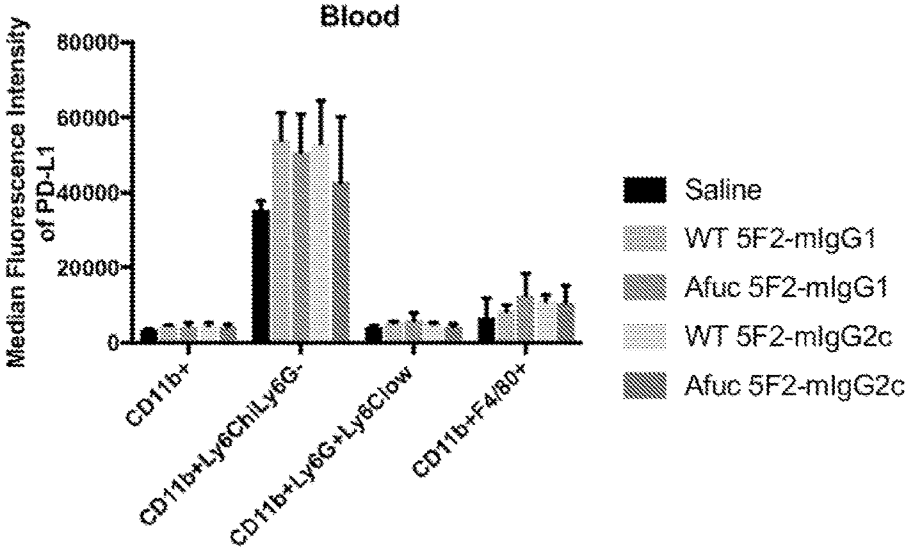

FIG. 12B. Average tumor volume of B16/F10-bearing mice received two Afuc 5F2-mIgG2c mAb treatments. $1.0\times10^5$ luc-B16/F10 cells were injected (s.c.) into the right lower flank of wildtype FoxP3-GFP knock-in reporter mice (females at ages of 8 weeks; in house) on day 0. Afuc 5F2-mIgG2c mAb (200 μg in 200 μl of saline via i.p.) were given to tumor-bearing mice on days 13 and 16 (mice were randomized to two groups based on tumor volume). Mice received 200 μl of saline were used as controls. Tumor volume was measured as described above and studies were terminated on day 17. n=4-5 per group.

FIGS. 13A-13D & 14A and 14B; BT271-308

Afucosylated anti-CD39 monoclonal antibody (mAb) 5F2-mIgG2c demonstrates anti-tumor activity toward established MC38 colorectal cancer in vivo. $1.0\times10^5$ MC38 cells were injected subcutaneously (s.c.) into the right lower flank of wildtype FoxP3-GFP knock-in reporter mice (both males and females at ages of 9-12 weeks; in house) on day 0. Afuc 5F2-mIgG2c mAb (200 μg in 200 μl of saline via i.p.) were given to tumor-bearing mice on days 7, 10, 14 and 21 (mice were randomized to two groups based on tumor volume per gender). Mice received 200 μl of saline served as controls. Tumor volume was measured as described above. Studies were terminated when any tumor volume reaches around 4000 $mm^3$. n=6 per group for males and n=8 per group for females.

FIGS. 15-23C; BT391-409.

Inhibition of MC38 growth by afucosylated 5F2-mIgG2c mAb is associated with decreased CD39 expression on major immune cell compartments and concurrent reduction of CTLA-4 in select immune cell subtypes. $1.0\times10^5$ MC38 cells were injected subcutaneously (s.c.) into the right lower flank of wildtype FoxP3-GFP knock-in reporter mice (males at ages of 10-12 weeks; in house) on day 0. Afuc 5F2-mIgG2c mAb (200 μg in 200 μl of saline via i.p.) were given to tumor-bearing mice on days 10, 13 and 16 (mice were randomized to two groups based on tumor volume). Mice received 200 μl of saline served as controls. Tumor volume was measured as described above and studies were terminated on day 18. Plasma were collected. Single-cell suspensions were prepared from spleen, the right Inguinal lymph node (considered as the Draining lymph node (DLN) and the entire tumor (using the Mouse Tumor Dissociation Kit and the gentleMACS Dissociator from Miltenyi Biotec) and subjected for FACS analysis using a CytoFLEX flow cytometer. CD45 was used as a surface marker to gate all lymphocytes. Duha59 (Biolegend), a rat anti-mouse CD39 antibody recognizes totally different epitope from 5F2 was used for FACS staining. n=8 per group.

FIGS. 24A-27; BT371-386. Healthy Tumor-Free Mice

Afucosylated 5F2-mIgG2c mAb treatment also results in decreased CD39 expression on major immune cell compartments in tumor-free healthy wildtype mice, to a much lesser extent than tumor-bearing mice. Healthy wildtype FoxP3-GFP knock-in reporter mice (males at ages of 8-10 weeks; in house) received two doses of Afuc 5F2-mIgG2c mAb (200 μg in 200 μl of saline via i.p.) on days 1 and 4. Mice received 200 μl of saline served as controls. Studies were terminated on day 5. Plasma were collected. Single-cell suspensions were prepared from spleen, the Inguinal lymph nodes on both legs and the liver and subjected for FACS analysis using a CytoFLEX flow cytometer. CD45 was used as a surface marker to gate all lymphocytes. Duha59, an anti-mouse CD39 antibody recognizes totally different epitope from 5F2 was used for FACS staining. n=6 per group.

FIG. 28; CTX1-10. Healthy Tumor-Free Mice for Liver and Renal Cytotoxicity

Safety evaluation of afucosylated 5F2-mIgG2c mAb in healthy wildtype mice. Healthy wildtype C57BL/6 mice (males at ages of 8-12 weeks; Taconic) received three doses of Afuc 5F2-mIgG2c mAb at two different concentrations (100 μg (CTX5-7) or 1000 μg (CTX8-10)) via i.p. on days 1, 4 and 7. Mice received 200 μl of saline (CTX1) or 100 μg of IgG2c isotype control antibody (Cat No. PZMU007; AB Biosciences, Concord, MA) (CTX2-4) served as controls. Studies were terminated on day 8. Plasma ALT, AST and BUN concentrations were measured by an automated autoanalyzer (ABL80 FLEX CO-OX; Radiometer America Inc., Brea, CA).

FIGS. 29A-34C; BT431-445. Healthy Tumor-Free Mice Received 4 Various 5F2 mAbs In tumor-free healthy wildtype mice, afucosylated 5F2-mIgG2c mAb treatment leads to the most dramatic reduction in CD39 expression on all major immune cell compartments, as compared to any other types of 5F2 mAbs. Healthy wildtype FoxP3-GFP knock-in reporter mice (females at ages of 15-16 weeks; in house) were treated with various 5F2 mAbs (200 μg of each mAb in 200 μl of saline via i.p.) on days 1 and 4. Mice received 200 μl of saline served as controls. Studies were terminated on day 6. Single-cell suspensions were prepared from spleen, the Inguinal lymph nodes on both legs and blood and subjected for FACS analysis using a CytoFLEX flow cytometer. CD45 was used as a surface marker to gate all lymphocytes. Duha59, a rat anti-mouse CD39 antibody that recognizes totally different epitope from 5F2 was used for FACS staining. n=3 per group.

Figure 35A:
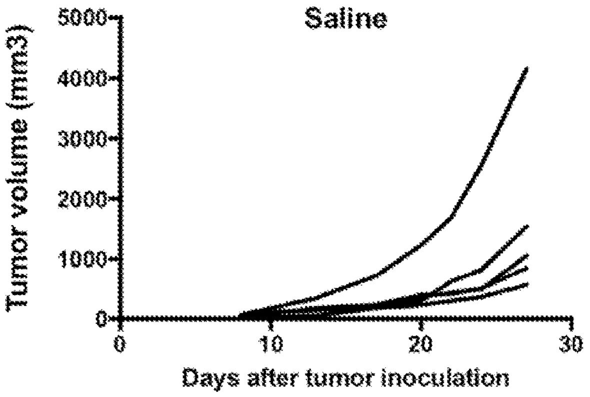
FIGS. 35A and 35B are a set of graphs showing the kinetics of MC38 tumor growth in each individual LysM-Cre/CD39KO mouse post Afuc 5F2-mIgG2c mAb (FIG. 35B) or saline treatment (FIG. 35A).
Figure 35B:
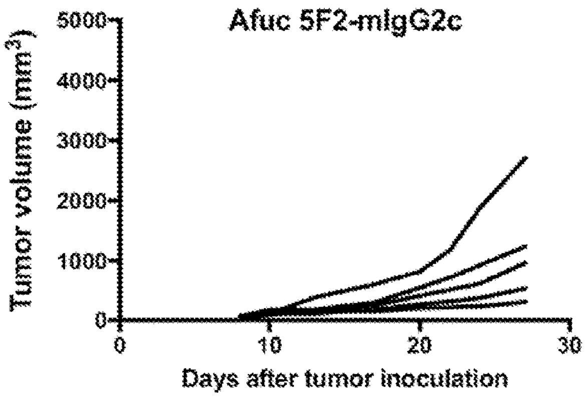
Figure 36:
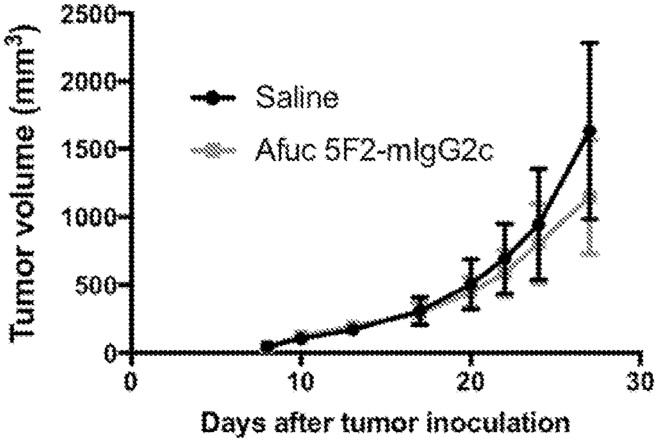
FIG. 36 is a graph showing average tumor volume of MC38-bearing LysMCre/CD39KO mice post Afuc 5F2-mIgG2c mAb treatment.
Figure 37A:
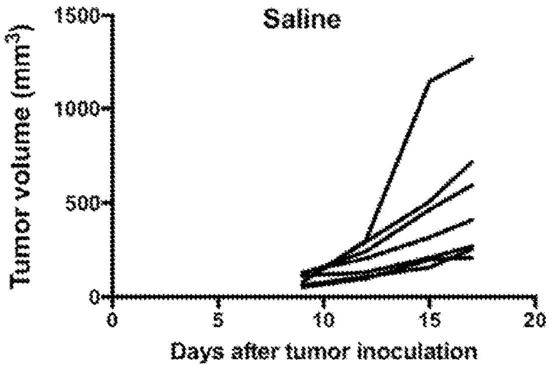
FIGS. 37A-37E are a set of graphs showing kinetics of MC38 tumor growth in each individual mouse post various types of 5F2 mAb treatment.
Figure 37B:
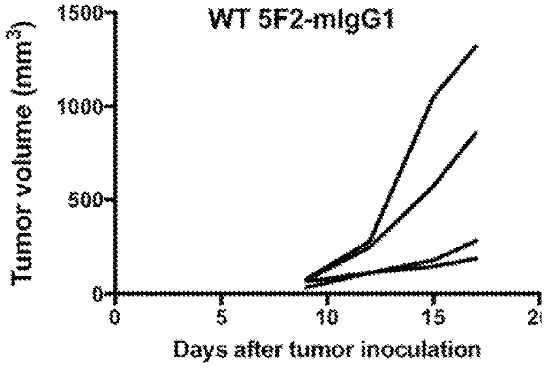
Figure 37C:
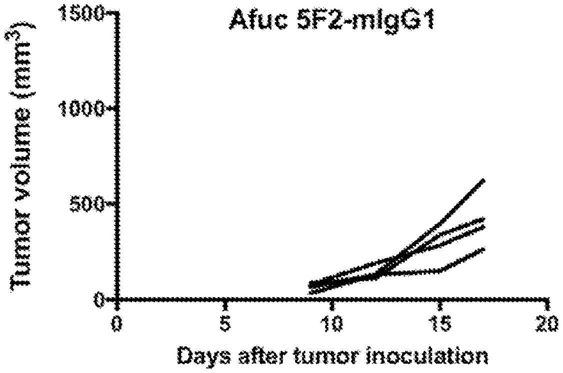
Figure 37D:
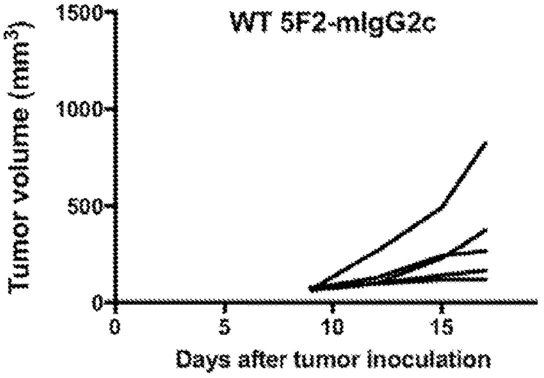
Figure 37E:
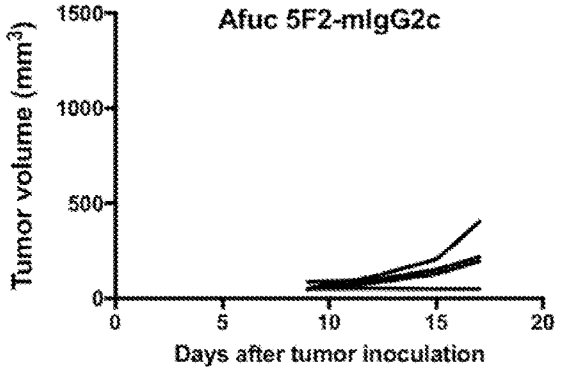
Figure 38:
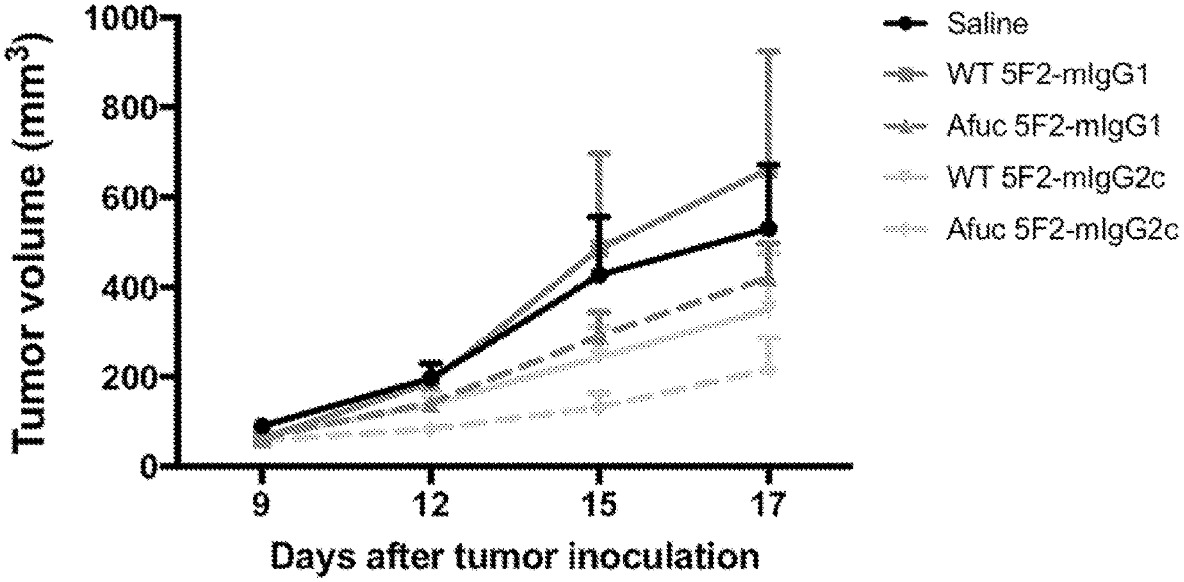
FIG. 38 is a graph showing average tumor volume of MC38-bearing mice post 5F2 mAb treatment.
Figure 39A:
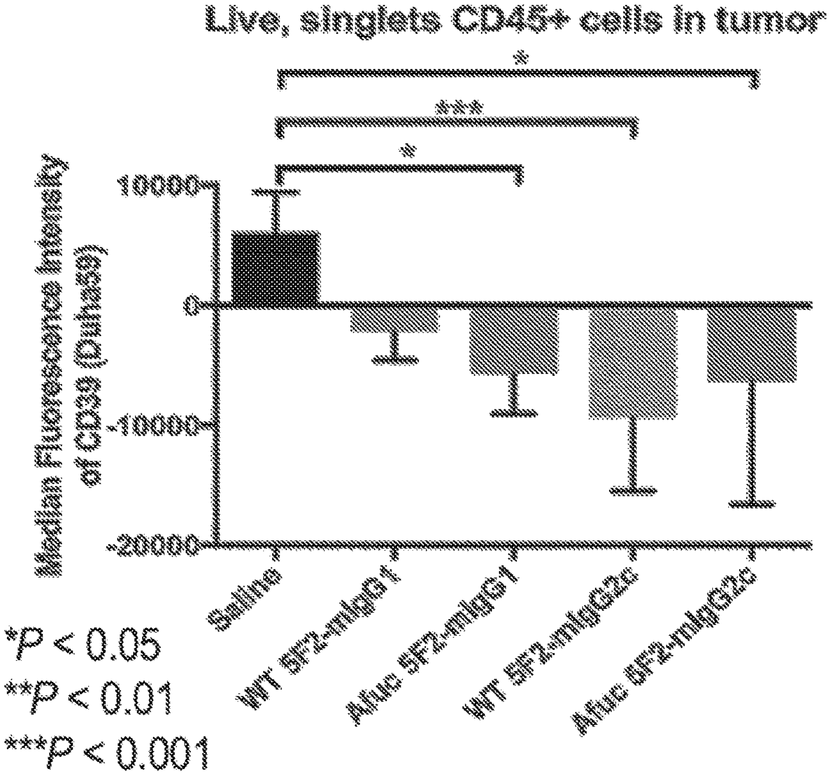
FIGS. 39A-39E are a set of graphs showing that in the tumor, decreases of CD39 expression are noted in all T cell subsets (CD45$^+$CD3$^+$) post 5F2 mAb treatments, in contrast to saline treated mice.
Figure 39B:
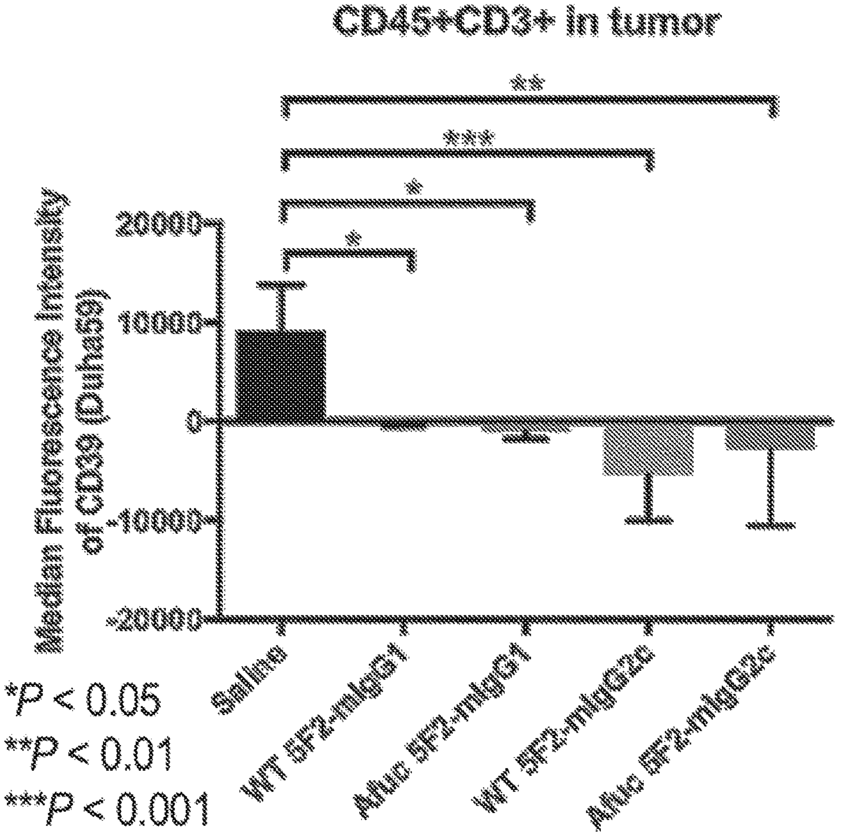
Figure 39C:
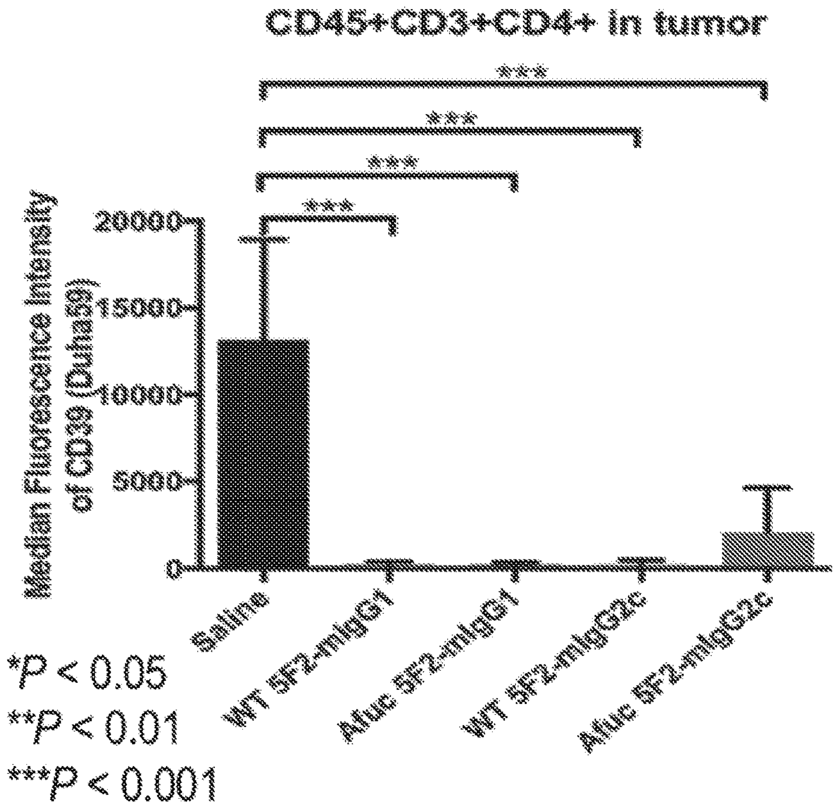
Figure 39D:
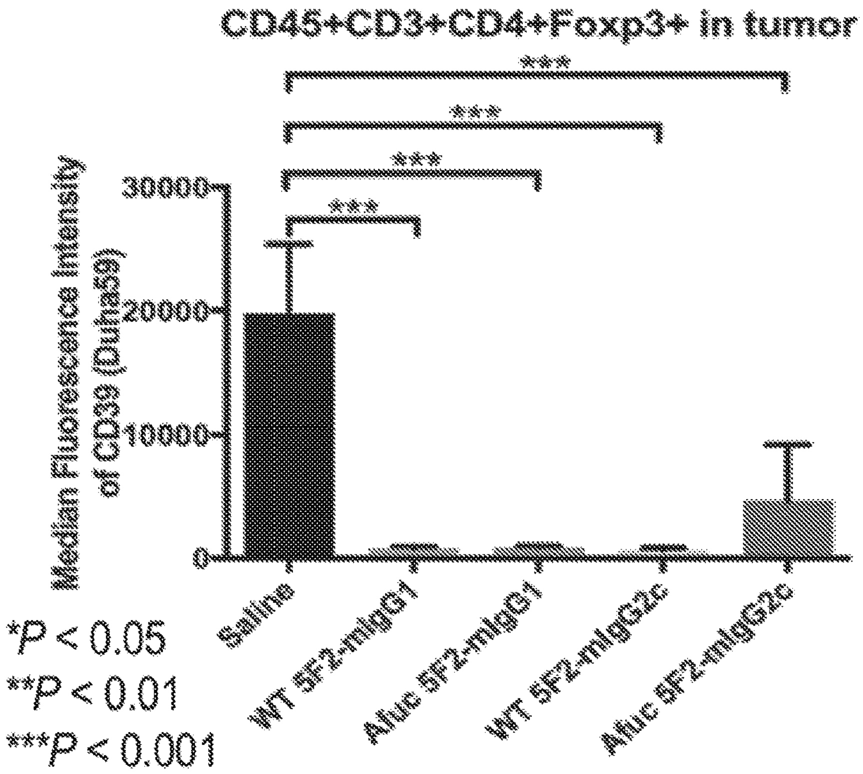
Figure 39E:
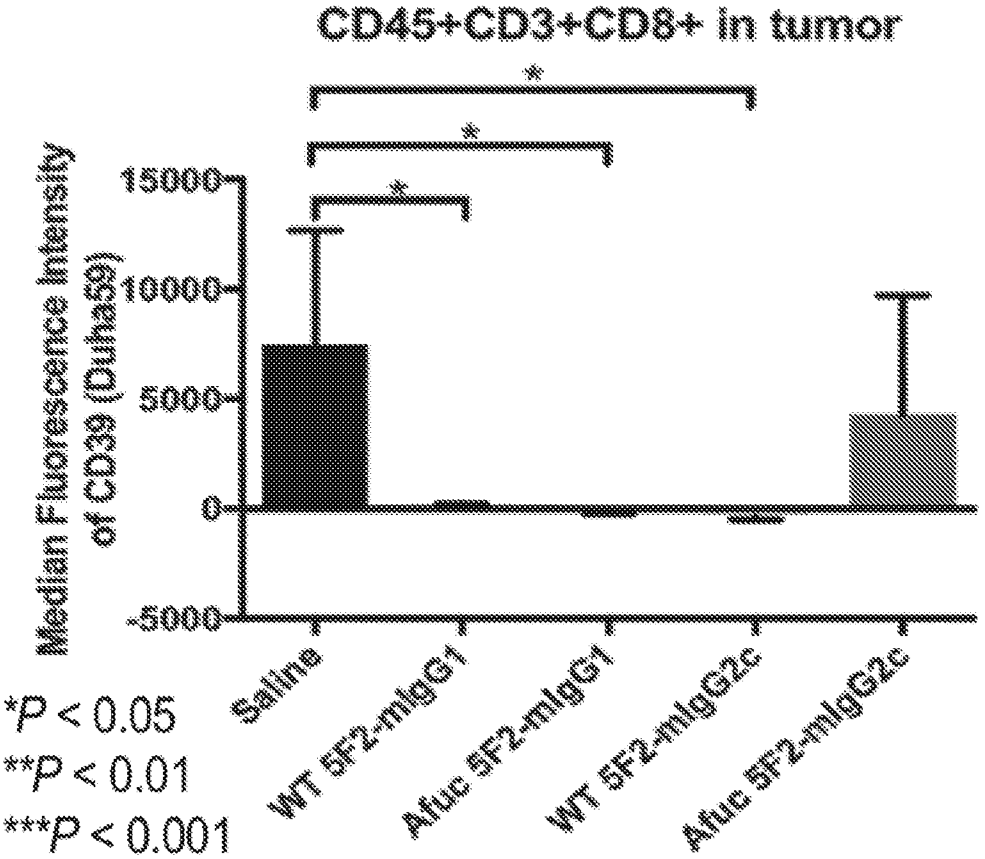
Figure 40A:
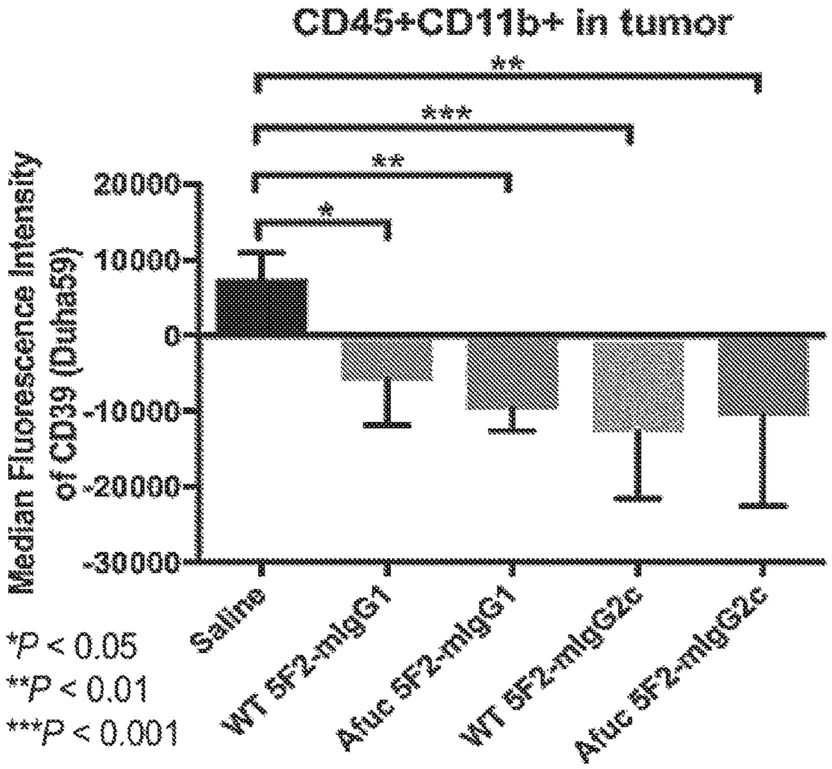
FIGS. 40A-40D are a set of graphs showing that in the tumor, decreases of CD39 expression are noted in all myeloid derived subpopulations (CD45$^+$CD11 b$^+$) post 5F2 mAb treatments, except for Gr1 high populations, in contrast to saline treated mice.
Figure 40B:
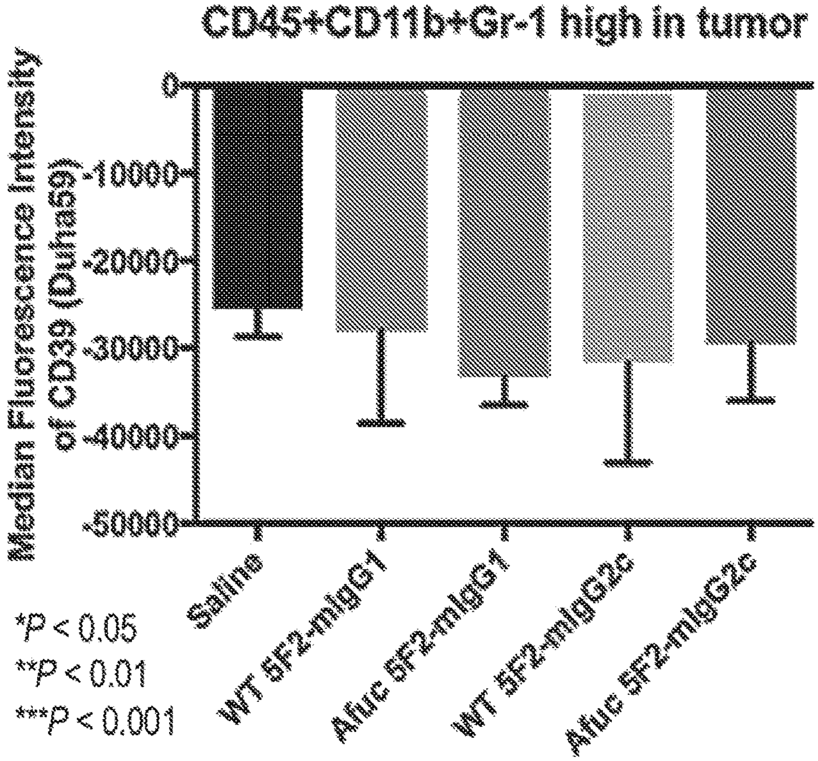
Figure 40C:
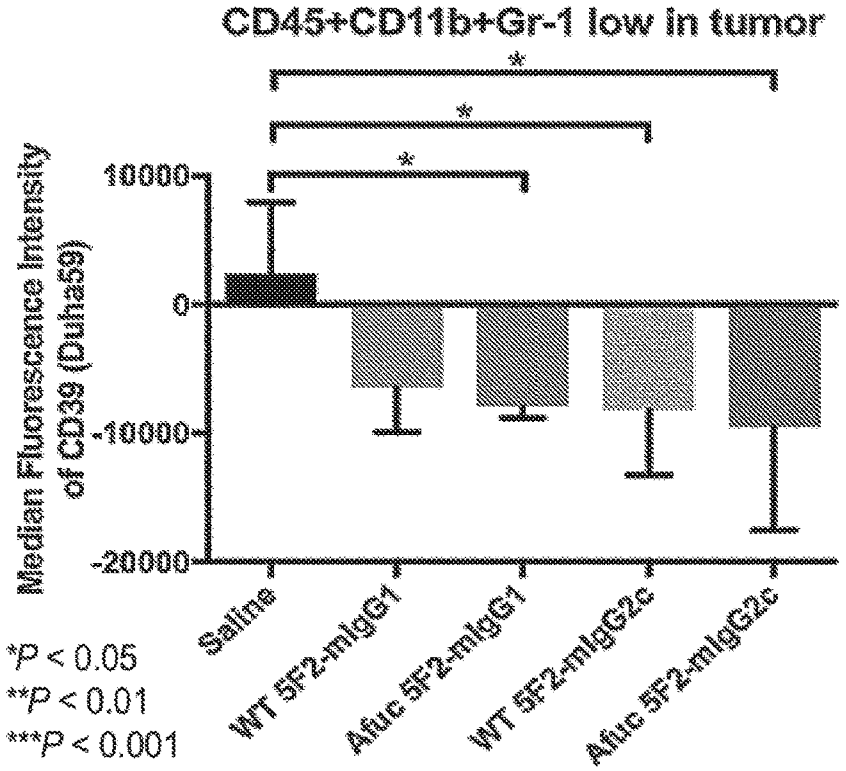
Figure 40D:
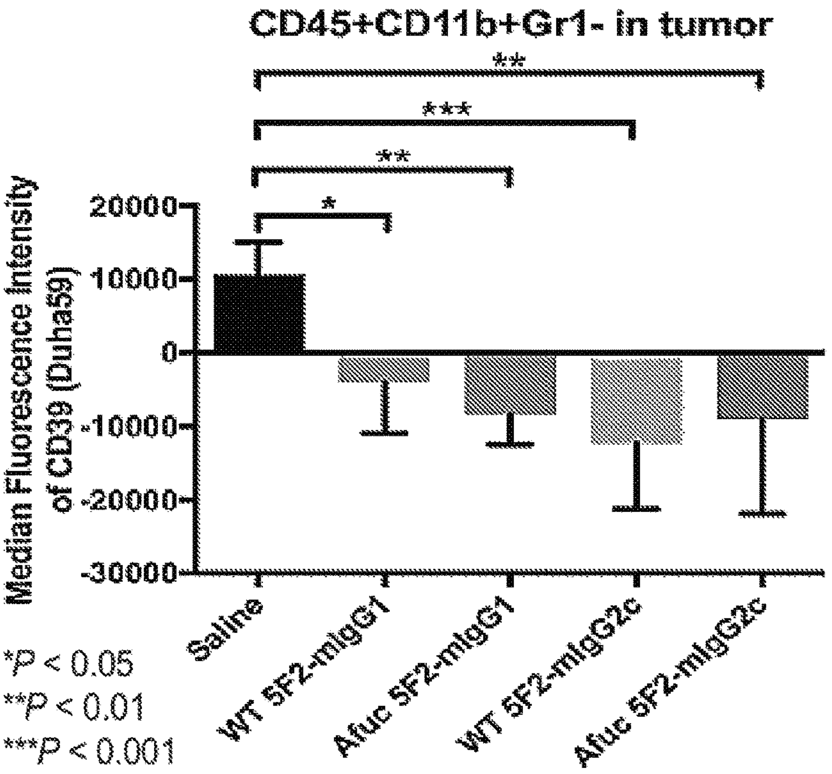
Figure 41A:
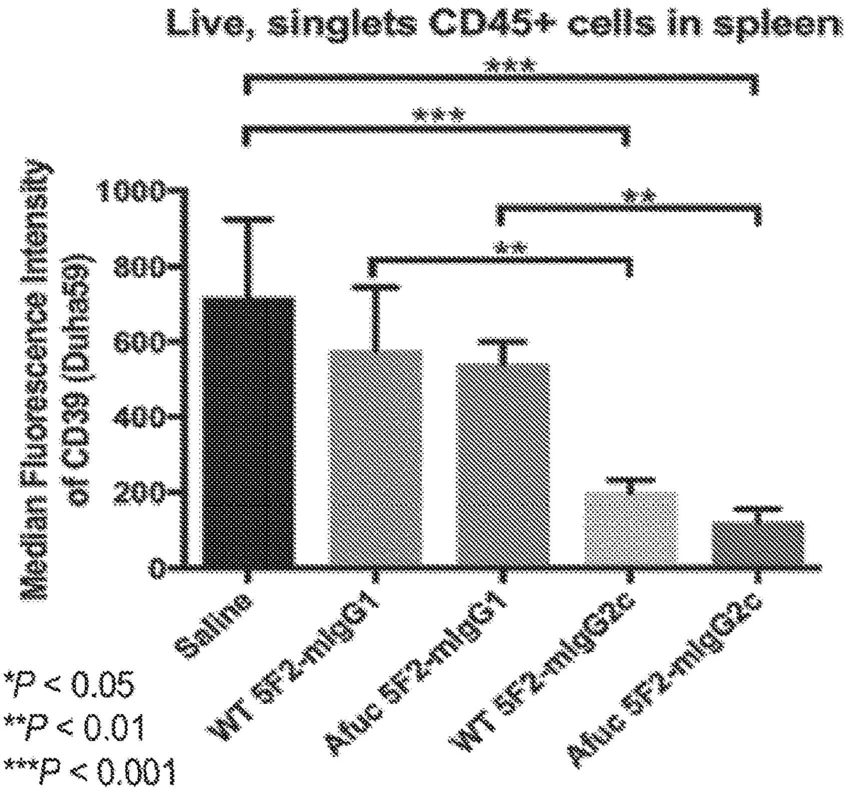
FIGS. 41A-41E are a set of graphs showing that in the spleen, decreases of CD39 expression are noted in all T cell subsets (CD45$^+$CD3$^+$) post 5F2 mAb treatments, in contrast to saline treated mice.
Figure 41B:
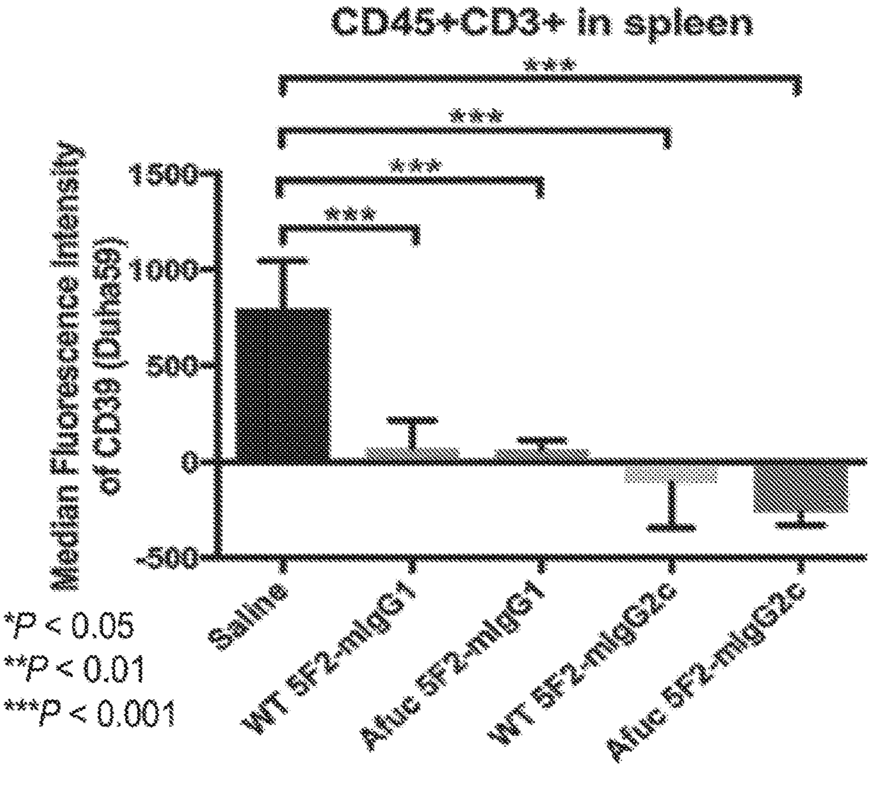
Figure 41C:
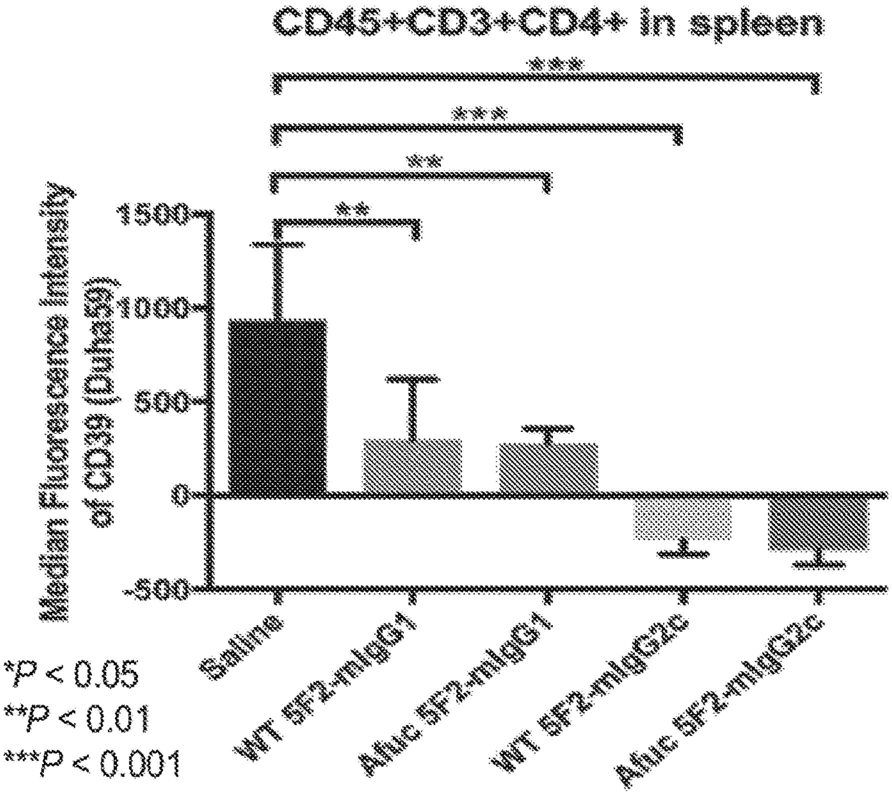
Figure 41D:
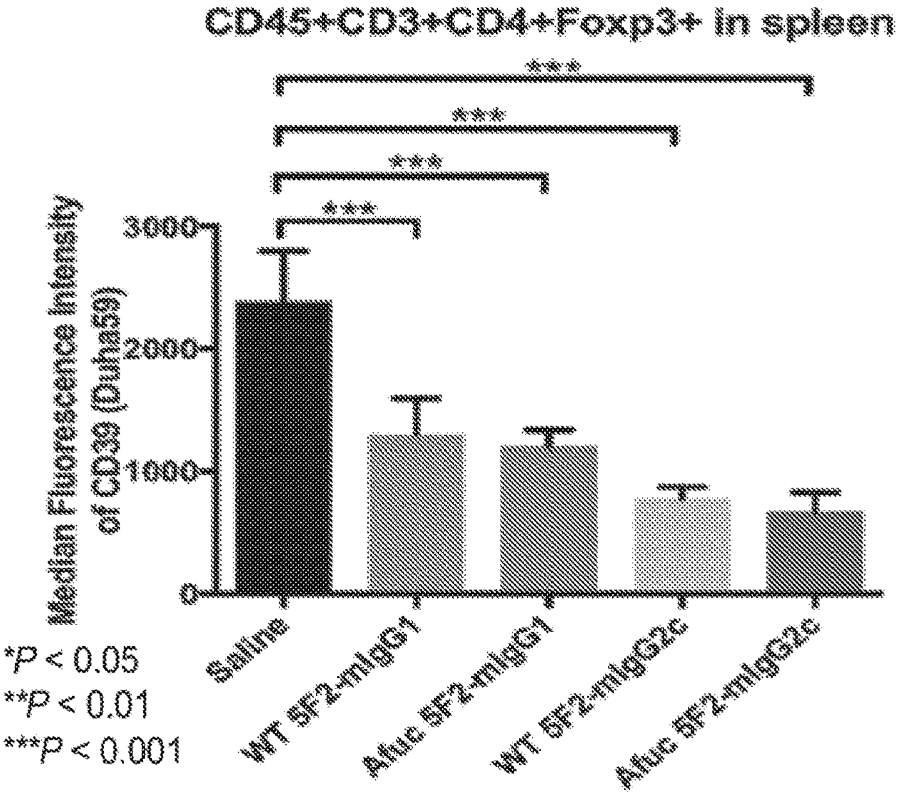
Figure 41E:
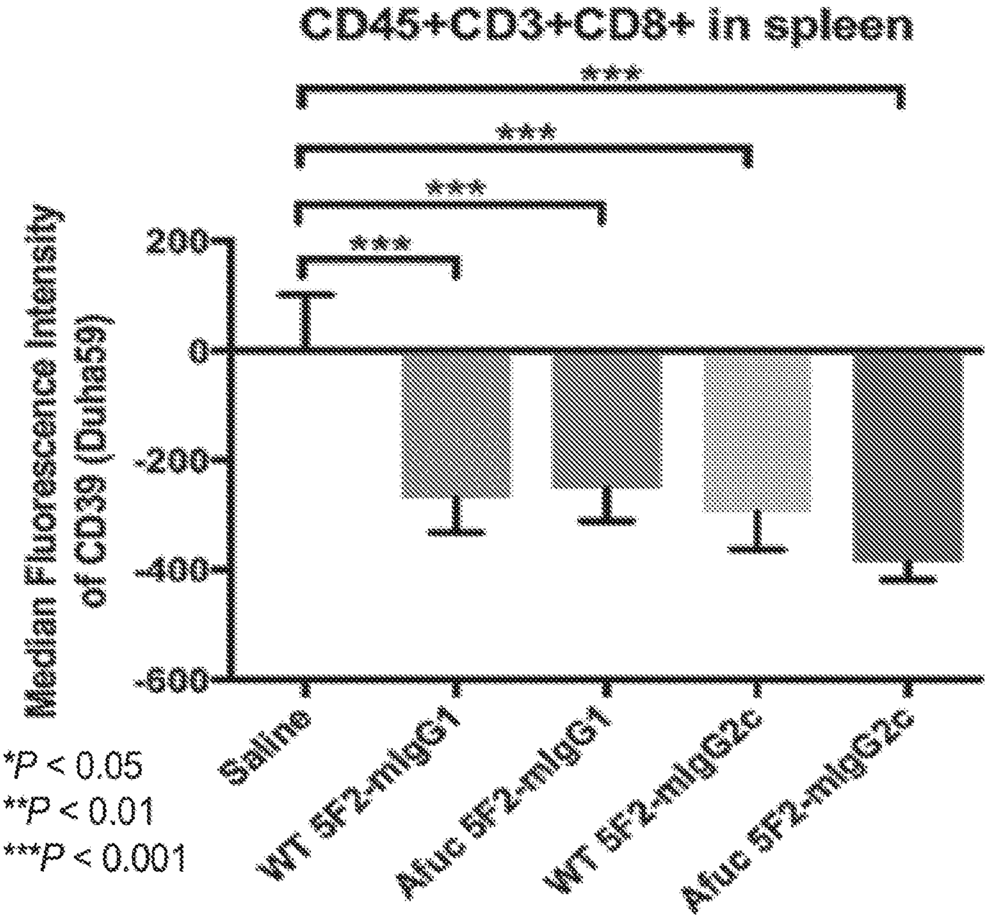
Figure 42A:
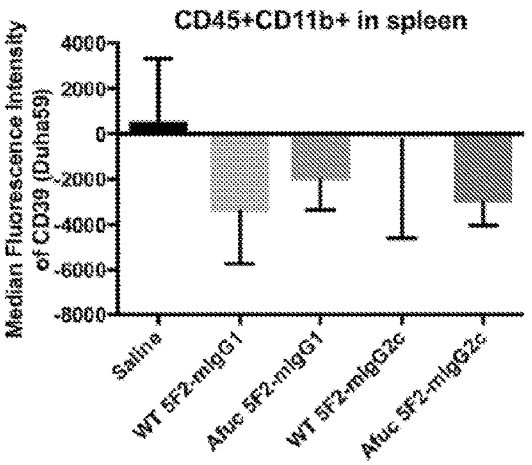
FIGS. 42A-42D are a set of graphs showing that in the spleen, decreases of CD39 expression are noted in all myeloid derived cell subpopulations (CD45$^+$CD11 b$^+$) post 5F2 mAb treatments, in contrast to saline treated mice.
Figure 42B:
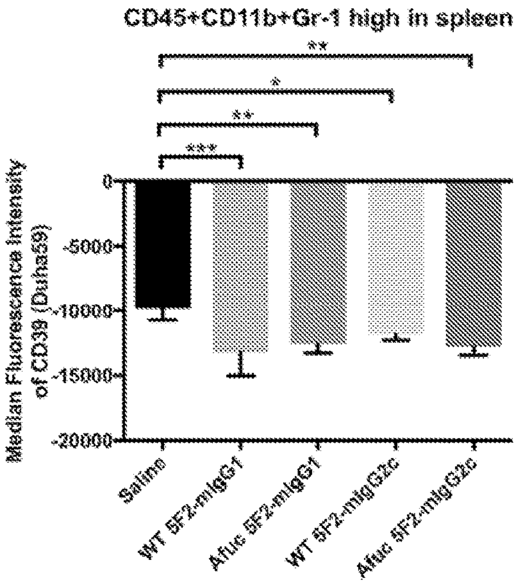
Figure 42C:
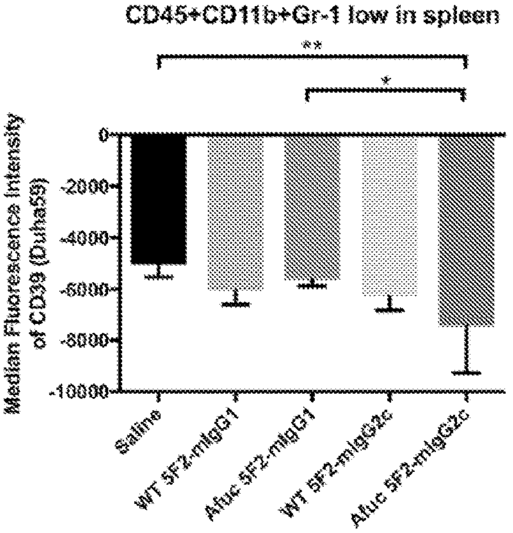
Figure 42D:
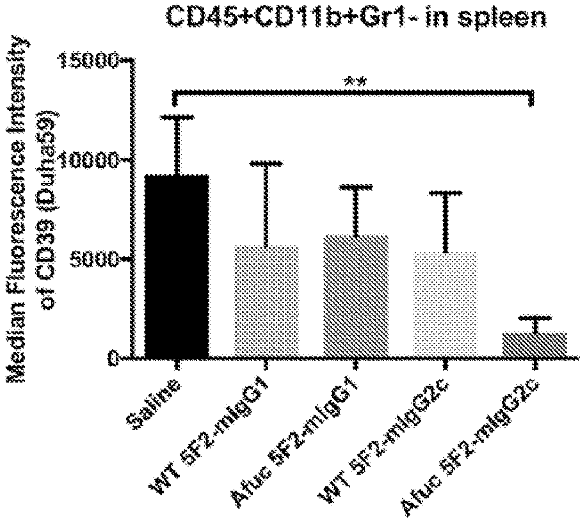
Figure 43A:
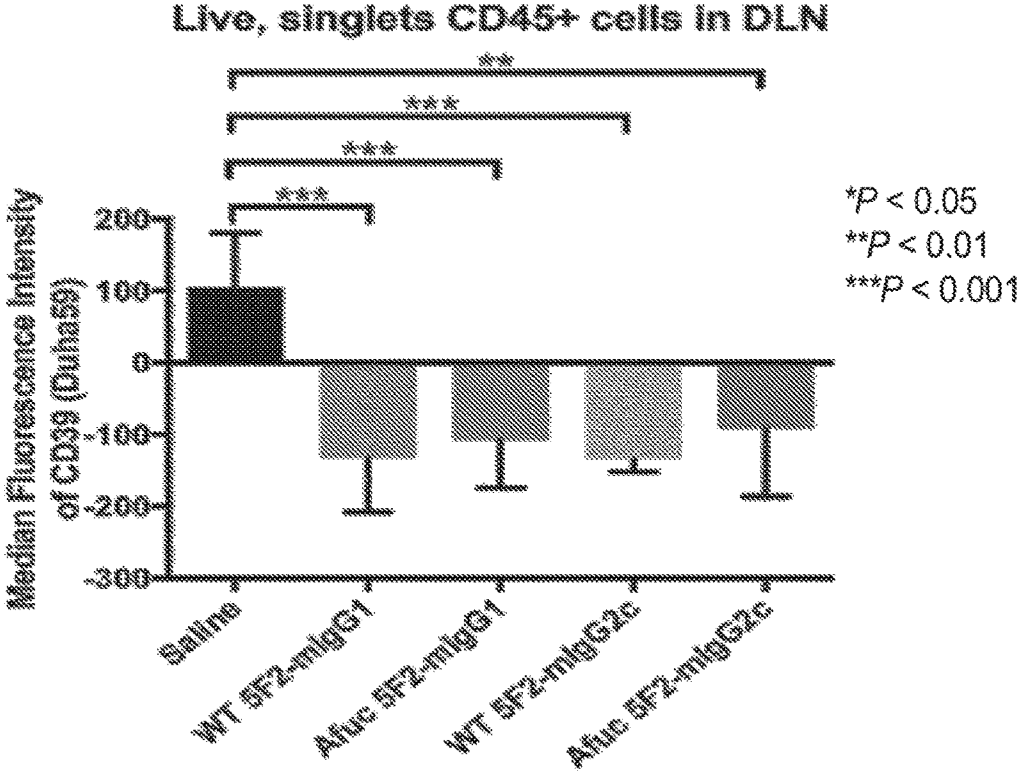
FIGS. 43A-43F are a set of graphs showing that in the draining lymph node (DLN), decreases of CD39 expression are noted in all T cell subsets (CD45$^+$CD3$^+$) (FIGS. 43A-43E) as well as myeloid derived subpopulations (CD45$^+$ CD11 b$^+$) (FIG. 43F) post 5F2 mAb treatments, in contrast to saline treated mice.
Figure 43B:
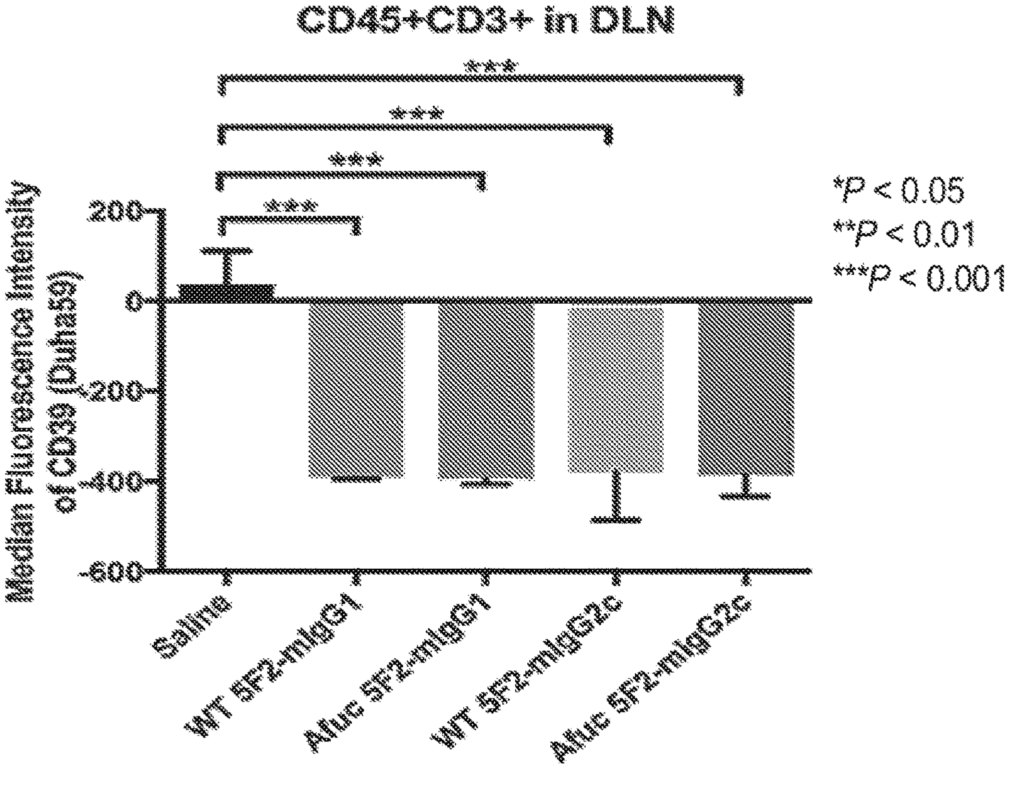
Figure 43C:
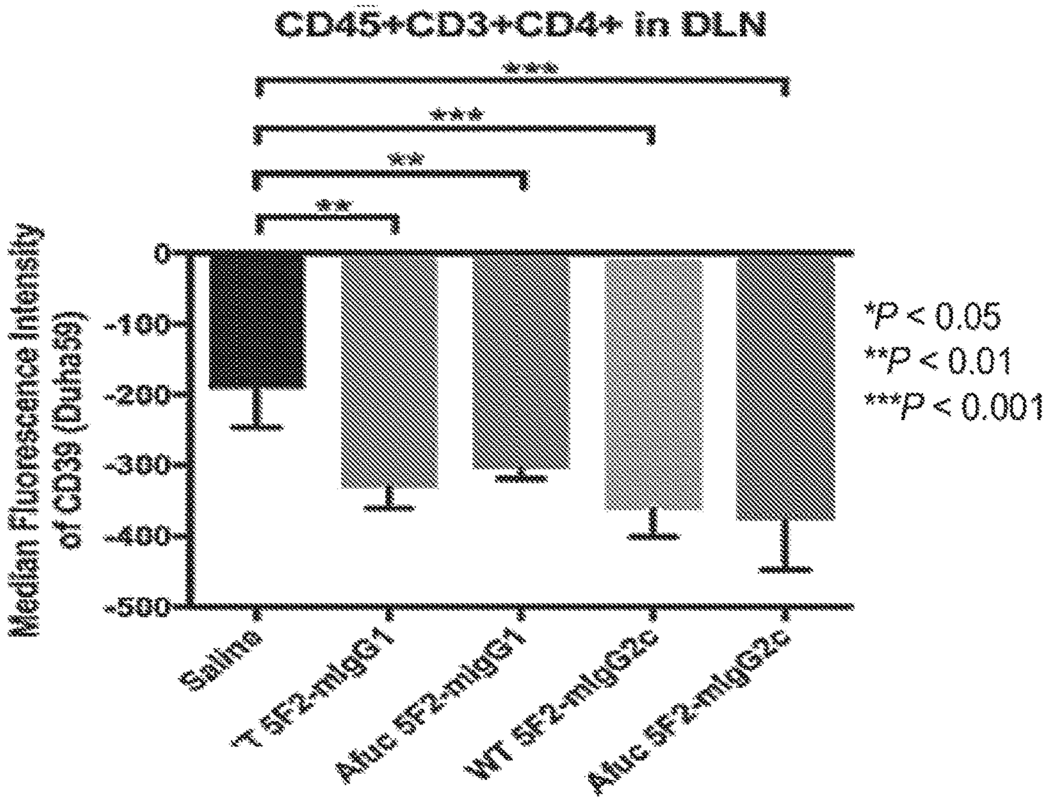
Figure 43D:
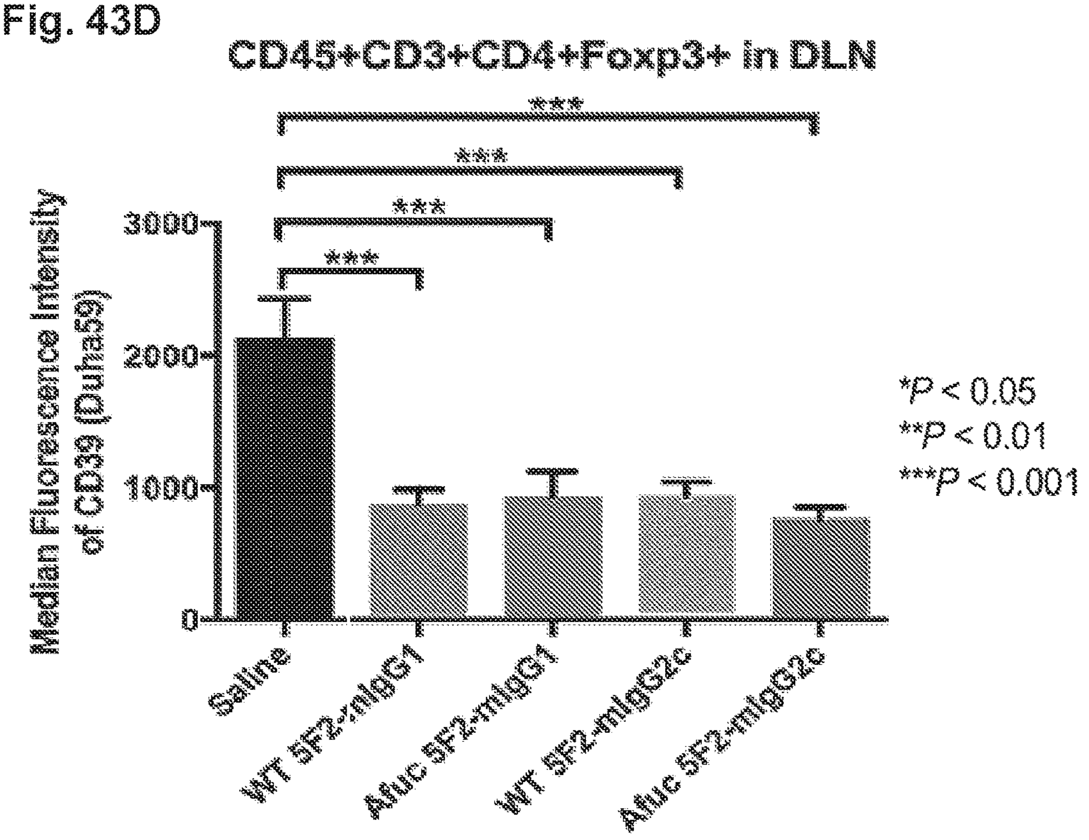
Figure 43E:
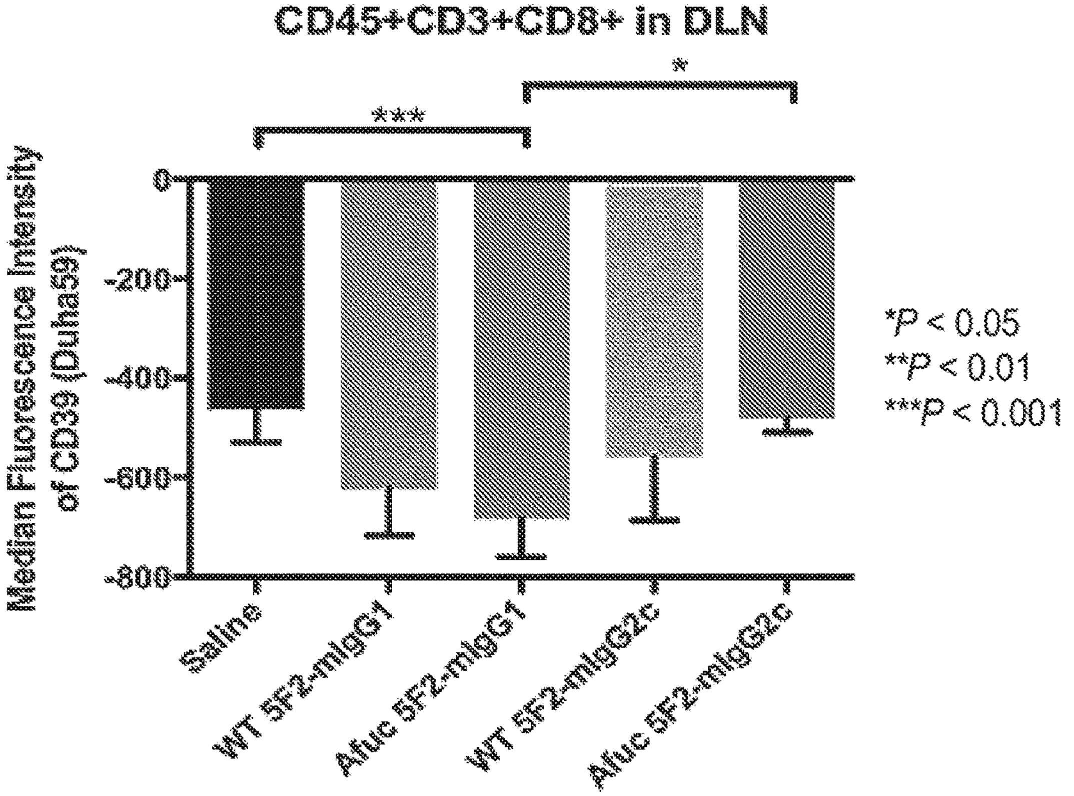
Figure 43F:
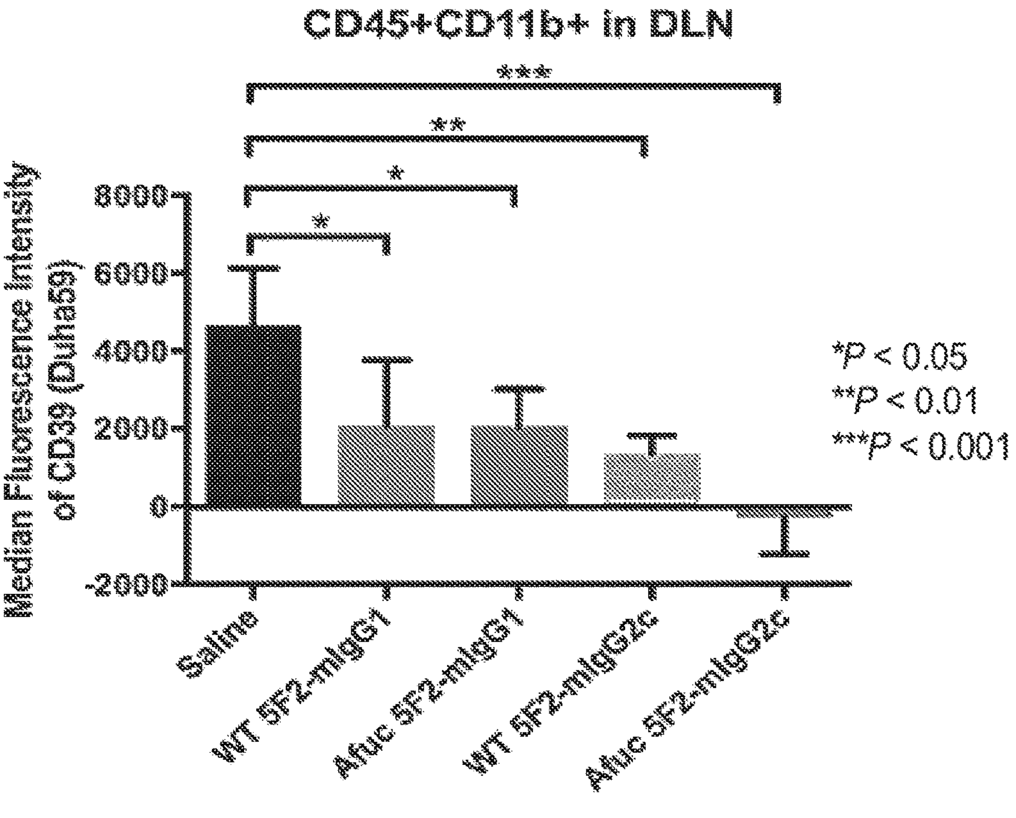
Figure 44A:
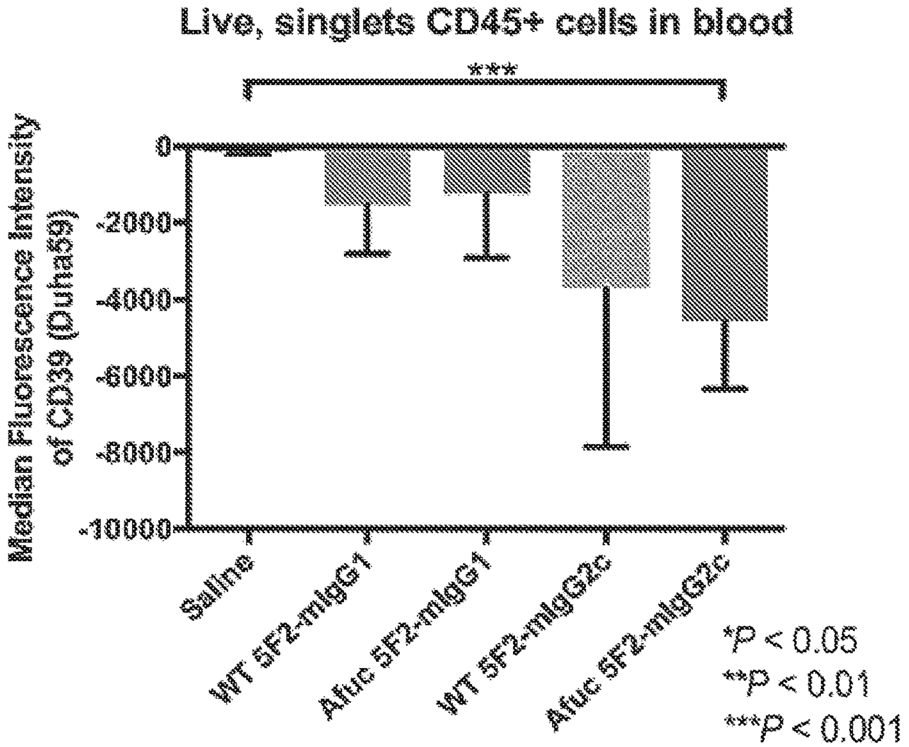
FIGS. 44A-44E are a set of graphs showing that in the blood, decreases of CD39 expression are noted in all T cell subsets (CD45$^+$CD3$^+$) post 5F2 mAb treatments, in contrast to saline treated mice.
Figure 44B:
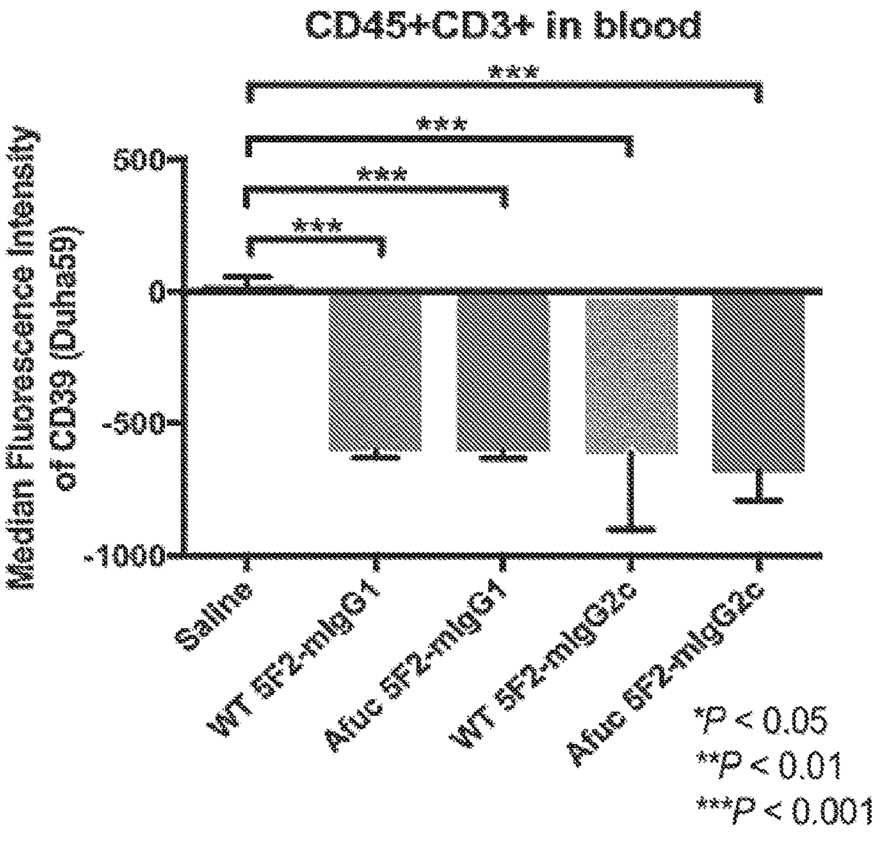
Figure 44C:
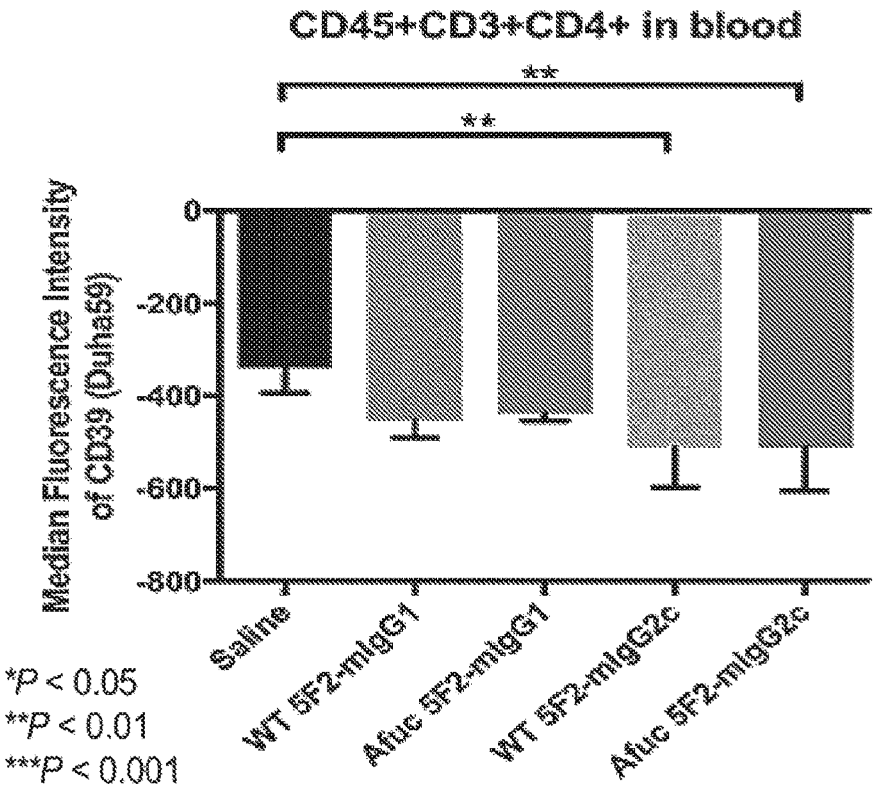
Figure 44D:
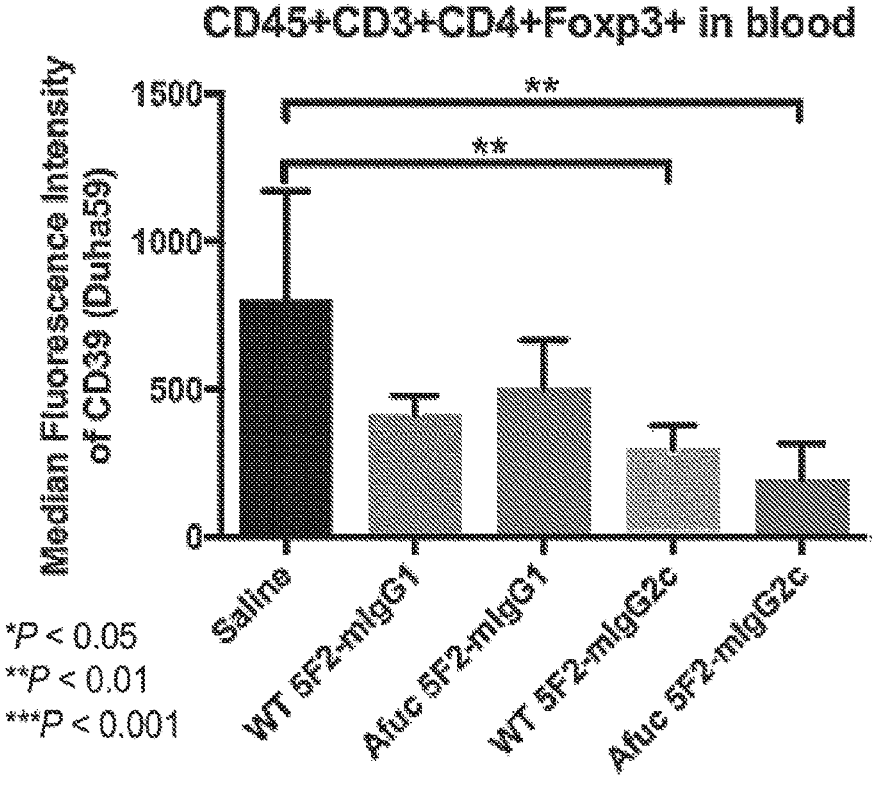
Figure 44E:
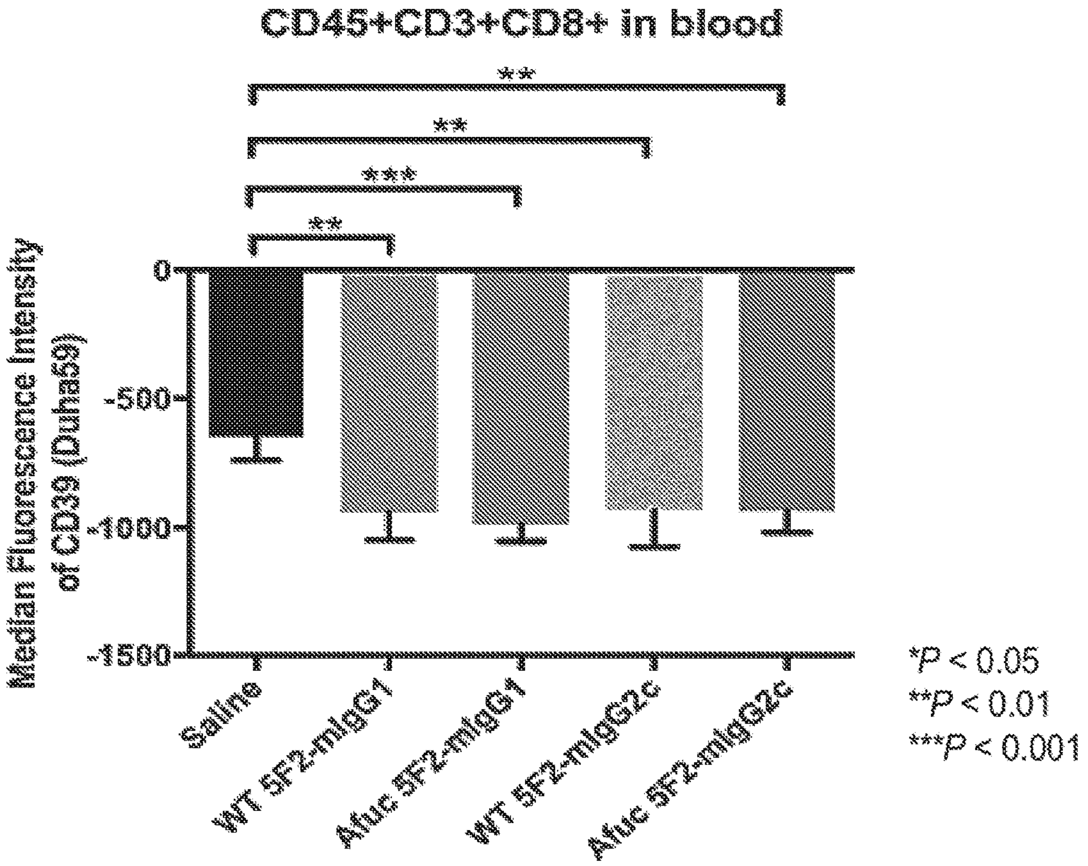
Figure 45A:
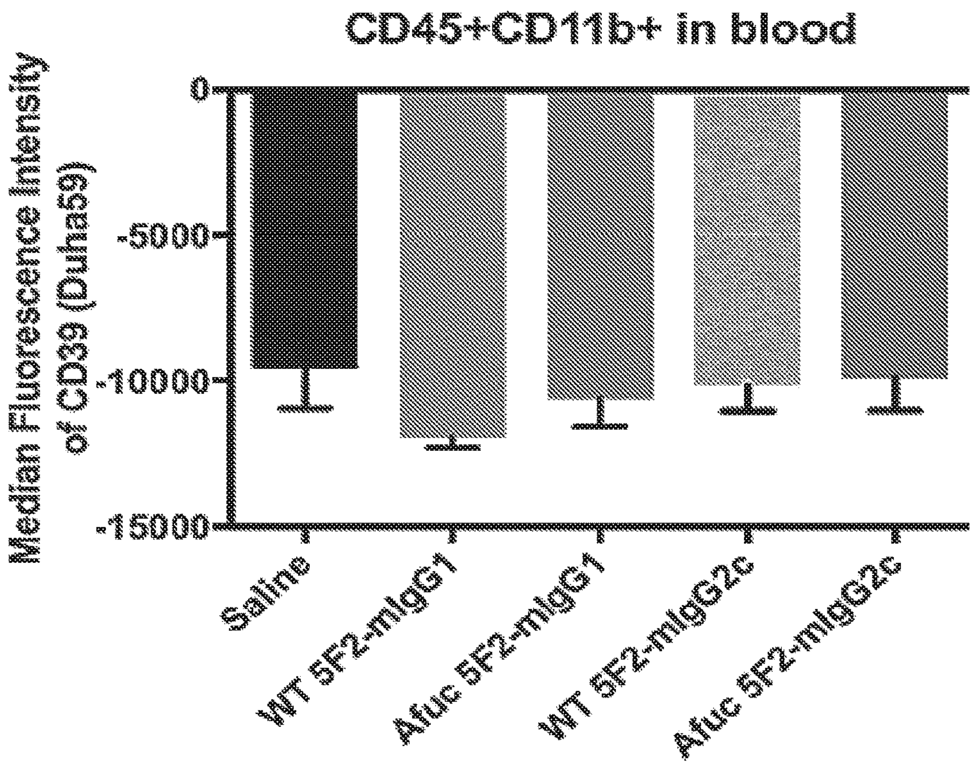
FIGS. 45A-45D are a set of graphs showing that in the blood, CD39 expression on myeloid derived subpopulations (CD45$^+$CD11 b$^+$) is not altered by any 5F2 mAb treatments, in contrast to saline treated mice.
Figure 45B:
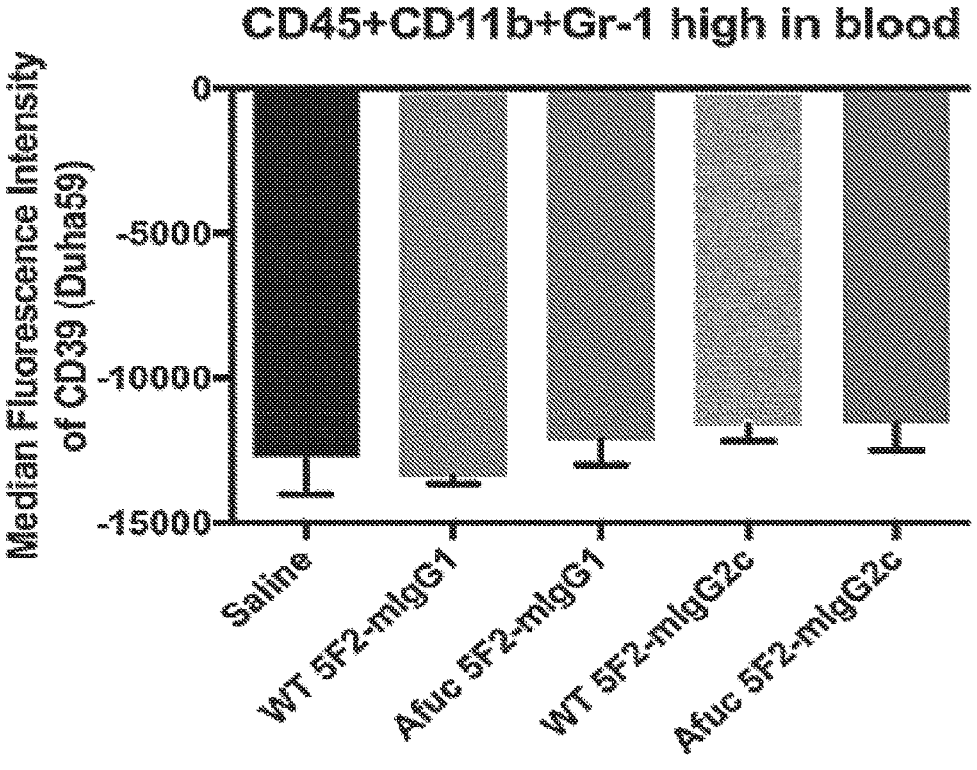
Figure 45C:
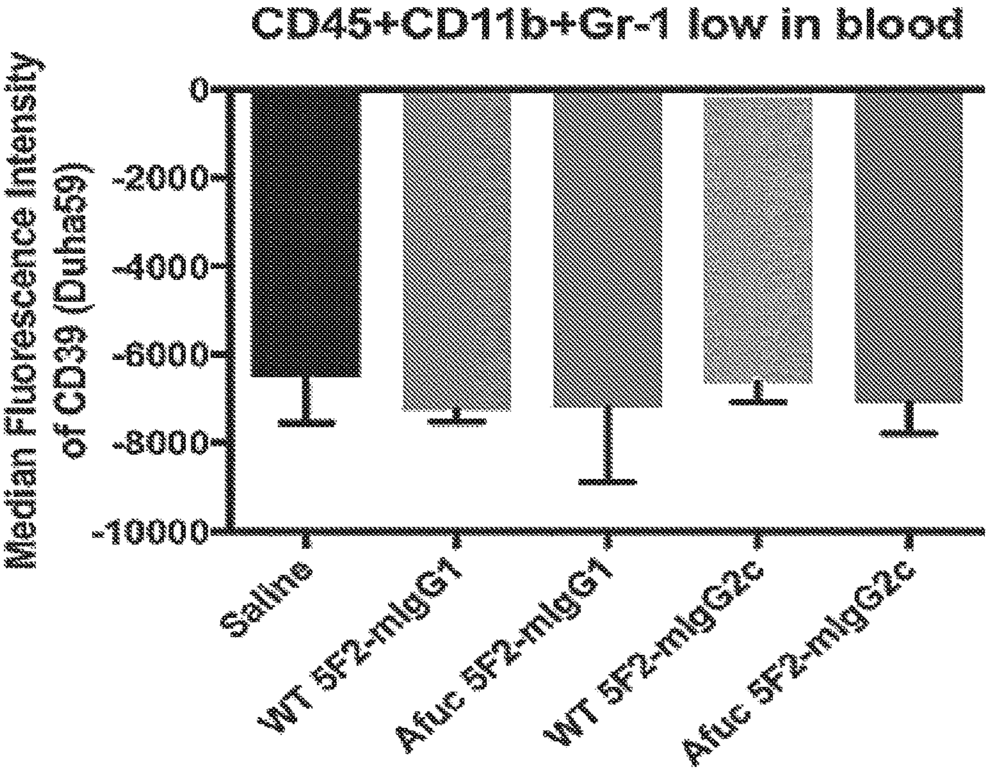
Figure 45D:
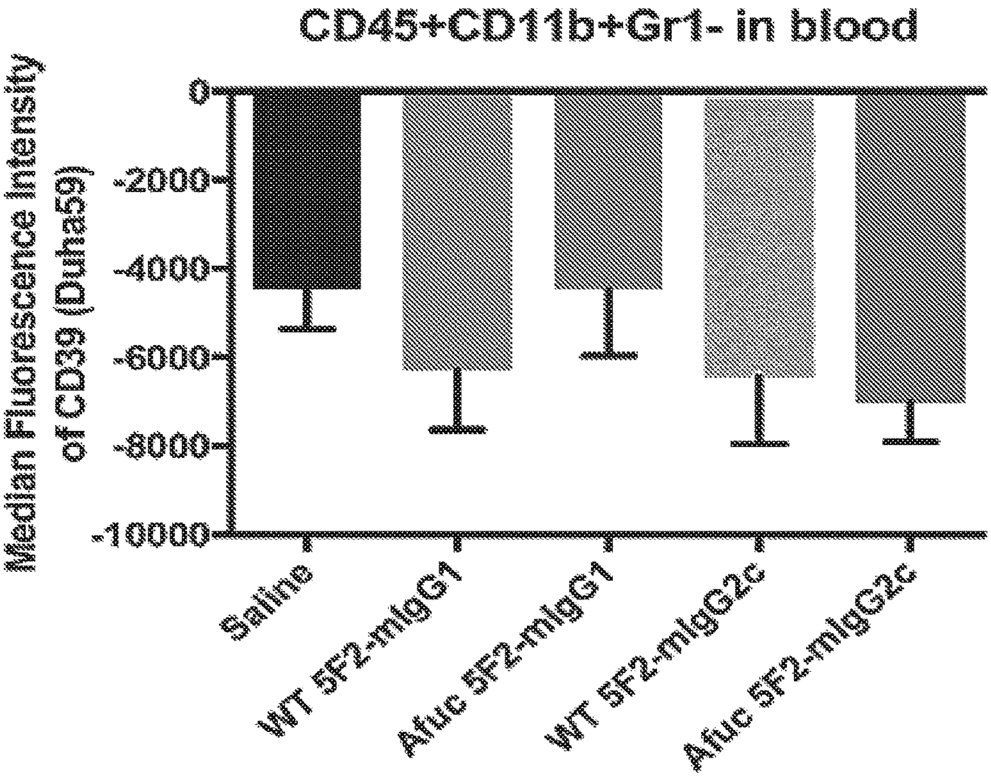
Figure 46A:
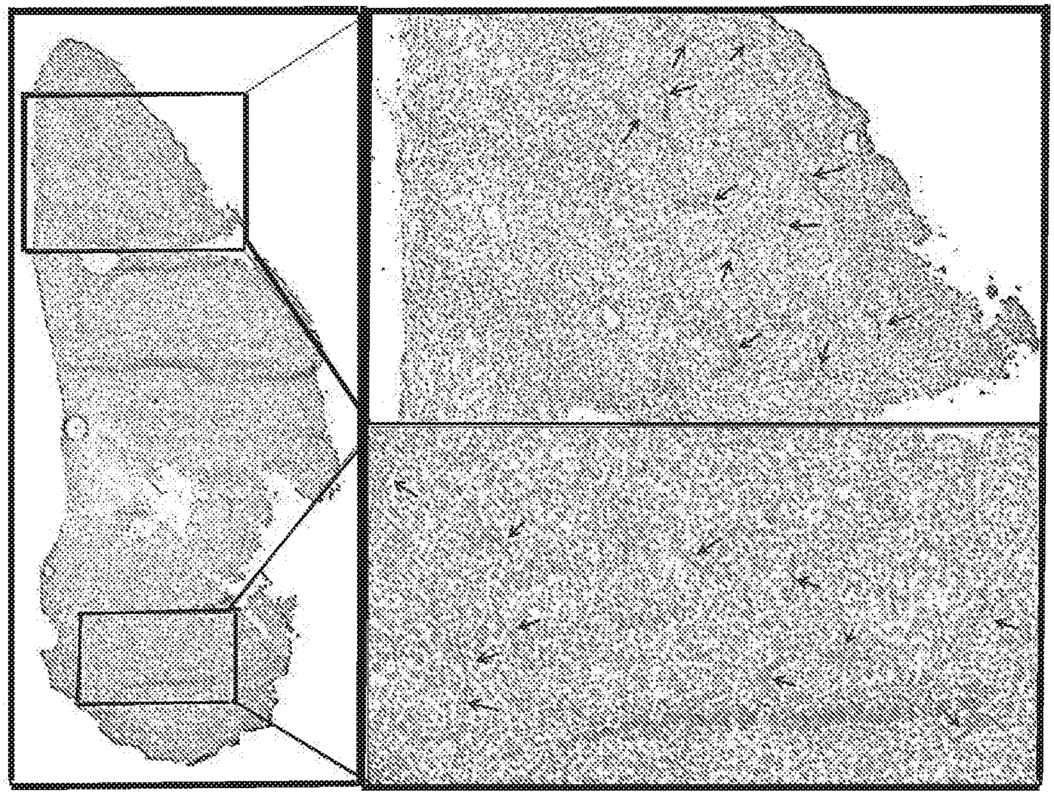
FIGS. 46A-46D are a set of IHC images showing CD39 staining of tumor vasculature treated with saline (FIGS. 46A and 46B) or afucosylated 5F2-mIgG2c (FIGS. 46C and 46D).
Figure 46B:
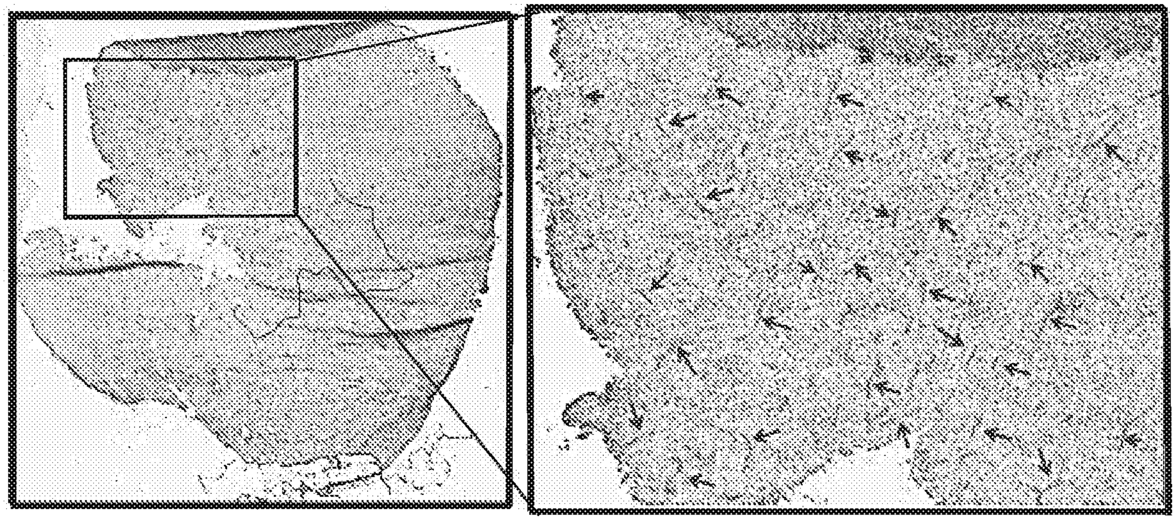
Figure 46C:
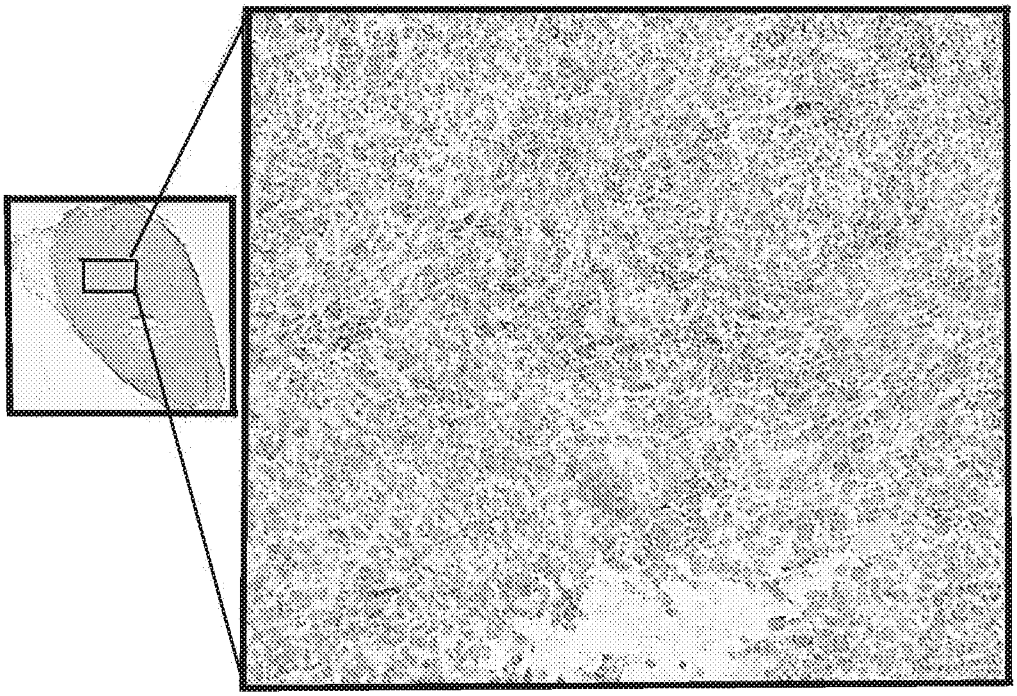
Figure 46D:
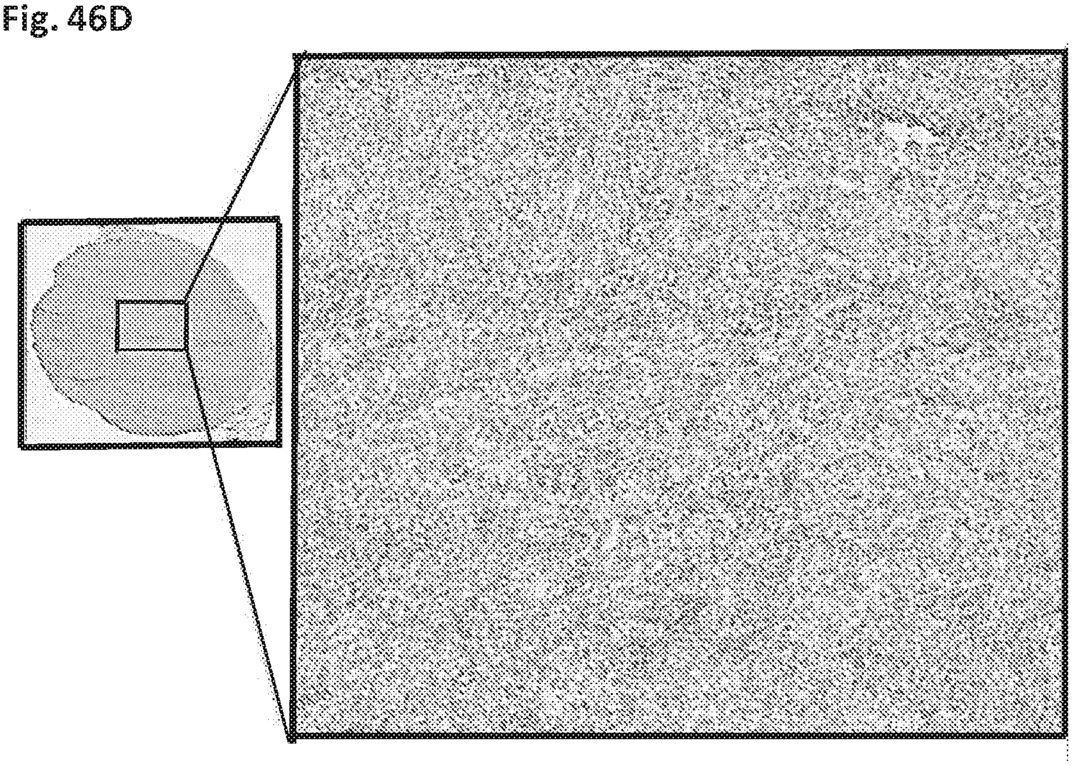

FIGS. 35A and 35B & 36; BT471-485. LysMCre/CD39 KO MC38 Tumor-Bearing Mice Received Afuc 5F2-mIgG2c Afucosylated 5F2-mIgG2c mAb fails to block MC38 tumor growth in mice with conditional deletion of CD39 on monocytes and macrophages (LysMCre/CD39KO). $1.0\times10^5$ MC38 cells were injected (s.c.) into the right lower flank of LysMCre/CD39KO mice (females at ages of 10-16 weeks; in house) on day 0. Afuc 5F2-mIgG2c mAb (200 μg in 200 μl of saline via i.p.) were given to tumor-bearing mice on days 8, 11 and 14 (mice were randomized to two groups based on tumor volume). Mice received 200 μl of saline served as controls. Tumor volume was measured as described above. Studies were terminated on day 27 (when any tumor volume reaches around 4000 $mm^3$). n=5 per group.

FIGS. 37A-46D; BT541-584. MC38 Tumor-Bearing Mice Received 4 Various 5F2 mAbs Afucosylated 5F2-mIgG2c shows superior in-vivo tumor-inhibitory activity against established MC38 colorectal cancer to any other types of 5F2 mAbs. $1.0\times10^5$ MC38 cells were injected (s.c.) into the right lower flank of wildtype FoxP3-GFP knock-in reporter mice (males at ages of 8-16 weeks; in house) on day 0. Various 5F2 mAbs (200 μg of each mAb in 200 μl of saline via i.p.) were given to tumor-bearing mice on days 9, 12 and 15 (mice were randomized to five groups). Tumor volume was measured as described above. Studies were terminated on day 17. Mice received 200 μl of saline served as controls. Single-cell suspensions were prepared from spleen, the right Inguinal lymph node (as the Draining lymph node (DLN)), blood as well as tumor, and subjected for FACS analysis using a CytoFLEX flow cytometer. CD45 was used as a surface marker to gate all lymphocytes. Duha59, an anti-mouse CD39 antibody recognizes totally different epitope from 5F2 was used for FACS staining. n=7 in saline group and n=4-5 per group in mAb treated mice.

Figure 47A:
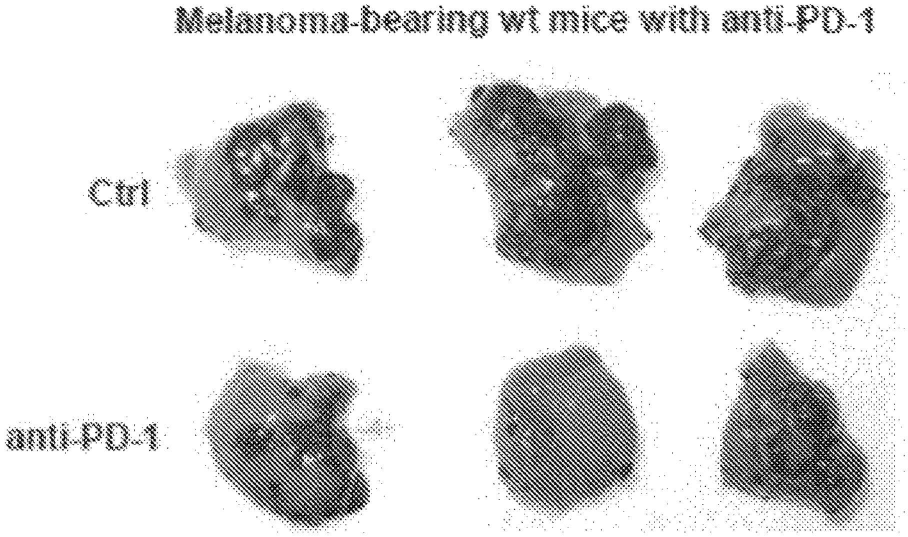
FIG. 47A is a photograph of tumors from melanoma-bearing wt mice treated with anti-PD-1 antibodies.
Figure 47B:
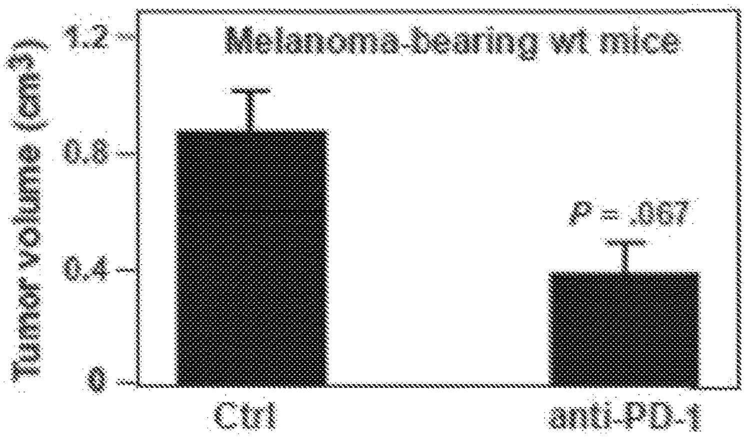
FIG. 47B is a graph showing tumor volume of melanoma-bearing wt mice treated with anti-PD-1 antibodies.
Figure 47C:
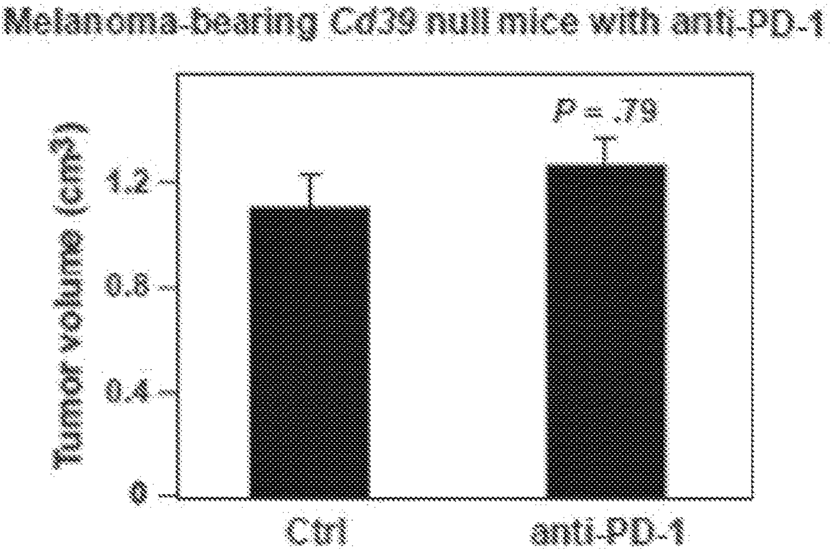
FIG. 47C is a graph showing tumor volume of melanoma-bearing CD39 null mice treated with anti-PD-1 antibodies.
Figure 48A:
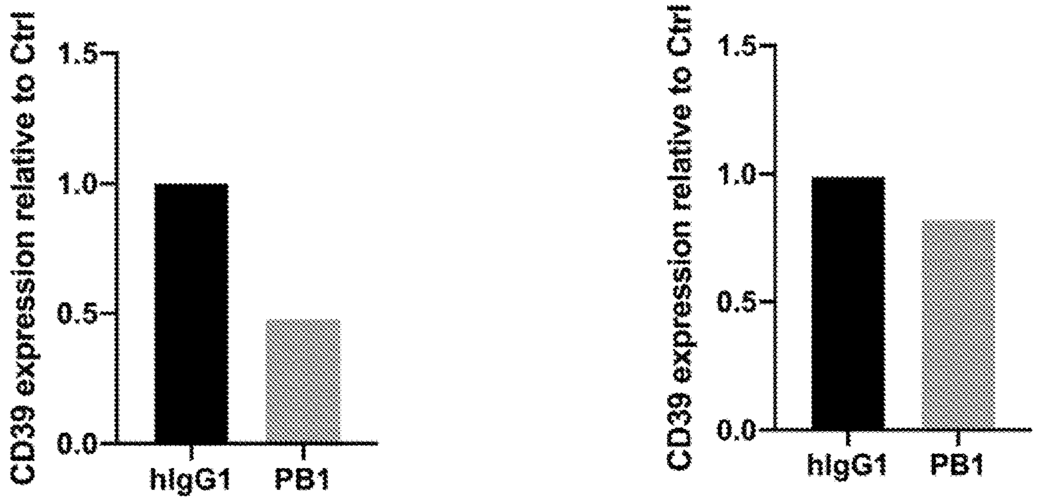
FIGS. 48A-48E are sets of graphs showing CD39 expression. Anti-hCD39 antibodies designated PB1 (FIG. 48A), PB2 (FIG. 48B), PB3 (FIG. 48C), PB4 (FIG. 48D) and PB5 (FIG. 48E) can deplete CD39 on otherwise CD39-positive human B lymphoblastoid cells (HCC1739BL) mediated at least in part through antibody-mediated target cytosis of CD39. CD39-expressing HCC1739BL cells were cocultured with or without THP-1 monocytic cells (THP-1: HCC1739BL=3:2), in the presence of rabbit anti-hCD39 antibody chimerized with a human Fc (IgG1) (4 μg/ml) or human IgG1 isotype control (4 μg/ml) for 43 hours or 2 hours. CD39 expression on HCC1739BL cells was detected by a staining antibody that recognizes different epitope from this chimeric antibody. THP-1 and HCC1739BL cells were gated separately by CD20 staining using a CytoFlexLX flow cytometer. The first panel in each figure is data representing as, within cocultures, relative intensity of cells treated with the chimeric antibody in contrast to cells treated with human IgG1 isotype control. The second panel in each figure is data representing is represented as relative intensity of cocultured cells compared with HCC1739BL cells alone.
Figure 48B:
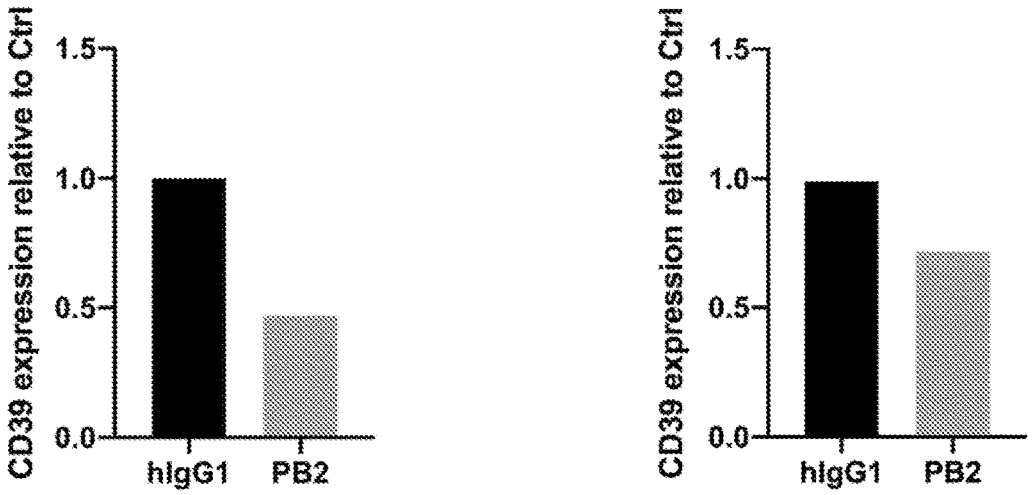
Figure 48C:
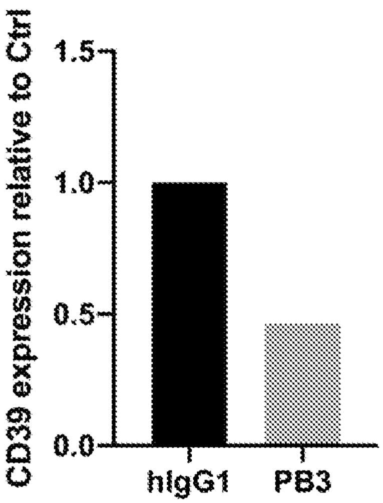
Figure 48C:
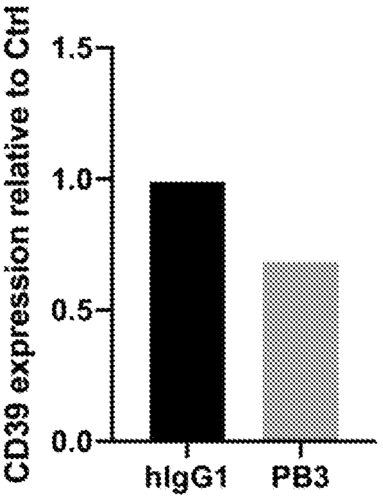
Figure 48D:
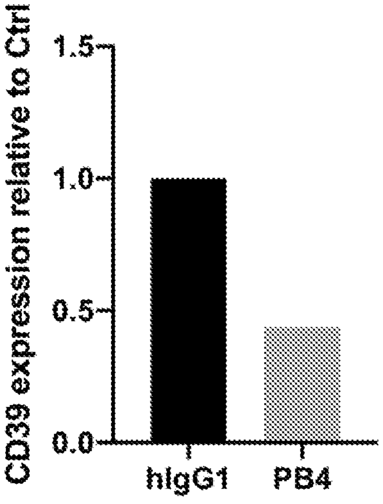
Figure 48D:
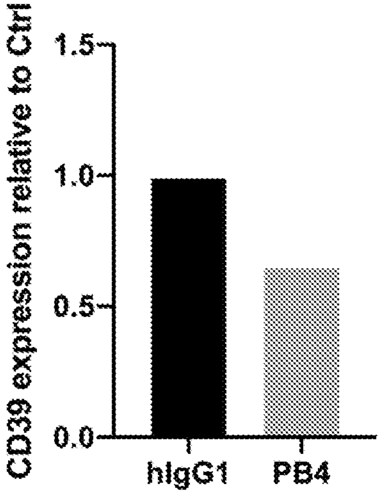
Figure 48E:
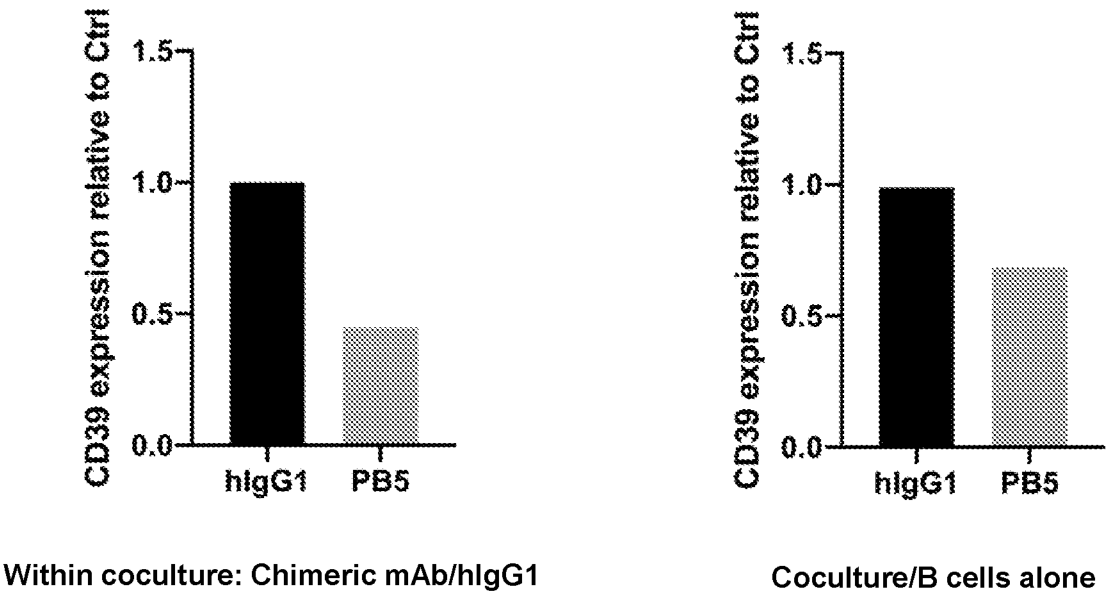

FIGS. 47A and 47B; Melanoma-Bearing Wt or CD39 Null Mice Received Anti-PD-1 Abs Melanoma-bearing wt mice were treated with anti-PD-1. Anti-PD-1 exhibited antitumor effects only in wt mice but not CD39 null mice. This suggests that PD-1 may function, at least in part, via harnessing of pathways common with those of purinergic signaling.

FIGS. 48A-48E and 49A-49D; CD39 Expression and Depletion

Anti-hCD39 antibodies designated PB1 (FIG. 48A), PB2 (FIG. 48B), PB3 (FIG. 48C), PB4 (FIG. 48D) and PB5 (FIG. 48E) can deplete CD39 on otherwise CD39-positive human B lymphoblastoid cells (HCC1739BL) mediated at least in part through antibody-mediated target cytosis of CD39. CD39-expressing HCC1739BL cells were cocultured with or without THP-1 monocytic cells (THP-1:HCC1739BL=3:2), in the presence of rabbit anti-hCD39 antibody chimerized with a human Fc (IgG1) (4 μg/ml) or human IgG1 isotype control (4 μg/ml) for 43 hours or 2 hours. CD39 expression on HCC1739BL cells was detected by a staining antibody that recognizes different epitope from this chimeric antibody. THP-1 and HCC1739BL cells were gated separately by CD20 staining using a CytoFlexLX flow cytometer. The first panel in each figure is data representing as, within cocultures, relative intensity of cells treated with the chimeric antibody in contrast to cells treated with human IgG1 isotype control. The second panel in each figure is data representing is represented as relative intensity of cocultured cells compared with HCC1739BL cells alone.

Figure 49A:
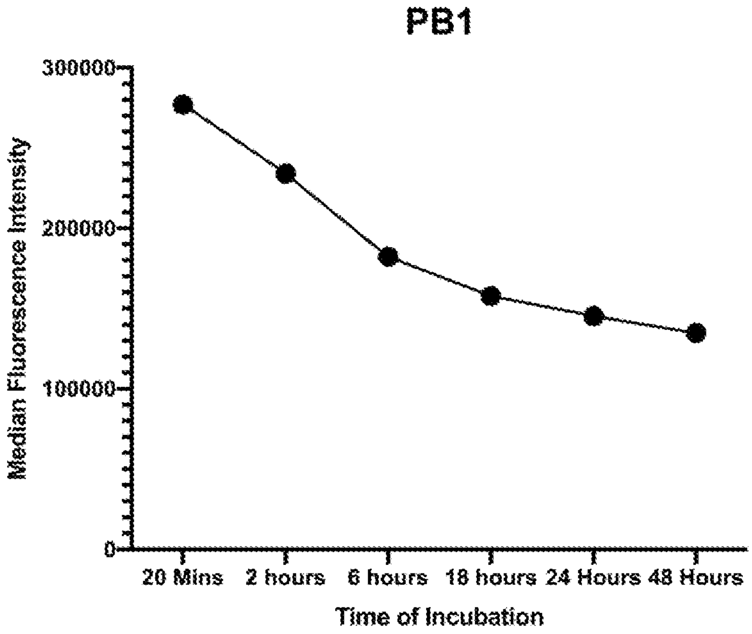
FIGS. 49A-49D are graphs showing CD39 depletion. Anti-hCD39 antibodies may cause depletion of CD39 through mechanisms also include shedding and/or internalization in HCC1739BL cells. CD39-expressing HCC1739BL cells were incubated with rabbit anti-hCD39 antibody chimerized with a human Fc (IgG1) (2 μg/ml) in a cell culture incubator for indicated times. After antibody incubation, cells were washed twice and stained with secondary antibody (Donkey anti-human IgG, Fcγ fragment specific antibody conjugated with AF488), followed by flow cytometric analysis on a CytoFlexLX machine.
Figure 49B:
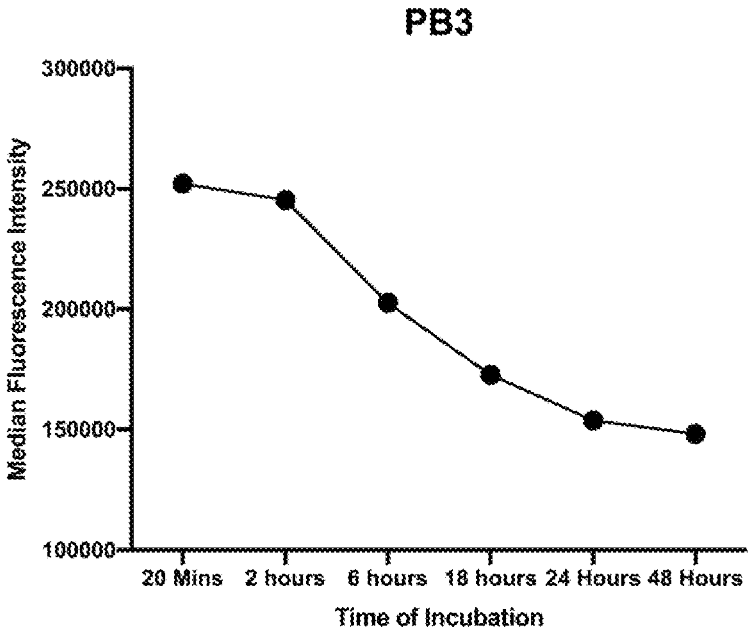
Figure 49C:
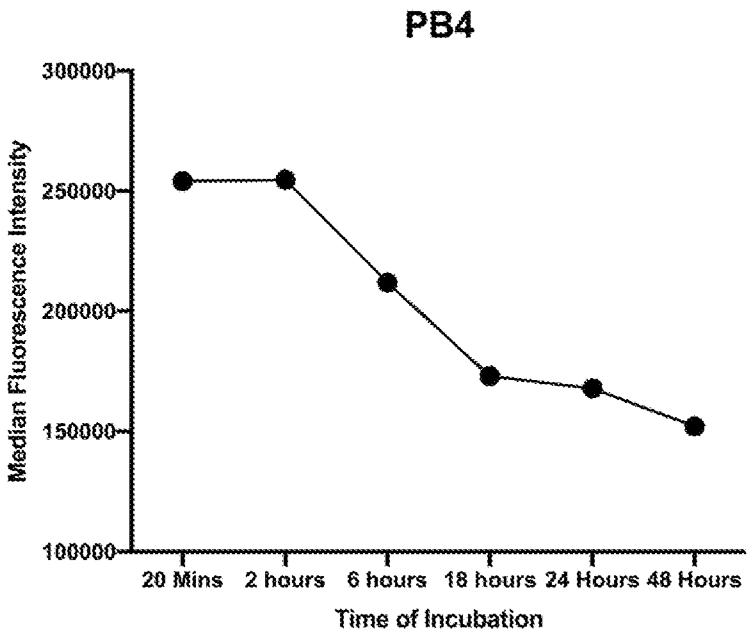
Figure 49D:
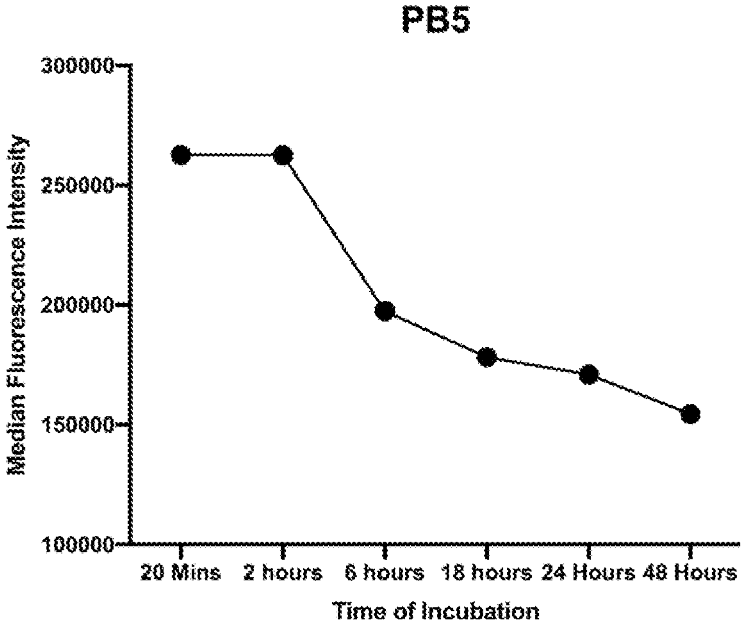

Anti-hCD39 antibodies may cause depletion of CD39 through mechanisms also include shedding and/or internalization in HCC1739BL cells. CD39-expressing HCC1739BL cells were incubated with rabbit anti-hCD39 antibody chimerized with a human Fc (IgG1) (2 μg/ml) in a cell culture incubator for indicated times. After antibody incubation, cells were washed twice and stained with secondary antibody (Donkey anti-human IgG, Fcγ fragment specific antibody conjugated with AF488), followed by flow cytometric analysis on a CytoFlexLX machine. FIG. 49A shows PB1, FIG. 49B shows PB3, FIG. 49C shows PB4, and FIG. 49D shows PB5.

Descriptions of IHC Data:

Immunohistochemical staining of s.c. tumor sections obtained from MC38-bearing mice revealed that protein expression of CD39 is strongly induced within the tumor sites from the saline-treated control mice, on both tumor-infiltrating lymphocytes and the tumor vasculature (as stained for CD31). Intriguingly, upon Afuc 5F2-mIgG2c mAb treatment, such high levels of CD39 on both tumor cell compartments were markedly decreased. These data indicate that blockade of CD39 using Afuc 5F2-mIgG2c mAb alone (as a monotherapy) is able to achieve enhanced anticancer activity by concurrent inhibition of CD39 functions within these two major tumor cell compartments, e.g., augmenting anticancer immunity and limiting tumor angiogenesis.

Materials and Methods

Animals:

Seven weeks old male or female wildtype C57BL/6 mice were purchased from Taconic (MA) or the Jackson Laboratory (Bar Harbor, ME) and hosted in the Animal Research Facility at Beth Israel Deaconess Medical Center (BIDMC) for at least 1-2 weeks before experimentation. Eight- to eighteen-week old male or female wildtype FoxP3-GFP knock-in mice of the C57BL/6 strain (a reporter mouse strain expresses Green Fluorescent Protein (GFP) in $FoxP3^+$ Treg cells, were generated as described previously (Deaglio et al. J. Exp Med (2007) 204:1257; and Sun et al. Gastroenterology (2010) 139:1030). Mice containing the CD39flox allele were crossed with mice expressing Cre recombinase under the control of the myeloid lineage-specific promoter, lysosome M (LysM) (Stock No. 004781 from the Jackson Laboratory) to generate mice in which CD39 was deleted in monocytes, mature macrophages and granulocytes (LysM-Cre/CD39KO). Animal Experimentation Protocols were reviewed and approved by the Institutional Animal Care and Use Committees (IACUC) of BIDMC.

Cell Lines:

The full-length mouse CD39 cDNA gene (AF037366) was cloned into pTOG3 vector (Antagen, Boston, MA) at MluI and XhoI sites. 1.0 μg of pTOG3-mCD39 was co-transfected with 20 ng of a Cre-expressing plasmid pOG231 (Addgene) into CHO-E cells (Antagen), using FuGene 6 reagent according to the instructions of the manufacturer. Two days after transfection, cells were selected with Hygromycin B (800 μg/mL) in 10 cm tissue culture plates in DMEM supplemented with 5% FBS, 2 mM L-Glutamine and 100 units/mL Penicillin and Streptomycin. After another 10 days, drug-resistant single colonies were dislodged under a microscope and transferred to 48-well plates using 200 μL pipette tips. Positive clones identified by FACS staining were expanded, and the best clone in morphology and growth was selected to establish the mCD39.CHO cell line.

The full-length human CD39 cDNA gene (isoform 2, P49961-2) was cloned into pLentiTdT vector (Antagen) at NotI and BamHI sites. 2.0 μg of pLentiTdT-hCD39 was co-transfected with packaging plasmids expressing Env, Gag, and Pol into HEK293 cells, using FuGene 6 reagent according to the instructions of the manufacturer. Lentivirus-containing supernatants were collected after 3 days and used to infect Raji cells. TdTomato-positive Raji cells were FACS-sorted to establish the hCD39.Raji cell line.

Jurkat cells, co-transfected with a plasmid encoding a firefly luciferase gene under the control of NFAT response element and another plasmid encoding human FcRγ common chain gene, were purchased from Promega as part of the ADCC Bioassay Core Kit (Cat. No. G7010). These cells were stained with anti-hFcγRIIIA, and FACS-sorted to obtain the hFcγRIIIA-negative population, followed by further infection with pLentiTdT-mFcγRIV. TdTomato positive Jurkat cells were FACS-sorted and used as effector cells to measure ADCC of mouse antibodies.

Tumor cell lines luciferase-expressing B16/F10 (luc-B16/F10) and MC38 colorectal cancer cells were maintained in DMEM (supplemented with 10% FBS, 2 mM L-Glutamine, 100 units/mL Penicillin and Streptomycin and 15 μg/mL Puromycin) and RPMI 1640 (supplemented with 10% FBS, 2 mM L-Glutamine and 100 units/mL Penicillin and Streptomycin), respectively, as previously described (Sun et al. Gastroenterology (2010) 139:1030; and Feng et al. Neoplasia (2011) 13:206).

Tumor Cell Inoculation:

Luc-B16/F10 or MC38 cells were harvested by trypsinization and resuspended with HBSS containing 2% FBS for injection. 1.0-2.0×$10^5$ cancer cells were injected subcutaneously (s.c.) into the right lower flank of mice. Perpendicular tumor diameters were directly measured at indicated time points using a digital caliper when tumor became palpable. Tumor volume was determined by integration: $\Sigma t_1+t_2+\ldots t_n$ ($t=a^2 \times b \times 0.52$; a=the smaller tumor diameter, b=the larger tumor diameter). Earlier euthanasia was conducted if tumor ulceration occurred.

Antibodies and Reagents:

All chemicals were obtained from Sigma-Aldrich (St. Louis, MO). InVivoMab anti-mouse PD-1 (CD279; Clone J43) for in vivo treatment was purchased from BioXCell (Cat No. BE0033-2; West Labanon, NH). The antibodies used for FACS analysis were from Biolegend (San Diego, CA), eBioscience/Thermofisher Scientific, BD Biosciences (San Jose, CA), and R&D Systems (Minneapolis, MN). The detailed list of FACS antibodies were appended as Table 1. Polyclonal antibodies used for immunohistochemistry were rabbit anti-mouse CD31 (Cat No. GWB-330879; Genway Biotech Inc., San Diego, CA) and polyclonal sheep anti-mouse CD39 (Cat No. AF4398; R&D Systems).

ADCC Assay:

One day before the assay, target cells were seeded in flat bottom white opaque tissue culture 96-well plates with low evaporation lid (Falcon, Cat No. 353296) at 10,000 cells/well in 100 μL medium. The next day, Jurkat effector cells (200,000 cells/well) and titrated doses of antibodies in total 75 μL medium were further added to the target cells and incubated at 37° C. for 6 hrs. After incubation, the plates were cooled at room temperature for 15 min, and 75 μL Bio Glo (Promega, Cat. No. G719A) was added to each well. The plates were read after 30 min for luminescence using a plate reader with glow-type luminescence read capabilities. Luciferase activities in fold increase over that of background were used as ADCC activities.

Preparation of Single-Cell Suspensions from Blood, Spleen, Lymph Node(s), Liver or Tumor:

Heparinized blood were drawn from the inferior vena cava of the mouse and 300 μL of blood were lysed using 6 mL of 1×BD RBC Lysing Buffer (Cat No. 555899; BD Biosciences) following the manufacturer's instructions.

Splenocytes were prepared by flushing the spleen using a syringe with a 25.5G needle and subsequent filtration by a 70 μM cell strainer. Blood cells were removed using 3 mL of 1×BD RBC Lysing Buffer (Cat No. 555899; BD Biosciences) by gently vortexing and brief centrifugation.

Lymph node(s) was simply meshed through a 70 μM cell strainer.

Liver and/or tumor was removed from euthanized mice, cut into small pieces using a scalpel, and subjected for enzymatic and physical dissociation using the Mouse Liver Dissociation Kit (Cat No. 130-105-807) and the Mouse Tumor Dissociation Kit (Cat No. 130-096-730), respectively, on the gentleMACS Dissociator (Miltenyi Biotec Inc., Auburn, CA), according to the manufacturer's instructions.

Flow Cytometric Analysis:

FACS studies were performed using conjugated antibodies to mouse CD45, CD3, CD4, CD8, CD11 b, Gr1, Ly6C, Ly6G, F4/80, B220, CTLA4, PD-1, and PD-L1 (as shown in Table 1) on a CytoFLEX flow cytometer (Beckman Coulter, Brea, CA). FACS data were analyzed using CytExpert 2.0 (Beckman Coulter).

Histology and Immunohistochemistry:

Paraffin-embedded or frozen sections of s.c. tumors were analyzed by immunohistochemical staining (IHC) as described with slight modifications (Sun et al. Gastroenterology (2010) 139:1030; and Sun et al. Hepatology (2013) 57:205), using rabbit anti-mouse antibody to CD31 or sheep anti-mouse CD39 antibody.

Statistical Analysis:

Results are expressed as means±SEM of values. For statistical analyses, the two-tailed Students t-test (between two groups) or ANOVA with Turkey post-test (between three or more groups) was used. Animal survival (time to euthanasia) were analyzed using the Kaplan-Meier method, and were compared using the log-rank test (GraphPad Prism, La Jolla, CA). Significance was defined as $P<0.05$.

TABLE 1

| Antibodies | | | | | |
|---|---|---|---|---|---|
| No. | Antibody | Conjugation | Company | Cat No. | Box |
| 1 | 7-AAD Viability | NA | Biolegend | 79993 | HZ Ab1 |
| 2 | Annexin V | FITC | Biolegend | 640906 | HZ Ab1 |

TABLE 1-continued

| Antibodies | | | | | |
|---|---|---|---|---|---|
| No. Antibody | Conjugation | Company | Cat No. | Box |
| 3 Annexin V | Apc | Biolegend | 640920 | HZ Ab1 |
| 4 CD11b | PerCP | Biolegend | 101230 | HZ/Robson Facs Ab |
| 5 CD11b | PerCP/Cy5.5 | Biolegend | 101228 | HZ/Robson Facs Ab |
| 6 CD11b | APC | Biolegend | 101212 | HZ/Robson Facs Ab |
| 7 CD11b | PE/Cy7 | Biolegend | 101216 | HZ/Robson Facs Ab |
| 8 CD11c | APC | Biolegend | 117310 | HZ/Robson Facs Ab |
| 9 CD11c | Pacific Blue | Biolegend | 117322 | HZ/Robson Facs Ab |
| 10 CD11c | APC/Fire ™ 750 | Biolegend | 117352 | HZ/Robson Facs Ab |
| 11 CD11c | PE/Cy7 | Biolegend | 117318 | HZ/Robson Facs Ab |
| 12 CD134(OX40) | PE/Cy7 | Biolegend | 119416 | HZ FACS Ab for mouse T cell |
| 13 CD134(OX40) | Brilliant Violet 605 | Biolegend | 119419 | Mingchen Zhu |
| 14 CD140a | APC | Biolegend | 135908 | HZ/Robson Facs Ab |
| 15 CD146 | PerCP/Cy5.5 | Biolegend | 134710 | HZ/Robson Facs Ab |
| 16 CD152 | PerCP/Cy5.5 | Biolegend | 106316 | HZ FACS Ab for mouse T cell |
| 17 CD19 | PE/Cy7 | Biolegend | 115519 | HZ/Robson Facs Ab |
| 18 CD223 (LAG-3) | PE/Cy7 | Biolegend | 125226 | Mingchen Zhu |
| 19 CD25 | PE | ebioscience | 12-0251-82 | HZ FACS Ab for mouse T cell |
| 20 CD25 | Brilliant Violet 510 | Biolegend | 102042 | HZ FACS Ab for mouse T cell |
| 21 CD274 | Brilliant Violet 605 | Biolegend | 124321 | HZ/Robson Facs Ab |
| 22 CD274 (B7-H1, PD-L1) | PE/Cy7 | Biolegend | 124313 | HZ/Robson Facs Ab |
| 23 CD279(PD-1) | Brilliant Violet 510 | Biolegend | 135241 | HZ/Robson Facs Ab |
| 24 CD279(PD-1) | APC | Biolegend | 135210 | HZ FACS Ab for mouse T cell |
| 25 CD31 | Pacific Blue | Biolegend | 102422 | HZ/Robson Facs Ab |
| 26 CD326(Ep-CAM) | PE/Cy7 | Biolegend | 118216 | HZ/Robson Facs Ab |
| 27 CD366(Tim-3) | APC | Biolegend | 134008 | Mingchen Zhu |
| 28 CD39 (Duha59) | PE/Cy7 | Biolegend | 143805 | HZ/Robson Facs Ab |
| 29 CD39 (Duha59) | PE | Biolegend | 143804 | HZ FACS Ab for mouse T cell |
| 30 CD39 (Duha59) | PE/Cy7 | Biolegend | 143806 | HZ FACS Ab for mouse T cell |
| 31 CD39 (5F2) | PE | ebioscience | 12-0391-82 | Mingchen Zhu |
| 32 CD39 (5F2) | PE | ebioscience | 12-3390-80 | Mingchen Zhu |
| 33 CD3ε | PerCP/Cy5.5 | Biolegend | 100328 | HZ/Robson Facs Ab |
| 34 CD3ε | PB | Biolegend | 100334 | HZ FACS Ab for mouse T cell |
| 35 CD3ε | PB | Biolegend | 100334 | HZ FACS Ab for mouse T cell |
| 36 CD3ε | Alexa Fluor ® 700 | Biolegend | 152316 | HZ FACS Ab for mouse T cell |
| 37 CD3ε | PE | Biolegend | 100308 | HZ FACS Ab for mouse T cell |
| 38 CD3ε | PE/Cy7 | Biolegend | 100320 | HZ FACS Ab for mouse T cell |
| 39 CD3ε | APC | ebioscience | 17-0031-82 | Mingchen Zhu |
| 40 CD3ε | PE/Cy5 | Biolegend | 100310 | Mingchen Zhu |
| 41 CD3ε | PE/Cy7 | Biolegend | 100320 | Mingchen Zhu |
| 42 CD4 | Alexa Fluor ® 700 | Biolegend | 100430 | HZ FACS Ab for mouse T cell |
| 43 CD4 | PE | ebioscience | 12-0041-82 | HZ FACS Ab for mouse T cell |
| 44 CD4 | PE | Biolegend | 100408 | HZ FACS Ab for mouse T cell |
| 45 CD4 | FITC | ebioscience | 11-0041-82 | HZ FACS Ab for mouse T cell |
| 46 CD4 | APC | Biolegend | 100412 | HZ FACS Ab for mouse T cell |
| 47 CD4 | AF647 | Biolegend | 100424 | HZ FACS Ab for mouse T cell |
| 48 CD4 | PerCP | Biolegend | 100432 | HZ FACS Ab for mouse T cell |

TABLE 1-continued

| No. | Antibody | Conjugation | Company | Cat No. | Box |
|---|---|---|---|---|---|
| | | Antibodies | | | |
| 49 | CD4 | PerCP/Cy5.5 | Biolegend | 100434 | HZ FACS Ab for mouse T cell |
| 50 | CD4 | PE-Cyanine7 | ebioscience | 25-0041-82 | HZ FACS Ab for mouse T cell |
| 51 | CD4 | Brilliant Violet 421 | Biolegend | 100437 | HZ FACS Ab for mouse T cell |
| 52 | CD4 | APC/Cy7 | Biolegend | 100414 | HZ FACS Ab for mouse T cell |
| 53 | CD4 | APC/Fire ™ 750 | Biolegend | 100460 | Mingchen Zhu |
| 54 | CD4 | APC | ebioscience | 17-0041-82 | Mingchen Zhu |
| 55 | CD41 | FITC | Biolegend | 133904 | HZ/Robson Facs Ab |
| 56 | CD45 | AF700 | Biolegend | 103128 | HZ/Robson Facs Ab |
| 57 | CD45 | PB | Biolegend | 103126 | HZ/Robson Facs Ab |
| 58 | CD45 | APC | Biolegend | 103112 | HZ/Robson Facs Ab |
| 59 | CD45 | APC/Cy7 | Biolegend | 103116 | HZ/Robson Facs Ab |
| 60 | CD45 | PB | Biolegend | 103125 | HZ FACS Ab for mouse T cell |
| 61 | CD45 | PE | Biolegend | 103106 | HZ FACS Ab for mouse T cell |
| 62 | CD45 | FITC | Biolegend | 103107 | HZ FACS Ab for mouse T cell |
| 63 | CD45 | PE-Cyanine7 | ebioscience | 25-0451-82 | HZ FACS Ab for mouse T cell |
| 64 | CD45 | APC/Cy7 | Biolegend | 103116 | Mingchen Zhu |
| 65 | CD45 | BUV661 | BD pharmingen | 565079 | Mingchen Zhu |
| 66 | CD45 | Alexa Fluor ® 594 | Biolegend | 103144 | HZ Ab1 |
| 67 | CD45a | PE | ebioscience | 12-0452-81 | HZ/Robson Facs Ab |
| 68 | CD45R/B220 | PerCP | Biolegend | 103234 | HZ/Robson Facs Ab |
| 69 | CD45R/B220 | APC | Biolegend | 103212 | HZ/Robson Facs Ab |
| 70 | CD45R/B220 | Pacific Blue | Biolegend | 103227 | HZ/Robson Facs Ab |
| 71 | CD8a | PB | Biolegend | 100725 | HZ FACS Ab for mouse T cell |
| 72 | CD8a | Alexa Fluor ® 700 | Biolegend | 100730 | HZ FACS Ab for mouse T cell |
| 73 | CD8a | FITC | Biolegend | 100706 | HZ FACS Ab for mouse T cell |
| 74 | CD8a | APC | Biolegend | 100712 | HZ FACS Ab for mouse T cell |
| 75 | CD8a | PerCP | Biolegend | 100732 | HZ FACS Ab for mouse T cell |
| 76 | CD8a | PerCP | Biolegend | 100732 | HZ FACS Ab for mouse T cell |
| 77 | CD8a | BV 605 | Biolegend | 100744 | HZ FACS Ab for mouse T cell |
| 78 | CD8a | BV 605 | Biolegend | 100744 | HZ FACS Ab for mouse T cell |
| 79 | CD8a | Brilliant Violet 510 | Biolegend | 100751 | Mingchen Zhu |
| 80 | CD8a | PE | Biolegend | 100708 | Mingchen Zhu |
| 81 | CD90.2 | Brilliant Violet 605 | Biolegend | 105343 | Mingchen Zhu |
| 82 | F4/80 | AF700 | Biolegend | 123130 | HZ/Robson Facs Ab |
| 83 | F4/80 | eFluor450 | ebioscience | 48-4801-80 | HZ/Robson Facs Ab |
| 86 | F4/80 | FITC | ebioscience | 11-4801-82 | HZ/Robson Facs Ab |
| 87 | F4/80 | PerCP | Biolegend | 123125 | HZ/Robson Facs Ab |
| 88 | F4/80 | PerCP/Cy5.5 | Biolegend | 123128 | HZ/Robson Facs Ab |
| 89 | F4/80 | APC | Biolegend | 123116 | HZ/Robson Facs Ab |
| 90 | F4/80 | APC | Biolegend | 123116 | HZ/Robson Facs Ab |
| 91 | F4/80 | AF700 | Biolegend | 123129 | HZ/Robson Facs Ab |
| 92 | F4/80 | NA | Biolegend | 123101 | Mingchen Zhu |
| 93 | Foxp3 | PE | ebioscience | 53-5773-82 | HZ FACS Ab for mouse T cell |
| 94 | Foxp3 | APC | ebioscience | 17-5773-80B | HZ FACS Ab for mouse T cell |
| 95 | Human BD FC Block | NA | BD pharmingen | 564220 | HZ Ab1 |
| 96 | I-A/I-E | APC | Biolegend | 107614 | HZ/Robson Facs Ab |
| 98 | I-A/I-E | PE/Cy7 | Biolegend | 107630 | HZ/Robson Facs Ab |
| 99 | IFN-γ | APC | Biolegend | 505810 | HZ/Robson Facs Ab |
| 100 | Ig1 iso ctrl | PE | ebioscience | 12-4714-41 | HZ/Robson Facs Ab |

TABLE 1-continued

Antibodies

| No. | Antibody | Conjugation | Company | Cat No. | Box |
|---|---|---|---|---|---|
| 101 | Ig1 iso ctrl | PE | Biolegend | 400112 | HZ/Robson Facs Ab |
| 102 | Ly-6C | AF700 | Biolegend | 128024 | HZ/Robson Facs Ab |
| 103 | Ly-6C | FITC | BD pharmingen | 553104 | HZ/Robson Facs Ab |
| 104 | Ly-6C | PE/Cy7 | Biolegend | 128018 | HZ/Robson Facs Ab |
| 105 | Ly-6G | APC | Biolegend | 127614 | HZ/Robson Facs Ab |
| 106 | Ly-6G | PE/Cy7 | Biolegend | 127618 | HZ/Robson Facs Ab |
| 107 | Ly-6G(Gr-1) | PE | ebioscience | 12-5931-81 | Mingchen Zhu |
| 108 | Ly-6G(Gr-1) | Brilliant Violet 510 | Biolegend | 127633 | Mingchen Zhu |
| 109 | Ly-6G/Ly-6C(Gr-1) | FITC | Biolegend | 108406 | HZ/Robson Facs Ab |
| 110 | Ly-6G/Ly-6C(Gr-1) | Pacific Blue | Biolegend | 108430 | HZ/Robson Facs Ab |
| 111 | Ly-6G/Ly-6C(Gr-1) | PE/Cy7 | Biolegend | 108416 | Mingchen Zhu |
| 112 | NCAM-1/CD56 | NA | R&D | 1487941 | New Ab-Awca CD39L6/NCAM/FAP |
| 113 | NK-1.1 | Pacific Blue | Biolegend | 108722 | HZ/Robson Facs Ab |
| 114 | NK-1.1 | FITC | Biolegend | 108705 | HZ/Robson Facs Ab |
| 115 | Rat IG2a isotype ctrol | PE | Biolegend | 400408 | HZ/Robson Facs Ab |
| 116 | Rat IG2a isotype ctrol | PE | Biolegend | 400408 | HZ/Robson Facs Ab |
| 117 | Rat IG2b isotype ctrol | Brilliant Violet 605 | Biolegend | 400649 | HZ/Robson Facs Ab |
| 118 | Rat IG2b isotype ctrol | APC | Biolegend | 400512 | HZ/Robson Facs Ab |
| 119 | Rat IgG1 Isotype Control | R&D | Biolegend | MAB005 | Mingchen Zhu |
| 120 | Rat IgG1 Isotype Control | Alexa Fluor 750 | R&D | IC005S | New Ab-Awca CD39L8/NCAM/FAP |
| 121 | Rat IgG2b, κ Isotype Ctrl | PerCP/Cy5.5 | Biolegend | 400631 | HZ Ab1 |
| 122 | Rat IgG2b, κ Isotype Ctrl | Apc | Biolegend | 400611 | HZ Ab1 |
| 123 | TCR β chain | Alexa Fluor ® 700 | Biolegend | 109224 | HZ FACS Ab for mouse T cell |
| 124 | TNF-a | PE | Biolegend | 506306 | HZ/Robson Facs Ab |

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

The invention claimed is:

1. A method for promoting an anti-tumor immune response in a human patient having a tumor with vascular endothelia and/or immune cells that overexpress cluster of differentiation 39 (CD39), the method comprising administering to the human patient with a tumor a hypofucosylated or afucosylated humanized anti-CD39 antibody or antigen-binding fragment thereof wherein the antibody or antigen-binding fragment thereof comprises an Fc domain that binds FcγRIIIa, wherein the antibody or antigen-binding fragment thereof retains antibody-dependent cellular cytotoxicity (ADCC), and wherein administration of the antibody to the human patient results in a reduction of CD39 expression on the immune cells and/or in the vascular endothelia in the tumor;

wherein the anti-CD39 antibody or antigen-binding fragment thereof comprises:

(a) a heavy chain variable region comprising the complementarity determining regions (CDRs) of SEQ ID NO: 2 and a light chain variable region comprising the CDRs of SEQ ID NO: 1;

(b) a heavy chain variable region comprising the CDRs of SEQ ID NO: 3 and a light chain variable region comprising the CDRs of SEQ ID NO: 4;

(c) a heavy chain variable region comprising the CDRs of SEQ ID NO: 5 and a light chain variable region comprising the CDRs of SEQ ID NO: 6;

(d) a heavy chain variable region comprising the CDRs of SEQ ID NO: 7 and a light chain variable region comprising the CDRs of SEQ ID NO: 8;

(e) a heavy chain variable region comprising the CDRs of SEQ ID NO: 9 and a light chain variable region comprising the CDRs of SEQ ID NO: 10; or (f) a heavy chain variable region comprising the CDRs of SEQ ID NO: 11 and a light chain variable region comprising the CDRs of SEQ ID NO: 12; wherein the CDRs are determined according to the Kabat numbering scheme.

2. The method of claim 1, wherein:

(a) the anti-CD39 antibody or antigen-binding fragment thereof (i) causes antibody-mediated target depletion cytosis of CD39 on CD45+ the immune cells, wherein the immune cells are CD45+ immune cells, (ii) causes antibody-mediated target depletion cytosis of CD39 from tumor the vascular endothelia of the tumor endothelium disruption; or (iii) or collapses the vasculature network in the tumor; or (b) the anti-CD39 antibody or antigen-binding fragment thereof is an IgG1 or IgG3 isotype.

3. The method of claim 1, wherein the tumor is a solid tumor.

4. The method of claim 3, wherein the solid tumor is pancreatic cancer, liver cancer, lung cancer, stomach cancer, esophageal cancer, head and neck squamous cell carcinoma, prostate cancer, colon cancer, breast cancer, lymphoma, gallbladder cancer, renal cancer, multiple myeloma, ovarian cancer, cervical cancer or glioma.

5. The method of claim 1 wherein the tumor is a liquid tumor.

6. The method of claim 5, wherein the liquid tumor is leukemia.

* * * * *

SEQUENCE LISTING

```
<160> NUMBER OF SEQ ID NOS: 27

<210> SEQ ID NO 1
<211> LENGTH: 107
<212> TYPE: PRT
<213> ORGANISM: Artificial Sequence
<220> FEATURE:
<223> OTHER INFORMATION: Synthetic Construct

<400> SEQUENCE: 1

Asp Ile Gln Leu Thr Gln Ser Pro Ala Ser Leu Ser Val Ala Thr Gly
1               5                   10                  15

Glu Lys Val Thr Ile Arg Cys Ile Thr Ser Thr Asp Val Asp Asp Asp
            20                  25                  30

Met Asn Trp Phe Gln Gln Lys Pro Gly Glu Pro Pro Asn Leu Leu Ile
        35                  40                  45
```

```
Ser Glu Gly Asp Thr Leu Arg Pro Gly Val Pro Ser Arg Phe Ser Ser
    50                  55                  60

Ser Gly Tyr Gly Thr Asp Phe Val Phe Thr Ile Glu Asn Thr Leu Ser
65                  70                  75                  80

Glu Asp Val Ala Asp Tyr Tyr Cys Leu Gln Ser Asp Asn Met Pro Leu
                85                  90                  95

Thr Phe Gly Gly Gly Thr Lys Leu Glu Ile Lys
            100                 105


<210> SEQ ID NO 2
<211> LENGTH: 120
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Glu Glu Ser Gly Pro Gly Leu Val Gln Pro Ser Gln
1               5                   10                  15

Arg Leu Ser Ile Thr Cys Thr Ile Ser Gly Phe Ser Leu Thr Ser Tyr
            20                  25                  30

Gly Ile His Trp Val Arg Gln Ser Pro Gly Lys Gly Leu Glu Trp Leu
        35                  40                  45

Gly Val Ile Trp Ser Gly Gly Asn Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Val Gly Asp Thr Ala Thr Tyr Tyr Cys Ala
                85                  90                  95

Arg Asn Gly His Gly Ser Asn Ile Pro Trp Phe Val Tyr Trp Gly Gln
            100                 105                 110

Gly Thr Leu Val Thr Val Ser Thr
        115                 120


<210> SEQ ID NO 3
<211> LENGTH: 466
<212> TYPE: PRT
<213> ORGANISM: Artificial Sequence
<220> FEATURE:
<223> OTHER INFORMATION: Synthetic Construct

<400> SEQUENCE: 3

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Asp Leu Val Gln
            20                  25                  30

Pro Gly Ala Ser Leu Thr Leu Thr Cys Thr Thr Ser Gly Phe Ser Phe
        35                  40                  45

Ser Ser Asn Tyr Trp Ile Cys Trp Val Arg Gln Ala Pro Gly Lys Gly
    50                  55                  60

Leu Glu Trp Ile Gly Cys Ile Tyr Thr Gly Ser Asp Thr Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Ser Cys Ala Arg Gly Gly Ala Val Tyr Ala Ala Tyr Ala Gly Val
```

```
        115                 120                 125

Phe Phe Gly Leu Trp Gly Pro Gly Ser Leu Val Thr Val Ser Ser Gly
    130                 135                 140

Gln Pro Lys Ala Pro Ser Val Phe Pro Leu Ala Pro Cys Cys Gly Asp
145                 150                 155                 160

Thr Pro Ser Ser Thr Val Thr Leu Gly Cys Leu Val Lys Gly Tyr Leu
                165                 170                 175

Pro Glu Pro Val Thr Val Thr Trp Asn Ser Gly Thr Leu Thr Asn Gly
            180                 185                 190

Val Arg Thr Phe Pro Ser Val Arg Gln Ser Ser Gly Leu Tyr Ser Leu
        195                 200                 205

Ser Ser Val Val Ser Val Thr Ser Ser Ser Gln Pro Val Thr Cys Asn
    210                 215                 220

Val Ala His Pro Ala Thr Asn Thr Lys Val Asp Lys Thr Val Ala Pro
225                 230                 235                 240

Ser Thr Cys Ser Lys Pro Met Cys Pro Pro Pro Glu Leu Pro Gly Gly
                245                 250                 255

Pro Ser Val Phe Ile Phe Pro Pro Lys Pro Lys Asp Thr Leu Met Ile
            260                 265                 270

Ser Arg Thr Pro Glu Val Thr Cys Val Val Val Asp Val Ser Gln Asp
        275                 280                 285

Asp Pro Glu Val Gln Phe Thr Trp Tyr Ile Asn Asn Glu Gln Val Arg
    290                 295                 300

Thr Ala Arg Pro Pro Leu Arg Glu Gln Gln Phe Asn Ser Thr Ile Arg
305                 310                 315                 320

Val Val Ser Thr Leu Pro Ile Ala His Gln Asp Trp Leu Arg Gly Lys
                325                 330                 335

Glu Phe Lys Cys Lys Val His Asn Lys Ala Leu Pro Ala Pro Ile Glu
            340                 345                 350

Lys Thr Ile Ser Lys Ala Arg Gly Gln Pro Leu Glu Pro Lys Val Tyr
        355                 360                 365

Thr Met Gly Pro Pro Arg Glu Glu Leu Ser Ser Arg Ser Val Ser Leu
    370                 375                 380

Thr Cys Met Ile Asn Gly Phe Tyr Pro Ser Asp Ile Ser Val Glu Trp
385                 390                 395                 400

Glu Lys Asn Gly Lys Ala Glu Asp Asn Tyr Lys Thr Thr Pro Thr Val
                405                 410                 415

Leu Asp Ser Asp Gly Ser Tyr Phe Leu Tyr Ser Lys Leu Ser Val Pro
            420                 425                 430

Thr Ser Glu Trp Gln Arg Gly Asp Val Phe Thr Cys Ser Val Met His
        435                 440                 445

Glu Ala Leu His Asn His Tyr Thr Gln Lys Ser Ile Ser Arg Ser Pro
    450                 455                 460

Gly Lys
465


<210> SEQ ID NO 4
<211> LENGTH: 237
<212> TYPE: PRT
<213> ORGANISM: Artificial Sequence
<220> FEATURE:
<223> OTHER INFORMATION: Synthetic Construct

<400> SEQUENCE: 4

Met Asp Thr Arg Ala Pro Thr Gln Leu Leu Gly Leu Leu Leu Leu Trp
```

-continued

```
1               5                   10                  15

Leu Pro Gly Ala Arg Cys Ala Asp Val Val Met Thr Gln Thr Pro Ala
            20                  25                  30

Ser Val Ser Glu Pro Val Gly Gly Thr Val Thr Ile Lys Cys Gln Ala
        35                  40                  45

Ser Glu Ser Ile Tyr Ser Gly Leu Ala Trp Tyr Gln Gln Lys Pro Gly
    50                  55                  60

Gln Pro Pro Lys Leu Leu Ile Tyr Gly Ala Ser Thr Leu Ala Ser Gly
65                  70                  75                  80

Val Pro Ser Arg Phe Lys Gly Ser Gly Ser Gly Thr Glu Phe Thr Leu
                85                  90                  95

Thr Ile Ser Asp Leu Glu Cys Ala Asp Ala Ala Thr Tyr Tyr Cys Gln
            100                 105                 110

Ser Tyr Phe Gly Ile Gly Gly Tyr Gly Leu Ala Phe Gly Gly Gly Thr
        115                 120                 125

Glu Val Val Val Leu Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235


<210> SEQ ID NO 5
<211> LENGTH: 458
<212> TYPE: PRT
<213> ORGANISM: Artificial Sequence
<220> FEATURE:
<223> OTHER INFORMATION: Synthetic Construct

<400> SEQUENCE: 5

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Ile Asp Phe Ser
        35                  40                  45

Asp Tyr Gly Tyr Met Cys Trp Val Arg Gln Ala Pro Gly Lys Gly Leu
    50                  55                  60

Glu Trp Ile Gly Cys Ile Tyr Val Gly Ser Ser Gly Ser Thr Tyr Tyr
65                  70                  75                  80

Ala Thr Trp Ala Lys Gly Arg Phe Thr Val Ser Arg Pro Ser Ser Thr
                85                  90                  95

Thr Val Thr Leu Gln Met Thr Ser Leu Thr Ala Ala Asp Thr Ala Thr
            100                 105                 110

Tyr Phe Cys Val Arg Arg Val Asn Gly Tyr Gly Leu Trp Gly Pro Gly
        115                 120                 125

Thr Leu Val Thr Val Ser Ser Gly Gln Pro Lys Ala Pro Ser Val Phe
```

```
    130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly Thr Leu Thr Asn Gly Val Arg Thr Phe Pro Ser Val Arg
            180                 185                 190

Gln Ser Ser Gly Leu Tyr Ser Leu Ser Ser Val Val Ser Val Thr Ser
        195                 200                 205

Ser Ser Gln Pro Val Thr Cys Asn Val Ala His Pro Ala Thr Asn Thr
    210                 215                 220

Lys Val Asp Lys Thr Val Ala Pro Ser Thr Cys Ser Lys Pro Met Cys
225                 230                 235                 240

Pro Pro Pro Glu Leu Pro Gly Gly Pro Ser Val Phe Ile Phe Pro Pro
                245                 250                 255

Lys Pro Lys Asp Thr Leu Met Ile Ser Arg Thr Pro Glu Val Thr Cys
            260                 265                 270

Val Val Val Asp Val Ser Gln Asp Asp Pro Glu Val Gln Phe Thr Trp
        275                 280                 285

Tyr Ile Asn Asn Glu Gln Val Arg Thr Ala Arg Pro Pro Leu Arg Glu
    290                 295                 300

Gln Gln Phe Asn Ser Thr Ile Arg Val Val Ser Thr Leu Pro Ile Ala
305                 310                 315                 320

His Gln Asp Trp Leu Arg Gly Lys Glu Phe Lys Cys Lys Val His Asn
                325                 330                 335

Lys Ala Leu Pro Ala Pro Ile Glu Lys Thr Ile Ser Lys Ala Arg Gly
            340                 345                 350

Gln Pro Leu Glu Pro Lys Val Tyr Thr Met Gly Pro Pro Arg Glu Glu
        355                 360                 365

Leu Ser Ser Arg Ser Val Ser Leu Thr Cys Met Ile Asn Gly Phe Tyr
    370                 375                 380

Pro Ser Asp Ile Ser Val Glu Trp Glu Lys Asn Gly Lys Ala Glu Asp
385                 390                 395                 400

Asn Tyr Lys Thr Thr Pro Thr Val Leu Asp Ser Asp Gly Ser Tyr Phe
                405                 410                 415

Leu Tyr Ser Lys Leu Ser Val Pro Thr Ser Glu Trp Gln Arg Gly Asp
            420                 425                 430

Val Phe Thr Cys Ser Val Met His Glu Ala Leu His Asn His Tyr Thr
        435                 440                 445

Gln Lys Ser Ile Ser Arg Ser Pro Gly Lys
    450                 455


<210> SEQ ID NO 6
<211> LENGTH: 237
<212> TYPE: PRT
<213> ORGANISM: Artificial Sequence
<220> FEATURE:
<223> OTHER INFORMATION: Synthetic Construct

<400> SEQUENCE: 6

Met Asp Thr Arg Val Pro Thr Gln Leu Leu Gly Leu Leu Leu Leu Trp
1               5                   10                  15

Leu Pro Gly Ala Arg Cys Ala Asp Val Val Met Thr Gln Thr Pro Ala
            20                  25                  30

Ser Val Ser Glu Pro Val Gly Gly Thr Val Thr Ile Lys Cys Gln Ala
```

```
        35                  40                  45

Ser Glu Asn Ile Tyr Thr Gly Leu Ala Trp Tyr Gln Gln Arg Pro Gly
    50                  55                  60

Gln Pro Pro Lys Leu Leu Ile Tyr Ala Ala Ser Thr Leu Ala Ser Gly
65                  70                  75                  80

Val Ser Ser Arg Phe Lys Gly Ser Arg Ser Gly Thr Glu Tyr Thr Leu
                85                  90                  95

Thr Ile Ser Asp Leu Glu Cys Ala Asp Ala Ala Thr Tyr Tyr Cys Gln
            100                 105                 110

Gly Cys Tyr Gly Ile Ser Ser Tyr Gly Asp Ser Phe Gly Gly Gly Thr
        115                 120                 125

Glu Val Val Val Arg Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235


<210> SEQ ID NO 7
<211> LENGTH: 462
<212> TYPE: PRT
<213> ORGANISM: Artificial Sequence
<220> FEATURE:
<223> OTHER INFORMATION: Synthetic Construct

<400> SEQUENCE: 7

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Ser Phe Ser
        35                  40                  45

Lys Asn Tyr Trp Met Cys Trp Val Arg Gln Ala Pro Gly Lys Gly Leu
    50                  55                  60

Glu Trp Ile Gly Cys Ile Tyr Thr Gly Ser Asp Ser Arg Tyr Tyr Ala
65                  70                  75                  80

Ser Trp Val Asn Gly Arg Phe Ser Ile Ser Lys Ser Ser Ser Thr Thr
                85                  90                  95

Val Thr Leu Gln Met Thr Ser Leu Thr Ala Ala Asp Thr Ala Thr Tyr
            100                 105                 110

Phe Cys Ala Ser Asp Ser Gly Ala Pro Gly Ser Ser Asp Ser Thr Leu
        115                 120                 125

Trp Gly Pro Gly Thr Leu Val Thr Val Ser Ser Gly Gln Pro Lys Ala
    130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
```

```
                165                 170                 175

Thr Val Thr Trp Asn Ser Gly Thr Leu Thr Asn Gly Val Arg Thr Phe
            180                 185                 190

Pro Ser Val Arg Gln Ser Ser Gly Leu Tyr Ser Leu Ser Ser Val Val
        195                 200                 205

Ser Val Thr Ser Ser Ser Gln Pro Val Thr Cys Asn Val Ala His Pro
    210                 215                 220

Ala Thr Asn Thr Lys Val Asp Lys Thr Val Ala Pro Ser Thr Cys Ser
225                 230                 235                 240

Lys Pro Met Cys Pro Pro Pro Glu Leu Pro Gly Gly Pro Ser Val Phe
                245                 250                 255

Ile Phe Pro Pro Lys Pro Lys Asp Thr Leu Met Ile Ser Arg Thr Pro
            260                 265                 270

Glu Val Thr Cys Val Val Val Asp Val Ser Gln Asp Asp Pro Glu Val
        275                 280                 285

Gln Phe Thr Trp Tyr Ile Asn Asn Glu Gln Val Arg Thr Ala Arg Pro
    290                 295                 300

Pro Leu Arg Glu Gln Gln Phe Asn Ser Thr Ile Arg Val Val Ser Thr
305                 310                 315                 320

Leu Pro Ile Ala His Gln Asp Trp Leu Arg Gly Lys Glu Phe Lys Cys
                325                 330                 335

Lys Val His Asn Lys Ala Leu Pro Ala Pro Ile Glu Lys Thr Ile Ser
            340                 345                 350

Lys Ala Arg Gly Gln Pro Leu Glu Pro Lys Val Tyr Thr Met Gly Pro
        355                 360                 365

Pro Arg Glu Glu Leu Ser Ser Arg Ser Val Ser Leu Thr Cys Met Ile
    370                 375                 380

Asn Gly Phe Tyr Pro Ser Asp Ile Ser Val Glu Trp Glu Lys Asn Gly
385                 390                 395                 400

Lys Ala Glu Asp Asn Tyr Lys Thr Thr Pro Thr Val Leu Asp Ser Asp
                405                 410                 415

Gly Ser Tyr Phe Leu Tyr Ser Lys Leu Ser Val Pro Thr Ser Glu Trp
            420                 425                 430

Gln Arg Gly Asp Val Phe Thr Cys Ser Val Met His Glu Ala Leu His
        435                 440                 445

Asn His Tyr Thr Gln Lys Ser Ile Ser Arg Ser Pro Gly Lys
    450                 455                 460


<210> SEQ ID NO 8
<211> LENGTH: 237
<212> TYPE: PRT
<213> ORGANISM: Artificial Sequence
<220> FEATURE:
<223> OTHER INFORMATION: Synthetic Construct

<400> SEQUENCE: 8

Met Asp Thr Arg Val Pro Thr Gln Leu Leu Gly Leu Leu Leu Leu Trp
1               5                   10                  15

Leu Pro Gly Ala Arg Cys Ala Asp Val Val Met Thr Gln Thr Pro Ala
            20                  25                  30

Ser Val Glu Ala Ala Val Gly Gly Thr Val Thr Ile Lys Cys Gln Ala
        35                  40                  45

Ser Glu Asn Ile Tyr Ser Gly Leu Ala Trp Tyr Gln Gln Lys Pro Gly
    50                  55                  60

Gln Pro Pro Lys Leu Leu Ile Tyr Leu Ala Ser Thr Leu Ala Ser Gly
```

```
65                  70                  75                  80

Val Ser Ser Arg Phe Lys Gly Ser Arg Ser Gly Thr Glu Tyr Thr Leu
                85                  90                  95

Thr Ile Ser Asp Leu Glu Cys Ala Asp Ala Ala Thr Tyr Tyr Cys Gln
            100                 105                 110

Ser Tyr Tyr Ala Leu Ser Thr Tyr Gly Thr Ala Phe Gly Gly Gly Thr
        115                 120                 125

Glu Val Val Val Lys Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235


<210> SEQ ID NO 9
<211> LENGTH: 460
<212> TYPE: PRT
<213> ORGANISM: Artificial Sequence
<220> FEATURE:
<223> OTHER INFORMATION: Synthetic Construct

<400> SEQUENCE: 9

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Ser Phe
        35                  40                  45

Ser Ser Ser Tyr Tyr Met Cys Trp Val Arg Gln Ala Pro Gly Lys Gly
    50                  55                  60

Leu Glu Trp Ile Gly Cys Ile Tyr Ile Gly Ser Ser Thr Thr Tyr Tyr
65                  70                  75                  80

Ala Thr Trp Ala Lys Gly Arg Phe Thr Ile Ser Lys Thr Ser Ser Thr
                85                  90                  95

Ala Val Thr Leu Gln Met Thr Gly Leu Thr Ala Ala Asp Thr Ala Thr
            100                 105                 110

Tyr Phe Cys Ala Arg Asp Gln Tyr Asp Asp Ser Gly Asn Leu Trp Gly
        115                 120                 125

Pro Gly Thr Leu Val Thr Val Ser Ser Gly Gln Pro Lys Ala Pro Ser
    130                 135                 140

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
                165                 170                 175

Thr Trp Asn Ser Gly Thr Leu Thr Asn Gly Val Arg Thr Phe Pro Ser
            180                 185                 190

Val Arg Gln Ser Ser Gly Leu Tyr Ser Leu Ser Ser Val Val Ser Val
```

```
        195                 200                 205

Thr Ser Ser Ser Gln Pro Val Thr Cys Asn Val Ala His Pro Ala Thr
    210                 215                 220

Asn Thr Lys Val Asp Lys Thr Val Ala Pro Ser Thr Cys Ser Lys Pro
225                 230                 235                 240

Met Cys Pro Pro Pro Glu Leu Pro Gly Gly Pro Ser Val Phe Ile Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Asp Pro Glu Val Gln Phe
        275                 280                 285

Thr Trp Tyr Ile Asn Asn Glu Gln Val Arg Thr Ala Arg Pro Pro Leu
    290                 295                 300

Arg Glu Gln Gln Phe Asn Ser Thr Ile Arg Val Val Ser Thr Leu Pro
305                 310                 315                 320

Ile Ala His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
    370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Thr Val Leu Asp Ser Asp Gly Ser
                405                 410                 415

Tyr Phe Leu Tyr Ser Lys Leu Ser Val Pro Thr Ser Glu Trp Gln Arg
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
    450                 455                 460


<210> SEQ ID NO 10
<211> LENGTH: 237
<212> TYPE: PRT
<213> ORGANISM: Artificial Sequence
<220> FEATURE:
<223> OTHER INFORMATION: Synthetic Construct

<400> SEQUENCE: 10

Met Asp Thr Arg Ala Pro Thr Gln Leu Leu Gly Leu Leu Leu Leu Trp
1               5                   10                  15

Leu Pro Gly Ala Arg Cys Ala Asp Val Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Ser Ile Tyr Ser Gly Leu Ala Trp Tyr Gln Gln Lys Pro Gly
    50                  55                  60

Gln Pro Pro Asn Leu Leu Ile Tyr Lys Ala Ser Asn Leu Ala Ser Gly
65                  70                  75                  80

Val Ser Ser Arg Phe Lys Gly Ser Arg Ser Gly Thr Glu Tyr Thr Leu
                85                  90                  95

Thr Ile Ser Asp Leu Glu Cys Ala Asp Ala Ala Thr Tyr Tyr Cys Gln
```

```
            100                 105                 110

Asn Trp Tyr Gly Ile Ser Ser Tyr Gly Arg Ala Phe Gly Gly Gly Thr
        115                 120                 125

Glu Val Val Val Lys Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235


<210> SEQ ID NO 11
<211> LENGTH: 460
<212> TYPE: PRT
<213> ORGANISM: Artificial Sequence
<220> FEATURE:
<223> OTHER INFORMATION: Synthetic Construct

<400> SEQUENCE: 11

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Gln
            20                  25                  30

Pro Glu Gly Ser Leu Thr Leu Thr Cys Lys Ala Ser Gly Phe Ala Leu
        35                  40                  45

Ser Ser Ser Tyr Tyr Met Cys Trp Val Arg Gln Ala Pro Gly Lys Gly
    50                  55                  60

Leu Glu Trp Ile Gly Cys Ile Tyr Ile Gly Ser Gly Thr Thr Tyr Tyr
65                  70                  75                  80

Ala Ser Trp Ala Lys Gly Arg Phe Thr Ile Ser Lys Thr Ser Ser Thr
                85                  90                  95

Ala Val Thr Leu Gln Met Thr Gly Leu Thr Ala Ala Asp Thr Ala Thr
            100                 105                 110

Tyr Phe Cys Ala Arg Asp Gln Tyr Asp Asp Ser Gly Asn Leu Trp Gly
        115                 120                 125

Pro Gly Thr Leu Val Thr Val Ser Ser Gly Gln Pro Lys Ala Pro Ser
    130                 135                 140

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
                165                 170                 175

Thr Trp Asn Ser Gly Thr Leu Thr Asn Gly Val Arg Thr Phe Pro Ser
            180                 185                 190

Val Arg Gln Ser Ser Gly Leu Tyr Ser Leu Ser Ser Val Val Ser Val
        195                 200                 205

Thr Ser Ser Ser Gln Pro Val Thr Cys Asn Val Ala His Pro Ala Thr
    210                 215                 220

Asn Thr Lys Val Asp Lys Thr Val Ala Pro Ser Thr Cys Ser Lys Pro
```

```
225                 230                 235                 240

Met Cys Pro Pro Pro Glu Leu Pro Gly Gly Pro Ser Val Phe Ile Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Asp Pro Glu Val Gln Phe
        275                 280                 285

Thr Trp Tyr Ile Asn Asn Glu Gln Val Arg Thr Ala Arg Pro Pro Leu
    290                 295                 300

Arg Glu Gln Gln Phe Asn Ser Thr Ile Arg Val Val Ser Thr Leu Pro
305                 310                 315                 320

Ile Ala His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
    370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Thr Val Leu Asp Ser Asp Gly Ser
                405                 410                 415

Tyr Phe Leu Tyr Ser Lys Leu Ser Val Pro Thr Ser Glu Trp Gln Arg
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
    450                 455                 460


<210> SEQ ID NO 12
<211> LENGTH: 237
<212> TYPE: PRT
<213> ORGANISM: Artificial Sequence
<220> FEATURE:
<223> OTHER INFORMATION: Synthetic Construct

<400> SEQUENCE: 12

Met Asp Thr Arg Val Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Asn Ile Tyr Ser Gly Leu Ala Trp Tyr Gln Gln Lys Pro Gly
    50                  55                  60

Gln Pro Pro Lys Leu Leu Ile Tyr Lys Ala Ser Asn Leu Ala Ser Gly
65                  70                  75                  80

Val Ser Ser Arg Phe Lys Gly Ser Arg Ser Gly Thr Glu Tyr Thr Leu
                85                  90                  95

Thr Ile Ser Asp Leu Glu Cys Ala Asp Ala Ala Thr Tyr Tyr Cys Gln
            100                 105                 110

Asn Trp Tyr Gly Ile Ser Thr Tyr Gly Arg Ala Phe Gly Gly Gly Thr
        115                 120                 125

Glu Val Val Val Lys Gly Asp Pro Val Ala Pro Thr Val Leu Ile Phe
```

```
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235


<210> SEQ ID NO 13
<211> LENGTH: 487
<212> TYPE: PRT
<213> ORGANISM: Artificial Sequence
<220> FEATURE:
<223> OTHER INFORMATION: Synthetic Construct

<400> SEQUENCE: 13

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Asp Leu Val Gln
            20                  25                  30

Pro Gly Ala Ser Leu Thr Leu Thr Cys Thr Thr Ser Gly Phe Ser Phe
        35                  40                  45

Ser Ser Asn Tyr Trp Ile Cys Trp Val Arg Gln Ala Pro Gly Lys Gly
    50                  55                  60

Leu Glu Trp Ile Gly Cys Ile Tyr Thr Gly Ser Asp Thr Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Ser Cys Ala Arg Gly Gly Ala Val Tyr Ala Ala Tyr Ala Gly Val
        115                 120                 125

Phe Phe Gly Leu Trp Gly Pro Gly Ser Leu Val Thr Val Ser Ser Gly
    130                 135                 140

Gln Pro Lys Ala Pro Ser Val Phe Pro Leu Ala Pro Cys Cys Gly Asp
145                 150                 155                 160

Thr Pro Ser Ser Thr Val Thr Leu Gly Cys Leu Val Lys Gly Tyr Leu
                165                 170                 175

Pro Glu Pro Val Thr Val Thr Trp Asn Ser Gly Thr Leu Thr Asn Gly
            180                 185                 190

Val Arg Thr Phe Pro Ser Val Arg Gln Ser Ser Gly Leu Tyr Ser Leu
        195                 200                 205

Ser Ser Val Val Ser Val Thr Ser Ser Ser Gln Pro Val Thr Cys Asn
    210                 215                 220

Val Ala His Pro Ala Thr Asn Thr Lys Val Asp Lys Thr Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
```

```
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys Gly Ser Gly Leu Asn Asp Ile Phe Glu Ala
465                 470                 475                 480

Gln Lys Ile Glu Trp His Glu
            485


<210> SEQ ID NO 14
<211> LENGTH: 479
<212> TYPE: PRT
<213> ORGANISM: Artificial Sequence
<220> FEATURE:
<223> OTHER INFORMATION: Synthetic Construct

<400> SEQUENCE: 14

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Ile Asp Phe Ser
        35                  40                  45

Asp Tyr Gly Tyr Met Cys Trp Val Arg Gln Ala Pro Gly Lys Gly Leu
    50                  55                  60

Glu Trp Ile Gly Cys Ile Tyr Val Gly Ser Ser Gly Ser Thr Tyr Tyr
65                  70                  75                  80

Ala Thr Trp Ala Lys Gly Arg Phe Thr Val Ser Arg Pro Ser Ser Thr
            85                  90                  95

Thr Val Thr Leu Gln Met Thr Ser Leu Thr Ala Ala Asp Thr Ala Thr
            100                 105                 110

Tyr Phe Cys Val Arg Arg Val Asn Gly Tyr Gly Leu Trp Gly Pro Gly
        115                 120                 125

Thr Leu Val Thr Val Ser Ser Gly Gln Pro Lys Ala Pro Ser Val Phe
```

```
    130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly Thr Leu Thr Asn Gly Val Arg Thr Phe Pro Ser Val Arg
            180                 185                 190

Gln Ser Ser Gly Leu Tyr Ser Leu Ser Ser Val Val Ser Val Thr Ser
        195                 200                 205

Ser Ser Gln Pro Val Thr Cys Asn Val Ala His Pro Ala Thr Asn Thr
    210                 215                 220

Lys Val Asp Lys Thr Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Gly Ser
    450                 455                 460

Gly Leu Asn Asp Ile Phe Glu Ala Gln Lys Ile Glu Trp His Glu
465                 470                 475


<210> SEQ ID NO 15
<211> LENGTH: 483
<212> TYPE: PRT
<213> ORGANISM: Artificial Sequence
<220> FEATURE:
<223> OTHER INFORMATION: Synthetic Construct

<400> SEQUENCE: 15

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
```

-continued

```
            20                  25                  30

Gly Ala Ser Leu Thr Leu Thr Cys Thr Ala Ser Gly Phe Ser Phe Ser
        35                  40                  45

Lys Asn Tyr Trp Met Cys Trp Val Arg Gln Ala Pro Gly Lys Gly Leu
    50                  55                  60

Glu Trp Ile Gly Cys Ile Tyr Thr Gly Ser Asp Ser Arg Tyr Tyr Ala
65                  70                  75                  80

Ser Trp Val Asn Gly Arg Phe Ser Ile Ser Lys Ser Ser Ser Thr Thr
                85                  90                  95

Val Thr Leu Gln Met Thr Ser Leu Thr Ala Ala Asp Thr Ala Thr Tyr
            100                 105                 110

Phe Cys Ala Ser Asp Ser Gly Ala Pro Gly Ser Ser Asp Ser Thr Leu
        115                 120                 125

Trp Gly Pro Gly Thr Leu Val Thr Val Ser Ser Gly Gln Pro Lys Ala
    130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
            180                 185                 190

Pro Ser Val Arg Gln Ser Ser Gly Leu Tyr Ser Leu Ser Ser Val Val
        195                 200                 205

Ser Val Thr Ser Ser Ser Gln Pro Val Thr Cys Asn Val Ala His Pro
    210                 215                 220

Ala Thr Asn Thr Lys Val Asp Lys Thr Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445
```

Glu Ala Leu His Asn His Tyr Thr Gln Lys Ser Leu Ser Leu Ser Pro
450 455 460

Gly Lys Gly Ser Gly Leu Asn Asp Ile Phe Glu Ala Gln Lys Ile Glu
465 470 475 480

Trp His Glu

<210> SEQ ID NO 16
<211> LENGTH: 481
<212> TYPE: PRT
<213> ORGANISM: Artificial Sequence
<220> FEATURE:
<223> OTHER INFORMATION: Synthetic Construct

<400> SEQUENCE: 16

Met Glu Thr Gly Leu Arg Trp Leu Leu Leu Val Ala Val Leu Lys Gly
1 5 10 15

Val Gln Cys Gln Glu Gln Leu Val Glu Ser Gly Gly Gly Leu Val Gln
20 25 30

Pro Glu Gly Ser Leu Thr Leu Thr Cys Thr Ala Ser Gly Phe Ser Phe
35 40 45

Ser Ser Ser Tyr Tyr Met Cys Trp Val Arg Gln Ala Pro Gly Lys Gly
50 55 60

Leu Glu Trp Ile Gly Cys Ile Tyr Ile Gly Ser Ser Thr Thr Tyr Tyr
65 70 75 80

Ala Thr Trp Ala Lys Gly Arg Phe Thr Ile Ser Lys Thr Ser Ser Thr
85 90 95

Ala Val Thr Leu Gln Met Thr Gly Leu Thr Ala Ala Asp Thr Ala Thr
100 105 110

Tyr Phe Cys Ala Arg Asp Gln Tyr Asp Asp Ser Gly Asn Leu Trp Gly
115 120 125

Pro Gly Thr Leu Val Thr Val Ser Ser Gly Gln Pro Lys Ala Pro Ser
130 135 140

Val Phe Pro Leu Ala Pro Cys Cys Gly Asp Thr Pro Ser Ser Thr Val
145 150 155 160

Thr Leu Gly Cys Leu Val Lys Gly Tyr Leu Pro Glu Pro Val Thr Val
165 170 175

Thr Trp Asn Ser Gly Thr Leu Thr Asn Gly Val Arg Thr Phe Pro Ser
180 185 190

Val Arg Gln Ser Ser Gly Leu Tyr Ser Leu Ser Ser Val Val Ser Val
195 200 205

Thr Ser Ser Ser Gln Pro Val Thr Cys Asn Val Ala His Pro Ala Thr
210 215 220

Asn Thr Lys Val Asp Lys Thr Val Glu Pro Lys Ser Cys Asp Lys Thr
225 230 235 240

His Thr Cys Pro Pro Cys Pro Ala Pro Glu Leu Leu Gly Gly Pro Ser
245 250 255

Val Phe Leu Phe Pro Pro Lys Pro Lys Asp Thr Leu Met Ile Ser Arg
260 265 270

Thr Pro Glu Val Thr Cys Val Val Val Asp Val Ser His Glu Asp Pro
275 280 285

Glu Val Lys Phe Asn Trp Tyr Val Asp Gly Val Glu Val His Asn Ala
290 295 300

Lys Thr Lys Pro Arg Glu Glu Gln Tyr Asn Ser Thr Tyr Arg Val Val
305 310 315 320

```
Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

Gly Ser Gly Leu Asn Asp Ile Phe Glu Ala Gln Lys Ile Glu Trp His
465                 470                 475                 480

Glu


<210> SEQ ID NO 17
<211> LENGTH: 481
<212> TYPE: PRT
<213> ORGANISM: Artificial Sequence
<220> FEATURE:
<223> OTHER INFORMATION: Synthetic Construct

<400> SEQUENCE: 17

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Gln
            20                  25                  30

Pro Glu Gly Ser Leu Thr Leu Thr Cys Lys Ala Ser Gly Phe Ala Leu
        35                  40                  45

Ser Ser Ser Tyr Tyr Met Cys Trp Val Arg Gln Ala Pro Gly Lys Gly
    50                  55                  60

Leu Glu Trp Ile Gly Cys Ile Tyr Ile Gly Ser Gly Thr Thr Tyr Tyr
65                  70                  75                  80

Ala Ser Trp Ala Lys Gly Arg Phe Thr Ile Ser Lys Thr Ser Ser Thr
                85                  90                  95

Ala Val Thr Leu Gln Met Thr Gly Leu Thr Ala Ala Asp Thr Ala Thr
            100                 105                 110

Tyr Phe Cys Ala Arg Asp Gln Tyr Asp Asp Ser Gly Asn Leu Trp Gly
        115                 120                 125

Pro Gly Thr Leu Val Thr Val Ser Ser Gly Gln Pro Lys Ala Pro Ser
    130                 135                 140

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
                165                 170                 175

Thr Trp Asn Ser Gly Thr Leu Thr Asn Gly Val Arg Thr Phe Pro Ser
            180                 185                 190

Val Arg Gln Ser Ser Gly Leu Tyr Ser Leu Ser Ser Val Val Ser Val
```

```
        195                 200                 205

Thr Ser Ser Ser Gln Pro Val Thr Cys Asn Val Ala His Pro Ala Thr
    210                 215                 220

Asn Thr Lys Val Asp Lys Thr Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

Gly Ser Gly Leu Asn Asp Ile Phe Glu Ala Gln Lys Ile Glu Trp His
465                 470                 475                 480

Glu
```

<210> SEQ ID NO 18
<211> LENGTH: 1401
<212> TYPE: DNA
<213> ORGANISM: Artificial Sequence
<220> FEATURE:
<223> OTHER INFORMATION: Synthetic Construct

<400> SEQUENCE: 18

```
atggagactg ggctgcgctg gcttctcctg gtcgctgtgc tcaaaggtgt ccagtgtcag      60

gagcagctgg tggagtccgg gggagacctg gtccagcctg gggcatccct gacactcacc     120

tgcacaactt ctggattctc cttcagtagc aattactgga tatgctgggt ccgccaggct     180

ccagggaagg ggctggagtg gatcggatgc atttatactg gtagtgatac cacttactac     240

gcgagctggg cgaaaggccg attcaccatc tccaaaacct cgtcgaccac ggtgactctg     300

cagatgacca gtctgacagc cgcggacacg gccacctatt cctgtgcgag aggggggggct     360

gtttatgctg cttatgctgg tgtcttcttt ggcttgtggg gcccaggctc cctggtcacc     420
```

gtctcctcag ggcaacctaa ggctccatca gtcttcccac tggccccctg ctgcggggac 480
acacccagct ccacggtgac cctgggctgc ctggtcaaag gctacctccc ggagccagtg 540
accgtgacct ggaactcggg caccctcacc aatggggtac gcaccttccc gtccgtccgg 600
cagtcctcag gcctctactc gctgagcagc gtggtgagcg tgacctcaag cagccagccc 660
gtcacctgca acgtggccca cccagccacc aacaccaaag tggacaagac cgttgcgccc 720
tcgacatgca gcaagcccat gtgcccaccc cctgaactcc cggggggacc gtctgtcttc 780
atcttccccc caaaacccaa ggacaccctc atgatctcac gcacccccga ggtcacatgc 840
gtggtggtgg acgtgagcca ggatgacccc gaggtgcagt tcacatggta cataaacaac 900
gagcaggtgc gcaccgcccg gccgccgcta cgggagcagc agttcaacag cacgatccgc 960
gtggtcagca ccctccccat cgcgcaccag gactggctga ggggcaagga gttcaagtgc 1020
aaagtccaca acaaggcact cccggccccc atcgagaaaa ccatctccaa agccagaggg 1080
cagcccctgg agccgaaggt ctacaccatg ggccctcccc gggaggagct gagcagcagg 1140
tcggtcagcc tgacctgcat gatcaacggc ttctaccctt ccgacatctc ggtggagtgg 1200
gagaagaacg ggaaggcaga ggacaactac aagaccacgc cgaccgtgct ggacagcgac 1260
ggctcctact tcctctacag caagctctca gtgcccacga gtgagtggca gcggggcgac 1320
gtcttcacct gctccgtgat gcacgaggcc ttgcacaacc actacacgca gaagtccatc 1380
tcccgctctc cgggtaaata g 1401

<210> SEQ ID NO 19
<211> LENGTH: 714
<212> TYPE: DNA
<213> ORGANISM: Artificial Sequence
<220> FEATURE:
<223> OTHER INFORMATION: Synthetic Construct

<400> SEQUENCE: 19
atggacacga gggcccccac tcagctgctg gggctcctgc tgctctggct cccaggtgcc 60
agatgtgccg atgttgtgat gacccagact ccagcctccg tgtctgaacc tgtgggaggc 120
acagtcacca tcaagtgcca ggccagtgag agcatttata gtggtttggc ctggtatcag 180
cagaaaccag ggcagcctcc caagctcctg atctatggtg catccactct ggcatctggg 240
gtcccgtcgc ggttcaaagg cagtggatct gggacagagt tcactctcac catcagcgac 300
ctggagtgtg ccgatgctgc cacttactac tgtcaaagct attttggtat tggtggttat 360
ggtcttgctt tcggcggagg gaccgaggtg gtggtcttgg gtgatccagt tgcacctact 420
gtcctcatct tcccaccagc tgctgatcag gtggcaactg gaacagtcac catcgtgtgt 480
gtggcgaata aatactttcc cgatgtcacc gtcacctggg aggtggatgg caccacccaa 540
acaactggca tcgagaacag taaaacaccg cagaattctg cagattgtac ctacaacctc 600
agcagcactc tgacactgac cagcacacag tacaacagcc acaaagagta cacctgcaag 660
gtgacccagg gcacgacctc agtcgtccag agcttcaata ggggtgactg ttag 714

<210> SEQ ID NO 20
<211> LENGTH: 1377
<212> TYPE: DNA
<213> ORGANISM: Artificial Sequence
<220> FEATURE:
<223> OTHER INFORMATION: Synthetic Construct

<400> SEQUENCE: 20
atggagactg ggctgcgctg gcttctcctg gtcgctgtgc tcaaaggtgt ccagtgtcag 60

-continued tcgttggagg agtccggggg agacctggtc aagcctgggg catccctgac actcacctgt 120
acagcctctg gaatcgactt cagtgactat ggctacatgt gctgggtccg ccaggctcca 180
gggaaggggc tggagtggat cggatgtatt tatgttggta gtagtggtag cacttattat 240
gcgacctggg cgaaaggccg attcaccgtc tccaggccct cgtcgaccac ggtgactctg 300
caaatgacca gtctgacagc cgcggacacg gccacttatt tctgtgtgag aagggttaat 360
ggttatgggt tgtggggccc aggcaccctg gtcaccgtct cctcagggca acctaaggct 420
ccatcagtct tcccactggc cccctgctgc ggggacacac ccagctccac ggtgaccctg 480
ggctgcctgg tcaaaggcta cctcccggag ccagtgaccg tgacctggaa ctcgggcacc 540
ctcaccaatg ggtacgcac cttcccgtcc gtccggcagt cctcaggcct ctactcgctg 600
agcagcgtgg tgagcgtgac ctcaagcagc cagcccgtca cctgcaacgt ggcccaccca 660
gccaccaaca ccaaagtgga caagaccgtt gcgccctcga catgcagcaa gcccatgtgc 720 ccacccccctg aactcccggg gggaccgtct gtcttcatct tcccccaaa acccaaggac 780 accctcatga tctcacgcac ccccgaggtc acatgcgtgg tggtggacgt gagccaggat 840
gaccccgagg tgcagttcac atggtacata aacaacgagc aggtgcgcac cgcccggccg 900
ccgctacggg agcagcagtt caacagcacg atccgcgtgg tcagcaccct ccccatcgcg 960
caccaggact ggctgagggg caaggagttc aagtgcaaag tccacaacaa ggcactcccg 1020
gcccccatcg agaaaaccat ctccaaagcc agagggcagc ccctggagcc gaaggtctac 1080
accatgggcc ctccccggga ggagctgagc agcaggtcgg tcagcctgac ctgcatgatc 1140
aacggcttct acccttccga catctcggtg gagtgggaga agaacgggaa ggcagaggac 1200
aactacaaga ccacgccgac cgtgctggac agcgacggct cctacttcct ctacagcaag 1260
ctctcagtgc ccacgagtga gtggcagcgg ggcgacgtct tcacctgctc cgtgatgcac 1320
gaggccttgc acaaccacta cacgcagaag tccatctccc gctctccggg taaatag 1377

<210> SEQ ID NO 21
<211> LENGTH: 714
<212> TYPE: DNA
<213> ORGANISM: Artificial Sequence
<220> FEATURE:
<223> OTHER INFORMATION: Synthetic Construct

<400> SEQUENCE: 21
atggacacga gggtccccac tcagctgctg gggctcctgc tgctctggct cccaggtgcc 60
agatgtgccg atgttgtgat gacccagact ccagcctccg tgtctgaacc tgtgggaggc 120
acagtcacca tcaagtgcca ggccagtgag aacatttata ctggtttggc ctggtatcag 180
cagagaccag ggcagcctcc caaactcctg atctatgctg catccactct ggcatctggg 240
gtctcatcgc ggttcaaagg cagtagatct gggacagagt acactctcac catcagcgac 300
ctggagtgtg ccgatgctgc cacttactac tgtcagggct gctatggtat tagtagttat 360
ggtgattctt tcggcggagg gaccgaggtg gtggtcagag gtgatccagt tgcacctact 420
gtcctcatct tcccaccagc tgctgatcag gtggcaactg gaacagtcac catcgtgtgt 480
gtggcgaata aatactttcc cgatgtcacc gtcacctggg aggtggatgg caccacccaa 540
acaactggca tcgagaacag taaaacaccg cagaattctg cagattgtac ctacaacctc 600
agcagcactc tgacactgac cagcacacag tacaacagcc acaaagagta cacctgcaag 660
gtgacccagg gcacgacctc agtcgtccag agcttcaata ggggtgactg ttag 714

<210> SEQ ID NO 22
<211> LENGTH: 1389
<212> TYPE: DNA
<213> ORGANISM: Artificial Sequence
<220> FEATURE:
<223> OTHER INFORMATION: Synthetic Construct

<400> SEQUENCE: 22
atggagactg ggctgcgctg gcttctcctg gtcgctgtgc tcaaaggtgt ccagtgtcag 60
tcgttggagg agtccggggg agacctggtc aagccggggg catccctgac actcacctgc 120
acagcctctg gattctcctt cagtaagaac tactggatgt gctgggtccg ccaggctcca 180
gggaagggtc tggagtggat cggatgcatt tatactggta gtgatagtag atactacgcg 240
agctgggtga atggccgatt ctccatctcc aaatcctcgt cgaccacggt gactctgcaa 300
atgaccagtc tgacagccgc ggacacggcc acttatttct gtgcgagcga tagtggtgct 360
cctggtagta gtgattcaac tttgtggggc ccaggcaccc tggtcaccgt ctcctcaggg 420
caacctaagg ctccatcagt cttcccactg gccccctgct gcggggacac acccagctcc 480
acggtgaccc tgggctgcct ggtcaaaggc tacctcccgg agccagtgac cgtgacctgg 540
aactcgggca ccctcaccaa tggggtacgc accttcccgt ccgtccggca gtcctcaggc 600
ctctactcgc tgagcagcgt ggtgagcgtg acctcaagca gccagcccgt cacctgcaac 660
gtggcccacc cagccaccaa caccaaagtg gacaagaccg ttgcgccctc gacatgcagc 720
aagcccatgt gcccaccccc tgaactcccg gggggaccgt ctgtcttcat cttcccccca 780
aaacccaagg acaccctcat gatctcacgc acccccgagg tcacatgcgt ggtggtggac 840
gtgagccagg atgaccccga ggtgcagttc acatggtaca taaacaacga gcaggtgcgc 900
accgcccggc cgccgctacg ggagcagcag ttcaacagca cgatccgcgt ggtcagcacc 960
ctccccatcg cgcaccagga ctggctgagg ggcaaggagt tcaagtgcaa agtccacaac 1020
aaggcactcc cggcccccat cgagaaaacc atctccaaag ccagagggca gcccctggag 1080
ccgaaggtct acaccatggg ccctccccgg gaggagctga gcagcaggtc ggtcagcctg 1140
acctgcatga tcaacggctt ctacccttcc gacatctcgg tggagtggga gaagaacggg 1200
aaggcagagg acaactacaa gaccacgccg accgtgctgg acagcgacgg ctcctacttc 1260
ctctacagca agctctcagt gcccacgagt gagtggcagc ggggcgacgt cttcacctgc 1320
tccgtgatgc acgaggcctt gcacaaccac tacacgcaga agtccatctc ccgctctccg 1380
ggtaaatag 1389

<210> SEQ ID NO 23
<211> LENGTH: 714
<212> TYPE: DNA
<213> ORGANISM: Artificial Sequence
<220> FEATURE:
<223> OTHER INFORMATION: Synthetic Construct

<400> SEQUENCE: 23
atggacacga gggtccccac tcagctgctg gggctcctgc tgctctggct cccaggtgcc 60
agatgtgccg atgttgtgat gacccagact ccagcctccg tggaggcagc tgtgggaggc 120
acagtcacca tcaagtgcca ggccagtgag aacatttata gtggtttggc ctggtatcag 180
cagaaaccag ggcagcctcc caaactcctg atctatctgg catccactct ggcatctggg 240
gtctcatcgc ggttcaaagg cagtagatct gggacagagt acactctcac catcagcgac 300
ctggagtgtg ccgatgctgc cacttactac tgtcaaagct attatgcgct tagtacttat 360

```
ggtactgctt tcggcggagg gaccgaggtg gtggtcaaag gtgatccagt tgcacctact    420

gtcctcatct tcccaccagc tgctgatcag gtggcaactg gaacagtcac catcgtgtgt    480

gtggcgaata aatactttcc cgatgtcacc gtcacctggg aggtggatgg caccacccaa    540

acaactggca tcgagaacag taaaacaccg cagaattctg cagattgtac ctacaacctc    600

agcagcactc tgacactgac cagcacacag tacaacagcc acaaagagta cacctgcaag    660

gtgacccagg gcacgacctc agtcgtccag agcttcaata ggggtgactg ttag          714
```

<210> SEQ ID NO 24
<211> LENGTH: 1383
<212> TYPE: DNA
<213> ORGANISM: Artificial Sequence
<220> FEATURE:
<223> OTHER INFORMATION: Synthetic Construct

<400> SEQUENCE: 24

```
atggagactg ggctgcgctg gcttctcctg gtcgctgtgc tcaaaggtgt ccagtgtcag     60

gagcagctgg tggagtccgg gggaggcctg gtccagcctg agggatccct gacactcacc    120

tgcacagctt ctggattctc cttcagtagc agctactaca tgtgctgggt ccgccaggct    180

ccagggaagg ggctggagtg gatcggatgc atttatattg gtagttctac cacttactac    240

gcgacctggg cgaaaggccg attcaccatc tccaaaacct cgtcgaccgc ggtgactctg    300

caaatgaccg gtctgacagc cgcggacacg gccacctatt tctgtgcgag agatcaatat    360

gatgatagtg gtaatttgtg ggcccaggc accctggtca ccgtctcctc agggcaacct    420

aaggctccat cagtcttccc actggccccc tgctgcgggg acacacccag ctccacggtg    480

accctgggct gcctggtcaa aggctacctc ccggagccag tgaccgtgac ctggaactcg    540

ggcaccctca ccaatggggt acgcaccttc ccgtccgtcc ggcagtcctc aggcctctac    600

tcgctgagca gcgtggtgag cgtgacctca agcagccagc ccgtcacctg caacgtggcc    660

cacccagcca ccaacaccaa agtggacaag accgttgcgc cctcgacatg cagcaagccc    720

atgtgcccac cccctgaact cccgggggga ccgtctgtct tcatcttccc cccaaaaccc    780

aaggacaccc tcatgatctc acgcaccccc gaggtcacat gcgtggtggt ggacgtgagc    840

caggatgacc ccgaggtgca gttcacatgg tacataaaca acgagcaggt gcgcaccgcc    900

cggccgccgc tacgggagca gcagttcaac agcacgatcc gcgtggtcag caccctcccc    960

atcgcgcacc aggactggct gaggggcaag gagttcaagt gcaaagtcca caacaaggca   1020

ctcccggccc ccatcgagaa aaccatctcc aaagccagag ggcagcccct ggagccgaag   1080

gtctacacca tgggccctcc ccgggaggag ctgagcagca ggtcggtcag cctgacctgc   1140

atgatcaacg gcttctaccc ttccgacatc tcggtggagt gggagaagaa cgggaaggca   1200

gaggacaact acaagaccac gccgaccgtg ctggacagcg acggctccta cttcctctac   1260

agcaagctct cagtgcccac gagtgagtgg cagcggggcg acgtcttcac ctgctccgtg   1320

atgcacgagg ccttgcacaa ccactacacg cagaagtcca tctcccgctc tccgggtaaa   1380

tag                                                                 1383
```

<210> SEQ ID NO 25
<211> LENGTH: 714
<212> TYPE: DNA
<213> ORGANISM: Artificial Sequence
<220> FEATURE:
<223> OTHER INFORMATION: Synthetic Construct

<400> SEQUENCE: 25
atggacacga gggcccccac tcagctgctg gggctcctgc tgctctggct cccaggtgcc 60
agatgtgccg atgttgtgat gacccagact ccagcctccg tgtctgaacc tgtgggaggc 120
acagtcacca tcaagtgcca ggccagtcag agcatttaca gtggtttggc ctggtatcag 180
cagaaaccag ggcagcctcc caacctcctg atctacaagg catccaatct ggcatctggg 240
gtctcatcgc ggttcaaagg cagtagatct gggacagagt acactctcac catcagcgac 300
ctggagtgtg ccgatgctgc cacttactac tgtcaaaact ggtatggtat tagtagttat 360
ggtcgggctt tcggcggagg gaccgaggtg gtggtcaaag gtgatccagt tgcacctact 420
gtcctcatct tcccaccagc tgctgatcag gtggcaactg gaacagtcac catcgtgtgt 480
gtggcgaata aatactttcc cgatgtcacc gtcacctggg aggtggatgg caccacccaa 540
acaactggca tcgagaacag taaaacaccg cagaattctg cagattgtac ctacaacctc 600
agcagcactc tgacactgac cagcacacag tacaacagcc acaaagagta cacctgcaag 660
gtgacccagg gcacgacctc agtcgtccag agcttcaata ggggtgactg ttag 714

<210> SEQ ID NO 26
<211> LENGTH: 1383
<212> TYPE: DNA
<213> ORGANISM: Artificial Sequence
<220> FEATURE:
<223> OTHER INFORMATION: Synthetic Construct

<400> SEQUENCE: 26
atggagactg ggctgcgctg gcttctcctg gtcgctgtgc tcaaaggtgt ccagtgtcag 60
gagcagctgg aggagtccgg gggaggcctg gtccagcctg agggatccct gacactcacc 120
tgcaaagcct ctggattcgc cctcagtagc agctactaca tgtgctgggt ccgccaggct 180
ccagggaagg ggctggagtg gatcggatgc atttatattg gtagtggtac cacttactac 240
gcgagctggg cgaaaggccg attcaccatc tccaaaacct cgtcgaccgc ggtgactctg 300
caaatgaccg gtctgacagc cgcggacacg gccacctatt tctgtgcgag agatcaatat 360
gatgatagtg gtaatttgtg gggcccaggc accctggtca ccgtctcctc agggcaacct 420
aaggctccat cagtcttccc actggccccc tgctgcgggg acacacccag ctccacggtg 480
accctgggct gcctggtcaa aggctacctc ccggagccag tgaccgtgac ctggaactcg 540
ggcaccctca ccaatggggt acgcaccttc ccgtccgtcc ggcagtcctc aggcctctac 600
tcgctgagca gcgtggtgag cgtgacctca agcagccagc ccgtcacctg caacgtggcc 660
cacccagcca ccaacaccaa agtggacaag accgttgcgc cctcgacatg cagcaagccc 720
atgtgcccac cccctgaact cccgggggga ccgtctgtct tcatcttccc cccaaaaccc 780
aaggacaccc tcatgatctc acgcaccccc gaggtcacat gcgtggtggt ggacgtgagc 840
caggatgacc ccgaggtgca gttcacatgg tacataaaca acgagcaggt gcgcaccgcc 900
cggccgccgc tacgggagca gcagttcaac agcacgatcc gcgtggtcag caccctcccc 960
atcgcgcacc aggactggct gaggggcaag gagttcaagt gcaaagtcca caacaaggca 1020
ctcccggccc ccatcgagaa aaccatctcc aaagccagag ggcagcccct ggagccgaag 1080
gtctacacca tgggccctcc ccgggaggag ctgagcagca ggtcggtcag cctgacctgc 1140
atgatcaacg gcttctaccc ttccgacatc tcggtggagt gggagaagaa cgggaaggca 1200
gaggacaact acaagaccac gccgaccgtg ctggacagcg acggctccta cttcctctac 1260
agcaagctct cagtgcccac gagtgagtgg cagcggggcg acgtcttcac ctgctccgtg 1320

```
atgcacgagg ccttgcacaa ccactacacg cagaagtcca tctcccgctc tccgggtaaa   1380

tag                                                                 1383


<210> SEQ ID NO 27
<211> LENGTH: 714
<212> TYPE: DNA
<213> ORGANISM: Artificial Sequence
<220> FEATURE:
<223> OTHER INFORMATION: Synthetic Construct

<400> SEQUENCE: 27

atggacacga gggtccccac tcagctgctg gggctcctgc tgctctggct cccaggtgcc     60

agatgtgccg atattgtgat gacccagact ccagcctccg tgtctgaacc tgtgggaggc    120

acagtcacca tcaagtgcca ggccagtcag aacatttaca gtggtttggc ctggtatcag    180

cagaaaccag ggcagcctcc caagctccta atctacaagg catccaatct ggcatctggg    240

gtctcatcgc ggttcaaagg cagtagatct gggacagagt acactctcac catcagcgac    300

ctggagtgtg ccgatgctgc cacttactac tgtcaaaact ggtatggtat tagtacttat    360

ggtcgggctt tcggcggagg gaccgaggtg gtggtcaaag gtgatccagt tgcacctact    420

gtcctcatct tcccaccagc tgctgatcag gtggcaactg gaacagtcac catcgtgtgt    480

gtggcgaata aatactttcc cgatgtcacc gtcacctggg aggtggatgg caccacccaa    540

acaactggca tcgagaacag taaaacaccg cagaattctg cagattgtac ctacaacctc    600

agcagcactc tgacactgac cagcacacag tacaacagcc acaaagagta cacctgcaag    660

gtgacccagg gcacgacctc agtcgtccag agcttcaata ggggtgactg ttag          714
```